(12) United States Patent
Brough et al.

(10) Patent No.: US 8,163,905 B2
(45) Date of Patent: Apr. 24, 2012

(54) COMPOUNDS AND THEIR USES 708

(75) Inventors: Stephen Brough, Leicestershire (GB); Richard Evans, Leicestershire (GB); Timothy Jon Luker, Leicestershire (GB); Piotr Raubo, Leicestershire (GB)

(73) Assignee: AstraZeneca AB, Sodertalje (SE)

( * ) Notice: Subject to any disclaimer, the term of this patent is extended or adjusted under 35 U.S.C. 154(b) by 972 days.

(21) Appl. No.: 12/147,132

(22) Filed: Jun. 26, 2008

(65) Prior Publication Data
US 2012/0065214 A1 Mar. 15, 2012

Related U.S. Application Data

(60) Provisional application No. 60/946,415, filed on Jun. 27, 2007, provisional application No. 60/978,167, filed on Oct. 8, 2007, provisional application No. 60/029,444, filed on Feb. 18, 2008.

(51) Int. Cl.
*C07D 241/00* (2006.01)
(52) U.S. Cl. ........ 544/336; 544/408; 544/406; 544/192; 544/410
(58) Field of Classification Search ............. 544/336, 544/406, 408, 192, 410
See application file for complete search history.

(56) References Cited

FOREIGN PATENT DOCUMENTS

| WO | WO 03/076405 | 9/2003 |
|---|---|---|
| WO | WO 2005/054230 | 6/2005 |
| WO | WO 2006/075438 | 8/2005 |
| WO | WO 2006/003517 | 1/2006 |
| WO | WO 2007/129036 | 11/2007 |
| WO | WO 2007/129040 | 11/2007 |
| WO | WO 2007/129963 | 11/2007 |
| WO | WO 2007/149448 | 12/2007 |

OTHER PUBLICATIONS

Database CAPLUS chemical Abstracts Service, Columbus, Ohio, US & WO 2007/149448, Bereznak et al. "Preparation of pyrazinones as cellular proleferation inhibitors", CAPLUS Registry No. 1008732-26-0; 1008732-61-3; 1008732-63-5; 1008733-11-6; 1008733-13-8; 1008733-48-9; 1008733-50-3; 1008733-98-9; 1008734-00-6; 1008734-86-8; 1008734-88-0; 1008735-23-6; 1008735-25-8; 1008735-74-7; 1008735-76-9; 1008736-01-03; 1008736-03-5; 1008744-49-7 Abstract, (2008).
Hanson "Inhibitors of p38 kinase" Expert Opinion on Therapeutic Patents 7(7): 729-733 (1997).

*Primary Examiner* — Jeffrey S. Lundgren
*Assistant Examiner* — Ibrahim D Bori
(74) *Attorney, Agent, or Firm* — AstraZeneca AB

(57) ABSTRACT

The present invention relates to pyrazinone derivatives of formula (I):

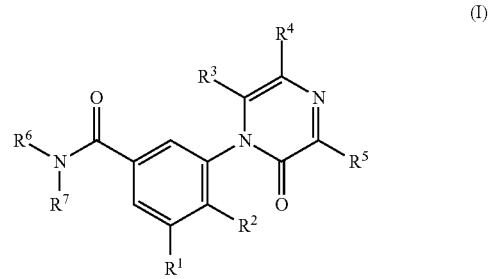

wherein $R^1$, $R^2$, $R^3$, $R^4$, $R^5$, $R^6$ and $R^7$ are as herein defined; processes for their preparation, pharmaceutical compositions containing them and their use in therapy.

4 Claims, 6 Drawing Sheets

Figure 1: XRPD for Example 167 Free Base Crystalline Form A
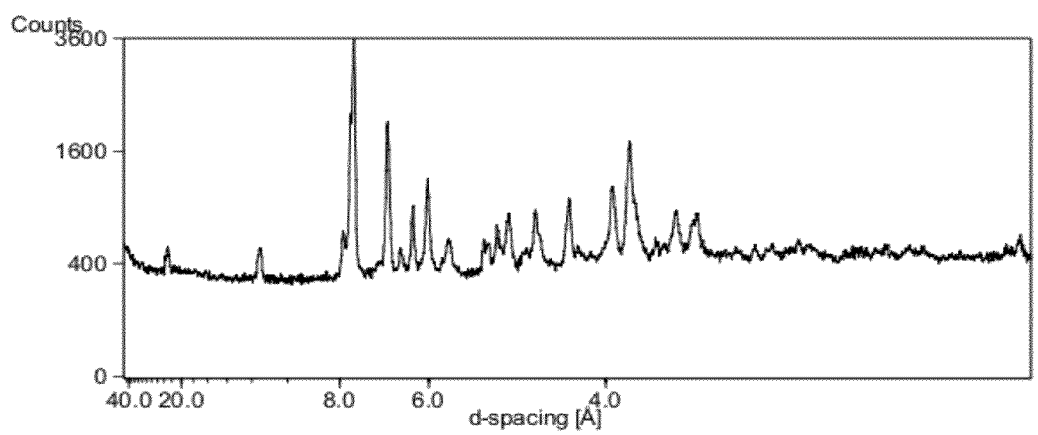
Figure 2: XRPD for Example 167 Free Base Crystalline Form B
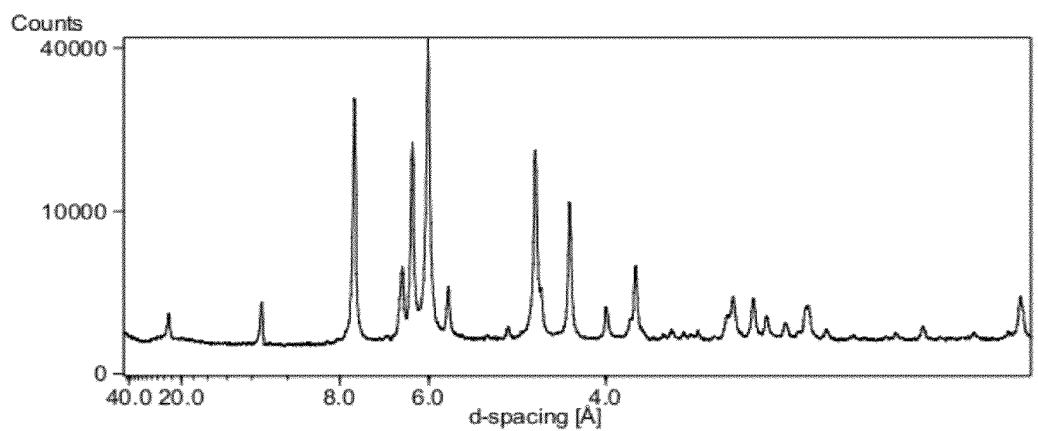

Figure 3: XRPD for Example 259 Free Base Crystalline Form A
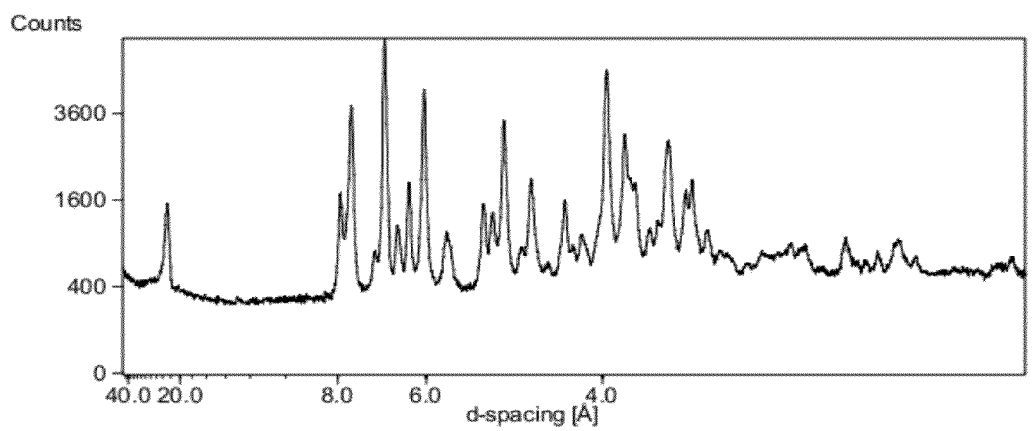
Figure 4: XRPD for Example 260 Free Base Crystalline Form A
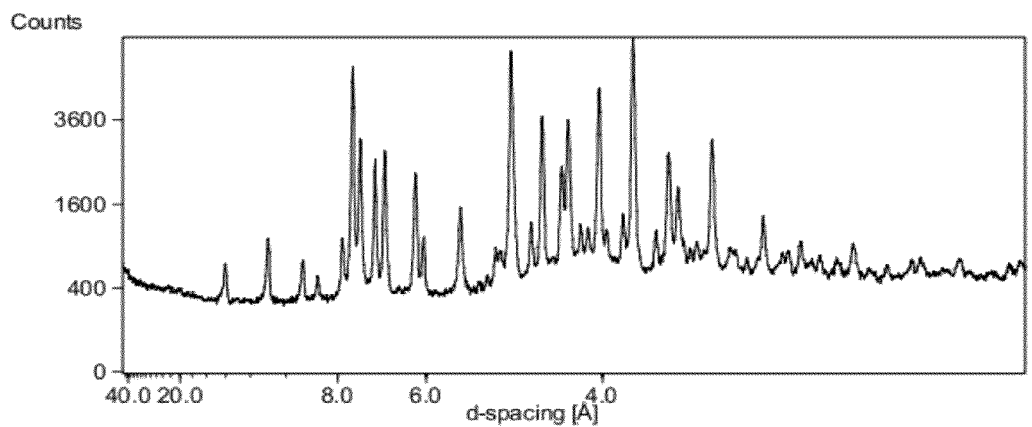

Figure 5: XRPD for Example 163 Free Base Crystaline Form A
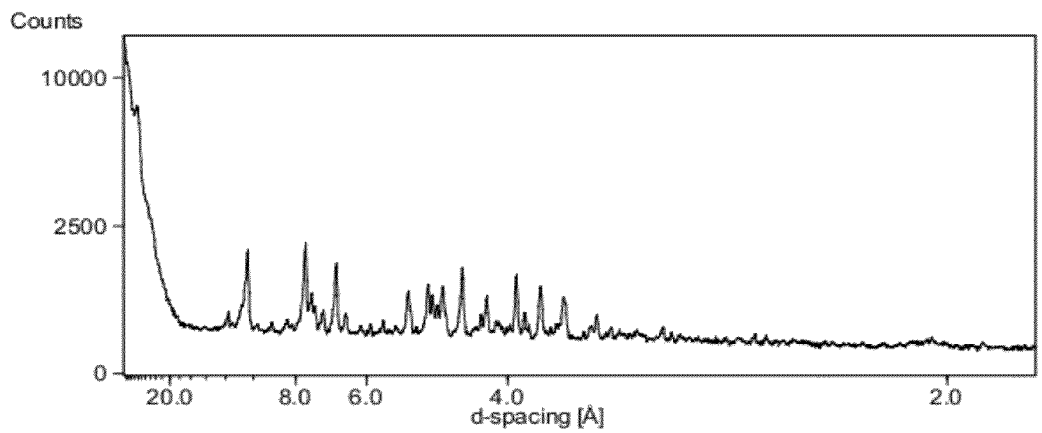
Figure 6: XRPD for Example 163 Free Base Crystaline Form B
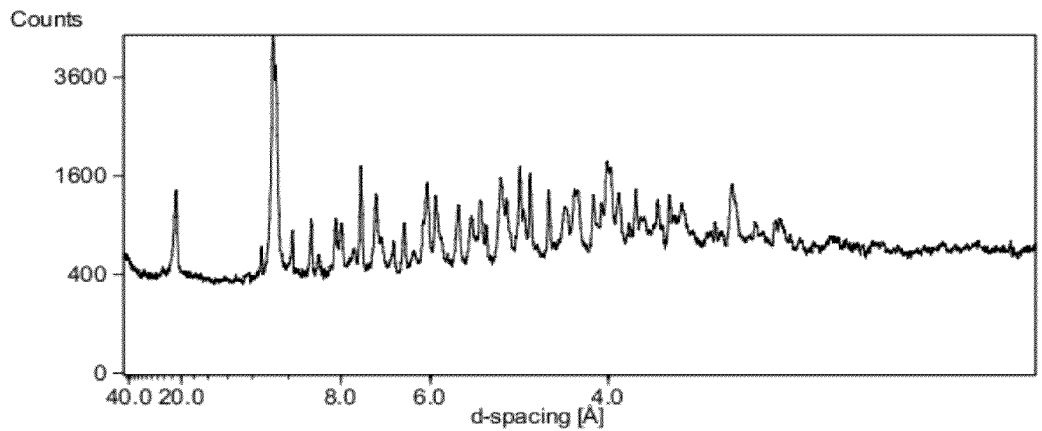

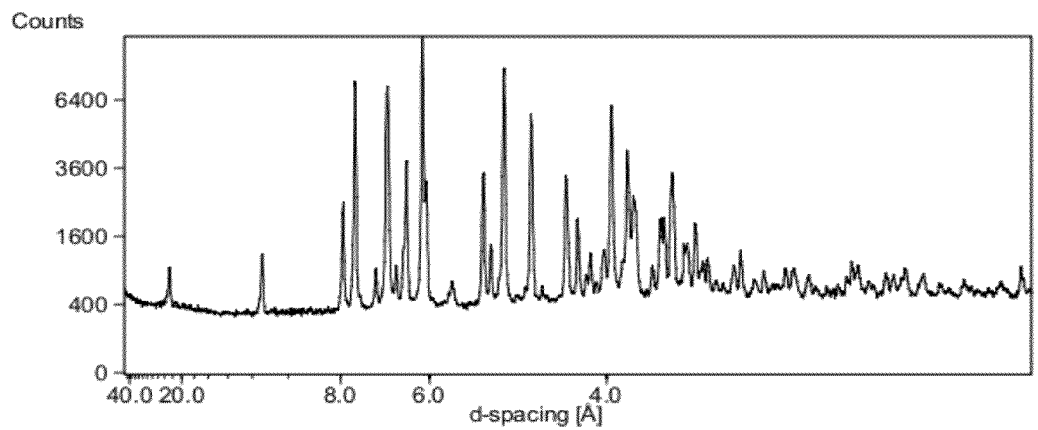
Figure 7: XRPD for Example 163 Free Base Crystaline Form C
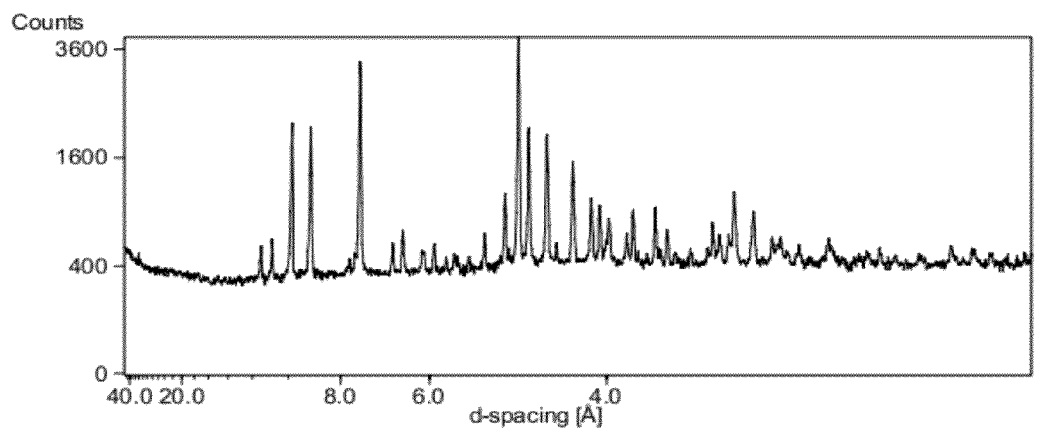
Figure 8: XRPD for Example 163 Free Base Crystaline Form D

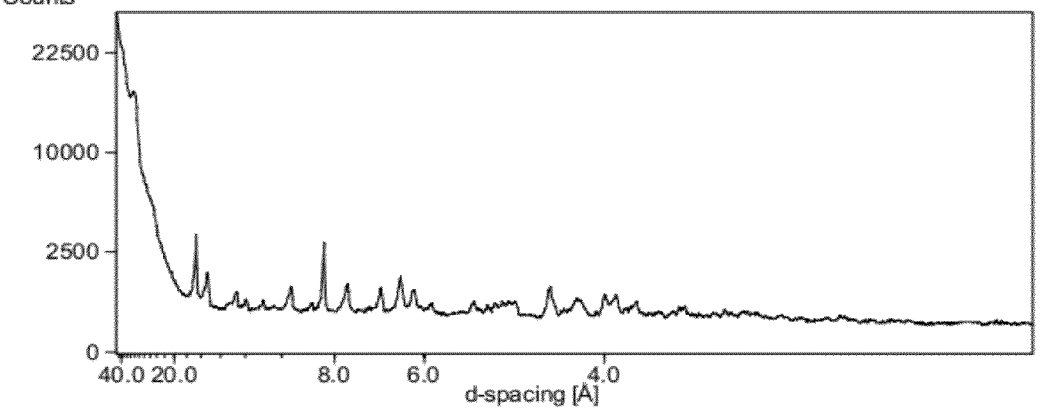
Figure 9: XRPD for Example 163 Saccharide Salt Crystaline Form A
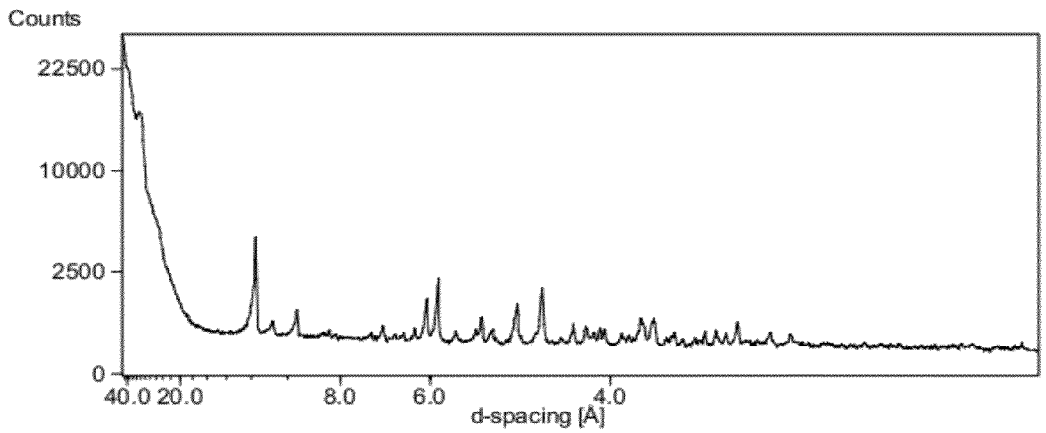
Figure 10: XRPD for Example 163 Tosylate salt Crystaline Form A

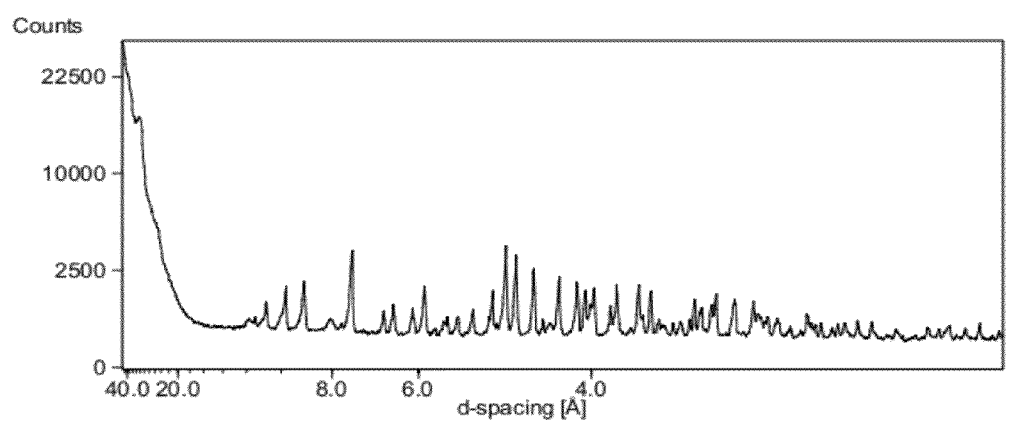
Figure 11: XRPD for Example 163 Tosylate salt Crystaline Form B
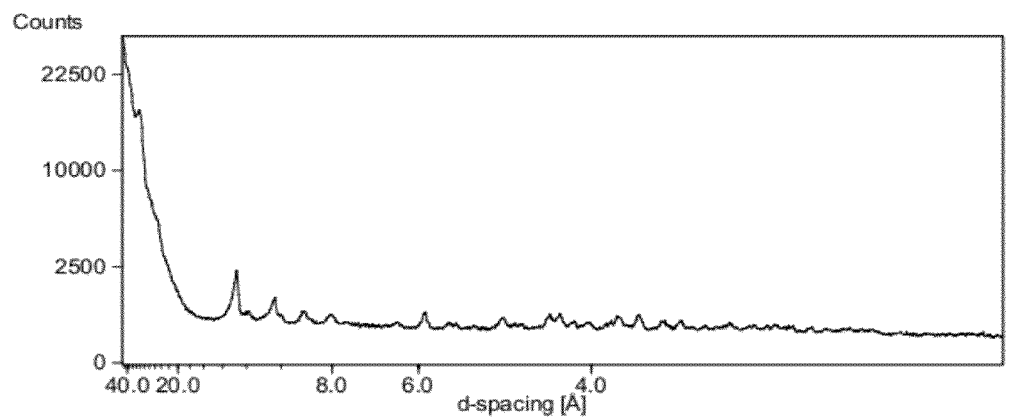
Figure 12: XRPD for Example 163 Hydrochloride salt Crystaline Form A

COMPOUNDS AND THEIR USES 708

This application claims the benefit of U.S. Provisional Application No. 60/946,415, filed Jun. 27, 2007, U.S. Provisional Application No. 60/978,167, filed Oct. 8, 2007, and U.S. Provisional Application No. 61/029,444, filed Feb. 18, 2008, all of which are herein incorporated by reference in their entirety.

The present invention relates to pyrazinone derivatives, processes for their preparation, pharmaceutical compositions containing them and their use in therapy.

The essential function of the lungs requires a fragile structure with enormous exposure to the environment, including pollutants, microbes, allergens, and carcinogens. Host factors, resulting from interactions of lifestyle choices and genetic composition, influence the response to this exposure. Damage or infection to the lungs can give rise to a wide range of diseases of the respiratory system (or respiratory diseases). A number of these diseases are of great public health importance. Respiratory diseases include Acute Lung Injury, Acute Respiratory Distress Syndrome (ARDS), occupational lung disease, lung cancer, tuberculosis, fibrosis, pneumoconiosis, pneumonia, emphysema, Chronic Obstructive Pulmonary Disease (COPD) and asthma.

Among the most common of the respiratory diseases is asthma. Asthma is generally defined as an inflammatory disorder of the airways with clinical symptoms arising from intermittent airflow obstruction. It is characterised clinically by paroxysms of wheezing, dyspnea and cough. It is a chronic disabling disorder that appears to be increasing in prevalence and severity. It is estimated that 15% of children and 5% of adults in the population of developed countries suffer from asthma. Therapy should therefore be aimed at controlling symptoms so that normal life is possible and at the same time provide basis for treating the underlying inflammation.

COPD is a term which refers to a large group of lung diseases which can interfere with normal breathing. Current clinical guidelines define COPD as a disease state characterized by airflow limitation that is not fully reversible. The airflow limitation is usually both progressive and associated with an abnormal inflammatory response of the lungs to noxious particles and gases. The most important contributory source of such particles and gases, at least in the western world, is tobacco smoke. COPD patients have a variety of symptoms, including cough, shortness of breath, and excessive production of sputum; such symptoms arise from dysfunction of a number of cellular compartments, including neutrophils, macrophages, and epithelial cells. The two most important conditions covered by COPD are chronic bronchitis and emphysema.

Chronic bronchitis is a long-standing inflammation of the bronchi which causes increased production of mucous and other changes. The patients' symptoms are cough and expectoration of sputum. Chronic bronchitis can lead to more frequent and severe respiratory infections, narrowing and plugging of the bronchi, difficult breathing and disability.

Emphysema is a chronic lung disease which affects the alveoli and/or the ends of the smallest bronchi. The lung loses its elasticity and therefore these areas of the lungs become enlarged. These enlarged areas trap stale air and do not effectively exchange it with fresh air. This results in difficult breathing and may result in insufficient oxygen being delivered to the blood. The predominant symptom in patients with emphysema is shortness of breath.

Therapeutic agents used in the treatment of respiratory diseases include corticosteroids. Corticosteroids (also known as glucocorticosteroids or glucocorticoids) are potent anti-inflammatory agents. Whilst their exact mechanism of action is not clear, the end result of corticosteroid treatment is a decrease in the number, activity and movement of inflammatory cells into the bronchial submucosa, leading to decreased airway responsiveness. Corticosteroids may also cause reduced shedding of bronchial epithelial lining, vascular permeability, and mucus secretion. Whilst corticosteroid treatment can yield important benefits, the efficacy of these agents is often far from satisfactory, particularly in COPD. Moreover, whilst the use of steroids may lead to therapeutic effects, it is desirable to be able to use steroids in low doses to minimise the occurrence and severity of undesirable side effects that may be associated with regular administration. Recent studies have also highlighted the problem of the acquisition of steroid resistance amongst patients suffering from respiratory diseases. For example, cigarette smokers with asthma have been found to be insensitive to short term inhaled corticosteroid therapy, but the disparity of the response between smokers and non-smokers appears to be reduced with high dose inhaled corticosteroid (Tomlinson et al., Thorax 2005; 60:282-287).

A further class of therapeutic agent used in the treatment of respiratory diseases are bronchodilators. Bronchodilators may be used to alleviate symptoms of respiratory diseases by relaxing the bronchial smooth muscles, reducing airway obstruction, reducing lung hyperinflation and decreasing shortness of breath. Types of bronchodilators in clinical use include $\beta_2$ adrenoceptor agonists, muscarinic receptor antagonists and methylxanthines. Bronchodilators are prescribed mainly for symptomatic relief and they are not considered to alter the natural history of respiratory diseases.

The serine/threonine kinase, p38, is a member of the stress and mitogen activated protein kinase family (SAPK/MAPK) and participates in intracellular signalling cascades involved in a number of responses associated with inflammatory processes. Four isoforms of p38 kinase are known to exist, identified as p38$\alpha$, p38$\beta$, p38$\gamma$ and p38$\delta$.

The p38 pathway is activated by stress (including tobacco smoke, infections or oxidative products) and pro-inflammatory cytokines (e.g. IL-1 or TNF-$\alpha$) and is involved in induction of cytokines such as TNF-$\alpha$, IL-1, IL-6 and matrix metalloprotease by bacterial lipopolysaccharide (LPS). Activation of p38 by dual phosphorylation of thr$^{180}$ and tyr$^{182}$ located in the activation loop is achieved by two dual specificity upstream MAP kinase kinases (MKK); MKK3 and MKK6. In turn p38 phosphorylates numerous targets including other kinases and transcription factors. In addition to effects on transcription, p38 is involved in the control of mRNA stability of several cytokines including TNF-$\alpha$, IL-3, IL-6 and IL-8. Thus through this cascade, p38 kinase is thought to play a significant role in the control of transcription and translation responsible for the induction of pro-inflammatory genes and the subsequent release of pro-inflammatory cytokines such as TNF-$\alpha$ from cells. This mechanism has been validated by investigation of the effects of inhibiting the p38 kinase enzyme on chronic inflammation and arthritis (Kumar et al, Nature Reviews Drug Discovery (2003) 2: 717-725). In particular, p38 kinase inhibitors have been described as potential agents for treating rheumatoid arthritis.

In addition to the links between p38 activation and chronic inflammation and arthritis, there is also data implicating a role for p38 in the pathogenesis of airway diseases in particular COPD and asthma. Stress stimuli (including tobacco smoke, infections or oxidative products) can cause inflammation within the lung environment. Inhibitors of p38 have been shown to inhibit LPS and ovalbumin induced airway TNF-$\alpha$, IL-1-13, IL-6, IL-4, IL-5 and IL-13 (Haddad et al Br J Pharmacol, 2001, 132 (8), 1715; Underwood et al., Am J Physiol Lung cell Mol 200, 279, L895; Duan et al., 2005 Am J Respir Crit. Care Med, 171, 571; Escott et al Br J. Pharmacol., 2000, 131, 173; Underwood et al., J Pharmacol Exp Ther. 293, 281). Furthermore, they significantly inhibit neutrophilia and the release of MMP-9 in LPS, ozone or cigarette smoke models. There is also a significant body of preclinical data highlighting the potential benefits of inhibition of the p38 kinase that could be relevant in the lung (Lee et al. Immunopharmacology, 2000, 47, 185-200). Thus, therapeutic inhibition of p38 activation may be important in the regulation of airway inflammation. Efficacy is anticipated when p38 kinase inhibitors are administered either locally to the lung (for example by inhalation and intranasal delivery) or via systemic routes (for example, oral, intravenous and subcutaneous delivery).

A particular aspect of the present invention relates to pharmaceutical compositions that are formulated to allow the compounds described herein to be administered locally to the lung. Advantages associated with such inhaled drug delivery include large lung surface area for dose absorption; rapid drug absorption, rapid onset of action; avoidance of the gastrointestinal tract and first-pass metabolism, lower dose and reduced side effects.

Known inhibitors of p38 kinase have been reviewed by G. J. Hanson in Expert Opinions on Therapeutic Patents, 1997, 7, 729-733, J Hynes et al Current Topics in Medicinal chemistry 2005, 5, 967-985, C Dominguez et al in Expert Opinions on Therapeutic Patents, 2005, 15, 801-816.

The present invention provides a compound of formula (I):

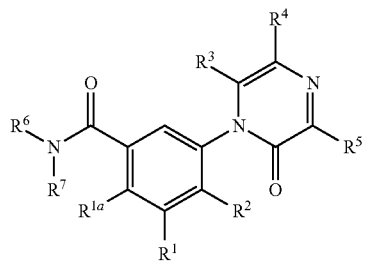

(I)

wherein:

$R^1$, $R^{1a}$ and $R^2$ are independently selected from H, $(C_1\text{-}C_6)$ alkyl, $(C_1\text{-}C_6)$alkoxy, halo, $CF_3$, and CN;

$R^3$ and $R^4$ are independently selected from H, $(C_1\text{-}C_6)$alkyl, $(C_1\text{-}C_6)$alkoxy, halo, OH, $NR^8R^9$, $CF_3$, CN, aryl, heteroaryl and $CONR^{19}R^{11}$, wherein said $(C_1\text{-}C_6)$alkyl and said $(C_1\text{-}C_6)$ alkoxy are, independently, optionally substituted with 1, 2 or 3 groups independently selected from OH, $(C_1\text{-}C_3)$alkoxy, $NR^{12}R^{13}$, $S(O)_pR^{55}$ and halo;

is $R^5$ is selected from H, aryl, heteroaryl, heterocycloalkyl, $(C_3\text{-}C_7)$cycloalkyl, $(CR^{14}R^{15})_mNR^{16}R^{17}$, $S(O)_pR^{16}$, $SO_2NR^{16}R^{17}$, $CH_2R^{16}$ and $OR^{16}$;

$R^6$ is selected from H, $(C_1\text{-}C_6)$alkyl, $(C_1\text{-}C_6)$alkoxy, $(C_3\text{-}C_7)$ cycloalkyl, —$(C_3\text{-}C_7)$cycloalkyl-$(C_1\text{-}C_6)$alkyl, heteroaryl and aryl; wherein said $(C_1\text{-}C_6)$alkyl may be optionally substituted by halo or OH;

$R^7$ is selected from H, $(C_1\text{-}C_6)$alkyl, $(C_1\text{-}C_6)$alkoxy, $(C_3\text{-}C_7)$ cycloalkyl and aryl;

or $R^6$ and $R^7$ together with the nitrogen atom to which they are attached form a 4 to 7 membered ring, optionally containing a further heteroatom selected from $NR^{18}$, S and O;

$R^8$ and $R^9$ are independently selected from H, $(C_1\text{-}C_6)$alkyl, $(C_1\text{-}C_6)$alkoxy and $(C_3\text{-}C_6)$cycloalkyl; or $R^8$ and $R^9$ together with the nitrogen atom to which they are attached form a 4 to 7 membered ring, optionally containing a further heteroatom selected from $NR^{19}$, S and O;

$R^{14}$ and $R^{15}$ are selected from H and $(C_1\text{-}C_6)$alkyl; or $R^{14}$ and $R^{15}$ together with the carbon to which they are attached form a carbonyl (C=O) group;

$R^{16}$ is selected from H, aryl, $(C_3\text{-}C_7)$cycloalkyl and

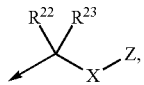

wherein said $(C_3\text{-}C_7)$cycloalkyl may be optionally substituted with an aryl group;

$R^{17}$ is selected from H, $(C_1\text{-}C_6)$alkyl, aryl, heteroaryl, heterocycloalkyl and $(C_3\text{-}C_7)$cycloalkyl, wherein said $(C_1\text{-}C_6)$alkyl may be optionally substituted with 1, 2 or 3 groups independently selected from $(C_1\text{-}C_6)$alkoxy, $(C_3\text{-}C_{10})$cycloalkyl, heterocycloalkyl, heteroaryl and $NR^{20}R^{21}$;

$R^{22}$ is selected from H, $(C_1\text{-}C_6)$alkyl, $(C_1\text{-}C_6)$alkoxy, OH, $NR^{29}R^{30}$, heterocycloalkyl and aryl, wherein said $(C_1\text{-}C_6)$ alkyl may be optionally substituted with 1, 2 or 3 $R^{28}$ groups; and wherein said aryl may be optionally substituted with 1, 2 or 3 groups independently selected from $(C_1\text{-}C_6)$alkyl, $(C_1\text{-}C_6)$alkoxy, halo, $CF_3$ and OH;

$R^{23}$ is selected from H and $(C_1\text{-}C_6)$alkyl;

or $R^{22}$ and $R^{23}$ together with the carbon atom to which they are attached form a $(C_3\text{-}C_7)$cycloalkyl or heterocycloalkyl ring;

X is a bond or a $(CR^{24}R^{25})_n$ group;

$R^{24}$ and $R^{25}$ are independently selected from H, $(C_1\text{-}C_6)$alkyl, $(C_1\text{-}C_6)$alkoxy, OH, heterocycloalkyl and $NR^{39}R^{40}$; or $R^{24}$ and $R^{25}$ together with the carbon atom to which they are attached may form a heterocycloalkyl ring;

Z is an aryl or heteroaryl ring, wherein said aryl or heteroaryl ring is substituted with $R^{26}$ and $R^{27}$;

$R^{26}$ is selected from H, $(C_1\text{-}C_6)$alkyl, $(C_1\text{-}C_6)$alkoxy, OH, aryl, O-aryl, halo, heterocycloalkyl, O-heterocycloalkyl, heteroaryl, O-heteroaryl, cycloalkyl, O-cycloalkyl, $S(O)_pR^{34}$, $NR^{34}R^{35}$ and $CONR^{34}R^{35}$, wherein said $(C_1\text{-}C_6)$alkyl or said $(C_1\text{-}C_6)$alkoxy may be optionally substituted with 1, 2 or 3 groups independently selected from halo, OH, heterocycloalkyl or $NR^{34}R^{35}$;

is $R^{27}$ is selected from H, halo and $(C_1\text{-}C_6)$alkyl, wherein said $(C_1\text{-}C_6)$alkyl may be optionally substituted with 1, 2 or 3 halo groups;

or $R^{26}$ and $R^{27}$ together may form a methylenedioxy group, when attached to adjacent carbon atoms of the aryl or heteroaryl ring;

each occurrence of $R^{28}$ is independently selected from $NR^{29}R^{30}$, halo, $CH_2CF_3$, $CF_3$, heterocycloalkyl, $(C_1\text{-}C_6)$ alkoxy, $OR^{36}$, $COOR^{42}$, $CONR^{31}R^{32}$ and $SO_2NR^{37}R^{38}$;

$R^{29}$ and $R^{30}$ are independently selected from H, $(C_1\text{-}C_6)$alkyl, $(C_3\text{-}C_7)$cycloalkyl, $SO_2R^{41}$ and $C(O)R^{41}$, wherein said $(C_1\text{-}C_6)$alkyl may be optionally substituted with, OH, $NR^{56}R^{57}$ or heterocycloalkyl;

$R^{31}$ and $R^{32}$ are independently selected from H, $(C_1\text{-}C_6)$alkyl and $(C_3\text{-}C_7)$cycloalkyl; or $R^{31}$ and $R^{32}$ together with the nitrogen atom to which they are attached form a 4 to 7 membered ring, optionally containing a further heteroatom selected from $NR^{33}$, S and O;

$R^{34}$ and $R^{35}$ are independently selected from H, $(C_1\text{-}C_6)$alkyl, $(C_3\text{-}C_7)$cycloalkyl, C-linked heterocycloalkyl and C(O)O $(C_1\text{-}C_6)$alkyl, wherein said $(C_1\text{-}C_6)$alkyl may be optionally substituted by OH, halo, $(C_1\text{-}C_6)$alkoxy, $NR^{58}R^{59}$, C(O)OH and heterocycloalkyl; or $R^{34}$ and $R^{35}$ together with the nitrogen to which they are attached form a 4 to 7 membered ring;
$R^{36}$ is selected from H, $(C_1-C_6)$alkyl and heterocycloalkyl, wherein said $(C_1-C_6)$alkyl may be optionally substituted with heterocycloalkyl;
$R^{10}, R^{11}, R^{12}, R^{13}, R^{18}, R^{19}, R^{20}, R^{21}, R^{33}, R^{37}, R^{38}, R^{39}, R^{40}, R^{41}$ and $R^{42}$ are independently selected from H and $(C_1-C_6)$alkyl;
m is 0 or 1;
n is 1 or 2;
each occurrence of p is independently selected from 0, 1 or 2;
cycloalkyl is a non-aromatic carbocyclic ring, optionally fused to an aryl group, wherein said cycloalkyl ring optionally contains, where possible, up to 2 double bonds; and wherein, unless otherwise stated, said cycloalkyl may be optionally substituted with 1 or 2 substituents independently selected from $(C_1-C_6)$alkyl, $(C_1-C_6)$alkoxy, OH, CN, $CF_3$, halo and $NR^{43}R^{44}$;
heterocycloalkyl is a C-linked or N-linked 3 to 9 membered non-aromatic, mono- or bi-cyclic ring, optionally fused to an aryl or heteroaryl group, wherein said heterocycloalkyl ring contains:
1 or 2 $NR^{45}$ atoms, or
one N-atom, or
one N-atom and one $NR^{45}$, or
one N-atom, one $NR^{45}$ and an $S(O)_p$ or an O atom, or
one N-atom and an $S(O)_p$ or an O atom, or
one S atom, or
one O atom;
optionally containing, where possible, 1 or 2 double bonds; and optionally substituted on carbon with 1 or 2 substituents independently selected from $(C_1-C_6)$alkyl, $(C_1-C_6)$alkoxy, OH, CN, $CF_3$, halo, $=O$, $NR^{46}R^{47}$, $-C(O)NR^{46}R^{47}$, bivalent substituent $-OCH_2CH_2O-$ (wherein the terminal oxygen atoms are attached to the same ring carbon atom), bivalent substituent $-CH_2NHCH_2-$ (wherein the terminal carbon atoms are attached to the same ring carbon atom), a tetrahydro-1,1-dioxido-3-thienyl group, and aryl, wherein said $(C_1-C_6)$alkyl may be optionally substituted by aryl, $(C_1-C_6)$alkoxy or OH; and wherein each aryl group may be optionally substituted with $(C_1-C_6)$alkoxy (which in turn may be optionally substituted by $NR^{34}R^{35}$), $(C_1-C_6)$alkyl, OH, $CF_3$ and halo;
aryl is an aromatic ring containing 6 or 10 carbon atoms; wherein, unless otherwise stated, said aryl may be optionally substituted with 1, 2 or 3 substituents independently selected from $(C_1-C_6)$alkyl, $(C_1-C_6)$alkoxy, OH, halo, CN, $CF_3$ and $NR^{48}R^{49}$;
heteroaryl is a 5, 6, 9 or 10 membered aromatic ring, containing from 1 or 2 N atoms and, optionally, an $NR^{50}$ atom, or one $NR^{50}$ atom and an S or an O atom, or one S atom, or one O atom; wherein, unless otherwise stated, said heteroaryl may be optionally substituted with 1, 2 or 3 substituents independently selected from $(C_1-C_6)$alkyl, $(C_1-C_6)$alkoxy, OH, halo, CN, $CF_3$ and $NR^{51}R^{52}$;
$R^{45}$ is selected from H, $(C_1-C_6)$alkyl, $C(O)(C_1-C_6)$alkyl, $C(O)O(C_1-C_6)$alkyl and aryl, wherein said $(C_1-C_6)$alkyl is optionally substituted with a group selected from $(C_1-C_3)$alkoxy, OH, halo, heterocycloalkyl and $NR^{29}R^{30}$; and wherein said $C(O)O(C_1-C_6)$alkyl is optionally substituted with an aryl group;
$R^{50}$ is selected from H, $(C_1-C_6)$alkyl and $C(O)O(C_1-C_6)$alkyl, wherein said $(C_1-C_6)$alkyl may be optionally substituted with a group selected from $(C_1-C_3)$alkoxy, OH, halo, $(C_3-C_6)$cycloalkyl and $NR^{53}R^{54}$;

$R^{43}, R^{44}, R^{46}, R^{47}, R^{48}, R^{49}, R^{51}, R^{52}, R^{53}, R^{54}, R^{55}, R^{56}, R^{57}$ and $R^{59}$ are each independently selected from H and $(C_1-C_6)$alkyl;
$R^{58}$ is selected from H and $(C_1-C_6)$alkyl wherein said $(C_1-C_6)$alkyl may be optionally substituted with a group selected from $(C_1-C_3)$alkoxy and OH;
or a pharmaceutically acceptable salt thereof.

In another aspect the present invention provides a prodrug of a compound of formula (I) as herein defined, or a pharmaceutically acceptable salt thereof.

In yet another aspect the present invention provides an N-oxide of a compound of formula (I) as herein defined, or a prodrug or pharmaceutically acceptable salt thereof.

It will be understood that certain compounds of the present invention may exist in solvated, for example hydrated, as well as unsolvated forms. It is to be understood that the present invention encompasses all such solvated forms.

The present invention also comprises the following embodiments and combinations thereof:

In one embodiment, the present invention provides a compound of formula (I) wherein $R^1$, $R^{1a}$ and $R^2$ are independently selected from H, $(C_1-C_4)$alkyl, halo and $CF_3$.

In another embodiment, the present invention provides a compound of formula (I) wherein $R^1$, $R^{1a}$ and $R^2$ are independently selected from H, $(C_1-C_4)$alkyl, F and Cl.

In yet another embodiment, the present invention provides a compound of formula (I) wherein $R^1$ and $R^{1a}$ are independently selected from H, F and Cl and $R^2$ is selected from $(C_1-C_4)$alkyl, F and Cl In yet another embodiment, the present invention provides a compound of formula (I) wherein $R^1$ and $R^{1a}$ are H and $R^2$ is selected from $(C_1-C_4)$alkyl, F and Cl.

In yet another embodiment, the present invention provides a compound of formula (I) wherein $R^1$ and $R^{1a}$ are H and $R^2$ is methyl.

In another embodiment, the present invention provides a compound of formula (I) wherein $R^1$, $R^{1a}$ and $R^2$ are independently selected from H, $(C_1-C_4)$alkyl and F.

In yet another embodiment, the present invention provides a compound of formula (I) wherein $R^1$ and $R^{1a}$ are independently selected from H and F and $R^2$ is selected from $(C_1-C_4)$alkyl and F.

In yet another embodiment, the present invention provides a compound of formula (I) wherein $R^1$ and $R^{1a}$ are H and $R^2$ is selected from $(C_1-C_4)$alkyl and F.

In yet another embodiment, the present invention provides a compound of formula (I) wherein $R^{1a}$ is H, $R^1$ is F and $R^2$ is $(C_1-C_4)$alkyl.

In yet another embodiment, the present invention provides a compound of formula (I) wherein $R^{1a}$ is H, $R^1$ is F and $R^2$ is methyl.

In one embodiment, the present invention provides a compound of formula (I) wherein $R^{1a}$ is H.

In one embodiment, the present invention provides a compound of formula (I) wherein $R^{1a}$ is H and $R^1$ and $R^2$ are independently selected from H, $(C_1-C_4)$alkyl, halo and $CF_3$.

In another embodiment, the present invention provides a compound of formula (I) wherein $R^{1a}$ is H and $R^1$ and $R^2$ are independently selected from H, $(C_1-C_4)$alkyl and F.

In yet another embodiment, the present invention provides a compound of formula (I) wherein $R^{1a}$ is H, $R^1$ is selected from H and F and $R^2$ is selected from $(C_1-C_4)$alkyl and F.

In yet another embodiment, the present invention provides a compound of formula (I) wherein $R^{1a}$ is H, $R^1$ is H and $R^2$ is selected from $(C_1-C_4)$alkyl and F.

In a yet further embodiment, the present invention provides a compound of formula (I) wherein $R^{1a}$ is H, $R^1$ is H and $R^2$ is methyl.

In one embodiment, the present invention provides a compound of formula (I) wherein $R^3$ and $R^4$ are independently selected from H, $(C_1-C_4)$alkyl, $(C_1-C_4)$alkoxy, Br, Cl, F, CN, aryl and $CONR^{10}R^{11}$, wherein said $(C_1-C_4)$alkyl and said $(C_1-C_4)$alkoxy are, independently, optionally substituted with 1, 2, or 3 groups independently selected from $NR^{12}R^{13}$ and halo.

In another embodiment, the present invention provides a compound of formula (I) wherein $R^3$ is H and $R^4$ is selected from H, methyl, ethyl, methoxy, ethoxy, Cl, Br, CN, phenyl and $CONH_2$, wherein methyl is optionally substituted with a $NR^{12}R^{13}$ group.

In yet another embodiment, the present invention provides a compound of formula (I) wherein $R^3$ and $R^4$ are H.

In one embodiment, the present invention provides a compound of formula (I) wherein $R^5$ is selected from H, aryl, heteroaryl, $NR^{16}R^{17}$ and heterocycloalkyl.

In another embodiment, the present invention provides a compound of formula (I) wherein $R^5$ is selected from heteroaryl, $NR^{16}R^{17}$ and heterocycloalkyl.

In yet another embodiment, the present invention provides a compound of formula (I) wherein $R^5$ is selected from $NR^{16}R^{17}$ and heterocycloalkyl.

In a yet further embodiment, the present invention provides a compound of formula (I) wherein $R^5$ is $NR^{16}R^{17}$.

In one embodiment, the present invention provides a compound of formula (I) wherein $R^6$ and $R^7$ are independently selected from H, $(C_1-C_4)$alkyl, $(C_1-C_4)$alkoxy and $(C_3-C_6)$cycloalkyl.

In another embodiment, the present invention provides a compound of formula (I) wherein $R^6$ is H and $R^7$ is selected from $(C_1-C_4)$alkyl, $(C_1-C_4)$alkoxy and $(C_3-C_6)$cycloalkyl.

In yet another embodiment, the present invention provides a compound of formula (I) wherein $R^6$ is H and $R^7$ is selected from methoxy ($OCH_3$), ethoxy ($OCH_2CH_3$) and $(C_3-C_6)$cycloalkyl.

In a yet further embodiment, the present invention provides a compound of formula (I) wherein $R^6$ is H and $R^7$ is cyclopropyl.

In one embodiment, the present invention provides a compound of formula (I) wherein $R^{16}$ is

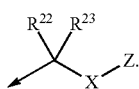

In another embodiment, the present invention provides a compound of formula (I) wherein $R^{16}$ is

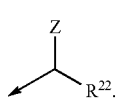

In yet another embodiment, the present invention provides a compound of formula (I) wherein $R^{16}$ is

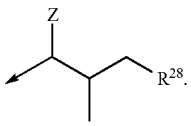

In yet another embodiment, the present invention provides a compound of formula (I) wherein $R^{16}$ is

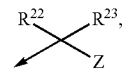

wherein $R^{22}$ and $R^{23}$ each independently represent $(C_1-C_6)$alkyl, or $R^{22}$ and $R^{23}$ together with the carbon atom to which they are attached form a $(C_3-C_7)$cycloalkyl ring.

In one embodiment, the present invention provides a compound of formula (I) wherein $R^{17}$ is selected from H and $(C_1-C_6)$alkyl.

In another embodiment, the present invention provides a compound of formula (I) wherein $R^{17}$ is H.

In one embodiment, the present invention provides a compound of formula (I) wherein $R^{22}$ is selected from H, $(C_1-C_6)$alkyl, heterocycloalkyl and aryl, wherein said $(C_1-C_6)$alkyl may be optionally substituted with 1 or 2 $R^{28}$ groups.

In another embodiment, the present invention provides a compound of formula (I) wherein $R^{22}$ is selected from H and $(C_1-C_6)$alkyl; wherein said $(C_1-C_6)$alkyl may be optionally substituted with a single $R^{28}$ group.

In yet another embodiment, the present invention provides a compound of formula (I) wherein $R^{22}$ is selected from H and branched $(C_1-C_6)$alkyl; wherein said branched $(C_1-C_6)$alkyl is substituted with a single $R^{28}$ group.

In yet another embodiment still, the present invention provides a compound of formula (I) wherein $R^{22}$ is selected from H and isopropyl; wherein said isopropyl is substituted with a single $R^{28}$ group.

In a further embodiment, the present invention provides a compound of formula (I) wherein $R^{22}$ is selected from H and $(C_1-C_6)$alkyl.

In a yet further embodiment, the present invention provides a compound of formula (I) wherein $R^{22}$ is H.

In a yet further still embodiment, the present invention provides a compound of formula (I) wherein $R^{22}$ is methyl.

In one embodiment, the present invention provides a compound of formula (I) wherein $R^{23}$ is H.

In another embodiment, the present invention provides a compound of formula (I) wherein $R^{23}$ is $(C_1-C_6)$alkyl.

In yet another embodiment, the present invention provides a compound of formula (I) wherein $R^{23}$ is methyl.

In one embodiment, the present invention provides a compound of formula (I) wherein X is a bond.

In another embodiment, the present invention provides a compound of formula (I) wherein X is a $(CR^{24}R^{25})_n$ group and n is 1.

In one embodiment, the present invention provides a compound of formula (I) wherein $R^{24}$ and $R^{25}$ are independently selected from H, OH and $(C_1-C_6)$alkyl.

In another embodiment, the present invention provides a compound of formula (I) wherein $R^{24}$ and $R^{25}$ are H.

In one embodiment, the present invention provides a compound of formula (I) wherein $R^{26}$ is selected from H, $(C_1$-$C_6)$alkyl, $(C_1$-$C_6)$alkoxy, OH, O-aryl, halo, aryl, $NR^{34}R^{35}$ and $CONR^{34}R^{35}$, wherein said $(C_1$-$C_6)$alkyl may be optionally substituted with 1, 2, or 3 groups independently selected from halo and $NR^{34}R^{35}$.

In another embodiment, the present invention provides a compound of formula (I) wherein $R^{26}$ is selected from H, $(C_1$-$C_6)$alkyl, $(C_1$-$C_6)$alkoxy, OH, halo, aryl, $NR^{34}R^{35}$ and $CF_3$.

In yet another embodiment, the present invention provides a compound of formula (I) wherein $R^{26}$ is selected from H, $(C_1$-$C_4)$alkyl, $(C_1$-$C_4)$alkoxy, OH, Cl and F.

In one embodiment, the present invention provides a compound of formula (I) wherein $R^{27}$ is H.

In one embodiment, the present invention provides a compound of formula (I) wherein each occurrence of $R^{28}$ is independently selected from heterocycloalkyl, halo, $CF_3$, $CH_2CF_3$ and $NR^{29}R^{30}$.

In another embodiment, the present invention provides a compound of formula (I) wherein each occurrence of $R^{28}$ is independently selected from heterocycloalkyl and $NR^{29}R^{30}$.

In yet another embodiment, the present invention provides a compound of formula (I) wherein $R^{28}$ is heterocycloalkyl.

In one embodiment, the present invention provides a compound of formula (I) wherein Z is an aryl ring substituted with $R^{26}$ and $R^{27}$.

In another embodiment, the present invention provides a compound of formula (I) wherein Z is a phenyl ring substituted with $R^{26}$ and $R^{27}$.

In one embodiment, the present invention provides a compound of formula (I) wherein heterocycloalkyl is a C-linked or N-linked 5 or 6 membered non-aromatic, monocyclic ring, optionally fused to an aryl group, wherein said heterocycloalkyl ring contains:

one N-atom, or one N-atom and one $NR^{45}$, or one N-atom and an $S(O)_p$ or an O atom, and is optionally substituted on carbon with 1 or 2 substituents independently selected from $(C_1$-$C_6)$alkyl, $(C_1$-$C_6)$alkoxy, OH, CN, $CF_3$, halo, $NR^{46}R^{47}$ and aryl, wherein said $(C_1$-$C_6)$alkyl may be optionally substituted by aryl, $(C_1$-$C_6)$alkoxy or OH; and wherein each aryl group may be optionally substituted with $(C_1$-$C_6)$alkoxy (which in turn may be optionally substituted by $NR^{34}R^{35}$), $(C_1$-$C_6)$alkyl, OH, $CF_3$ and halo.

In one embodiment, the present invention provides a compound of formula (I) wherein halo is selected from Cl and F.

In one embodiment, the present invention provides a compound of formula (I) wherein halo is F.

In one embodiment, the present invention provides a compound of formula (I) wherein n is 1.

In one embodiment, the present invention provides a compound of formula (I) wherein m is 0.

In one embodiment, the present invention provides a compound of formula (IA), or a pharmaceutically acceptable salt thereof

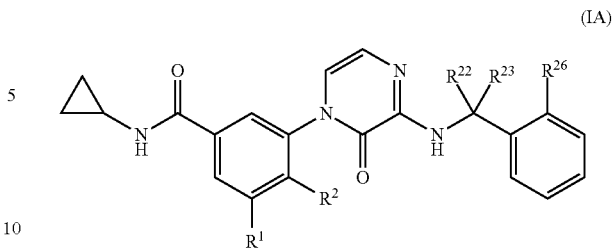

(IA)

wherein:
$R^1$ and $R^2$ are independently selected from H, $(C_1$-$C_4)$alkyl and F;
$R^{22}$ and $R^{23}$ are each independently selected from H and $(C_1$-$C_6)$alkyl;
or $R^{22}$ and $R^{23}$ together with the carbon atom to which they are both attached form a $(C_3$-$C_4)$cycloalkyl;
$R^{26}$ is $(C_1$-$C_6)$alkoxy which may be optionally substituted with $NR^{34}R^{35}$; and
$R^{34}$ and $R^{35}$ are independently selected from H and $(C_1$-$C_6)$alkyl wherein said $(C_1$-$C_6)$alkyl may be optionally substituted by OH.

In one embodiment, the present invention provides a compound of formula (IA), wherein $R^1$ is selected from H and F.

In one embodiment, the present invention provides a compound of formula (IA), wherein $R^1$ is H.

In one embodiment, the present invention provides a compound of formula (IA), wherein $R^1$ is F.

In one embodiment, the present invention provides a compound of formula (IA), wherein $R^2$ is methyl.

In one embodiment, the present invention provides a compound of formula (IA) wherein $R^1$ is F and $R^2$ is methyl.

In one embodiment, the present invention provides a compound of formula (IA), wherein $R^{22}$ and $R^{23}$ together with the carbon atom to which they are both attached form a cyclopropyl ring.

In one embodiment, the present invention provides a compound of formula (IA), wherein $R^{22}$ and $R^{23}$ each independently represent methyl or ethyl.

In one embodiment, the present invention provides a compound of formula (IA), wherein $R^{26}$ $(C_1$-$C_6)$alkoxy substituted with $NR^{34}R^{35}$, wherein $R^{34}$ and $R^{35}$ are independently selected from H and $(C_1$-$C_4)$alkyl wherein said $(C_1$-$C_4)$alkyl may be optionally substituted by OH.

In one embodiment, the present invention provides a compound of formula (IA), wherein $R^{26}$ is selected from
—$OCH_2CH_2NH_2$,
—$OCH_2CH_2NHCH_3$,
—$OCH_2CH_2NHCH_2CH_3$,
—$OCH_2CH_2NHCH(CH_3)_2$,
—$OCH_2CH_2N(CH_2CH_3)_2$,
—$OCH_2CH_2CH_2NHCH_3$,
—$OCH_2CH_2CH_2CH_2NHCH_3$,
—$OCH_2CH_2NHCH_2CH_2OH$,
—$OCH_2CH_2N(CH_3)CH_2CH_2OH$,
—$OCH_2CH_2NHCH(CH_3)CH_2OH$,
—$OCH_2CH_2NHCH_2CH_2CH_2OH$, and
—$OCH_2CH_2NHCH_2CH(OH)CH_3$.

In one embodiment, the present invention provides a compound of formula (IA) selected from:
N-Cyclopropyl-4-methyl-3-[3-[[1-methyl-1-[2-[2-(methylamino)ethoxy]phenyl]ethyl]amino]-2-oxo-1(2H)-pyrazinyl]-benzamide N-Cyclopropyl-4-methyl-3-[[1-[2-[2-(methylamino)ethoxy]phenyl]cyclopropyl]amino]-2-oxo-1(2H)-pyrazinyl]-benzamide N-Cyclopropyl-3-fluoro-5-[3-[[1-[2-[2-[(2-hydroxyethyl)amino]ethoxy]phenyl]-1-methylethyl]amino]-2-oxo-1(2H)-pyrazinyl]-4-methyl-benzamide N-Cyclopropyl-3-fluoro-5-[3-[[1-[2-[2-[[(2R)-2-hydroxypropyl]amino]ethoxy]phenyl]-1-methylethyl]amino]-2-oxo-1(2H)-pyrazinyl]-4-methyl-benzamide N-Cyclopropyl-3-fluoro-5-[3-[[1-[2-[2-[[(2S)-2-hydroxypropyl]amino]ethoxy]phenyl]-1-methylethyl]amino]-2-oxo-1(2H)-pyrazinyl]-4-methyl-benzamide N-Cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide N-Cyclopropyl-3-fluoro-5-[3-[[1-[2-[2-[(2-hydroxyethyl)amino]ethoxy]phenyl]cyclopropyl]amino]-2-oxo-1(2H)-pyrazinyl]-4-methyl-benzamide 3-[3-({1-[2-(2-Aminoethoxy)phenyl]-1-methylethyl}amino)-2-oxopyrazin-1(2H)-yl]-N-cyclopropyl-5-fluoro-4-methylbenzamide 3-[3-({1-[2-(2-Aminoethoxy)phenyl]cyclopropyl}amino)-2-oxopyrazin-1(2H)-yl]-N-cyclopropyl-5-fluoro-4-methylbenzamide and N-Cyclopropyl-3-fluoro-5-[3-{[1-(2-{2-[(2-hydroxyethyl)(methyl)amino]ethoxy}phenyl)cyclopropyl]amino}-2-oxopyrazin-1(2H)-yl]-4-methylbenzamide or a pharmaceutically acceptable salt thereof.

In one embodiment, the present invention provides a compound of formula (IA) selected from:
N-Cyclopropyl-4-methyl-3-[3-[[1-methyl-1-[2-[2-(methylamino)ethoxy]phenyl]ethyl]amino]-2-oxo-1(2H)-pyrazinyl]-benzamide N-Cyclopropyl-4-methyl-3-[3-[[1-[2-[2-(methylamino)ethoxy]phenyl]cyclopropyl]amino]-2-oxo-1(2H)-pyrazinyl]-benzamide N-Cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide and N-Cyclopropyl-3-fluoro-5-[3-[[1-[2-[2-[(2-hydroxyethyl)amino]ethoxy]phenyl]cyclopropyl]amino]-2-oxo-1(2H)-pyrazinyl]-4-methyl-benzamide or a pharmaceutically acceptable salt thereof.

In one embodiment, the present invention provides a compound of formula (ID), or a pharmaceutically acceptable salt thereof

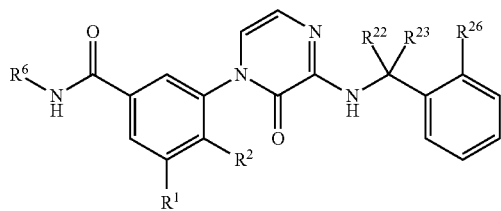

(ID)

wherein:
$R^1$ and $R^2$ are independently selected from H, $(C_1-C_4)$alkyl and F;
$R^6$ is $(C_1-C_4)$alkoxy;
$R^{22}$ and $R^{23}$ are each independently selected from H and $(C_1-C_6)$alkyl;
or $R^{22}$ and $R^{23}$ together with the carbon atom to which they are both attached form a $(C_3-C_4)$cycloalkyl;

$R^{26}$ $(C_1-C_6)$alkoxy which may be optionally substituted with $NR^{34}R^{35}$; and
$R^{34}$ and $R^{35}$ are independently selected from H and $(C_1-C_6)$alkyl wherein said $(C_1-C_6)$alkyl may be optionally substituted by OH.

In one embodiment, the present invention provides a compound of formula (ID), wherein $R^1$ is selected from H and F.

In one embodiment, the present invention provides a compound of formula (ID), wherein $R^1$ is H.

In one embodiment, the present invention provides a compound of formula (ID), wherein $R^1$ is F.

In one embodiment, the present invention provides a compound of formula (ID), wherein $R^2$ is methyl.

In one embodiment, the present invention provides a compound of formula (ID), wherein $R^6$ is methoxy.

In one embodiment, the present invention provides a compound of formula (ID), wherein $R^{22}$ and $R^{23}$ together with the carbon atom to which they are both attached form a cyclopropyl ring.

In one embodiment, the present invention provides a compound of formula (ID), wherein $R^{22}$ and $R^{23}$ each independently represent methyl or ethyl.

In one embodiment, the present invention provides a compound of formula (ID), wherein $R^{26}$ is $(C_1-C_6)$alkoxy substituted with $NR^{34}R^{35}$, wherein $R^{34}$ and $R^{35}$ are independently selected from H and $(C_1-C_4)$alkyl wherein said $(C_1-C_4)$alkyl may be optionally substituted by OH.

In one embodiment, the present invention provides a compound of formula (ID), wherein $R^{26}$ is —$OCH_2CH_2NHCH_3$.

In one embodiment, the present invention provides a compound of formula (ID) selected from:
3-Fluoro-N-methoxy-4-methyl-5-{3-[(1-methyl-1-{2-[2-(methylamino)ethoxy]phenyl}ethyl)amino]-2-oxopyrazin-1(2H)-yl}benzamide and N-Methoxy-4-methyl-3-{3-[(1-{2-[2-(methylamino)ethoxy]phenyl}cyclopropyl)amino]-2-oxopyrazin-1(2H)-yl}benzamide or a pharmaceutically acceptable salt thereof.

In one embodiment, the present invention provides a compound of formula (IE), or a pharmaceutically acceptable salt thereof

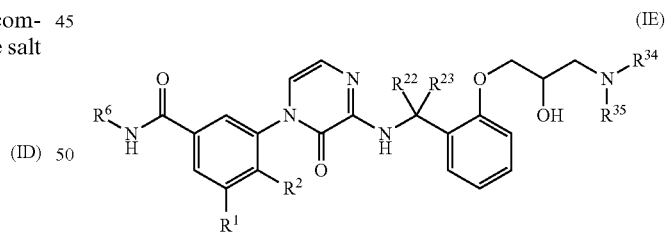

(IE)

wherein:
$R^1$ and $R^2$ are independently selected from H, $(C_1-C_4)$alkyl and F;
$R^6$ is cyclopropyl or $(C_1-C_4)$alkoxy;
$R^{22}$ and $R^{23}$ are each independently selected from H and $(C_1-C_6)$alkyl;
or $R^{22}$ and $R^{23}$ together with the carbon atom to which they are both attached form a $(C_3-C_4)$cycloalkyl; and
$R^{34}$ and $R^{35}$ are independently selected from H and $(C_1-C_6)$alkyl wherein said $(C_1-C_6)$alkyl may be optionally substituted by OH.

In one embodiment, the present invention provides a compound of formula (IE), wherein $R^1$ is selected from H and F.

In one embodiment, the present invention provides a compound of formula (IE), wherein $R^1$ is H.

In one embodiment, the present invention provides a compound of formula (IE), wherein $R^1$ is F.

In one embodiment, the present invention provides a compound of formula (IE), wherein $R^2$ is methyl.

In one embodiment, the present invention provides a compound of formula (IE), wherein $R^6$ is cyclopropyl.

In one embodiment, the present invention provides a compound of formula (IE), wherein $R^{22}$ and $R^{23}$ together with the carbon atom to which they are both attached form a cyclopropyl ring.

In one embodiment, the present invention provides a compound of formula (IE), wherein $R^{22}$ and $R^{23}$ each independently represent methyl or ethyl.

In one embodiment, the present invention provides a compound of formula (IE), wherein $R^{34}$ and $R^{35}$ are independently selected from H and $(C_1-C_4)$alkyl.

In one embodiment, the present invention provides a compound of formula (IE) selected from:

N-Cyclopropyl-3-fluoro-5-[3-{[1-(2-{[(2R)-2-hydroxy-3-(methylamino)propyl]oxy}phenyl)-1-methylethyl]amino}-2-oxopyrazin-1(2H)-yl]-4-methylbenzamide N-Cyclopropyl-3-[3-{[1-(2-{[(2R)-3-(ethylamino)-2-hydroxypropyl]oxy}phenyl)-1-methylethyl]amino}-2-oxopyrazin-1(2H)-yl]-5-fluoro-4-methylbenzamide and N-Cyclopropyl-3-fluoro-5-[3-{[1-(2-{[(2S)-2-hydroxy-3-(methylamino)propyl]oxy}phenyl)-1-methylethyl]amino}-2-oxopyrazin-1(2H)-yl]-4-methylbenzamide or a pharmaceutically acceptable salt thereof.

In one embodiment, the present invention provides a compound of formula (I) selected from:

N-methoxy-4-methyl-3-[3-[[(1R,2S)-2-methyl-3-(4-morpholinyl)-1-phenylpropyl]amino]-2-oxo-1(2H)-pyrazinyl]-benzamide;

N-methoxy-4-methyl-3-[2-oxo-3-[[(1R)-1-phenylpropyl]amino]-1(2H)-pyrazinyl]-benzamide;

N-methoxy-4-methyl-3-[3-[[(1R,2S)-2-methyl-1-phenyl-3-(1-pyrrolidinyl)propyl]amino]-2-oxo-1(2H)-pyrazinyl]-benzamide;

N-cyclopropyl-4-methyl-3-[3-[[1-methyl-1-[2-[2-(methylamino)ethoxy]phenyl]ethyl]amino]-2-oxo-1(2H)-pyrazinyl]-benzamide;

N-cyclopropyl-4-methyl-3-[3-[[1-methyl-1-[2-[3-(methylamino)propoxy]phenyl]ethyl]amino]-2-oxo-1(2H)-pyrazinyl]-benzamide;

N-cyclopropyl-4-methyl-3-[3-[[1-methyl-1-[2-[2-(1-pyrrolidinyl)ethoxy]phenyl]ethyl]amino]-2-oxo-1(2H)-pyrazinyl]-benzamide;

N-methoxy-4-methyl-3-[3-[(1-methyl-1-phenylethyl)amino]-2-oxo-1(2H)-pyrazinyl]-benzamide;

3-[3-[[(1R,2R)-3-hydroxy-2-methyl-1-phenylpropyl]amino]-2-oxo-1(2H)-pyrazinyl]-N-methoxy-4-methylbenzamide;

N-cyclopropyl-4-methyl-3-[2-oxo-3-[[(1R)-1-[2-[2-(1-pyrrolidinyl)ethoxy]phenyl]propyl]amino]-1(2H)-pyrazinyl]-benzamide;

N-cyclopropyl-3-[3-[[(1R,2S)-3-[(1,1-dimethylethyl)amino]-2-methyl-1-phenylpropyl]amino]-2-oxo-1(2H)-pyrazinyl]-4-methyl-benzamide;

N-methoxy-4-methyl-3-[3-[[(1R,2S)-2-methyl-3-(4-morpholinyl)-1-(1-naphthalenyl)propyl]amino]-2-oxo-1(2H)-pyrazinyl]-benzamide;

N-cyclopropyl-3-[3-[[(1R,2S)-3-[[2-(dimethylamino)ethyl]amino]-2-methyl-1-phenylpropyl]amino]-2-oxo-1(2H)-pyrazinyl]-4-methyl-benzamide;

N-cyclopropyl-3-[3-[[(1R,2S)-3-[4-(hydroxymethyl)-1-piperidinyl]-2-methyl-1-phenylpropyl]amino]-2-oxo-1(2H)-pyrazinyl]-4-methyl-benzamide;

N-methoxy-4-methyl-3-[3-[[(1R,2S)-2-methyl-1-(1-naphthalenyl)-3-(1-pyrrolidinyl)propyl]amino]-2-oxo-1(2H)-pyrazinyl]-benzamide;

N-cyclopropyl-3-[3-[[(1R,2S)-3-[(2,2-dimethylpropyl)amino]-2-methyl-1-phenylpropyl]amino]-2-oxo-1(2H)-pyrazinyl]-4-methyl-benzamide;

N-cyclopropyl-3-[3-[[(1R,2S)-3-[(1,1-dimethylethyl)methylamino]-2-methyl-1-phenylpropyl]amino]-2-oxo-1(2H)-pyrazinyl]-4-methyl-benzamide;

N-cyclopropyl-3-[3-[[(1R,2S)-3-[(2R)-2-(methoxymethyl)-1-pyrrolidinyl]-2-methyl-1-phenylpropyl]amino]-2-oxo-1(2H)-pyrazinyl]-4-methyl-benzamide;

N-cyclopropyl-3-[3-[[(1R,2S)-3-[(2S)-2-(methoxymethyl)-1-pyrrolidinyl]-2-methyl-1-phenylpropyl]amino]-2-oxo-1(2H)-pyrazinyl]-4-methyl-benzamide;

N-cyclopropyl-4-methyl-3-[3-[[(1R,2S)-2-methyl-3-(4-morpholinyl)-1-phenylpropyl]amino]-2-oxo-1(2H)-pyrazinyl]-benzamide;

N-cyclopropyl-4-methyl-3-[2-oxo-3-[[(1R)-1-phenylpropyl]amino]-1(2H)-pyrazinyl]-benzamide;

N-cyclopropyl-3-[3-[[(1R,2S)-3-(4-hydroxy-1-piperidinyl)-2-methyl-1-phenylpropyl]amino]-2-oxo-1(2H)-pyrazinyl]-4-methyl-benzamide;

N-cyclopropyl-3-[3-[[(1R,2S)-3-(diethylamino)-2-methyl-1-phenylpropyl]amino]-2-oxo-1(2H)-pyrazinyl]-4-methyl-benzamide;

N-cyclopropyl-3-[3-[[(1R,2S)-3-[[2-(dimethylamino)ethyl]methylamino]-2-methyl-1-phenylpropyl]amino]-2-oxo-1(2H)-pyrazinyl]-4-methyl-benzamide;

N-cyclopropyl-4-methyl-3-[3-[[(1R,2S)-2-methyl-1-phenyl-3-(1-piperidinyl)propyl]amino]-2-oxo-1(2H)-pyrazinyl]-benzamide;

N-cyclopropyl-4-methyl-3-[3-[[(1R,2S)-2-methyl-1-phenyl-3-(1-pyrrolidinyl)propyl]amino]-2-oxo-1(2H)-pyrazinyl]-benzamide;

N-cyclopropyl-3-[3-[[(1R,2S)-3-(dimethylamino)-2-methyl-1-phenylpropyl]amino]-2-oxo-1(2H)-pyrazinyl]-4-methyl-benzamide;

N-cyclopropyl-4-methyl-3-[3-[[(1R,2S)-2-methyl-3-(4-methyl-1-piperazinyl)-1-phenylpropyl]amino]-2-oxo-1(2H)-pyrazinyl]-benzamide;

3-[3-[[(1R,2S)-3-(4-acetyl-1-piperazinyl)-2-methyl-1-phenylpropyl]amino]-2-oxo-1(2H)-pyrazinyl]-N-cyclopropyl-4-methyl-benzamide;

N-cyclopropyl-3-[3-[[1-(2-hydroxyphenyl)-1-methylethyl]amino]-2-oxo-1(2H)-pyrazinyl]-4-methyl-benzamide;

N-cyclopropyl-4-methyl-3-[3-[2-(3-methylphenyl)-1-pyrrolidinyl]-2-oxo-1(2H)-pyrazinyl]-benzamide;

N-cyclopropyl-3-[3-[2-(2-methoxyphenyl)-1-pyrrolidinyl]-2-oxo-1(2H)-pyrazinyl]-4-methyl-benzamide;

N-cyclopropyl-4-methyl-3-[3-[[1-[2-[2-(methylamino)ethoxy]phenyl]cyclopropyl]amino]-2-oxo-1(2H)-pyrazinyl]-benzamide;

N-cyclopropyl-4-methyl-3-[3-[[1-[2-[2-(ethylamino)ethoxy]phenyl]cyclopropyl]amino]-2-oxo-1(2H)-pyrazinyl]-benzamide; and N-cyclopropyl-3-fluoro-4-methyl-5-[3-[[1-methyl-1-[2-[2-(methylamino)ethoxy]phenyl]ethyl]amino]-2-oxo-1(2H)-pyrazinyl]-benzamide, N-Cyclopropyl-4-methyl-3-[3-[[(1R,2S)-2-methyl-3-(4-methyl-1-piperidinyl)-1-phenylpropyl]amino]-2-oxo-1(2H)-pyrazinyl]-benzamide N-Cyclopropyl-4-methyl-3-[3-[[(1R,2S)-2-methyl-3-[4-(1-methylethyl)-1-piperazinyl]-1-phenylpropyl]amino]-2-oxo-1(2H)-pyrazinyl]-benzamide
N-Cyclopropyl-4-methyl-3-[3-[[(1R,2S)-2-methyl-1-phenyl-3-(1-piperazinyl)propyl]amino]-2-oxo-1(2H)-pyrazinyl]-benzamide
N-Cyclopropyl-3-[3-[[(1R,2S)-3-(hexahydro-4-methyl-1H-1,4-diazepin-1-yl)-2-methyl-1-phenylpropyl]amino]-2-oxo-1(2H)-pyrazinyl]-4-methyl-benzamide
N-Cyclopropyl-3-[3-[[(1R,2S)-3-(4-fluoro-1-piperidinyl)-2-methyl-1-phenylpropyl]amino]-2-oxo-1(2H)-pyrazinyl]-4-methyl-benzamide
N-Cyclopropyl-3-[3-[[(1R,2S)-3-(4,4-difluoro-1-piperidinyl)-2-methyl-1-phenylpropyl]amino]-2-oxo-1(2H)-pyrazinyl]-4-methyl-benzamide
N-Cyclopropyl-3-[3-[[(1R,2S)-3-[4-(dimethylamino)-1-piperidinyl]-2-methyl-1-phenylpropyl]amino]-2-oxo-1(2H)-pyrazinyl]-4-methyl-benzamide
N-Cyclopropyl-4-methyl-3-[3-[[(1R,2S)-2-methyl-1-phenyl-3-[4-(trifluoromethyl)-1-piperidinyl]propyl]amino]-2-oxo-1(2H)-pyrazinyl]-benzamide
N-Cyclopropyl-4-methyl-3-[3-[[(1R,2S)-2-methyl-3-(3-oxo-1-piperazinyl)-1-phenylpropyl]amino]-2-oxo-1(2H)-pyrazinyl]-benzamide
N-Cyclopropyl-3-[3-[[(1R,2S)-3-(1,4-dioxa-8-azaspiro[4.5]dec-8-yl)-2-methyl-1-phenylpropyl]amino]-2-oxo-1(2H)-pyrazinyl]-4-methyl-benzamide
N-Cyclopropyl-4-methyl-3-[3-[[(1R,2S)-2-methyl-3-[(3R)-3-methyl-1-piperazinyl]-1-phenylpropyl]amino]-2-oxo-1(2H)-pyrazinyl]-benzamide
N-Cyclopropyl-4-methyl-3-[3-[[(1R,2S)-2-methyl-3-[(3S)-3-methyl-1-piperazinyl]-1-phenylpropyl]amino]-2-oxo-1(2H)-pyrazinyl]-benzamide
N-Cyclopropyl-4-methyl-3-[3-[[(1R,2S)-2-methyl-3-[(2-methylpropyl)amino]-1-phenylpropyl]amino]-2-oxo-1(2H)-pyrazinyl]-benzamide
N-Cyclopropyl-3-[3-[[(1R,2S)-3-(cyclopropylamino)-2-methyl-1-phenylpropyl]amino]-2-oxo-1(2H)-pyrazinyl]-4-methyl-benzamide
N-Cyclopropyl-4-methyl-3-[3-[[(1R,2S)-2-methyl-3-[(2R)-2-methyl-1-pyrrolidinyl]-1-phenylpropyl]amino]-2-oxo-1(2H)-pyrazinyl]-benzamide
N-Cyclopropyl-3-[3-[[(1R,2S)-3-[(3S)-3-hydroxy-1-piperidinyl]-2-methyl-1-phenylpropyl]amino]-2-oxo-1(2H)-pyrazinyl]-4-methyl-benzamide
N-Cyclopropyl-3-[3-[[(1R,2S)-3-[(3R)-3-hydroxy-1-piperidinyl]-2-methyl-1-phenylpropyl]amino]-2-oxo-1(2H)-pyrazinyl]-4-methyl-benzamide
N-Cyclopropyl-4-methyl-3-[3-[[(1R,2S)-2-methyl-3-[(2R)-2-methyl-1-piperazinyl]-1-phenylpropyl]amino]-2-oxo-1(2H)-pyrazinyl]-benzamide
N-Cyclopropyl-3-[3-[[(1R,2S)-3-(2,7-diazaspiro[3.5]non-7-yl)-2-methyl-1-phenylpropyl]amino]-2-oxo-1(2H)-pyrazinyl]-4-methyl-benzamide
N-Cyclopropyl-4-methyl-3-[3-[[(1R,2S)-2-methyl-1-phenyl-3-(4-thiomorpholinyl)propyl]amino]-2-oxo-1(2H)-pyrazinyl]-benzamide
N-Cyclopropyl-3-[3-[[(1R,2S)-3-[(3S)-3-hydroxy-1-pyrrolidinyl]-2-methyl-1-phenylpropyl]amino]-2-oxo-1(2H)-pyrazinyl]-4-methyl-benzamide
N-Cyclopropyl-4-methyl-3-[3-[[(1R,2S)-2-methyl-1-phenyl-3-[4-(tetrahydro-1,1-dioxido-3-thienyl)-1-piperazinyl]propyl]amino]-2-oxo-1(2H)-pyrazinyl]-benzamide
1-[(2S,3R)-3-[[4-[5-[(cyclopropylamino)carbonyl]-2-methylphenyl]-3,4-dihydro-3-oxopyrazinyl]amino]-2-methyl-3-phenylpropyl]-4-piperidinecarboxamide
N-Cyclopropyl-3-[3-[[(1R,2S)-3-[(2-hydroxy-1,1-dimethylethyl)amino]-2-methyl-1-phenylpropyl]amino]-2-oxo-1(2H)-pyrazinyl]-4-methyl-benzamide
N-Cyclopropyl-3-[3-[[(1R,2S)-3-[(3R,5S)-3,5-dimethyl-1-piperazinyl]-2-methyl-1-phenylpropyl]amino]-2-oxo-1(2H)-pyrazinyl]-4-methyl-benzamide
N-Cyclopropyl-4-methyl-3-[3-[[(1R,2S)-2-methyl-1-phenyl-3-(4-piperidinylamino)propyl]amino]-2-oxo-1(2H)-pyrazinyl]-benzamide
N-Cyclopropyl-4-methyl-3-[3-[[(1R,2S)-2-methyl-3-(5-methyl-2,5-diazabicyclo[2.2.1]hept-2-yl)-1-phenylpropyl]amino]-2-oxo-1(2H)-pyrazinyl]-benzamide
N-Cyclopropyl-3-[3-[[(1R,2S)-3-(2,2-dimethyl-1-pyrrolidinyl)-2-methyl-1-phenylpropyl]amino]-2-oxo-1(2H)-pyrazinyl]-4-methyl-benzamide
N-Cyclopropyl-3-[3-[[1-[2-[2-(ethylamino)ethoxy]phenyl]-1-methylethyl]amino]-2-oxo-1(2H)-pyrazinyl]-4-methyl-benzamide.
N-Cyclopropyl-4-methyl-3-[3-[[1-methyl-1-[2-[2-(1-piperazinyl)ethoxy]phenyl]ethyl]amino]-2-oxo-1(2H)-pyrazinyl]-benzamide
N-Cyclopropyl-3-[3-[[1-[2-[2-(diethylamino)ethoxy]phenyl]-1-methylethyl]amino]-2-oxo-1(2H)-pyrazinyl]-4-methyl-benzamide
N-Cyclopropyl-4-methyl-3-[3-[[1-methyl-1-[2-[2-(1-piperidinyl)ethoxy]phenyl]ethyl]amino]-2-oxo-1(2H)-pyrazinyl]-benzamide
N-Cyclopropyl-4-methyl-3-[3-[[1-methyl-1-[2-[2-(4-methyl-1-piperazinyl)ethoxy]phenyl]ethyl]amino]-2-oxo-1(2H)-pyrazinyl]-benzamide
N-Cyclopropyl-4-methyl-3-[3-[[1-methyl-1-[2-[2-(4-morpholinyl)ethoxy]phenyl]ethyl]amino]-2-oxo-1(2H)-pyrazinyl]-benzamide
N-Cyclopropyl-4-methyl-3-[3-[[1-methyl-1-[2-[4-(methylamino)butoxy]phenyl]ethyl]amino]-2-oxo-1(2H)-pyrazinyl]-benzamide
N-Cyclopropyl-4-methyl-3-[3-[[1-methyl-1-[2-[4-[(2,2,2-trifluoroethyl)amino]butoxy]phenyl]ethyl]amino]-2-oxo-1(2H)-pyrazinyl]-benzamide
N-Cyclopropyl-4-methyl-3-[3-[[1-methyl-1-[2-[4-(4-methyl-1-piperazinyl)butoxy]phenyl]ethyl]amino]-2-oxo-1(2H)-pyrazinyl]-benzamide
N-Cyclopropyl-4-methyl-3-[3-[[1-methyl-1-[2-[3-[(2,2,2-trifluoroethyl)amino]propoxy]phenyl]ethyl]amino]-2-oxo-1(2H)-pyrazinyl]-benzamide
N-Cyclopropyl-4-methyl-3-[3-[[1-methyl-1-[2-[3-(4-methyl-1-piperazinyl)propoxy]phenyl]ethyl]amino]-2-oxo-1(2H)-pyrazinyl]-benzamide
N-Cyclopropyl-4-methyl-3-[3-[[1-methyl-1-[2-[1-methyl-2-(4-methyl-1-piperazinyl)ethoxy]phenyl]ethyl]amino]-2-oxo-1(2H)-pyrazinyl]-benzamide
N-Cyclopropyl-3-[3-[[1-[2-[2-[(2-methoxyethyl)amino]ethoxy]phenyl]-1-methylethyl]amino]-2-oxo-1(2H)-pyrazinyl]-4-methyl-benzamide
N-Cyclopropyl-3-[3-[[1-[2-[2-[(2-hydroxyethyl)amino]ethoxy]phenyl]-1-methylethyl]amino]-2-oxo-1(2H)-pyrazinyl]-4-methyl-benzamide
N-Cyclopropyl-4-methyl-3-[3-[[1-methyl-1-[2-[2-[(1-methylethyl)amino]ethoxy]phenyl]ethyl]amino]-2-oxo-1(2H)-pyrazinyl]-benzamide
N-Cyclopropyl-3-[3-[[1-[2-[2-[[(2S)-2-hydroxypropyl]amino]ethoxy]phenyl]-1-methylethyl]amino]-2-oxo-1(2H)-pyrazinyl]-4-methyl-6-benzamide
N-Cyclopropyl-4-methyl-3-[3-[[1-methyl-1-[2-(4-piperidinylmethoxy)phenyl]ethyl]amino]-2-oxo-1(2H)-pyrazinyl]-benzamide N-Cyclopropyl-4-methyl-3-[3-[[1-[2-(3-azetidinyloxy)phenyl]-1-methylethyl]amino]-2-oxo-1(2H)-pyrazinyl]-benzamide N-Cyclopropyl-4-methyl-3-[3-[[1-methyl-1-[2-(3-pyrrolidinyloxy)phenyl]ethyl]amino]-2-oxo-1(2H)-pyrazinyl]-benzamide N-Cyclopropyl-4-methyl-3-[3-[[1-methyl-1-[2-[2-(4-piperidinyl)ethoxy]phenyl]ethyl]amino]-2-oxo-1(2H)-pyrazinyl]-benzamide N-Cyclopropyl-4-methyl-3-[3-[[1-methyl-1-[2-(3-piperidinylmethoxy)phenyl]ethyl]amino]-2-oxo-1(2H)-pyrazinyl]-benzamide N-Cyclopropyl-4-methyl-3-[3-[[1-methyl-1-[2-(4-piperidinyloxy)phenyl]ethyl]amino]-2-oxo-1(2H)-pyrazinyl]-benzamide N-Ethoxy-4-methyl-3-[3-[[1-methyl-1-[2-[2-(methylamino)ethoxy]phenyl]ethyl]amino]-2-oxo-1(2H)-pyrazinyl]-benzamide 4-Methyl-N-(1-methylcyclopropyl)-3-[3-[[1-methyl-1-[2-[2-(methylamino)ethoxy]phenyl]ethyl]amino]-2-oxo-1(2H)-pyrazinyl]-benzamide 4-Methyl-3-[3-[[1-methyl-1-[2-[2-(methylamino)ethoxy]phenyl]ethyl]amino]-2-oxo-1(2H)-pyrazinyl]-benzamide N-Cyclopropyl-3-[3-[[1-[2-[2-[[(2S)-2-hydroxypropyl]amino]ethoxy]phenyl]cyclopropyl]amino]-2-oxo-1(2H)-pyrazinyl]-4-methyl-benzamide N-Cyclopropyl-3-[3-[[1-[2-[2-[(2-methoxyethyl)amino]ethoxy]phenyl]cyclopropyl]amino]-2-oxo-1(2H)-pyrazinyl]-4-methyl-benzamide N-Cyclopropyl-3-[3-[[1-[2-[2-[4-(2-hydroxyethyl)-1-piperazinyl]ethoxy]phenyl]cyclopropyl]amino]-2-oxo-1(2H)-pyrazinyl]-4-methyl-benzamide N-Cyclopropyl-3-[3-[[1-[2-[2-[(2-hydroxyethyl)amino]ethoxy]phenyl]cyclopropyl]amino]-2-oxo-1(2H)-pyrazinyl]-4-methyl-benzamide N-Cyclopropyl-4-methyl-3-[3-[[1-[2-[2-[(1-methylethyl)amino]ethoxy]phenyl]cyclopropyl]amino]-2-oxo-1(2H)-pyrazinyl]-benzamide N-Cyclopropyl-3-[3-[[1-[2-[2-(hexahydro-4-methyl-1H-1,4-diazepin-1-yl)ethoxy]phenyl]cyclopropyl]amino]-2-oxo-1(2H)-pyrazinyl]-4-methyl-benzamide N-Cyclopropyl-3-[3-[[1-[2-[2-[(3R)-3-hydroxy-1-pyrrolidinyl]ethoxy]phenyl]cyclopropyl]amino]-2-oxo-1(2H)-pyrazinyl]-4-methyl-benzamide N-Cyclopropyl-3-[3-[[1-[2-[2-(dimethylamino)ethoxy]phenyl]cyclopropyl]amino]-2-oxo-1(2H)-pyrazinyl]-4-methyl-benzamide N-Cyclopropyl-4-methyl-3-[2-oxo-3-[[1-[2-[2-(1-pyrrolidinyl)ethoxy]phenyl]cyclopropyl]amino]-1(2H)-pyrazinyl]-benzamide N-Cyclopropyl-3-[3-[[1-[2-[2-[(2S)-2-(hydroxymethyl)-1-pyrrolidinyl]ethoxy]phenyl]cyclopropyl]amino]-2-oxo-1(2H)-pyrazinyl]-4-methyl-benzamide N-Cyclopropyl-4-methyl-3-[2-oxo-3-[[1-[2-[2-[(2,2,2-trifluoroethyl)amino]ethoxy]phenyl]cyclopropyl]amino]-1(2H)-pyrazinyl]-benzamide N-Cyclopropyl-3-[3-[[1-[2-[2-(ethyl methylamino)ethoxy]phenyl]cyclopropyl]amino]-2-oxo-1(2H)-pyrazinyl]-4-methyl-benzamide N-Cyclopropyl-3-[3-[[1-[2-[2-[(3-hydroxy-2,2-dimethylpropyl)amino]ethoxy]phenyl]cyclopropyl]amino]-2-oxo-1(2H)-pyrazinyl]-4-methyl-benzamide N-Cyclopropyl-4-methyl-3-[2-oxo-3-[[1-[2-[2-(1-piperazinyl)ethoxy]phenyl]cyclopropyl]amino]-1(2H)-pyrazinyl]-benzamide N-Cyclopropyl-3-[3-[[1-[2-[2-(3,3-difluoro-1-pyrrolidinyl)ethoxy]phenyl]cyclopropyl]amino]-2-oxo-1(2H)-pyrazinyl]-4-methyl-benzamide N-Cyclopropyl-3-[3-[[1-[2-[2-[(2-fluoroethyl)amino]ethoxy]phenyl]cyclopropyl]amino]-2-oxo-1(2H)-pyrazinyl]-4-methyl-benzamide N-Cyclopropyl-4-methyl-3-[3-[[1-[2-[2-[(1-methylpropyl)amino]ethoxy]phenyl]cyclopropyl]amino]-2-oxo-1(2H)-pyrazinyl]-benzamide N-Cyclopropyl-4-methyl-3-[3-[[1-[2-[2-[(2R)-2-methyl-1-pyrrolidinyl]ethoxy]phenyl]cyclopropyl]amino]-2-oxo-1(2H)-pyrazinyl]-benzamide 3-[3-[[1-[2-[2-(cyclobutylamino)ethoxy]phenyl]cyclopropyl]amino]-2-oxo-1(2H)-pyrazinyl]-N-Cyclopropyl-4-methyl-benzamide N-Cyclopropyl-3-[3-[[1-[2-[2-[[(1R)-2-hydroxy-1-methylethyl]amino]ethoxy]phenyl]cyclopropyl]amino]-2-oxo-1(2H)-pyrazinyl]-4-methyl-benzamide N-Cyclopropyl-3-[3-[[1-[2-[2-[(3-hydroxypropyl)amino]ethoxy]phenyl]cyclopropyl]amino]-2-oxo-1(2H)-pyrazinyl]-4-methyl-benzamide 3-[3-[[1-[2-(2-aminoethoxy)phenyl]cyclopropyl]amino]-2-oxo-1(2H)-pyrazinyl]-N-cyclopropyl-4-methyl-benzamide N-Cyclopropyl-3-[3-[[1-[2-[2-(ethylamino)ethoxy]phenyl]-1-methylethyl]amino]-2-oxo-1(2H)-pyrazinyl]-5-fluoro-4-methyl-benzamide N-Cyclopropyl-3-fluoro-5-[3-[[1-[2-[2-[(2-hydroxyethyl)amino]ethoxy]phenyl]-1-methylethyl]amino]-2-oxo-1(2H)-pyrazinyl]-4-methyl-benzamide N-Cyclopropyl-3-fluoro-4-methyl-5-[3-[[1-methyl-1-[2-[2-[(1-methylethyl)amino]ethoxy]phenyl]ethyl]amino]-2-oxo-1(2H)-pyrazinyl]-benzamide N-Cyclopropyl-3-fluoro-5-[3-[[1-[2-[2-[(2-methoxyethyl)amino]ethoxy]phenyl]-1-methylethyl]amino]-2-oxo-1(2H)-pyrazinyl]-4-methyl-benzamide N-Cyclopropyl-3-fluoro-5-[3-[[1-[2-[2-[[(2R)-2-hydroxypropyl]amino]ethoxy]phenyl]-1-methylethyl]amino]-2-oxo-1(2H)-pyrazinyl]-4-methyl-benzamide N-Cyclopropyl-3-fluoro-5-[3-[[1-[2-[2-[(2-hydroxy-2-methylpropyl)amino]ethoxy]phenyl]-1-methylethyl]amino]-2-oxo-1(2H)-pyrazinyl]-4-methyl-benzamide N-Cyclopropyl-3-fluoro-5-[3-[[1-[2-[2-[[(2S)-2-hydroxypropyl]amino]ethoxy]phenyl]-1-methylethyl]amino]-2-oxo-1(2H)-pyrazinyl]-4-methyl-benzamide N-Cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide N-Cyclopropyl-3-fluoro-5-[3-[[1-[2-[2-[(2-hydroxyethyl)amino]ethoxy]phenyl]cyclopropyl]amino]-2-oxo-1(2H)-pyrazinyl]-4-methyl-benzamide N-Cyclopropyl-3-fluoro-5-[3-[[1-[2-[2-[(2-methoxyethyl)amino]ethoxy]phenyl]cyclopropyl]amino]-2-oxo-1(2H)-pyrazinyl]-4-methyl-benzamide N-Cyclopropyl-3-[3-[[1-[2-[2-(ethylamino)ethoxy]phenyl]cyclopropyl]amino]-2-oxo-1(2H)-pyrazinyl]-5-fluoro-4-methyl-benzamide N-Cyclopropyl-3-fluoro-5-[3-[[1-[2-[2-[[2S)-2-hydroxypropyl]amino]ethoxy]phenyl]cyclopropyl]amino]-2-oxo-1(2H)-pyrazinyl]-4-methyl-benzamide N-Cyclopropyl-3-fluoro-4-methyl-5-[3-[[1-[2-[2-[(1-methylethyl)amino]ethoxy]phenyl]cyclopropyl]amino]-2-oxo-1(2H)-pyrazinyl]-benzamide N-Cyclopropyl-3-fluoro-5-[3-[[1-[2-[2-[[(2R)-2-hydroxypropyl]amino]ethoxy]phenyl]cyclopropyl]amino]-2-oxo-1(2H)-pyrazinyl]-4-methyl-benzamide N-Cyclopropyl-3-[3-[[1-[2-[2-(ethylamino)ethoxy]phenyl]-1-methylethyl]amino]-2-oxo-1(2H)-pyrazinyl]-4-methyl-benzamide N-Cyclopropyl-3-[3-[[1-ethyl-1-[2-[2-(ethylamino)ethoxy]phenyl]propyl]amino]-2-oxo-1(2H)-pyrazinyl]-4-methyl-benzamide N-Cyclopropyl-4-methyl-3-[3-[[1-[2-[2-(methylamino)ethoxy]phenyl]cyclobutyl]amino]-2-oxo-1(2H)-pyrazinyl]-benzamide N-Cyclopropyl-3-[3-[[1-[2-[2-(ethylamino)ethoxy]phenyl]cyclobutyl]amino]-2-oxo-1(2H)-pyrazinyl]-4-methyl-benzamide N-Cyclopropyl-3-[3-[[1-[2-[2-[(2-hydroxyethyl)amino]ethoxy]phenyl]cyclobutyl]amino]-2-oxo-1(2H)-pyrazinyl]-4-methyl-benzamide N-Cyclopropyl-4-methyl-3-[3-[[1-[2-[2-[(1-methylethyl)amino]ethoxy]phenyl]cyclobutyl]amino]-2-oxo-1(2H)-pyrazinyl]-benzamide N-Cyclopropyl-3-[3-[[(1R,2R)-3-hydroxy-1-(2-methylphenyl)-2-methylpropyl]amino]-2-oxo-1(2H)-pyrazinyl]-4-methyl-benzamide N-Cyclopropyl-3-[3-[[(1R,2R)-3-hydroxy-1-(3-methylphenyl)-2-methylpropyl]amino]-2-oxo-1(2H)-pyrazinyl]-4-methyl-benzamide N-Cyclopropyl-3-[3-[[(1R,2R)-3-hydroxy-1-(2-methoxyphenyl)-2-methylpropyl]amino]-2-oxo-1(2H)-pyrazinyl]-4-methyl-benzamide N-Cyclopropyl-3-[3-[[(1R,2S)-1-(2-methylphenyl)-2-methyl-3-(1-pyrrolidinyl)propyl]amino]-2-oxo-1(2H)-pyrazinyl]-4-methyl-benzamide N-Cyclopropyl-3-[3-[[(1R,2S)-1-(3-methylphenyl)-2-methyl-3-(1-pyrrolidinyl)propyl]amino]-2-oxo-1(2H)-pyrazinyl]-4-methyl-benzamide N-Cyclopropyl-3-[3-[[(1R,2S)-1-(2-methoxyphenyl)-2-methyl-3-(1-pyrrolidinyl)propyl]amino]-2-oxo-1(2H)-pyrazinyl]-4-methyl-benzamide N-Cyclopropyl-3-[3-[[1-[5-fluoro-2-[2-(methylamino)ethoxy]phenyl]cyclopropyl]amino]-2-oxo-1(2H)-pyrazinyl]-4-methyl-benzamide N-Cyclopropyl-3-[3-[[1-[5-fluoro-2-[2-[(2-hydroxyethyl)amino]ethoxy]phenyl]cyclopropyl]amino]-2-oxo-1(2H)-pyrazinyl]-4-methyl-benzamide N-Cyclopropyl-3-[3-[[1-[2-[2-(ethylamino)ethoxy]-5-fluorophenyl]cyclopropyl]amino]-2-oxo-1(2H)-pyrazinyl]-4-methyl-benzamide N-Cyclopropyl-3-fluoro-5-{3-[(1-{5-fluoro-2-[2-(methylamino)ethoxy]phenyl}cyclopropyl)amino]-2-oxopyrazin-1(2H)-yl}-4-methylbenzamide N-Cyclopropyl-3-fluoro-5-[3-{[1-(5-fluoro-2-{2-[(2-hydroxyethyl)amino]ethoxy}phenyl)cyclopropyl]amino}-2-oxopyrazin-1(2H)-yl]-4-methylbenzamide N-Cyclopropyl-3-[3-({1-[3-fluoro-2-(2-{[(2R)-2-hydroxypropyl]amino}ethoxy)phenyl]cyclopropyl}amino)-2-oxopyrazin-1(2H)-yl]-4-methylbenzamide 3-[3-({1-[2-(2-Aminoethoxy)-3-fluorophenyl]cyclopropyl}amino)-2-oxopyrazin-1(2H)-yl]-N-cyclopropyl-4-methylbenzamide N-Cyclopropyl-3-[3-{[1-(3-fluoro-2-{2-[(2-hydroxyethyl)amino]ethoxy}phenyl)cyclopropyl]amino}-2-oxopyrazin-1(2H)-yl]-4-methylbenzamide N-Cyclopropyl-3-{3-[(1-{2-[2-(ethylamino)ethoxy]-3-fluorophenyl}cyclopropyl)amino]-2-oxopyrazin-1(2H)-yl}-4-methylbenzamide N-Cyclopropyl-3-{3-[(1-{3-fluoro-2-[2-(methylamino)ethoxy]phenyl}cyclopropyl)amino]-2-oxopyrazin-1(2H)-yl}-4-methylbenzamide N-Cyclopropyl-4-ethyl-3-({1-[2-(2-{[(2S)-2-hydroxypropyl]amino}ethoxy)phenyl]-1-methylethyl}amino)-2-oxopyrazin-1(2H)-yl]benzamide N-Cyclopropyl-4-ethyl-3-{3-[(1-{2-[2-(ethylamino)ethoxy]phenyl}-1-methylethyl)amino]-2-oxopyrazin-1(2H)-yl}benzamide N-Cyclopropyl-3-[3-({1-[2-(2-{[(1R)-1-(hydroxymethyl)-2-methylpropyl]amino}ethoxy)phenyl]cyclopropyl}amino)-2-oxopyrazin-1(2H)-yl]-4-methylbenzamide N-Cyclopropyl-3-[3-({1-[2-(2-{[(2-hydroxy-1-(hydroxymethyl)ethyl]amino}ethoxy)phenyl]cyclopropyl}amino)-2-oxopyrazin-1(2H)-yl]-4-methylbenzamide N-Cyclopropyl-3-[3-{[1-(2-{2-[(1,1-dioxidotetrahydrothiophen-3-yl)amino]ethoxy}phenyl)cyclopropyl]amino}-2-oxopyrazin-1(2H)-yl]-4-methylbenzamide N-Cyclopropyl-3-{3-[(1-{2-[2-(5,6-dihydroimidazo[1,2-a]pyrazin-7(8H)-yl)ethoxy]phenyl}cyclopropyl)amino]-2-oxopyrazin-1(2H)-yl}-4-methylbenzamide N-Cyclopropyl-4-methyl-3-{3-[(1-{2-[2-(1-methyl-1,4,6,7-tetrahydro-5H-imidazo[4,5-c]pyridin-5-yl)ethoxy]phenyl}cyclopropyl)amino]-2-oxopyrazin-1(2H)-yl}benzamide N-Cyclopropyl-4-methyl-3-{2-oxo-3-[(1-{2-[2-(propylamino)ethoxy]phenyl}cyclopropyl)amino]pyrazin-1(2H)-yl}benzamide N-Cyclopropyl-3-[3-({1-[2-({(2R)-2-hydroxy-3-[(2-hydroxyethyl)amino]propyl}oxy)phenyl]cyclopropyl}amino)-2-oxopyrazin-1(2H)-yl]-4-methylbenzamide N-Cyclopropyl-3-[3-{[1-(2-{[(2R)-3-(ethylamino)-2-hydroxypropyl]oxy}phenyl)cyclopropyl]amino}-2-oxopyrazin-1(2H)-yl]-4-methylbenzamide N-Cyclopropyl-3-[3-{[1-(2-{[(2R)-2-hydroxy-3-(methylamino)propyl]oxy}phenyl)cyclopropyl]amino}-2-oxopyrazin-1(2H)-yl]-4-methylbenzamide N-Cyclopropyl-3-[3-({1-[2-({(2S)-2-hydroxy-3-[(2-hydroxyethyl)amino]propyl}oxy)phenyl]cyclopropyl}amino)-2-oxopyrazin-1(2H)-yl]-4-methylbenzamide N-cyclopropyl-3-[3-{[1-(2-{[(2S)-3-(ethylamino)-2-hydroxypropyl]oxy}phenyl)cyclopropyl]amino}-2-oxopyrazin-1(2H)-yl]-4-methylbenzamide N-Cyclopropyl-3-[3-{[1-(2-{[(2S)-2-hydroxy-3-(methylamino)propyl]oxy}phenyl)cyclopropyl]amino}-2-oxopyrazin-1(2H)-yl]-4-methylbenzamide 3-[3-{[1-(2-{[(2R)-2-Amino-3-hydroxypropyl]oxy}phenyl)-1-methylethyl]amino}-2-oxopyrazin-1(2H)-yl]-N-cyclopropyl-4-methylbenzamide N-Cyclopropyl-3-[3-{[1-(2-{[(2R)-2-(dimethylamino)-3-hydroxypropyl]oxy}phenyl)-1-methylethyl]amino}-2-oxopyrazin-1(2H)-yl]-4-methylbenzamide N-Cyclopropyl-3-fluoro-5-[3-{[1-(2-{[(2R)-2-hydroxy-3-(methylamino)propyl]oxy}phenyl)-1-methylethyl]amino}-2-oxopyrazin-1(2H)-yl]-4-methylbenzamide N-Cyclopropyl-3-[3-{[1-(2-{[(2R)-3-(ethylamino)-2-hydroxypropyl]oxy}phenyl)-1-methylethyl]amino}-2-oxopyrazin-1(2H)-yl]-5-fluoro-4-methylbenzamide N-Cyclopropyl-3-[3-{[1-(2-{[(2S)-3-(ethylamino)-2-hydroxypropyl]oxy}phenyl)-1-methylethyl]amino}-2-oxopyrazin-1(2H)-yl]-5-fluoro-4-methylbenzamide N-Cyclopropyl-3-fluoro-5-[3-{[1-(2-{[(2S)-2-hydroxy-3-(methylamino)propyl]oxy}phenyl)-1-methylethyl]amino}-2-oxopyrazin-1(2H)-yl]-4-methylbenzamide 3-[3-({1-[2-(2-Aminoethoxy)phenyl]-1-methylethyl}amino)-2-oxopyrazin-1(2H)-yl]-N-cyclopropyl-5-fluoro-4-methylbenzamide N-(2-{2-[1-({4-[5-(Cyclopropylcarbamoyl)-3-fluoro-2-methylphenyl]-3-oxo-3,4-dihydropyrazin-2-yl}amino)-1-methylethyl]phenoxy}ethyl)glycine N-(2-{2-[1-({4-[5-(Cyclopropylcarbamoyl)-3-fluoro-2-methylphenyl]-3-oxo-3,4-dihydropyrazin-2-yl}amino)-1-methylethyl]phenoxy}ethyl)-beta-alanine 3-[3-({1-[2-(2-Aminoethoxy)phenyl]cyclopropyl}amino)-2-oxopyrazin-1(2H)-yl]-N-cyclopropyl-5-fluoro-4-methylbenzamide N-Cyclopropyl-3-fluoro-5-[3-{[1-(2-{2-[(2-hydroxyethyl)(methyl)amino]ethoxy}phenyl)cyclopropyl]amino}-2-oxopyrazin-1(2H)-yl]-4-methylbenzamide 3-Fluoro-N-methoxy-4-methyl-5-{3-[(1-methyl-1-{2-[2-(methylamino)ethoxy]phenyl}ethyl)amino]-2-oxopyrazin-1(2H)-yl}benzamide N-Methoxy-4-methyl-3-{3-[(1-{2-[2-(methylamino)ethoxy]phenyl}cyclopropyl)amino]-2-oxopyrazin-1(2H)-yl}benzamide N-Cyclopropyl-3-fluoro-4-methyl-5-[3-{[1-methyl-1-(2-{[2-(methylamino)ethyl]sulfanyl}phenyl)ethyl]amino}-2-oxopyrazin-1(2H)-yl]benzamide 3-{3-[(1-{2-[(2-Aminoethyl)sulfanyl]phenyl}-1-methylethyl)amino]-2-oxopyrazin-1(2H)-yl}-N-cyclopropyl-5-fluoro-4-methylbenzamide N-Cyclopropyl-3-fluoro-4-methyl-5-{3-[(1-methyl-1-{2-[3-(methylamino)propyl]phenyl}ethyl)amino]-2-oxopyrazin-1(2H)-yl}benzamide N-Cyclopropyl-4-methyl-3-[3-(2-{2-[3-(methylamino)propoxy]phenyl}pyrrolidin-1-yl)-2-oxopyrazin-1(2H)-yl]benzamide N-Cyclopropyl-3-fluoro-4-methyl-5-[3-{[(1R,2S)-2-methyl-1-phenyl-3-pyrrolidin-1-ylpropyl]amino}-2-oxopyrazin-1(2H)-yl]benzamide N-Cyclopropyl-3-fluoro-4-methyl-5-[3-{[(1R,2S)-2-methyl-1-phenyl-3-piperidin-1-ylpropyl]amino}-2-oxopyrazin-1(2H)-yl]benzamide 4-Chloro-N-cyclopropyl-3-[3-[(1-methyl-1-{2-[2-(methylamino)ethoxy]phenyl}ethyl)amino]-2-oxopyrazin-1(2H)-yl]benzamide 4-Chloro-N-cyclopropyl-3-[3-{[1-(2-{2-[(2-hydroxyethyl)amino]ethoxy}phenyl)-1-methylethyl]amino}-2-oxopyrazin-1(2H)-yl]benzamide 4-Chloro-N-cyclopropyl-3-[3-({1-[2-(2-{[(2R)-2-hydroxypropyl]amino}ethoxy)phenyl]-1-methylethyl}amino)-2-oxopyrazin-1(2H)-yl]benzamide 4-Chloro-N-cyclopropyl-3-[3-[(1-{2-[2-(ethylamino)ethoxy]phenyl}-1-methylethyl)amino]-2-oxopyrazin-1(2H)-yl]benzamide 3-[3-({1-[2-(2-Aminoethoxy)phenyl]-1-methylethyl}amino)-2-oxopyrazin-1(2H)-yl]-4-chloro-N-cyclopropylbenzamide or a pharmaceutically acceptable salt thereof.

In one embodiment, the present invention provides compounds of formula (IB):

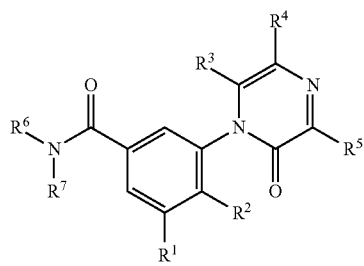

(IB)

wherein:

$R^1$ and $R^2$ are independently selected from H, $(C_1-C_6)$alkyl, $(C_1-C_6)$alkoxy, halo, $CF_3$, and CN;

$R^3$ and $R^4$ are independently selected from H, $(C_1-C_6)$alkyl, $(C_1-C_6)$alkoxy, halo, OH, $NR^8R^9$, $CF_3$, CN, aryl, heteroaryl and $CONR^{16}R^{11}$, wherein said $(C_1-C_6)$alkyl and said $(C_1-C_6)$alkoxy are, independently, optionally substituted with 1, 2 or 3 groups independently selected from OH, $(C_1-C_3)$alkoxy, $NR^{12}R^{13}$, $S(O)_pR^{55}$ and halo;

$R^5$ is selected from H, aryl, heteroaryl, heterocycloalkyl, $(C_3-C_7)$cycloalkyl, $(CR^{14}R^{15})_mNR^{16}R^{17}$, $S(O)_pR^{16}$, $SO_2NR^{16}R^{17}$, $CH_2R^{16}$ and $OR^{16}$;

$R^6$ is selected from H, $(C_1-C_6)$alkyl, $(C_1-C_6)$alkoxy, $(C_3-C_7)$cycloalkyl, heteroaryl and aryl;

$R^7$ is selected from H, $(C_1-C_6)$alkyl, $(C_1-C_6)$alkoxy, $(C_3-C_7)$cycloalkyl and aryl;

or $R^6$ and $R^7$ together with the nitrogen atom to which they are attached form a 4 to 7 membered ring, optionally containing a further heteroatom selected from $NR^{18}$, S and O;

$R^8$ and $R^9$ are independently selected from H, $(C_1-C_6)$alkyl, $(C_1-C_6)$alkoxy and $(C_3-C_6)$cycloalkyl; or $R^8$ and $R^9$ together with the nitrogen atom to which they are attached form a 4 to 7 membered ring, optionally containing a further heteroatom selected from $NR^{19}$, S and O;

$R^{14}$ and $R^{15}$ are selected from H and $(C_1-C_6)$alkyl; or $R^{14}$ and $R^{15}$ together with the carbon to which they are attached form a carbonyl (C=O) group;

$R^{16}$ is selected from H, aryl, $(C_1-C_7)$cycloalkyl and

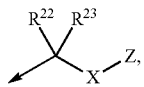

wherein said $(C_3-C_7)$cycloalkyl may be optionally substituted with an aryl group;

$R^{17}$ is selected from H, $(C_1-C_6)$alkyl, aryl, heteroaryl, heterocycloalkyl and $(C_3-C_7)$cycloalkyl, wherein said $(C_1-C_6)$alkyl may be optionally substituted with 1, 2 or 3 groups independently selected from $(C_1-C_6)$alkoxy, $(C_3-C_{10})$cycloalkyl, heterocycloalkyl, heteroaryl and $NR^{20}R^{21}$;

$R^{22}$ is selected from H, $(C_1-C_6)$alkyl, $(C_1-C_6)$alkoxy, OH, $NR^{29}R^{30}$, heterocycloalkyl and aryl, wherein said $(C_1-C_6)$alkyl may be optionally substituted with 1, 2 or 3 $R^{28}$ groups; and wherein said aryl may be optionally substituted with 1, 2 or 3 groups independently selected from $(C_1-C_6)$alkyl, $(C_1-C_6)$alkoxy, halo, $CF_3$ and OH;

$R^{23}$ is selected from H and $(C_1-C_6)$alkyl;

or $R^{22}$ and $R^{23}$ together with the carbon atom to which they are attached form a $(C_3-C_7)$cycloalkyl or heterocycloalkyl ring;

X is a bond or a $(CR^{24}R^{25})_n$ group;

$R^{24}$ and $R^{25}$ are independently selected from H, $(C_1-C_6)$alkyl, $(C_1-C_6)$alkoxy, OH, heterocycloalkyl and $NR^{39}R^{40}$; or $R^{24}$ and $R^{25}$ together with the carbon atom to which they are attached may form a heterocycloalkyl ring;

Z is an aryl or heteroaryl ring, wherein said aryl or heteroaryl ring is substituted with $R^{26}$ and $R^{27}$;

$R^{26}$ is selected from H, $(C_1-C_6)$alkyl, $(C_1-C_6)$alkoxy, OH, aryl, O-aryl, halo, heterocycloalkyl, O-heterocycloalkyl, heteroaryl, O-heteroaryl, cycloalkyl, O-cycloalkyl, $S(O)_pR^{34}$, $NR^{34}R^{35}$ and $CONR^{34}R^{35}$, wherein said $(C_1-C_6)$alkyl or said $(C_1-C_6)$alkoxy may be optionally substituted with 1, 2 or 3 groups independently selected from halo, heterocycloalkyl or $NR^{34}R^{35}$;

$R^{27}$ is selected from H, halo and $(C_1-C_6)$alkyl, wherein said $(C_1-C_6)$alkyl may be optionally substituted with 1, 2 or 3 halo groups;

or $R^{26}$ and $R^{27}$ together may form a methylenedioxy group, when attached to adjacent carbon atoms of the aryl or heteroaryl ring;

each occurrence of $R^{28}$ is independently selected from $NR^{29}R^{30}$, halo, $CH_2CF_3$, $CF_3$, heterocycloalkyl, $(C_1-C_6)$alkoxy, $OR^{36}$, $COOR^{42}$, $CONR^{31}R^{32}$ and $SO_2NR^{37}R^{38}$;

$R^{29}$ and $R^{30}$ are independently selected from H, $(C_1-C_6)$alkyl, $SO_2R^{41}$ and $C(O)R^{41}$, wherein said $(C_1-C_6)$alkyl may be optionally substituted with $NR^{56}R^{57}$ or heterocycloalkyl;

$R^{31}$ and $R^{32}$ are independently selected from H, $(C_1-C_6)$alkyl and $(C_3-C_7)$cycloalkyl; or $R^{31}$ and $R^{32}$ together with the nitrogen atom to which they are attached form a 4 to 7 membered ring, optionally containing a further heteroatom selected from $NR^{33}$, S and O;

$R^{34}$ and $R^{35}$ are independently selected from H, $(C_1-C_6)$alkyl, $(C_3-C_7)$cycloalkyl and $C(O)O(C_1-C_6)$alkyl, wherein said $(C_1-C_6)$alkyl may be optionally substituted by OH, halo, $(C_1-C_6)$alkoxy, $NR^{58}R^{59}$ and heterocycloalkyl; or $R^{34}$ and $R^{35}$ together with the nitrogen to which they are attached form a 4 to 7 membered ring;

$R^{36}$ is selected from H, $(C_1-C_6)$alkyl and heterocycloalkyl, wherein said $(C_1-C_6)$alkyl may be optionally substituted with heterocycloalkyl;

$R^{10}$, $R^{11}$, $R^{12}$, $R^{13}$, $R^{18}$, $R^{19}$, $R^{20}$, $R^{21}$, $R^{33}$, $R^{37}$, $R^{38}$, $R^{39}$, $R^{40}$, $R^{41}$ and $R^{42}$ are independently selected from H and $(C_1-C_6)$alkyl;

m is 0 or 1;

n is 1 or 2;

each occurrence of p is independently selected from 0, 1 or 2;

cycloalkyl is a non-aromatic carbocyclic ring, optionally fused to an aryl group, wherein said cycloalkyl ring optionally contains, where possible, up to 2 double bonds; and wherein, unless otherwise stated, said cycloalkyl may be optionally substituted with 1 or 2 substituents independently selected from $(C_1-C_6)$alkyl, $(C_1-C_6)$alkoxy, OH, CN, $CF_3$, halo and $NR^{43}R^{44}$;

heterocycloalkyl is a C-linked or N-linked 3 to 9 membered non-aromatic, mono- or bi-cyclic ring, optionally fused to an aryl group, wherein said heterocycloalkyl ring contains:
1 or 2 $NR^{45}$ atoms, or
one N-atom, or
one N-atom and one $NR^{45}$, or
one N-atom, one $NR^{45}$ and an $S(O)_p$ or an O atom, or
one N-atom and an $S(O)_p$ or an O atom, or
one S atom, or
one O atom;
optionally containing, where possible, 1 or 2 double bonds; and optionally substituted on carbon with 1 or 2 substituents independently selected from $(C_1-C_6)$alkyl, $(C_1-C_6)$alkoxy, OH, CN, $CF_3$, halo, $NR^{46}R^{47}$ and aryl, wherein said $(C_1-C_6)$alkyl may be optionally substituted by aryl, $(C_1-C_6)$alkoxy or OH; and wherein each aryl group may be optionally substituted with $(C_1-C_6)$alkoxy (which in turn may be optionally substituted by $NR^{34}R^{35}$), $(C_1-C_6)$alkyl, OH, $CF_3$ and halo;

aryl is an aromatic ring containing 6 or 10 carbon atoms; wherein, unless otherwise stated, said aryl may be optionally substituted with 1, 2 or 3 substituents independently selected from $(C_1-C_6)$alkyl, $(C_1-C_6)$alkoxy, OH, halo, CN, $CF_3$ and $NR^{48}R^{49}$;

heteroaryl is a 5, 6, 9 or 10 membered aromatic ring, containing from 1 or 2 N atoms and, optionally, an $NR^{50}$ atom, or one $NR^{50}$ atom and an S or an O atom, or one S atom, or one O atom; wherein, unless otherwise stated, said heteroaryl may be optionally substituted with 1, 2 or 3 substituents independently selected from $(C_1-C_6)$alkyl, $(C_1-C_6)$alkoxy, OH, halo, CN, $CF_3$ and $NR^{51}R^{52}$;

$R^{45}$ is selected from H, $(C_1-C_6)$alkyl, $C(O)(C_1-C_6)$alkyl, $C(O)O(C_1-C_6)$alkyl and aryl, wherein said $(C_1-C_6)$alkyl is optionally substituted with a group selected from $(C_1-C_3)$alkoxy, OH, halo, heterocycloalkyl and $NR^{29}R^{30}$; and wherein said $C(O)O(C_1-C_6)$alkyl is optionally substituted with an aryl group;

$R^{50}$ is selected from H, $(C_1-C_6)$alkyl and $C(O)O(C_1-C_6)$alkyl, wherein said $(C_1-C_6)$alkyl may be optionally substituted with a group selected from $(C_1-C_3)$alkoxy, OH, halo, $(C_3-C_6)$cycloalkyl and $NR^{53}R^{54}$;

$R^{43}$, $R^{44}$, $R^{46}$, $R^{47}$, $R^{48}$, $R^{49}$, $R^{51}$, $R^{52}$, $R^{53}$, $R^{54}$, $R^{55}$, $R^{56}$, $R^{57}$ $R^{58}$ and $R^{59}$ are each independently selected from H and $(C_1-C_6)$alkyl;

or pharmaceutically acceptable salts thereof.

For compounds of formula (IB), embodiments of the invention include those wherein each of $R^1$, $R^2$, $R^3$, $R^4$, $R^5$, $R^6$ and $R^7$ are as defined herein above in embodiments of the invention concerning compounds of formula (I).

In one embodiment, the present invention provides a compound of formula (IC):

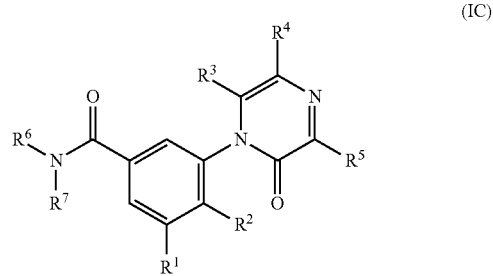

is wherein:

$R^1$ and $R^2$ are independently selected from H, $(C_1-C_6)$alkyl, $(C_1-C_6)$alkoxy, halo, $CF_3$, and CN;

$R^3$ and $R^4$ are independently selected from H, $(C_1-C_6)$alkyl, $(C_1-C_6)$alkoxy, halo, OH, $NR^8R^9$, $CF_3$, CN, aryl, heteroaryl and $CONR^{16}R^{11}$, wherein said $(C_1-C_6)$alkyl and said $(C_1-C_6)$alkoxy are, independently, optionally substituted with 1, 2 or 3 groups independently selected from OH, $(C_1-C_3)$alkoxy, $NR^{12}R^{13}$, $S(O)_pR^{55}$ and halo;

$R^5$ is selected from H, aryl, heteroaryl, heterocycloalkyl, $(C_3-C_7)$cycloalkyl, $(CR^{14}R^{15})_mNR^{16}R^{17}$, $S(O)_pR^{16}$, $SO_2NR^{16}R^{17}$, $CH_2R^{16}$ and $OR^{16}$;

$R^6$ is selected from H, $(C_1-C_6)$alkyl, $(C_1-C_6)$alkoxy, $(C_3-C_7)$cycloalkyl, $—(C_3-C_7)$cycloalkyl-$(C_1-C_6)$alkyl, heteroaryl and aryl; wherein said $(C_1-C_6)$alkyl may be optionally substituted by halo or OH;

$R^7$ is selected from H, $(C_1-C_6)$alkyl, $(C_1-C_6)$alkoxy, $(C_3-C_7)$cycloalkyl and aryl;

or $R^6$ and $R^7$ together with the nitrogen atom to which they are attached form a 4 to 7 membered ring, optionally containing a further heteroatom selected from $NR^{18}$, S and O;

$R^8$ and $R^9$ are independently selected from H, $(C_1-C_6)$alkyl, $(C_1-C_6)$alkoxy and $(C_3-C_6)$cycloalkyl; or $R^8$ and $R^9$ together with the nitrogen atom to which they are attached form a 4 to 7 membered ring, optionally containing a further heteroatom selected from $NR^{19}$, S and O;

$R^{14}$ and $R^{15}$ are selected from H and $(C_1-C_6)$alkyl; or $R^{14}$ and $R^{15}$ together with the carbon to which they are attached form a carbonyl (C=O) group;

$R^{16}$ is selected from H, aryl, $(C_3-C_7)$cycloalkyl and

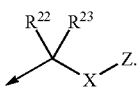

wherein said $(C_3-C_7)$cycloalkyl may be optionally substituted with an aryl group;

$R^{17}$ is selected from H, $(C_1-C_6)$alkyl, aryl, heteroaryl, heterocycloalkyl and $(C_3-C_7)$cycloalkyl, wherein said $(C_1-C_6)$alkyl may be optionally substituted with 1, 2 or 3 groups independently selected from $(C_1-C_6)$alkoxy, $(C_3-C_{10})$cycloalkyl, heterocycloalkyl, heteroaryl and $NR^{20}R^{21}$;

$R^{22}$ is selected from H, $(C_1-C_6)$alkyl, $(C_1-C_6)$alkoxy, OH, $NR^{29}R^{30}$, heterocycloalkyl and aryl, wherein said $(C_1-C_6)$alkyl may be optionally substituted with 1, 2 or 3 $R^{28}$ groups; and wherein said aryl may be optionally substituted with 1, 2 or 3 groups independently selected from $(C_1-C_6)$alkyl, $(C_1-C_6)$alkoxy, halo, $CF_3$ and OH;

$R^{23}$ is selected from H and $(C_1-C_6)$alkyl;

or $R^{22}$ and $R^{23}$ together with the carbon atom to which they are attached form a $(C_3-C_7)$cycloalkyl or heterocycloalkyl ring;

X is a bond or a $(CR^{24}R^{25})_n$ group;

$R^{24}$ and $R^{25}$ are independently selected from H, $(C_1-C_6)$alkyl, $(C_1-C_6)$alkoxy, OH, heterocycloalkyl and $NR^{39}R^{40}$; or $R^{24}$ and $R^{25}$ together with the carbon atom to which they are attached may form a heterocycloalkyl ring;

Z is an aryl or heteroaryl ring, wherein said aryl or heteroaryl ring is substituted with $R^{26}$ and $R^{27}$;

$R^{26}$ is selected from H, $(C_1-C_6)$alkyl, $(C_1-C_6)$alkoxy, OH, aryl, O-aryl, halo, heterocycloalkyl, O-heterocycloalkyl, heteroaryl, O-heteroaryl, cycloalkyl, O-cycloalkyl, $S(O)_pR^{34}$, $NR^{34}R^{35}$ and $CONR^{34}R^{35}$, wherein said $(C_1-C_6)$alkyl or said $(C_1-C_6)$alkoxy may be optionally substituted with 1, 2 or 3 groups independently selected from halo, heterocycloalkyl or $NR^{34}R^{35}$;

$R^{27}$ is selected from H, halo and $(C_1-C_6)$alkyl, wherein said $(C_1-C_6)$alkyl may be optionally substituted with 1, 2 or 3 halo groups;

or $R^{26}$ and $R^{27}$ together may form a methylenedioxy group, when attached to adjacent carbon atoms of the aryl or heteroaryl ring;

each occurrence of $R^{28}$ is independently selected from $NR^{29}R^{30}$, halo, $CH_2CF_3$, $CF_3$, heterocycloalkyl, $(C_1-C_6)$alkoxy, $OR^{36}$, $COOR^{42}$, $CONR^{31}R^{32}$ and $SO_2NR^{37}R^{38}$;

$R^{29}$ and $R^{30}$ are independently selected from H, $(C_1-C_6)$alkyl, $(C_3-C_7)$cycloalkyl, $SO_2R^{41}$ and $C(O)R^{41}$, wherein said $(C_1-C_6)$alkyl may be optionally substituted with, OH, $NR^{56}R^{57}$ or heterocycloalkyl;

$R^{31}$ and $R^{32}$ are independently selected from H, $(C_1-C_6)$alkyl and $(C_3-C_7)$cycloalkyl; or $R^{31}$ and $R^{32}$ together with the nitrogen atom to which they are attached form a 4 to 7 membered ring, optionally containing a further heteroatom selected from $NR^{33}$, S and O;

$R^{34}$ and $R^{35}$ are independently selected from H, $(C_1-C_6)$alkyl, $(C_3-C_7)$cycloalkyl and $C(O)O(C_1-C_6)$alkyl, wherein said $(C_1-C_6)$alkyl may be optionally substituted by OH, halo, $(C_1-C_6)$alkoxy, $NR^{58}R^{59}$ and heterocycloalkyl; or $R^{34}$ and $R^{35}$ together with the nitrogen to which they are attached form a 4 to 7 membered ring;

$R^{36}$ is selected from H, $(C_1-C_6)$alkyl and heterocycloalkyl, wherein said $(C_1-C_6)$alkyl may be optionally substituted with heterocycloalkyl;

$R^{10}$, $R^{11}$, $R^{12}$, $R^{13}$, $R^{18}$, $R^{19}$, $R^{20}$, $R^{21}$, $R^{33}$, $R^{37}$, $R^{38}$, $R^{39}$, $R^{40}$, $R^{41}$ and $R^{42}$ are independently selected from H and $(C_1-C_6)$alkyl;

m is 0 or 1;

n is 1 or 2;

each occurrence of p is independently selected from 0, 1 or 2;

cycloalkyl is a non-aromatic carbocyclic ring, optionally fused to an aryl group, wherein said cycloalkyl ring optionally contains, where possible, up to 2 double bonds; and wherein, unless otherwise stated, said cycloalkyl may be optionally substituted with 1 or 2 substituents independently selected from $(C_1-C_6)$alkyl, $(C_1-C_6)$alkoxy, OH, CN, $CF_3$, halo and $NR^{43}R^{44}$;

heterocycloalkyl is a C-linked or N-linked 3 to 9 membered non-aromatic, mono- or bi-cyclic ring, optionally fused to an aryl group, wherein said heterocycloalkyl ring contains:

1 or 2 $NR^{45}$ atoms, or one N-atom, or one N-atom and one $NR^{45}$, or one N-atom, one $NR^{45}$ and an $S(O)_p$ or an O atom, or one N-atom and an $S(O)_p$ or an O atom, or one S atom, or one O atom;

optionally containing, where possible, 1 or 2 double bonds; and optionally substituted on carbon with 1 or 2 substituents independently selected from $(C_1-C_6)$alkyl, $(C_1-C_6)$alkoxy, OH, CN, $CF_3$, halo, =O, $NR^{46}R^{47}$, $-C(O)NR^{46}R^{47}$, bivalent substituent $-OCH_2CH_2O-$ (wherein the terminal oxygen atoms are attached to the same ring carbon atom), bivalent substituent $-CH_2NHCH_2-$ (wherein the terminal carbon atoms are attached to the same ring carbon atom), a tetrahydro-1,1-dioxido-3-thienyl group, and aryl, wherein said $(C_1-C_6)$alkyl may be optionally substituted by aryl, $(C_1-C_6)$alkoxy or OH; and wherein each aryl group may be optionally substituted with $(C_1-C_6)$alkoxy (which in turn may be optionally substituted by $NR^{34}R^{35}$), $(C_1-C_6)$alkyl, OH, $CF_3$ and halo;

aryl is an aromatic ring containing 6 or 10 carbon atoms; wherein, unless otherwise stated, said aryl may be optionally substituted with 1, 2 or 3 substituents independently selected from $(C_1-C_6)$alkyl, $(C_1-C_6)$alkoxy, OH, halo, CN, $CF_3$ and $NR^{46}R^{47}$;

heteroaryl is a 5, 6, 9 or 10 membered aromatic ring, containing from 1 or 2 N atoms and, optionally, an $NR^{50}$ atom, or one $NR^{50}$ atom and an S or an O atom, or one S atom, or one O atom; wherein, unless otherwise stated, said heteroaryl may be optionally substituted with 1, 2 or 3 substituents independently selected from $(C_1-C_6)$alkyl, $(C_1-C_6)$alkoxy, OH, halo, CN, $CF_3$ and $NR^{51}R^{52}$;

$R^{45}$ is selected from H, $(C_1-C_6)$alkyl, $C(O)(C_1-C_6)$alkyl, $C(O)O(C_1-C_6)$alkyl and aryl, wherein said $(C_1-C_6)$alkyl is optionally substituted with a group selected from $(C_1-C_3)$alkoxy, OH, halo, heterocycloalkyl and $NR^{29}R^{30}$; and wherein said $C(O)O(C_1-C_6)$alkyl is optionally substituted with an aryl group;

$R^{50}$ is selected from H, $(C_1-C_6)$alkyl and $C(O)O(C_1-C_6)$alkyl, wherein said $(C_1-C_6)$alkyl may be optionally substituted with a group selected from $(C_1-C_3)$alkoxy, OH, halo, $(C_3-C_6)$cycloalkyl and $NR^{53}R^{54}$;

$R^{43}, R^{44}, R^{46}, R^{47}, R^{48}, R^{49}, R^{51}, R^{52}, R^{53}, R^{54}, R^{55}, R^{56}, R^{57}$ $R^{58}$ and $R^{59}$ are each independently selected from H and $(C_1-C_6)$alkyl;

or pharmaceutically acceptable salts thereof.

For compounds of formula (IC), embodiments of the invention include those wherein each of $R^1, R^2, R^3, R^4, R^5, R^6$ and $R^7$ are as defined herein above in embodiments of the invention concerning compounds of formula (I).

In one embodiment, the present invention provides a compound of formula (I), (IA), (IB), (IC), (ID) or (IE) having a p38 alpha $pIC_{50}$ figure of 5.0 or greater.

In another embodiment, the present invention provides a compound of formula (I), (IA), (IB), (IC), (ID) or (IE) having a p38 alpha $pIC_{50}$ figure of 6.0 or greater.

In yet another embodiment, the present invention provides a compound of formula (I), (IA), (IB), (IC), (ID) or (IE) having a p38 alpha $pIC_{50}$ figure of 7.0 or greater.

In a yet further embodiment, the present invention provides a compound of formula (I), (IA), (IB), (IC), (ID) or (IE) having a p38 alpha $pIC_{50}$ figure of 8.5 or greater.

In the context of the above embodiments, p38 alpha $pIC_{50}$ figures are determined according to the p38 alpha enzyme assay described herein below.

DEFINITIONS

Unless otherwise stated, halo is selected from Cl, F, Br and I;

Cycloalkyl is as defined above. Examples of suitable cycloalkyl groups include cyclopropyl, cyclobutyl, cyclopentyl, cyclohexyl, cycloheptyl, cyclopentene, cyclopenta-1,3-diene, cyclohexene and cyclohexa-1,4-diene (optionally substituted as stated above). Examples of suitable cycloalkyl groups, when fused with aryl, include indanyl and 1,2,3,4-s tetrahydronaphthyl (optionally substituted as stated above).

Heterocycloalkyl is as defined above. Examples of suitable heterocycloalkyl groups include oxiranyl, aziridinyl, azetidinyl, tetrahydrofuranyl, pyrrolidinyl, tetrahydropyranyl, piperidinyl, N-methylpiperidinyl, morpholinyl, N-methyl morpholinyl, thiomorpholinyl, thiomorpholinyl-1-oxide, thiomorpholinyl-1,1-dioxide, piperazinyl, N-methylpiperazinyl, azepinyl oxazepinyl, diazepinyl, 1,2,3,4-tetrahydropyridinyl and

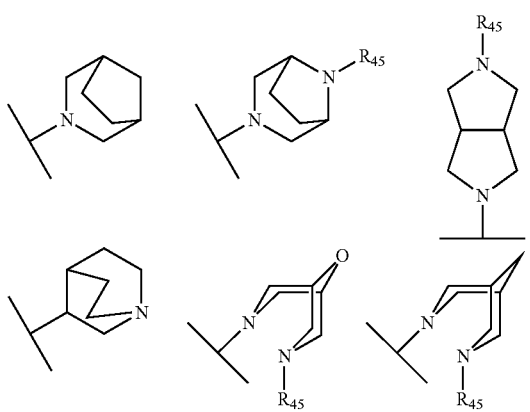

(optionally substituted as stated above). Examples of suitable heterocycloalkyl groups, when fused with aryl or heteroaryl, include 1,2,3,4-tetrahydroquinolinyl, 1,2,3,4-tetrahydroisoquinolinyl, tetrahydroimidazopyrazine, tetrahydroimidazopyridine and indolinyl (optionally substituted as stated above).

Aryl is as defined above. Examples of suitable aryl groups include phenyl and naphthyl (optionally substituted as stated above).

Heteroaryl is as defined above. Examples of suitable heteroaryl groups include thienyl, furanyl, pyrrolyl, pyrazolyl, imidazoyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, indolyl, benzimidazolyl, benzotriazolyl, quinolinyl and isoquinolinyl (optionally substituted as stated above).

Unless otherwise stated alkyl, alkoxy, alkenyl and alkynyl groups containing the requisite number of carbon atoms can be branched or unbranched. Examples of suitable alkyl groups include methyl, ethyl, n-propyl, i-propyl, n-butyl, sec-butyl and t-butyl. Examples of suitable alkoxy groups include methoxy ($—OCH_3$), ethoxy ($—OCH_2CH_3$), n-propoxy, i-propoxy, n-butoxy, sec-butoxy and t-butoxy. Examples of suitable alkenyl groups include 1,1-ethylenyl, 1,2-ethylenyl, 1,1-propylenyl, 1,2-propylenyl, 1,3-propylenyl and 2,2-propylene. Examples of suitable alkynyl groups include prop-1-ynyl, but-1-ynyl, but-2-ynyl, pent-1-ynyl, pent-2-ynyl and hex-1-ynyl.

The term 'C-linked', such as in 'C-linked heterocycloalkyl', means that the heterocycloalkyl group is joined via a ring carbon atom.

The term 'N-linked', such as in 'N-linked heterocycloalkyl', means that the heterocycloalkyl group is joined via a ring nitrogen atom.

"Pharmaceutically acceptable salt" means a physiologically or toxicologically tolerable salt and includes, when appropriate, pharmaceutically acceptable base addition salts and pharmaceutically acceptable acid addition salts. For example (i) where a compound of the invention contains one or more acidic groups, for example carboxy groups, pharmaceutically acceptable base addition salts that can be formed include sodium, potassium, calcium, magnesium and ammonium salts, or salts with organic amines, such as, diethylamine, N-methyl-glucamine, diethanolamine or amino acids (e.g. lysine) and the like; (ii) where a compound of the invention contains a basic group, such as an amino group, pharmaceutically acceptable acid addition salts that can be formed include hydrochlorides, hydrobromides, sulfates, phosphates, acetates, citrates, lactates, tartrates, mesylates, tosylates, benzenesulfonates, maleates, fumarates, xinafoates, p-acetamidobenzoates, succinates, ascorbates, oleates, bisulfates and the like.

In one embodiment, pharmaceutically acceptable salts may include salts of pharmaceutically acceptable organic acids, especially carboxylic and sulfonic acids, including, but not limited to, acetate, adipate, alginate, ascorbate, aspartate, benzenesulfonate (besylate), benzoate, butyrate, camphorate, camphorsulfonate, camsylate, citrate, p-chlorobenzenesulfonate, cyclopentate, 2,5-dichlorobesylate, digluconate, edisylate, esylate, fumarate, formate, gluconate, glucoheptanoate, glutamate, glutarate, glycerophosphate, glycolate, heptanoate, hexanoate, hippurate, 2-hydroxyethane sulfonate, lactate, lactobionate, laurate, malate, maleate, malonate, mandelate, methanesulfonate, 2-naphthalenesulfonate, napsylate, nicotinate, orotate, oxalate, pantothenate, pamoate, pamoic, pectinate, 3-phenylpropionate, pivalate, propionate, pivalate, saccharin, salicylate, stearate, succinate, tartrate, trans-cinnamate, trifluoroacetate, xinafoate, xylate (p-xylene-2-sulfonic acid), undecanoate; and of inorganic acids such as hydrobromide, hydrochloride, hydroiodide, sulphate, bisulfate, phosphate, nitrate, hemisulfate, thiocyanate, persulfate, phosphoric and sulfonic acids.

Salts which are not pharmaceutically acceptable may still be valuable as intermediates.

Hemisalts of acids and bases can also be formed, for example, hemisulfate and hemicalcium salts.

For a review of suitable salts, see "Handbook of Pharmaceutical Salts: Properties, Selection and Use" by Stahl and Wermuth (Wiley-VCH, Weinheim, Germany, 2002).

"Prodrug" refers to a compound which is convertible in vivo by metabolic means (e.g. by hydrolysis, reduction or oxidation) to a compound of the invention. Suitable groups for forming pro-drugs are described in The Practice of Medicinal Chemistry, $2^{nd}$ Ed. pp 561-585 (2003) and in F. J. Leinweber, Drug Metab. Res., 18, 379. (1987).

The compounds of the invention can exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when the solvent is water.

Where compounds of the invention exist in one or more geometrical, optical, enantiomeric, diastereomeric and tautomeric forms, including but not limited to cis- and trans-forms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers can be prepared by the application of adaptation of known methods (e.g. asymmetric synthesis).

The skilled person will recognise that the compounds of the invention may be prepared, in known manner, in a variety of ways. The routes below are merely illustrative of some of the methods that can be employed for the synthesis of compounds of formula (I).

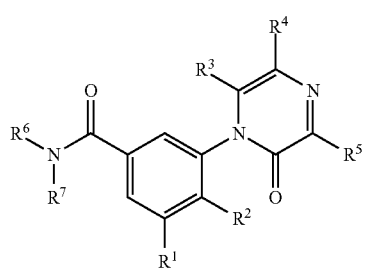
(I)

Accordingly, the present invention provides a process for preparing a compound of formula (I) or a pharmaceutically-acceptable salt thereof which comprises functionalisation of compound of formula (II) wherein $R^1$, $R^2$, $R^3$, $R^5$, $R^6$ and $R^7$ are as defined in claim 1 and $L_1$ is a leaving group, typically halogen, and optionally carrying out one or more of the following:
  (i) converting the compound to another compound of formula (I);
  (ii) forming a pharmaceutically-acceptable salts of the compound.

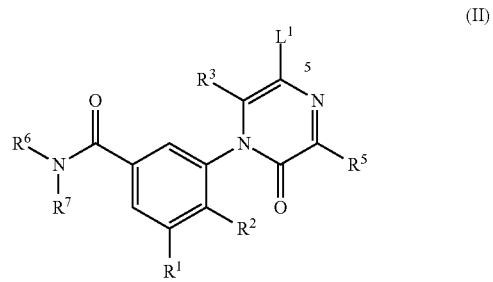
(II)

The functionalisation of the $C^5$ position of 2(1H)-pyrazinone ring of compound of formula (II) may involve formation of a C—H, C—C, C—N, C—S or C-0 bond. The reaction may be catalysed by a transition metal such as palladium, or copper and conveniently performed in an organic solvent such toluene, N-methylpyrrolidin-2-one, tetrahydrofuran, 1,4-dioxane, methanol, ethanol, ethyl acetate, N,N-dimethylformamide, N,N-dimethylacetamide, 1,2-dimethoxyethane and optionally in the presence of an appropriate base such as triethylamine, N,N-diisopropylethylamine, sodium carbonate, potassium carbonate, cesium carbonate, potassium phosphate, sodium tert-butoxide and at a temperature in the range, for example, of from 0 to 200° C. In the dehalogenation reactions, reducing agents such as hydrogen gas, sodium formate, ammonium formate, formic acid, 1,3- or 1,4-cyclohexadiene may be used. Typically, where $R^4$ is H, ammonium formate in ethanol in the presence of N,N-diisopropylethylamine can be used.

Alternatively, a compound of formula (I) or a pharmaceutically-acceptable salt thereof may be prepared by reacting a compound of formula (III) wherein $W^1$ represents a leaving group (for example hydroxyl, alkoxy, acyloxy or halogen) with a compound of formula (IV).

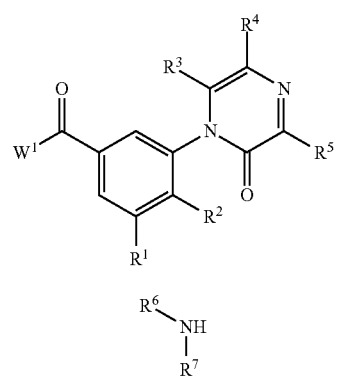
(III)

(IV)

Typically, if compound (III) is in an ester form such as methyl or ethyl ester, the reaction may be carried out by treating a compound of formula (III) with a compound of formula (IV) in the presence of an organomagnesium halide, typically iso-propylmagnesium chloride or cyclopentylmagnesium bromide, or trialkylaluminium in a suitable anhydrous solvent such as diethyl ether, tetrahydrofuran, 1,4-dioxane, toluene, 1,2-dimethoxyethane, and at a temperature in the range, for example, of from −78° C. to ambient temperature (25° C.). Alternatively, reaction of (III) and (IV) may be performed under thermal conditions in a suitable organic solvent or diluent, for example toluene, tetrahydrofuran, 1,4- dioxane, 1,2-dimethoxyethane, N,N-dimethylformamide, N,N-dimethylacetamide, N-methylpyrrolidin-2-one at elevated temperature, for example in the range of from 40 to 130° C.

In the case where $W^1$ is OH, the carboxylic acid can be first converted to an acid halide by treatment with oxalyl halide at a temperature between −5° C. and 35° C. in an inert solvent such as dichloromethane. Typically, the acid halide is then treated with the amine of formula (IV) in an inert solvent such as dichloromethane in the presence of a non-nucleophilic base such as N,N-diisopropylethylamine or triethylamine; or, when $W^1$ is OH, the carboxylic acid can be first converted to other suitable reactive derivative of formula (III), for example, a mixed anhydride, for example an anhydride formed by the reaction of the acid and a chloroformate such as isobutyl chloroformate; an ester, formed by reaction with an alcohol in the presence of acid or base; an active ester, for example an ester formed by the reaction of the acid with a phenol such as pentafluorophenol, with an ester such as pentafluorophenyl trifluoroacetate or with an alcohol such as N-hydroxybenzotriazole;

or, the acid of formula (III, $W^1$=OH) can be reacted with an amine of formula (IV) in the presence of an amide coupling agent such as dicyclohexylcarbodiimide, Pybop (benzotriazole-1-yl-oxy-tris-pyrrolidino-phosphonium hexafluorophosphate), 1-ethyl-3-(3'-dimethylaminopropyl)carbodiimide, HATU (2-(1H-7-azabenzotriazol-1-yl)-1,1,3,3-tetramethyluroniumhexafluorophosphate methanaminium) or PyBroP (bromo-tris-pyrrolidino-phosphonium hexafluorophosphate).

If the compound (III) is an acid form, such compounds may be prepared by hydrolysis of corresponding ester under basic (for example treating with lithium hydroxide in methanol-water mixture), hydrogenolytic (for example treating with hydrogen in appropriate solvent in the presence of palladium on charcoal) or acidic conditions (for example treating with 48% HBr or trifluoroacetic acid).

Compounds of formula (II) can be prepared from the compound of formula (V) wherein $W^1$ represents a leaving group (for example hydroxyl, alkoxy, acyloxy or halogen), $R^1$, $R^2$, $R^3$ and $R^5$ as defined in the formula (I) and $L^1$ is a leaving group, typically halogen, using methods described for preparation of compound of formula (I) from a compound of formula (III).

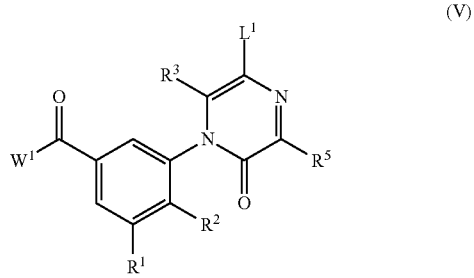

(V)

Additionally, compounds of formula (III) can be conveniently prepared from the compound of formula (V) wherein $W^1$ represents the alkoxy group and $R^1$, $R^2$, $R^3$, $R^5$ and $L^1$ are as defined above, using methods described for preparation of a compound of formula (I) from compound of formula (II).

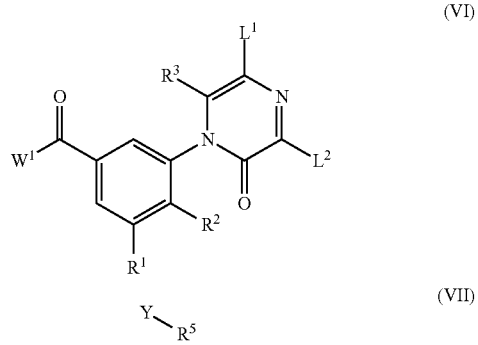

(VI)

(VII)

Compounds of formula (V) can be conveniently prepared from the compound of formula (VI), wherein $L^1$ and $L^2$ are leaving groups, typically halogen, and $R^1$, $R^2$, $R^3$ are as defined above and $W^1$ in an alkoxy group, by selective nucleophilic aromatic substitution of the $L^2$ leaving group with a variety nucleophiles of formula (VII) wherein Y represents hydrogen (for example in amines, anilines, alcohols, phenols, thioalcohols, thiophenols) or a metal (for example in cyanides, Grignard reagents). The reaction can be performed in a suitable organic solvent such toluene, N-methylpyrrolidin-2-one, tetrahydrofuran, 1,4-dioxane, methanol, ethanol, ethyl acetate, N,N-dimethylformamide, N,N-dimethylacetamide, 1,2-s dimethoxyethane and optionally in the presence of an appropriate base such as triethylamine, N,N-diisopropylethylamine, 1,8-diazabicyclo[5.4.0]undec-7-ene (DBU), sodium carbonate, potassium carbonate, cesium carbonate, sodium tert-butoxide, sodium hydride and at a temperature in the range, for example, of from −78 to 200° C., most conveniently at ambient temperature (25° C.). In the case where $R^5$ is $(CR^{14}R^{15})_m NR^{16}R^{17}$ wherein $R^{14}$, $R^{15}$, $R^{16}$ and $R^{17}$ are as defined in claim 1 and m=0, the reaction is typically carried out in tetrahydrofuran at ambient or elevated temperature in the presence of tertiary amine such as N,N-diisopropylethylamine.

Also, compounds of formula (V) where $R^5$ aryl, heteroaryl, alkenyl, alkynyl or $CH_2R^{16}$, wherein, $R^{16}$ is as defined in claim 1, can be prepared in transition metal catalysed cross-coupling reactions (for example Suzuki, Negishi, Kumada, Stille, Sonogashira, Hiyama or Heck cross-coupling reactions) from the compound of formula (VI) and formula (VII) such as alkenes, alkynes, boronic acids and esters thereof, stannanes and silanes. The reaction can be performed in an organic solvent such toluene, N-methylpyrrolidin-2-one, tetrahydrofuran, 1,4-dioxane, methanol, ethanol, ethyl acetate, N,N-dimethylformamide, N,N-dimethylacetamide, 1,2-dimethoxyethane in the presence of an appropriate base such as triethylamine, N,N-diisopropylethylamine, sodium carbonate, potassium carbonate, cesium carbonate, potassium phosphate, sodium tert-butoxide, sodium hydride and at a temperature in the range, for example, of from 0 to 150° C.

In another method, compounds of formula (VI) can be prepared from the compound of formula (IX) wherein $R^1$, $R^2$, $R^3$ are as defined above and $W^1$ in an alkoxy group, by treatment with suitable halogenating reagents, such as N-halosuccinimide in the presence of a base like sodium carbonate and a suitable solvent such as, for example N,N-dimethylformamide.

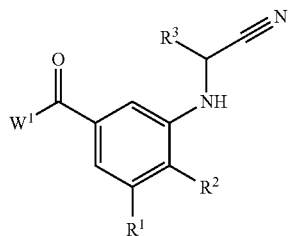

(VIII)

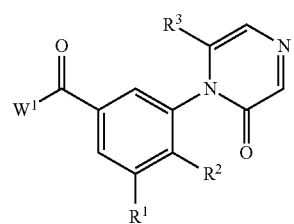

(IX)

Compounds of formula (VI) can be conveniently prepared by treatment of the compound of formula (VIII) or a salt thereof, wherein $R^1$, $R^2$, $R^3$ are as defined above and $W^1$ is an alkoxy group, with the corresponding oxalyl halides such as oxalyl bromide or oxalyl chloride in a suitable solvent such as for example N,N-dimethylformamide, chlorobenzene, dichlorobenzene, chloroform optionally in the presence of suitable salt such as for example tetraethylammonium bromide and at a temperature in the range, for example, of from 20 to 200° C. Typically, the reaction is carried out with oxalyl bromide in 1,2-dichlorobenzene at 100° C.

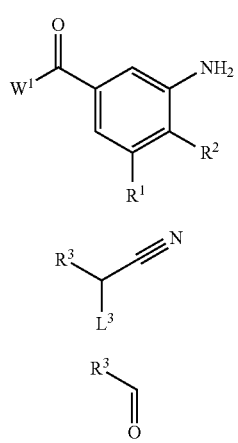

(X)

(XI)

(XII)

Compounds of formula (VIII), where $R^1$, $R^2$ and $R^3$ areas defined above and $W^1$ is an alkoxy group can be conveniently prepared by treatment of the compound of formula (X) or a salt thereof, with a compound of formula (XI) wherein $L^3$ is a leaving group, typically halogen, and is as defined above. The reaction can be performed in the presence of a non-nucleophilic base, such as N,N-diisopropylethylamine, triethylamine, sodium carbonate, in an inert solvent, such as toluene, N-methylpyrrolidin-2-one, tetrahydrofuran, 1,2-dimethoxyethane, 1,4-dioxane, ethyl acetate, N,N-dimethylformamide, N,N-dimethylacetamide and at a temperature in the range, for example, of from 0 to 150° C., preferably in tetrahydrofuran in the presence N,N-diisopropylethylamine at reflux.

Alternatively, compounds of formula (VIII) can be prepared in reaction of a compound of formula (X) with a compound of formula (XII), wherein $R^3$ is as defined above, and cyanides such as, for example sodium cyanide, potassium cyanide or trimethylsilyl cyanide in a suitable solvent such for example acetonitrile, acetic acid, methanol, ethanol, water, acetone, toluene optionally in the presence of suitable Lewis acid such as for example trifluoromethanesulphonic acid, magnesium sulphate, nickel chloride, zinc chloride and at a temperature in the range, for example, of from 0 to 200° C. most conveniently at ambient temperature (25° C.).

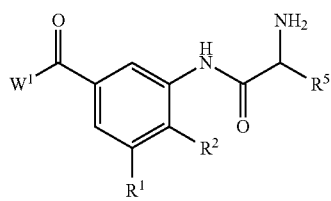

(XIII)

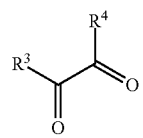

(XIV)

Compounds of formula (III) can also be conveniently prepared by treatment of a compound of formula (XIII), wherein $R^1$, $R^2$, $R^5$ are as defined above and $W^1$ is an alkoxy group, with a compound of formula (XIV), wherein $R^3$ and $R^4$ are as defined above, in the presence of base in a suitable organic solvent such as for example methanol.

Compounds of formula (IX), wherein $R^1$, $R^2$ and $R^3$ areas defined above and $W^1$ is an alkoxy or alkylamino group can similarly be prepared by treatment of a compound of formula (XIII) with a compound of formula (XIV), where $R^3$ in H.

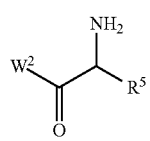

(XV)

Compounds of formula (XIII) can be conveniently prepared from a compound of formula (X) and a corresponding amino acid derivative (XV), wherein $R^5$ is defined hereinabove and $W^2$ is the hydroxyl or alkoxy group, in the standard amide coupling reactions using the methods described for preparation of compound of formula (I) from a compound of formula (III).

Homochiral compounds of formula (VII), wherein $R^5$ is $(CR^{14}R^{15})_m NR^{16}R^{17}$ where m=0, $R^{17}$=H and $R^{16}$ is as defined in claim 1, can by conveniently prepared from a compound of formula (XVI) wherein Z, X, $R^{22}$ and $R^{23}$ are as defined in claim 1 by treatment with a suitable acid, such as for example hydrochloric or trifluoroacetic acid, in a suitable organic solvent, such as for example methanol, ethanol or 1,4-dioxane and at a temperature in the range, for example, of from 0 to 100° C., most conveniently at ambient temperature (25° C.). Typically, the reaction is carried out with hydrogen chloride in 1,4-dioxane/methanol at ambient temperature (25° C.).

Compounds of formula (XVI) wherein Z, X, $R^{22}$ and $R^{23}$ are as defined in claim 1, can by conveniently prepared by reacting a compound of formula (XVII) with a suitable derivative of a compound of formula (XVIII), wherein Z and X are as defined in claim 1 and M is a metal (for example magnesium, aluminium, cerium, lithium, indium) or metalloid (for example boron) in a suitable solvent, such as for example toluene, tetrahydrofuran, 1,4-dioxane, diethyl ether, 1,2-dimethoxyethane or dichloromethane and optionally in the presence of appropriate metal catalyst, such as for example bis(acetonitrile)[(1,2,5,6-n)-1,5-cyclooctadiene]-rhodium, tetrafluoroborate and at a temperature in the range, for example, of from −78 to 100° C. Typically, the reaction is carried out with Grignard reagents in dichloromethane at a temperature in the range, for example, of from −40 to 0° C.

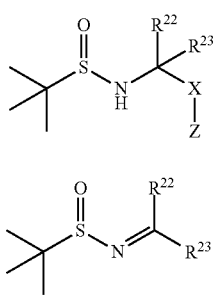

(XVI)

(XVII)

Compound of formula (XVII) wherein $R^{22}$ and $R^{23}$ are as defined in claim 1 can by conveniently prepared by reacting a compound of formula (XIX) with a suitable sulfinimine in a suitable solvent, such as for example toluene, tetrahydrofuran, 1,4-dioxane, diethyl ether, 1,2-dimethoxyethane, dichloromethane in the presence of suitable dehydrating agent, such as for example titanium(IV) ethoxide, copper(II) sulphate, sodium(I) sulphate and at a temperature in the range, for example, of from 0 to 100° C., most conveniently at ambient temperature (25° C.). Typically, the reaction is carried out with (R) or (S) 2-methyl-2-propanesulfinamide in the presence of titanium(IV) ethoxide in tetrahydrofuran at ambient temperature (25° C.).

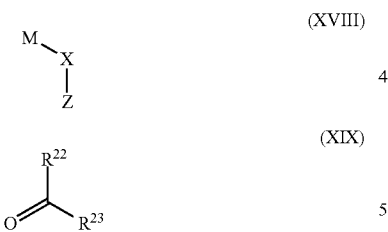

(XVIII)

(XIX)

Compounds of formula (IV), (VII), (X), (XI), (XII), (XIV), (XV), (XIX) are commercially available, are known in the literature, or may be prepared using known techniques by those skilled in the art.

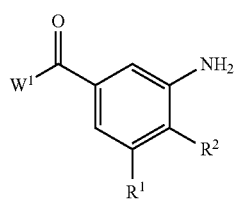

(X)

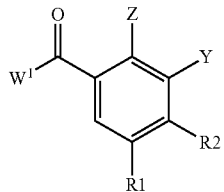

(XX)

Compounds of formula (X), where $R^1$, $R^2$ and $R^3$ areas defined above (in particular $R^1$=F and $R^2$=Me) and $W^1$ is an alkoxy group can be conveniently prepared by reduction of compound of formula (XX) where Z=hydrogen, chloro, bromo or iodo, and Y=nitro, nitroso or amino. Typical reducing agents include, for example, hydrogen gas, sodium formate, ammonium formate, formic acid, 1,3- or 1,4-cyclohexadiene. Typically the reaction may be catalysed by a transition metal such as palladium and conveniently performed in an organic solvent such as, but not limited by, toluene, N-methylpyrrolidin-2-one, tetrahydrofuran, 1,4-dioxane, methanol, ethanol, ethyl acetate, N,N-dimethylformamide, N,N-dimethylacetamide, 1,2-dimethoxyethane and optionally in the presence of an appropriate base such as triethylamine, N,N-diisopropylethylamine, sodium carbonate, potassium carbonate, cesium carbonate, potassium phosphate, sodium hydroxide and at a temperature in the range, for example, of from 0 to 200° C. Preferably when $R^1$=F and $R^2$=Me and $W^1$=OMe, X=Cl and Y=nitro the reaction is carried out using Pd/C and either hydrogen gas/N,N-diisopropylethylamine or ammonium formate in ethanol at temperatures between room temperature and 80° C.

Compounds of formula (XX) where $W^1$ is alkoxy can conveniently be prepared from (XX) where $W^1$ is OH by an esterification reaction. This can be carried out using the an alcohol solvent such as methanol or ethanol under for example acid catalysis. Such acids can include sulfuric acid or hydrochloric acid or via addition of excess chlorotrimethylsilane and can be at a temperature in the range, for example, of from 0 to 150° C., preferably in methanol at room temperature with excess chlorotrimethylsilane.

Compounds of the type (XX) $W^1$ is OH, Z=Cl, $R^1$=F $R^2$=Me are known in the literature (such as DE 3441788), or may be prepared using known techniques by those skilled in the art.

This route offers significant advantages over alternative literature routes which proceed via potentially explosive nitroaryl diazonium salts (J Chem Soc 1960, 672-6).

In one embodiment, the present invention provides a process for preparing a compound of formula (I) as defined herein above, or a pharmaceutically-acceptable salt thereof, by the reaction of a compound of formula (III):

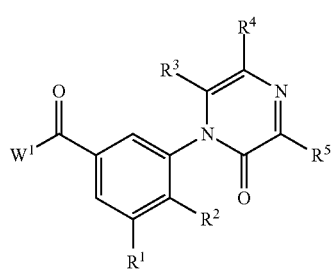

(III)

wherein $R^1$, $R^2$, $R^3$, $R^4$ and $R^5$ are as defined in formula (I) and $W^1$ is a leaving group;

with a compound of formula (IV):

(IV)

wherein $R^6$ and $R^7$ are as defined in formula (I).

It will be appreciated by those skilled in the art that in the processes of the present invention certain functional groups such as hydroxy, carboxy or amino groups in the starting reagents or intermediate compounds may need to be protected by protecting groups. Thus, the preparation of the compounds of formula (I) may involve at a certain stage protection with and/or the removal of one or more protecting groups. The protection and deprotection of functional groups is described in 'Protective Groups in Organic Synthesis', 2nd edition, T. W. Greene and P. G. M. Wuts, Wiley-Interscience (1991) and 'Protecting Groups', P. J. Kocienski, Georg Thieme Verlag (1994). The compounds of formula (I) above may be converted to a pharmaceutically acceptable salt using conventional methods.

Some of the intermediate compounds used in the preparation of compounds of formula (I) are themselves novel compounds. Accordingly, in one embodiment the present invention further provides a compound of formula (VA) or a salt thereof

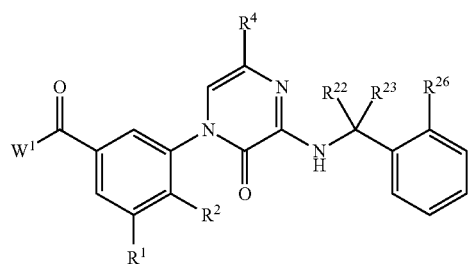

(VA)

wherein:

$W^1$ is OH or ($C_1$-$C_4$)alkoxy;

$R^1$ and $R^2$ are independently selected from H, ($C_1$-$C_4$)alkyl and F;

$R^4$ is H or Br;

$R^{22}$ and $R^{23}$ each independently represent methyl, or $R^{22}$ and $R^{23}$ together with the carbon atom to which they are both attached form a cyclopropyl ring; and $R^{26}$ is selected from OH, $OCH_2Ph$ or $OCH_2CH_2Cl$.

In one embodiment, the present invention provides a compound of formula (VA), or a salt thereof, wherein $W^1$ is OH or OMe; $R^1$ is H or F; $R^2$ is methyl; $R^4$ is H or Br;

$R^{22}$ and $R^{23}$ each independently represent methyl, or $R^{22}$ and $R^{23}$ together with the carbon atom to which they are both attached form a cyclopropyl ring; and $R^{26}$ is OH, $OCH_2Ph$ or $OCH_2CH_2Cl$.

In another embodiment the present invention further provides a compound of formula (VIA) or a salt thereof

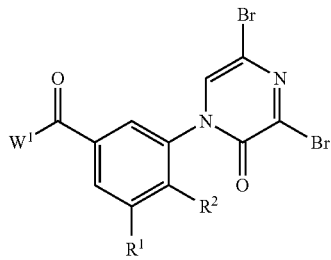

(VIA)

wherein:

$W^1$ is OH or ($C_1$-$C_4$)alkoxy; and $R^1$ and $R^2$ are independently selected from H, ($C_1$-$C_4$)alkyl and F.

In one embodiment, the present invention provides a compound of formula (VIA), or a salt thereof, wherein $W^1$ is OH or OMe; $R^1$ is H or F; and $R^2$ is methyl.

In another embodiment the present invention provides the compound (XXI), or a salt thereof,

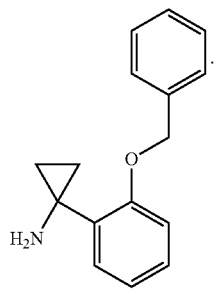

(XXI)

The compounds of the invention have activity as pharmaceuticals, in particular as p38 kinase inhibitors. Diseases and conditions which may be treated with the compounds include:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. bone and joints: arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthritides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritits, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, malepattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 15. gastrointestinal tract: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

Accordingly, the present invention further provides a compound of formula (I), (IA), (IB), (IC), (ID) or (IE) as hereinbefore defined, or a pharmaceutically acceptable salt thereof, for use in therapy.

In another aspect, the invention provides the use of a compound of formula (I), (IA), (IB), (IC), (ID) or (IE) as hereinbefore defined, or a pharmaceutically acceptable salt thereof, in the manufacture of a medicament for use in therapy.

In the context of the present specification, the term "therapy" also includes "prophylaxis" unless there are specific indications to the contrary. The terms "therapeutic" and "therapeutically" should be construed accordingly.

A further aspect of the invention provides a method of treating a disease state in a mammal suffering from, or at risk of, said disease, which comprises administering to a mammal in need of such treatment a therapeutically effective amount of a compound of formula (I), (IA), (IB), (IC), (ID) or (IE) as hereinbefore defined, or a pharmaceutically acceptable salt thereof.

The present invention also provides the use of a compound of formula (I), (IA), (IB), (IC), (ID) or (IE) as hereinbefore defined, or a pharmaceutically acceptable salt thereof, in the manufacture of a medicament for use in the treatment of chronic obstructive pulmonary disease (COPD) (such as irreversible COPD).

The present invention also provides a compound of formula (I), (IA), (IB), (IC), (ID) or (IE) as hereinbefore defined, or a pharmaceutically acceptable salt thereof, for treating COPD.

The present invention also provides the use of a compound of formula (I), (IA), (IB), (IC), (ID) or (IE) as hereinbefore defined, or a pharmaceutically acceptable salt thereof, in the manufacture of a medicament for use in the treatment of asthma.

The present invention also provides a compound of formula (I), (IA), (IB), (IC), (ID) or (IE) as hereinbefore defined, or a pharmaceutically acceptable salt thereof, for treating asthma.

The present invention further provides a method of treating chronic obstructive pulmonary disease (COPD) (such as irreversible COPD), in a warm-blooded animal, such as man, which comprises administering to a mammal in need of such treatment an effective amount of a compound of formula (I), (IA), (IB), (IC), (ID) or (IE) as hereinbefore defined, or a pharmaceutically acceptable salt thereof.

The present invention further provides a method of treating asthma in a warm-blooded animal, such as man, which comprises administering to a mammal in need of such treatment an effective amount of a compound of formula (I), (IA), (IB), (IC), (ID) or (IE) as hereinbefore defined, or a pharmaceutically acceptable salt thereof.

In order to use a compound of the invention for the therapeutic treatment of a warm-blooded animal, such as man, said ingredient is normally formulated in accordance with standard pharmaceutical practice as a pharmaceutical composition.

Therefore in another aspect the present invention provides a pharmaceutical composition that comprises a compound of the invention as hereinbefore defined and a pharmaceutically acceptable adjuvant, diluent or carrier. In a further aspect the present invention provides a process for the preparation of said composition, which comprises mixing active ingredient with a pharmaceutically acceptable adjuvant, diluent or carrier. Depending on the mode of administration, the pharmaceutical composition will, for example, comprise from 0.05 to 99% w (percent by weight), such as from 0.05 to 80% w, for example from 0.10 to 70% w, such as from 0.10 to 50% w, of active ingredient, all percentages by weight being based on total composition.

The pharmaceutical compositions of this invention may be administered in standard manner for the disease condition that it is desired to treat, for example by topical (such as to the lung and/or airways or to the skin), oral, rectal or parenteral administration. For these purposes the compounds of this invention may be formulated by means known in the art into the form of, for example, aerosols, dry powder formulations, tablets, capsules, syrups, powders, granules, aqueous or oily solutions or suspensions, (lipid) emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule, which contains between 0.1 mg and 1 g of active ingredient.

In another aspect a pharmaceutical composition of the invention is one suitable for intravenous, subcutaneous or intramuscular injection. Each patient may receive, for example, an intravenous, subcutaneous or intramuscular dose of 0.01 mgkg$^{-1}$ to 100 mgkg$^{-1}$ of the compound, for example in the range of 0.1 mgkg$^{-1}$ to 20 mgkg$^{-1}$ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose, which is approximately equivalent to the daily parenteral dose, the composition being administered 1 to 4 times per day Another suitable pharmaceutical composition of this invention is one suitable for inhaled administration, inhalation being a particularly useful method for administering the compounds of the invention when treating respiratory diseases such as chronic obstructive pulmonary disease (COPD) or asthma. When administered by inhalation the compounds of formula (I) may be used effectively at doses in the µg range, for example 0.1 to 500 µg, 0.1 to 50 µg, 0.1 to 40 µg, 0.1 to 30 µg, 0.1 to 20 µg, 0.1 to 10 µg, 5 to 10 µg, 5 to 50 µg, 5 to 40 µg, 5 to 30 µg, 5 to 20 µg, 5 to 10 µg, 10 to 50 µg, 10 to 40 µg 10 to 30 µg, or 10 to 20 µg of active ingredient.

In an embodiment of the invention, there is provided a pharmaceutical composition comprising a compound of the invention as hereinbefore defined, in association with a pharmaceutically acceptable adjuvant, diluent or carrier, which is formulated for inhaled administration.

When administered by inhalation, metered dose inhaler devices may be used to administer the active ingredient, dispersed in a suitable propellant and with or without additional excipients such as ethanol, surfactants, lubricants or stabilising agents. Suitable propellants include hydrocarbon, chlorofluorocarbon and hydrofluoroalkane (e.g. heptafluoroalkane) propellants, or mixtures of any such propellants. Preferred propellants are P134a and P227, each of which may be used alone or in combination with other propellants and/or surfactant and/or other excipients. Nebulised aqueous suspensions or, preferably, solutions may also be employed, with or without a suitable pH and/or tonicity adjustment, either as a unit-dose or multi-dose formulations.

Dry powder inhalers may be used to administer the active ingredient, alone or in combination with a pharmaceutically acceptable carrier, in the later case either as a finely divided powder or as an ordered mixture. The dry powder inhaler may be single dose or multi-dose and may utilise a dry powder or a powder-containing capsule.

Metered dose inhaler, nebuliser and dry powder inhaler devices are well known and a variety of such devices are available.

The invention further relates to combination therapies wherein a compound of the invention or a pharmaceutical composition or formulation comprising a compound of the invention, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with agents listed below.

Non-steroidal anti-inflammatory agents (hereinafter NSAIDs) including non-selective cyclo-oxygenase COX-1/ COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention with a monoclonal antibody targeting B-Lymphocytes (such as CD20 (rituximab), MRA-aILI6R and T-Lymphocytes, CTLA4-Ig, HuMax II-15).

The present invention still further relates to the combination of a compound of the invention with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY x 1005.

The present invention further relates to the combination of a compound of the invention and a receptor antagonist for leukotrienes (LT) B4, LTC4, LTD4, and LTE4 selected from the group consisting of the phenothiazin-3-1s such as L-651, 392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention and a proton pump inhibitor (such as omeprazole) or a gastroprotective histamine type 2 receptor antagonist.

The present invention further relates to the combination of a compound of the invention and an antagonist of the histamine type 4 receptor.

The present invention still further relates to the combination of a compound of the invention and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agent including a muscarinic receptor (M1, M2, and M3) antagonist such as atropine, hyoscine, glycopyrrrolate, ipratropium bromide, tiotropium bromide, oxitropium bromide, pirenzepine or telenzepine.

The present invention still further relates to the combination of a compound of the invention and a beta-adrenoceptor agonist (including beta receptor subtypes 1-4) such as isoprenaline, salbutamol, formoterol, salmeterol, terbutaline, orciprenaline, bitolterol mesylate, pirbuterol, or indacaterol or a chiral enantiomer thereof.

The present invention further relates to the combination of a compound of the invention and a chromone, such as sodium cromoglycate or nedocromil sodium.

The present invention still further relates to the combination of a compound of the invention with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention with an agent that modulates a nuclear hormone receptor such as PPARs.

The present invention still further relates to the combination of a compound of the invention together with an immunoglobulin (Ig) or Ig preparation or an antagonist or antibody modulating Ig function such as anti-IgE (for example omalizumab).

The present invention further relates to the combination of a compound of the invention and another systemic or topically-applied anti-inflammatory agent, such as thalidomide or a derivative thereof, a retinoid, dithranol or calcipotriol.

The present invention still further relates to the combination of a compound of the invention and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention and an agent for the treatment of acute or chronic pain, such as a centrally or peripherally-acting analgesic (for example an opioid or derivative thereof), carbamazepine, phenyloin, sodium valproate, amitryptiline or other anti-depressant agent-s, paracetamol, or a non-steroidal anti-inflammatory agent.

The present invention further relates to the combination of a compound of the invention together with a parenterally or topically-applied (including inhaled) local anaesthetic agent such as lignocaine or a derivative thereof.

A compound of the present invention can also be used in combination with an anti-osteoporosis agent including a hormonal agent such as raloxifene, or a biphosphonate such as alendronate.

The present invention still further relates to the combination of a compound of the invention together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B1.- or B2.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK1 or NK3 receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2×7; or (xxvii) inhibitor of transcription factor activation such as NFkB, API, or STATS.

A compound of the invention can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy) quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy) quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin avβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a further embodiment the present invention provides a pharmaceutical product comprising, in combination, a first active ingredient which is a compound of formula (I), (IA), (IB), (IC), (ID) or (IE) as hereinbefore described, or a pharmaceutically acceptable salt thereof, and at least one further active ingredient selected from:— a phosphodiesterase inhibitor
a β2. adrenoceptor agonist
a modulator of chemokine receptor function
a protease inhibitor
a steroidal glucocorticoid receptor agonist
an anticholinergic agent, and a
a non-steroidal glucocorticoid receptor agonist.

The pharmaceutical product according to this embodiment may, for example, be a pharmaceutical composition comprising the first and further active ingredients in admixture. Alternatively, the pharmaceutical product may, for example, comprise the first and further active ingredients in separate pharmaceutical preparations suitable for simultaneous, sequential or separate administration to a patient in need thereof. The pharmaceutical product of this embodiment is of particular use in treating respiratory diseases such as asthma, COPD or rhinitis.

Examples of a phosphodiesterase inhibitor that may be used in the pharmaceutical product according to this embodiment include a PDE4 inhibitor such as an inhibitor of the isoform PDE4D, a PDE3 inhibitor and a PDE5 inhibitor. Examples include the compounds (Z)-3-(3,5-dichloro-4-pyridyl)-2-[4-(2-indanyloxy-5-methoxy-2-pyridyl]propenenitrile, N-[9-amino-4-oxo-1-phenyl-3,4,6,7-tetrahydropyrrolo[3,2,1-jk][1,4]benzodiazepin-3(R)-yl]pyridine-3-carboxamide (CI-1044), 3-(benzyloxy)-1-(4-fluorobenzyl)-N-[3-(methylsulphonyl)phenyl]-1H-indole-2-carboxamide, (1S-exo)-5-[3-(bicyclo[2.2.1]hept-2-yloxy)-4-methoxyphenyl]tetrahydro-2(1H)-pyrimidinone (Atizoram), N-(3,5,dichloro-4-pyridinyl)-2-[1-(4-fluorobenzyl)-5-hydroxy-1H-indol-3-yl]-2-oxoacetamide (AWD-12-281), 6-[3-(cyclopentyloxy)-4-methoxyphenyl]-1,3-dihydro-1,3-dioxo-2H-isoindole-2-propanamide (CDC-801), N-[9-methyl-4-oxo-1-phenyl-3,4,6,7-tetrahydropyrrolo[3,2,1-jk][1,4]benzodiazepin-3(R)-yl]pyridine-4-carboxamide (CI-1018), cis-[4-cyano-4-(3-cyclopentyloxy-4-methoxyphenyl)cyclohexane-1-carboxylic acid (Cilomilast), 8-amino-1,3-bis(cyclopropylmethyl)xanthine (Cipamfylline), N-(2,5-dichloro-3-pyridinyl)-8-methoxy-5-quinolinecarboxamide (D-4418), 5-(3,5-di-tert-butyl-4-hydroxybenzylidene)-2-iminothiazolidin-4-one (Darbufelone), 2-methyl-1-[2-(1-methylethyl)pyrazolo[1,5-a]pyridin-3-yl]-1-propanone (Ibudilast), 2-(2,4-dichlorophenylcarbonyl)-3-ureidobenzofuran-6-yl methanesulphonate (Lirimilast), (−)-(R)-5-(4-methoxy-3-propoxyphenyl)-5-methyloxazolidin-2-one (Mesopram), (−)-cis-9-ethoxy-8-methoxy-2-methyl-1,2,3,4,4a,10b-hexahydro-6-(4-diisopropylaminocarbonylphenyl)-benzo[c][1,6]naphthyridine (Pumafentrine), 3-(cyclopropylmethoxy)-N-(3,5-dichloro-4-pyridyl)-4-(difluoromethoxy)benzamide (Roflumilast), the N-oxide of Roflumilast, 5,6-diethoxybenzo[b]thiophene-2-carboxylic acid (Tibenelast), 2,3,6,7-tetrahydro-2-(mesitylimino)-9,10-dimethoxy-3-methyl-4H-pyrimido[6,1-a]isoquinolin-4-one (trequinsin) and 3-[[3-(cyclopentyloxy)-4-methoxyphenyl]-methyl]-N-ethyl-8-(1-methylethyl)-3H-purine-6-amine (V-11294A).

Examples of a β$_2$-adrenoceptor agonist that may be used in the pharmaceutical product according to this embodiment include metaproterenol, isoproterenol, isoprenaline, albuterol, salbutamol (e.g. as sulphate), formoterol (e.g. as fumarate), salmeterol (e.g. as xinafoate), terbutaline, orciprenaline, bitolterol (e.g. as mesylate), pirbuterol or indacaterol. The β$_2$-adrenoceptor agonist of this embodiment may be a long-acting β$_2$-agonists, for example salmeterol (e.g. as xinafoate), formoterol (e.g. as fumarate), bambuterol (e.g. as hydrochloride), carmoterol (TA 2005, chemically identified as 2(1H)-Quinolone, 8-hydroxy-5-[1-hydroxy-2-[2-(4-methoxy-phenyl)-1-methylethyl]-amino]ethylFmonohydrochloride, [R—(R*,R*)] also identified by Chemical Abstract Service Registry Number 137888-11-0 and disclosed in U.S. Pat. No. 4,579,854), indacaterol (CAS no 312753-06-3; QAB-149), formanilide derivatives e.g. 3-(4-{[6-({(2R)-2-[3-(formylamino)-4-hydroxyphenyl]-2-hydroxyethyl}amino)hexyl]oxy}-butyl)benzenesulfonamide as disclosed in WO 2002/76933, benzenesulfonamide derivatives e.g. 3-(4-{[6-({(2R)-2-hydroxy-2-[4-hydroxy-3-(hydroxy-methyl)phenyl]ethyl}amino)-hexyl]oxy}butyl)benzenesulfonamide as disclosed in WO 2002/88167, aryl aniline receptor agonists as disclosed in WO 2003/042164 and WO 2005/025555, indole derivatives as disclosed in WO 2004/032921, in US 2005/222144, compounds GSK 159797, GSK 159802, GSK 597901, GSK 642444 and GSK 678007.

Examples of a modulator of chemokine receptor function that may be used in the pharmaceutical product according to this embodiment include a CCR1 receptor antagonist.

Examples of a protease inhibitor that may be used in the pharmaceutical product according to this embodiment include an inhibitor of neutrophil elastase or an inhibitor of MMP12.

Examples of a steroidal glucocorticoid receptor agonist that may be used in the pharmaceutical product according to this embodiment include budesonide, fluticasone (e.g. as propionate ester), mometasone (e.g. as furoate ester), beclomethasone (e.g. as 17-propionate or 17,21-dipropionate esters), ciclesonide, loteprednol (as e.g. etabonate), etiprednol (as e.g. dicloacetate), triamcinolone (e.g. as acetonide), flunisolide, zoticasone, flumoxonide, rofleponide, butixocort (e.g. as propionate ester), prednisolone, prednisone, tipredane, steroid esters e.g. 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl)ester and 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, steroid esters according to DE 4129535, steroids according to WO 2002/00679, WO 2005/041980, or steroids GSK 870086, GSK 685698 and GSK 799943.

Examples of an anticholinergic agent that may be used in the pharmaceutical product according to this embodiment include for example a muscarinic receptor antagonist (for example a M1, M2 or M3 antagonist, such as a M3 antagonist) for example ipratropium (e.g. as bromide), tiotropium (e.g. as bromide), oxitropium (e.g. as bromide), tolterodine, pirenzepine, telenzepine, glycopyrronium bromide (such as R,R-glycopyrronium bromide or a mixture of R,S- and S,R-glycopyrronium bromide); mepensolate (e.g. as bromide), a quinuclidine derivative such as 3(R)-(2-hydroxy-2,2-dithien-2-ylacetoxy)-1-(3-phenoxypropyl)-1-azonia-bicyclo[2.2.2]octane bromide as disclosed in US 2003/0055080, quinuclidine derivatives as disclosed in WO 2003/087096 and WO 2005/115467 and DE 10050995; or GSK 656398 or GSK 961081.

Examples of a modulator of a non-steroidal glucocorticoid receptor agonist that may be used in the pharmaceutical product according to this embodiment include those described in WO2006/046916.

EXPERIMENTAL METHODS

The following abbreviations have been used:

| DMF | N,N-dimethylformamide |
| DMSO | dimethylsulphoxide |
| THF | tetrahydrofuran |
| DMA | N,N-dimethylacetamide |
| DCM | dichloromethane. |

In the examples the NMR spectra were measured on a Varian Unity Inova spectrometer at a proton frequency of either 300 or 400 MHz. Reactions that were heated by microwave irradiation were pereperformed using a CEM Discover Microwave. Examples having chiral centre might appear in NMR as a mixture of rotamers. The MS spectra were measured on either an Agilent 1100 MSD G1946D spectrometer or a Hewlett Packard HP1100 MSD G1946A spectrometer. Preparative HPLC separations were performed using a Waters Symmetry® or Xterra® column or Phenomenex Gemini® using 0.1% aqueous trifluoroacetic acid:acetonitrile, 0.1% aqueous ammonia:acetonitrile or 0.1% ammonium acetate:acetonitrile as the eluent. SCX and NH$_2$ resin were obtained from Varian Incorporated. Compound names were generated using the commercially available chemical naming software package Index ACDLABS 8.0.

Example 1

N-Cyclopropyl-3-[3-(2-fluoro-benzylamino)-2-oxo-2H-pyrazin-1-yl]-4-methyl-benzamide

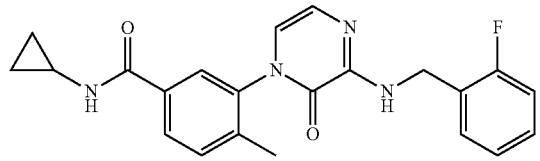

a) 3-[(Cyanomethyl)amino]-4-methyl-benzoic acid, methyl ester

To a stirred solution of 3-amino-4-methyl-benzoic acid, methyl ester (10.0 g) in dry tetrahydrofuran was added N,N-diisopropylethylamine (12.6 mL) followed by the addition of bromoacetonitrile (5.1 mL). The reaction was heated at reflux under an atmosphere of nitrogen with stirring for 12 h. Water was added and the mixture extracted with ethyl acetate. The pooled organics were washed with brine, dried (MgSO$_4$), filtered and the solvent removed under reduced pressure to afford the subtitle compound as a solid (12.4 g).

MS: APCI (+ve) 178 (M+H$^+$).

$^1$H NMR δ(DMSO-d$_6$, 300 MHz) 7.31 (1H, dd), 7.23-7.17 (2H, m), 5.91 (1H, t), 4.33 (2H, d), 3.83 (3H, s), 2.17 (3H, s).

b) 3-(3,5-Dibromo-2-oxo-2H-pyrazin-1-yl)-4-methyl-benzoic acid, methyl ester

To 3-[(cyanomethyl)amino]-4-methyl-benzoic acid, methyl ester (Example 1a, 5.0 g) was added 1,2-dichlorobenzene (50 mL) and oxalyl bromide (11.5 mL). The reaction was heated at 100° C. for four h before the volatiles were removed under reduced pressure and the residue azeotroped twice with toluene. Purification (SiO$_2$ chromatography eluting with dichloromethane) afforded the subtitle compound as a solid (7.2 g).

MS: APCI (+ve) 401/403/405 (M+H$^+$).

$^1$H NMR δ(DMSO-d$_6$, 400 MHz) 8.08 (1H, dd), 7.87 (1H, d), 7.46 (1H, d), 7.29 (1H, s), 3.92 (3H, s), 2.25 (3H, s).

c) N-Cyclopropyl-3-[3-(2-fluoro-benzylamino)-2-oxo-2H-pyrazin-1-yl]-4-methyl-benzamide To a stirred solution of 3-(3,5-dibromo-2-oxo-2H-pyrazin-1-yl)-4-methyl-benzoic acid, methyl ester (Example 1b, 0.1 g) in tetrahydrofuran (1 mL) within a microwave vial was added triethylamine (38 μL) and 2-fluoro-benzenemethanamine (31 μL). The reaction was stirred overnight before the addition of cyclopropylamine (0.13 mL) and cyclopentylmagnesium bromide (2M in diethyl ether, 750 μL) dropwise. After stirring for 30 minutes, ethanol (2 mL) was added followed by the addition of ammonium formate (0.3 g) and 10% palladium on carbon (30 mg). The reaction mixture was heated within a microwave for 60 minutes at 100° C. before being cooled to room temperature, filtered and washed with ethanol. The filtrate was concentrated in vacuo. Purification by preparative HPLC (Gemini column, 0.1% ammonia:acetonitrile eluent) afforded the title compound as a solid (58 mg).

MS: APCI (+ve) 393 (M+H$^+$).

¹H NMR δ(DMSO-d₆, 400 MHz) 8.44 (1H, d), 7.90-7.85 (2H, m), 7.76 (1H, d), 7.50 (1H, d), 7.35-7.26 (2H, m), 7.20-7.13 (2H, m), 6.82 (1H, d), 6.72 (1H, d), 4.64 (1H, dd), 4.54 (1H, dd), 2.89-2.81 (1H, m), 2.12 (3H, s), 0.72-0.66 (2H, m), 0.58-0.53 (2H, m).

The following examples 2-49 (Table 1) were prepared and purified in a similar manner to Example 1c.

Example 2

N-Cyclopropyl-4-methyl-3-[3-(4-methyl-1-piperazinyl)-2-oxo-1(2H)-pyrazinyl]-benzamide

Example 3

N-Cyclopropyl-3-[3-[[3-(dimethylamino)propyl]amino]-2-oxo-1(2H)-pyrazinyl]-4-methyl-benzamide

Example 4

N-Cyclopropyl-4-methyl-3-[3-[[3-(4-methyl-1-piperazinyl)propyl]amino]-2-oxo-1(2H)-pyrazinyl]-benzamide

Example 5

N-Cyclopropyl-3-[3-[[2-(dimethylamino)ethyl]amino]-2-oxo-1(2H)-pyrazinyl]-4-methyl-benzamide

Example 6

N-Cyclopropyl-4-methyl-3-[3-[[3-(4-morpholinyl)propyl]amino]-2-oxo-1(2H)-pyrazinyl]-benzamide

Example 7

N-Cyclopropyl-4-methyl-3-[3-(methylamino)-2-oxo-1(2H)-pyrazinyl]-benzamide,

Example 8 is N-Cyclopropyl-3-[3-[(3-methoxypropyl)amino]-2-oxo-1(2H)-pyrazinyl]-4-methyl-benzamide

Example 9

N-Cyclopropyl-4-methyl-3-[2-oxo-3-[[2-(2-pyridinyl)ethyl]amino]-1(2H)-pyrazinyl]-benzamide

Example 10

N-Cyclopropyl-4-methyl-3-[2-oxo-3-[(2-phenylethyl)amino]-1(2H)-pyrazinyl]-benzamide

Example 11

N-Cyclopropyl-4-methyl-3-[2-oxo-3-[(phenylmethyl)amino]-1(2H)-pyrazinyl]-benzamide

Example 12

N-Cyclopropyl-4-methyl-3-[2-oxo-3-(phenylamino)-1(2H)-pyrazinyl]-benzamide

Example 13

N-Cyclopropyl-3-[3-[[(3-methoxyphenyl)methyl]amino]-2-oxo-1(2H)-pyrazinyl]-4-methyl-benzamide

Example 14

4-Methyl-3-[3-[[[4-(4-methyl-1-piperazinyl)phenyl]methyl]amino]-2-oxo-1(2H)-pyrazinyl]-N-(1-methylpropyl)-benzamide

Example 15

N-Cyclopropyl-4-methyl-3-[2-oxo-3-[[(1R)-1-phenylethyl]amino]-1(2H)-pyrazinyl]-benzamide

Example 16

N-Cyclopropyl-4-methyl-3-[2-oxo-3-[[(1R)-1,2,3,4-tetrahydro-1-naphthalenyl]amino]-1(2H)-pyrazinyl]-benzamide

Example 17

N-Cyclopropyl-3-[3-[[(1R)-2,3-dihydro-1H-inden-1-yl]amino]-2-oxo-1(2H)-pyrazinyl]-4-methyl-benzamide

Example 18

N-Cyclopropyl-4-methyl-3-[3-[(1-methyl-1-phenylethyl)amino]-2-oxo-1(2H)-pyrazinyl]-benzamide

Example 19

N-Cyclopropyl-4-methyl-3-[3-[methyl(phenylmethyl)amino]-2-oxo-1(2H)-pyrazinyl]-benzamide

Example 20

N-Cyclopropyl-3-[3-[[(4-methoxyphenyl)methyl]amino]-2-oxo-1(2H)-pyrazinyl]-4-methyl-benzamide

Example 21

N-Cyclopropyl-4-methyl-3-[2-oxo-3-[[(1S)-1-phenylethyl]amino]-1(2H)-pyrazinyl]-benzamide

Example 22

N-Cyclopropyl-3-[3-[[(3-fluorophenyl)methyl]amino]-2-oxo-1(2H)-pyrazinyl]-4-methyl-benzamide

Example 23

N-Cyclopropyl-4-methyl-3-[2-oxo-3-[(2-pyridinylmethyl)amino]-1(2H)-pyrazinyl]-benzamide

Example 24

N-Cyclopropyl-4-methyl-3-[2-oxo-3-[(3-pyridinylmethyl)amino]-1(2H)-pyrazinyl]-benzamide

Example 25

N-Cyclopropyl-4-methyl-3-[3-[[[4-(methylsulfonyl)phenyl]methyl]amino]-2-oxo-1(2H)-pyrazinyl]-benzamide

Example 26

N-Cyclopropyl-3-[3-[[(2-methoxyphenyl)methyl]amino]-2-oxo-1(2H)-pyrazinyl]-4-methyl-benzamide

Example 27

3-[3-[(1H-Benzimidazol-2-ylmethyl)amino]-2-oxo-1(2H)-pyrazinyl]-N-cyclopropyl-4-methyl-benzamide

Example 28

N-Cyclopropyl-4-methyl-3-[2-oxo-3-[(3-quinolinylmethyl)amino]-1(2H)-pyrazinyl]-benzamide

Example 29

N-Cyclopropyl-4-methyl-3-[2-oxo-3-[[(1,2,3,4-tetrahydro-3-quinolinyl)methyl]amino]-1(2H)-pyrazinyl]-benzamide

Example 30

N-Cyclopropyl-3-[3-(3,4-dihydro-2(1H)-isoquinolinyl)-2-oxo-1(2H)-pyrazinyl]-4-methyl-benzamide

Example 31

N-Cyclopropyl-4-methyl-3-[2-oxo-3-[(2-thienylmethyl)amino]-1(2H)-pyrazinyl]-benzamide

Example 32

3-[3-[(1,3-Benzodioxol-5-ylmethyl)amino]-2-oxo-1(2H)-pyrazinyl]-N-cyclopropyl-4-methyl-benzamide

Example 33

N-Cyclopropyl-3-[3-[[(4-fluorophenyl)methyl]amino]-2-oxo-1(2H)-pyrazinyl]-4-methyl-benzamide

Example 34

N-Cyclopropyl-4-methyl-3-[2-oxo-3-[[1-phenyl-2-(1-pyrrolidinyl)ethyl]amino]-1(2H)-pyrazinyl]-benzamide

Example 35

N-Cyclopropyl-4-methyl-3-[3-[[(1-methyl-4-phenyl-4-piperidinyl)methyl]amino]-2-oxo-1(2H)-pyrazinyl]-benzamide

Example 36

N-Cyclopropyl-4-methyl-3-[2-oxo-3-[(3-phenylpropyl)amino]-1(2H)-pyrazinyl]-benzamide

Example 37

N-Cyclopropyl-3-[3-[[[4-(1,1-dimethylethyl)phenyl]methyl]amino]-2-oxo-1(2H)-pyrazinyl]-4-methyl-benzamide

Example 38

N-Cyclopropyl-4-methyl-3-[2-oxo-3-[[(1R)-1-phenylpropyl]amino]-1(2H)-pyrazinyl]-benzamide

Example 39

N-Cyclopropyl-4-methyl-3-[3-[[(2-methylphenyl)methyl]amino]-2-oxo-1(2H)-pyrazinyl]-benzamide

Example 40

N-Cyclopropyl-4-methyl-3-[3-[[[3-[(4-methyl-1-piperazinyl)methyl]phenyl]methyl]amino]-2-oxo-1(2H)-pyrazinyl]-benzamide

Example 41

N-Cyclopropyl-4-methyl-3-[3-[[[2-[(4-methyl-1-piperazinyl)methyl]phenyl]methyl]amino]-2-oxo-1(2H)-pyrazinyl]-benzamide

Example 42

N-Cyclopropyl-4-methyl-3-[3-[[(4-methylphenyl)methyl]amino]-2-oxo-1(2H)-pyrazinyl]-benzamide

Example 43

3-[3-[(Cyclohexylmethyl)amino]-2-oxo-1(2H)-pyrazinyl]-N-cyclopropyl-4-methyl-benzamide

Example 44

3-[3-[([1,1'-Biphenyl]-2-ylmethyl)amino]-2-oxo-1(2H)-pyrazinyl]-N-cyclopropyl-4-methyl-benzamide

Example 45

N-Cyclopropyl-4-methyl-3-[2-oxo-3-[[(4-phenoxyphenyl)methyl]amino]-1(2H)-pyrazinyl]-benzamide

Example 46

N-Cyclopropyl-4-methyl-3-[3-[[(3-methylphenyl)methyl]amino]-2-oxo-1(2H)-pyrazinyl]-benzamide

Example 47

N-Cyclopropyl-4-methyl-3-[2-oxo-3-[[(1S,2R)-2-phenylcyclopropyl]amino]-1(2H)-pyrazinyl]-benzamide

Example 48

N-Cyclopropyl-4-methyl-3-[2-oxo-3-[[(1S)-1,2,3,4-tetrahydro-1-naphthalenyl]amino]-1(2H)-pyrazinyl]-benzamide

Example 49

N-Cyclopropyl-3-[3-[(2,2-dimethylpropyl)amino]-2-oxo-1(2H)-pyrazinyl]-4-methyl-benzamide a) Where the amine was present as the salt extra triethylamine was used (38 µL).

b) Heating was required for the initial displacement (120° C. for 60 minutes within a microwave) before cooling followed by the addition of the cyclopropylamine (0.13 mL) and cyclopentylmagnesium bromide (2M in diethyl ether, 750 µL) dropwise.

c) Final purification by preparative HPLC (Gemini column, 0.1% trifluoroacetic acid:acetonitrile eluent)

TABLE 1
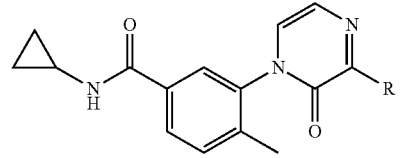
| Example | R | MS [M + H]+ m/z | ¹H NMR δ (DMSO-d₆) |
|---|---|---|---|
| 2 | 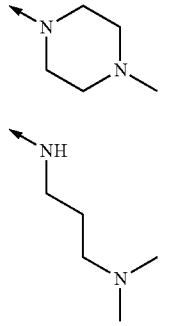 | 368 | 8.43 (1H, d), 7.85 (1H, dd), 7.71 (1H, d), 7.47 (1H, d), 6.99 (1H, d), 6.97 (1H, d), 3.76 – 3.64 (4H, m), 2.88 – 2.81 (1H, m), 2.39 (4H, t), 2.19 (3H, s), 2.09 (3H, s), 0.71 – 0.66 (2H, m), 0.58 – 0.53 (2H, m) |
| 3 | 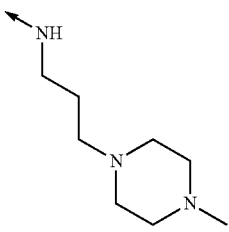 | 370 | 8.44 (1H, d), 7.86 (1H, dd), 7.73 (1H, d), 7.50 – 7.44 (2H, m), 6.84 (1H, d), 6.65 (1H, d), 3.43 – 3.26 (2H, m), 2.89 – 2.81 (1H, m), 2.26 (2H, t), 2.12 (6H, s), 2.10 (3H, s), 1.69 (2H, quintet), 0.71 – 0.65 (2H, m), 0.58 – 0.53 (2H, m) |
| 4 | 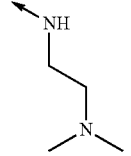 | 425 | 8.44 (1H, d), 7.86 (1H, dd), 7.73 (1H, d), 7.52 – 7.46 (2H, m), 6.84 (1H, d), 6.65 (1H, d), 3.43 – 3.27 (2H, m), 2.89 – 2.81 (1H, m), 2.43 – 2.23 (10H, m), 2.13 (3H, s), 2.10 (3H, s), 1.76 – 1.66 (2H, m), 0.72 – 0.66 (2H, m), 0.58 – 0.53 (2H, m) |
| 5 | 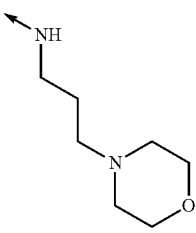 | 356 | 8.44 (1H, d), 7.86 (1H, dd), 7.73 (1H, d), 7.48 (1H, d), 7.08 (1H, t), 6.86 (1H, d), 6.68 (1H, d), 3.48 – 3.32 (2H, m), 2.89 – 2.80 (1H, m), 2.45 (2H, td), 2.18 (6H, s), 2.10 (3H, s), 0.72 – 0.66 (2H, m), 0.58 – 0.53 (2H, m) |
| 6 |  | 412 | 8.44 (1H, d), 7.86 (1H, dd), 7.73 (1H, s), 7.65 (1H, t), 7.49 (1H, d), 6.85 (1H, dd), 6.66 (1H, dd), 3.58 (4H, t), 3.46 – 3.28 (2H, m), 2.90 – 2.79 (1H, m), 2.41 – 2.30 (6H, m), 2.10 (3H, s), 1.73 (2H, quintet), 0.73 – 0.65 (2H, m), 0.60 – 0.52 (2H, m) |
| 7 | 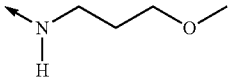 | 299 | 8.44 (1H, d), 7.86 (1H, dd), 7.73 (1H, d), 7.48 (1H, d), 7.41 – 7.36 (1H, m), 6.86 (1H, d), 6.66 (1H, d), 2.88 – 2.81 (4H, m), 2.10 (3H, s), 0.71 – 0.66 (2H, m), 0.58 – 0.53 (2H, m) |
| 8 | 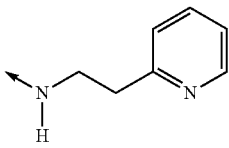 | 357 | 8.44 (1H, d), 7.86 (1H, dd), 7.74 (1H, d), 7.48 (1H, d), 7.35 (1H, t), 6.85 (1H, d), 6.66 (1H, d), 3.45 – 3.28 (4H, m), 3.23 (3H, s), 2.89 – 2.81 (1H, m), 2.10 (3H, s), 1.81 (2H, quintet), 0.72 – 0.66 (2H, m), 0.58 – 0.53 (2H, m) |
| 9 |  | 390 | 8.51 – 8.48 (1H, m), 8.43 (1H, d), 7.86 (1H, dd), 7.74 – 7.68 (2H, m), 7.48 (1H, d), 7.44 (1H, t), 7.29 (1H, d), 7.24 – 7.20 (1H, m), 6.87 (1H, d), 6.69 (1H, d), 3.77 – 3.62 (2H, m), 3.09 – 3.01 (2H, m), 2.88 – 2.81 (1H, m), 2.10 (3H, s), 0.71 – 0.66 (2H, m), 0.58 – 0.53 (2H, m) |

TABLE 1-continued

| Example | R | MS [M + H]+ m/z | 1H NMR δ (DMSO-d6) |
|---|---|---|---|
| 10 | (N-H linked to CH2CH2-phenyl) | 389 | 8.44 (1H, d), 7.86 (1H, dd), 7.73 (1H, d), 7.48 (1H, d), 7.38 – 7.17 (6H, m), 6.88 (1H, d), 6.68 (1H, d), 3.64 – 3.47 (2H, m), 2.94 – 2.80 (3H, m), 2.10 (3H, s), 0.72 –0.65 (2H, m), 0.58 – 0.52 (2H, m) |
| 11 | (N-H linked to CH2-phenyl) | 375 | 8.43 (1H, d), 7.92 (1H, t), 7.87 (1H, dd), 7.75 (1H, d), 7.49 (1H, d), 7.36 – 7.28 (4H, m), 7.25 – 7.20 (1H, m), 6.82 (1H, d), 6.70 (1H, d), 4.59 (1H, dd), 4.48 (1H, dd), 2.89– 2.81 (1H, m), 2.11 (3H, s), 0.71 – 0.66 (2H, m), 0.58 – 0.53 (2H, m) |
| 12 | (N-H linked to phenyl) | 361 | 9.27 (1H, s), 8.46 (1H, d), 8.02 – 7.98 (2H, m), 7.89 (1H, dd), 7.81 (1H, d), 7.52 (1H, d), 7.32 (2H, t), 7.04 – 6.99 (2H, m), 6.96 (1H, d), 2.89 – 2.82 (1H, m), 2.16 (3H, s), 0.72 – 0.67 (2H, m), 0.59 – 0.54 (2H, m) |
| 13 | (N-H-CH2-3-methoxyphenyl) | 405 | 8.43 (1H, d), 7.94 – 7.84 (2H, m), 7.75 (1H, d), 7.49 (1H, d), 7.22 (1H, t), 6.92 – 6.87 (2H, m), 6.84 – 6.77 (2H, m), 6.70 (1H, d), 4.56 (1H, dd), 4.45 (1H, dd), 3.73 (3H, s), 2.90 – 2.79 (1H, m), 2.11 (3H, s), 0.73 – 0.65 (2H, m), 0.59 – 0.51 (2H, m) |
| 14 | (N-H-CH2-4-(4-methylpiperazin-1-yl)phenyl) | 473 | 8.42 (1H, d), 7.86 (1H, dd), 7.76 – 7.72 (2H, m), 7.48 (1H, d), 7.19 (2H, d), 6.89 – 6.85 (2H, m), 6.83 (1H, d), 6.68 (1H, d), 4.47 (1H, dd), 4.37 (1H, dd), 3.08 (4H, t), 2.88 – 2.81 (1H, m), 2.43 (4H, t), 2.21 (3H, s), 2.10 (3H, s), 0.71 – 0.65 (2H, m), 0.57 – 0.53 (2H, m) |
| 15 | (N-H-CH(CH3)-phenyl) | 389 | 8.47 – 8.37 (1H, m), 7.86 (1H, d), 7.74 (1H, d), 7.63 – 7.53 (1H, m), 7.52 – 7.45 (1H, m), 7.44 – 7.38 (2H, m), 7.36 – 7.27 (2H, m), 7.25 – 7.17 (1H, m), 6.83 – 6.78 (1H, m), 6.71 – 6.65 (1H, m), 5.15 (1H, quintet), 2.90– 2.79 (1H, m), 2.13 (1.5H, s), 2.08 (1.5H, s), 1.51 (3H, t), 0.73 – 0.63 (2H, m), 0.61 – 0.50 (2H, m) |
| 16 | (N-H-tetrahydronaphthalen-1-yl) | 415 | 8.48 – 8.40 (1H, m), 7.87 (1H, d), 7.78 (1H, d), 7.49 (1H, d), 7.25 – 7.08 (5H, m), 6.90 (1H, d), 6.75 (1H, d), 5.26 (1H, quintet), 2.91 – 2.67 (3H, m), 2.15 (1.5H, s), 2.13 (1.5H, s), 2.03 – 1.84 (3H, m), 1.83 – 1.69 (1H, m), 0.74 – 0.64 (2H, m), 0.60 – 0.51 (2H, m) |
| 17 | (N-H-indan-1-yl) | 401 | 8.51 – 8.40 (1H, m), 7.93 – 7.84 (1H, m), 7.83 – 7.74 (1H, m), 7.55 – 7.46 (1H, m), 7.43 – 7.12 (5H, m), 6.96 – 6.87 (1H, m), 6.81 – 6.73 (1H, m), 5.67 – 5.52 (1H, m), 3.09 – 2.94 (1H, m), 2.93 – 2.77 (2H, m), 2.60 – 2.40 (1H, m), 2.21 – 2.00 (4H, m), 0.76 – 0.64 (2H, m), 0.62 – 0.53 (2H, m) |

TABLE 1-continued

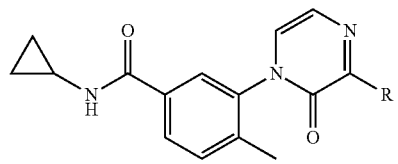

| Example | R | MS [M + H]+ m/z | 1H NMR δ (DMSO-d6) |
|---|---|---|---|
| 18[b] | 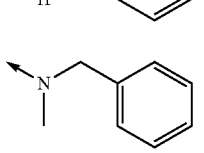 | 403 | 8.44 (1H, d), 7.87 (1H, dd), 7.76 (1H, d), 7.49 (1H, d), 7.41 – 7.36 (2H, m), 7.33 – 7.27 (2H, m), 7.21 – 7.16 (1H, m), 6.93 (1H, s), 6.67 (2H, s), 2.89 – 2.81 (1H, m), 2.12 (3H, s), 1.76 (3H, s), 1.72 (3H, s), 0.72 – 0.66 (2H, m), 0.58 – 0.53 (2H, m) |
| 19 | 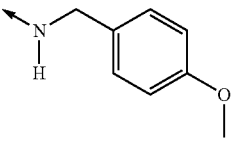 | 389 | 8.45 (1H, d), 7.85 (1H, dd), 7.74 (1H, d), 7.47 (1H, d), 7.36 – 7.30 (2H, m), 7.27 – 7.21 (3H, m), 6.98 (1H, d), 6.91 (1H, d), 5.09 (1H, d), 4.95(1H, d), 3.03 (3H, s), 2.88 – 2.81 (1H, m), 2.09 (3H, s), 0.72 – 0.66 (2H, m), 0.58 – 0.54 (2H, m) |
| 20 | 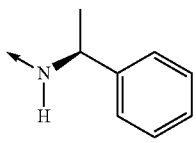 | 405 | 8.43 (1H, d), 7.86 (1H, dd), 7.82 (1H, t), 7.74 (1H, d), 7.49 (1H, d), 7.27 (2H, dd), 6.90 – 6.85 (2H, m), 6.83 (1H, d), 6.69 (1H, d), 4.51 (1H, dd), 4.41 (1H, dd), 3.72 (3H, s), 2.88 – 2.81 (1H, m), 2.11 (3H, s), 0.71 – 0.66 (2H, m), 0.57 – 0.53 (2H, m) |
| 21 | 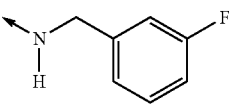 | 389 | 8.46 – 8.37 (1H, m), 7.86 (1H, dd), 7.75 – 7.71 (1H, m), 7.62 – 7.53 (1H, m), 7.51 – 7.46 (1H, m), 7.44 – 7.38 (2H, m), 7.34 – 7.28 (2H, m), 7.24 – 7.19 (1H, m), 6.82 – 6.78 (1H, m), 6.70 – 6.65 (1H, m), 5.15(11 – 1, quintet), 2.88 – 2.80 (1H, m), 2.12 (1.5H, s), 2.08 (1.5H, s), 1.51 (3H, t), 0.72 – 0.65 (2H, m), 0.59 – 0.51 (2H, m) |
| 22 | 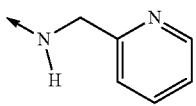 | 393 | 8.43 (1H, d), 8.01 (1H, t), 7.87 (1H, dd), 7.76 (1H, d), 7.49 (1H, d), 7.36 (1H, td), 7.17(1H, d), 7.15 – 7.11 (1H, m), 7.08 – 7.02 (1H, m), 6.82 (1H, d), 6.71 (1H, d), 4.60 (1H, dd), 4.49 (1H, dd), 2.88 – 2.81 (1H, m), 2.12 (3H, s), 0.71 – 0.66 (2H, m), 0.58 – 0.53 (2H, m) |
| 23 | 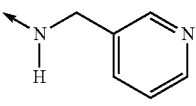 | 376 | 8.53 – 8.51 (1H, m), 8.45 (1H, d), 7.92 (1H, t), 7.87 (1H, dd), 7.78 – 7.73 (2H, m), 7.50 (1H, d), 7.31 (1H, d), 7.28 – 7.24 (1H, m), 6.82 (1H, d), 6.74 (1H, d), 4.68 (1H, dd), 4.59 (1H, dd), 2.89 – 2.82 (1H, m), 2.13 (3H, s), 0.72 – 0.66 (2H, m), 0.59 – 0.53 (2H, m) |
| 24 | 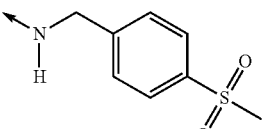 | 376 | 8.56 (1H, d), 8.46 – 8.40 (2H, m), 8.05 (1H, t), 7.89 – 7.84 (1H, m), 7.77 – 7.71 (2H, m), 7.49 (1H, d), 7.34 (1H, dd), 6.83 (1H, d), 6.72 (1H, d), 4.60 (1H, dd), 4.50 (1H, dd), 2.90 – 2.79 (1H, m), 2.11 (3H, s), 0.73 – 0.65 (2H, m), 0.59 – 0.52 (2H, m) |
| 25[a] | 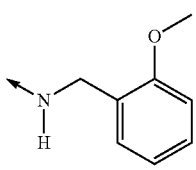 | 453 | 8.44 (1H, d), 8.13 (1H, t), 7.87 (3H, d), 7.76 (1H, d), 7.57 (2H, d), 7.49 (1H, d), 6.81 (1H, d), 6.72(1H, d), 4.68 (1H, dd), 4.57 (1H, dd), 3.19 (3H, s), 2.91 – 2.80 (1H, m), 2.12 (3H, s), 0.73 – 0.65 (2H, m), 0.59 – 0.52 (2H, m) |
| 26 |  | 405 | 8.44 (1H, d), 7.87 (1H, dd), 7.77 (1H, d), 7.58 (1H,t), 7.50 (1H, d), 7.25 – 7.20 (1H, m), 7.12 (1H, d), 6.99 (1H, d), 6.89 (1H, t), 6.81 (1H, d), 6.70 (1H, d), 4.56 (1H, dd), 4.47 (1H, dd), 3.83 (3H, s), 2.89 - 2.82 (1H, m), 2.13 (3H, s), 0.72 – 0.66 (2H, m), 0.58 – 0.54 (2H, m) |

TABLE 1-continued

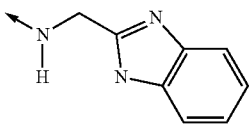

| Example | R | MS [M + H]+ mz | ¹H NMR δ (DMSO-d₆) |
|---|---|---|---|
| 27[b] | 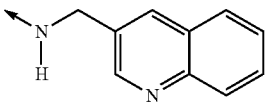 | 415 | 12.19 (1H, s), 8.48 (1H, d), 7.92 – 7.85 (2H, m), 7.76 (1H, s), 7.57 – 7.48 (2H, m), 7.47 – 7.41 (1H, m), 7.18 – 7.09 (2H, m), 6.84 (1H, dd), 6.76 (1H, dd), 4.80 (1H, dd), 4.71 (1H, dd), 2.91 – 2.81 (1H, m), 2.15 (3H, s), 0.74 – 0.65 (2H, m), 0.60 – 0.53 (2H, m) |
| 28[a] | 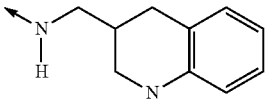 | 426 | 8.94 (1H, d), 8.42 (1H, d), 8.23 (1H, d), 8.16 (1H, t), 7.98 (2H, dd), 7.86 (1H, dd), 7.76 – 7.70 (2H, m), 7.62 – 7.57 (1H, m), 7.49 (1H, d), 6.84 (1H, d), 6.72 (1H, d), 4.78 (1H, dd), 4.69 (1H, dd), 2.88 – 2.81 (1H, m), 2.12 (3H, s), 0.71 – 0.65 (2H, m), 0.57 – 0.53 (2H, m) |
| 29 | 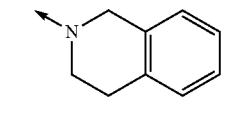 | 430 | 8.43 (1H, d), 7.87 (1H, dd), 7.75 (1H, t), 7.54 – 7.47 (2H, m), 6.86 – 6.81 (3H, m), 6.68 (1H, d), 6.44 – 6.38 (2H, m), 5.62 (1H, s), 3.43 – 3.27 (2H, m), 3.27 – 3.20 (1H, m), 2.91 – 2.81 (2H, m), 2.48 – 2.39 (1H, m), 2.31 – 2.21 (1H, m), 2.75 – 2.68 (1H, m), 2.12 (3H, s), 0.72 – 0.66 (2H, m), 0.58 – 0.53 (2H, m) |
| 30 | 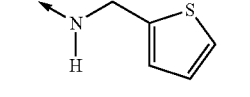 | 401 | 8.43 (1H, d), 7.86 (1H, dd), 7.73 (1H, d), 7.48 (1H, d), 7.18 – 7.15 (4H, m), 7.02 (1H, d), 6.96 (1H, d), 4.86 (2H, dd), 4.09 – 3.98 (2H, m), 2.91 (2H, t), 2.88 – 2.81 (1H, m), 2.11 (3H, s), 0.71 – 0.66 (2H, m), 0.57 – 0.53 (2H, m) |
| 31 | 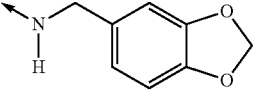 | 381 | 8.43 (1H, d), 7.93 (1H, t), 7.87 (1H, dd), 7.74 (1H, d), 7.49 (1H, d), 7.35 (1H, dd), 7.02 (1H, dd), 6.95 (1H, dd), 6.89 (1H, dd), 6.73 (1H, d), 4.73 (1H, dd), 4.63 (1H, dd), 2.88 – 2.81 (1H, m), 2.10 (3H, s), 0.71 – 0.65 (2H, m), 0.57 – 0.53 (2H, m) |
| 32 | 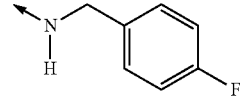 | 419 | 8.42 (1H, d), 7.89 – 7.82 (2H, m), 7.74 (1H, d), 7.49 (1H, d), 6.92 (1H, d), 6.86 – 6.79 (3H, m), 6.69 (1H, d), 5.97 (2H, d), 4.48 (1H, dd), 4.38 (1H, dd) 2.88 – 2.81 (1H, m), 2.11 (3H, s), 0.71 – 0.66 (2H, m), 0.57 – 0.53 (2H, m) |
| 33 | 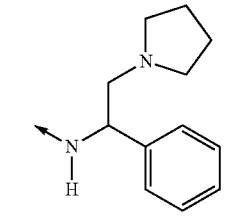 | 393 | 8.43 (1H, d), 7.96 (1H, t), 7.86 (1H, dd), 7.75 (1H, d), 7.49 (1H, d), 7.40 – 7.34 (2H, m), 7.17 – 7.10 (2H, m), 6.83 (1H, d), 6.70 (1H, d), 4.56 (1H, dd), 4.45 (1H, dd), 2.88 – 2.81 (1H, m), 2.11 (3H, s), 0.72 – 0.66 (2H, m), 0.58 – 0.53 (2H, m) |
| 34[a] |  | 458 | 8.44 (0.5H, d), 8.40 (0.5H, d), 7.86 (1H, dd), 7.75 (0.5H, d), 7.72 (0.5H, d), 7.54 – 7.46 (2H, m), 7.43 – 7.38 (2H, m), 7.34 – 7.28 (2H, m), 7.25 – 7.19 (1H, m), 6.78 – 6.76 (1H, m), 6.69 – 6.67 (1H, m), 5.10 – 5.01 (1H, m), 3.07 – 2.99 (1H, m), 2.89 – 2.80 (1H, m), 2.70 – 2.57 (1H, m), 2.52 – 2.44 (4H, m), 2.13 (1.5H, s), 2.08 (1.5H, s), 1.68 – 1.62 (4H, m), 0.72 – 0.65 (2H, m), 0.58 – 0.51 (2H, m) |

TABLE 1-continued

| Example | R | MS [M + H]+ m/z | ¹H NMR δ (DMSO-d₆) |
|---|---|---|---|
| 35 | | 472 | 8.41 (1H, d), 7.85 (1H, dd), 7.70 (1H, d), 7.46 (1H, d), 7.43 – 7.32 (4H, m), 7.21 (1H, t), 6.81 (1H, d), 6.66 (1H, d), 6.27 – 6.20 (1H, m), 3.61 (1H, dd), 3.44 (1H, dd), 2.88 – 2.80 (1H, m), 2.54 – 2.43 (2H, m), 2.16 – 2.03 (4H, m), 2.08 (3H, s), 2.05 (3H, s), 1.91 – 1.82 (2H, m), 0.71 – 0.65 (2H, m), 0.57 – 0.52 (2H, m) |
| 36 | | 403 | 8.44 (1H, d), 7.86 (1H, dd), 7.74 (1H, d), 7.48 (1H, d), 7.40 (1H,t), 7.31 – 7.25 (2H, m), 7.24 – 7.15 (3H, m), 6.84 (1H, d), 6.66 (1H, d), 3.43 – 3.27 (2H, m), 2.89 – 2.81 (1H, m), 2.63 (2H, t), 2.10 (3H, s), 1.89 (2H, quintet), 0.72 – 0.66 (2H, m), 0.58 – 0.53 (2H, m) |
| 37 | | 431 | 8.42 (1H, d), 7.90 – 7.84 (2H, m), 7.74 (1H, d), 7.49 (1H, d), 7.35 – 7.31 (2H, m), 7.28 – 7.24 (2H, m), 6.82 (1H, d), 6.69 (1H, d), 4.57 – 4.51 (1H, m), 4.47 – 4.41 (1H, m), 2.88 – 2.81 (1H, m), 2.11 (3H, s), 1.26 (9H, s), 0.71 – 0.66 (2H, m), 0.58 – 0.53 (2H, m) |
| 38 | | 403 | 8.44 (0.5H, d), 8.38 (0.5H, d), 7.88 – 7.84 (1H, m), 7.76 (0.5H, d), 7.71 (0.5H, d), 7.61 – 7.56 (1H, m), 7.51 – 7.46 (1H, m), 7.45 – 7.39 (2H, m), 7.34 – 7.28 (2H, m), 7.24 – 7.19 (1H, m), 6.81 – 6.78 (1H, m), 6.68 – 6.65 (1H, m), 4.91 (1H, dd), 2.89 – 2.79 (1H, m), 2.13 (1.5H, s), 2.06 (1.5H, s), 2.03 – 1.90 (1H, m), 1.88 – 1.74 (1H, m), 0.86 (3H, td), 0.72 – 0.64 (2H, m), 0.59 – 0.50 (2H, m) |
| 39 | | 389 | 8.44 (1H, d), 7.87 (1H, dd), 7.81 – 7.74 (2H, m), 7.50 (1H, d), 7.23 7.10 (4H, m), 6.82 (1H, d), 6.71 (1H, d), 4.61 – 4.52 (1H, m), 4.50 – 4.41 (1H, m), 2.90 – 2.80 (1H, m), 2.33 (3H, s), 2.13 (3H, s), 0.73 – 0.65 (2H, m), 0.59 – 0.52 (2H, m) |
| 40ᵃ | | 487 | 8.44 (1H, d), 7.90 (1H, t), 7.86 (1H, dd), 7.74 (1H, d), 7.49 (1H, d), 7.28 – 7.18 (3H, m), 7.13 (1H, d), 6.82 (1H, d), 6.70 (1H, d), 4.56 (1H, dd), 4.48 (1H, dd), 3.42 (2H, s), 2.88 – 2.81 (1H, m), 2.43 – 2.21 (8H, m), 2.13 (3H, s), 2.12 (3H, s), 0.71 – 0.66 (2H, m), 0.58 – 0.53 (2H, m) |
| 41ᵃ | | 487 | 8.42 (1H, d), 7.85 (1H, dd), 7.77 (1H, t), 7.74 (1H, d), 7.48 (1H, d), 7.37 – 7.34 (1H, m), 7.27 – 7.18 (3H, m), 6.86 (1H, d), 6.69 (1H, d), 4.69 (1H, dd), 4.59 (1H, dd), 3.60 (1H, d), 3.50 (1H, d), 2.88 – 2.81 (1H, m), 2.45 – 2.26 (8H, m), 2.10 (6H, s), 0.71 – 0.66 (2H, m), 0.57 – 0.52 (2H, m) |

TABLE 1-continued
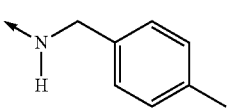
| Example | R | MS [M + H]+ mz | ¹H NMR δ (DMSO-d₆) |
|---|---|---|---|
| 42 | 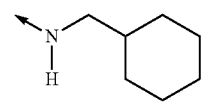 | 389 | 8.43 (1H, d), 7.88 – 7.82 (2H, m), 7.74 (1H, d), 7.49 (1H, d), 7.22 (2H, d), 7.11 (2H, d), 6.82 (1H, d), 6.69 (1H, d), 4.53 (1H, dd), 4.43 (1H, dd), 2.88 – 2.81 (1H, m), 2.27 (3H, s), 2.11 (3H, s), 0.71 – 0.65 (2H, m), 0.58 – 0.53 (2H, m) |
| 43 | 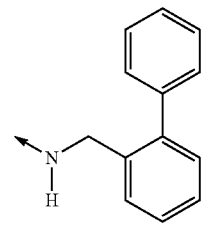 | 381 | 8.43 (1H, d), 7.86 (1H, dd), 7.74 (1H, d), 7.48 (1H, d), 7.30 (1H, t), 6.84 (1H, d), 6.65 (1H, d), 3.29 – 3.19 (1H, m), 3.17 – 3.06 (1H, m), 2.90 – 2.80 (1H, m), 2.10 (3H, s), 1.75 – 1.55 (6H, m), 1.27 – 1.09 (3H, m), 1.00 – 0.82 (2H, m), 0.73 – 0.65 (2H, m), 0.59 – 0.52 (2H, m) |
| 44[c] | 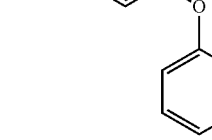 | 451 | 8.47 (1H, d), 7.87 (1H, dd), 7.77 (1H, d), 7.51 – 7.45 (3H, m), 7.43 – 7.32 (7H, m), 7.25 – 7.21 (1H, m), 6.79 (1H, d), 6.76 (1H, d), 4.56 (1H, dd), 4.48 (1H, dd), 2.89 – 2.81 (1H, m), 2.12 (3H, s), 0.72 – 0.67 (2H, m), 0.59 – 0.54 (2H, m) |
| 45 | 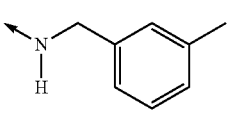 | 467 | 8.43 (1H, d), 7.92 (1H, t), 7.87 (1H, dd), 7.75 (1H, d), 7.49 (1H, d), 7.41 – 7.34 (4H, m), 7.15 – 7.10 (1H, m), 7.01 – 6.95 (4H, m), 6.84 (1H, d), 6.70 (1H, d), 4.57 (1H, dd), 4.46 (1H, dd), 2.89 – 2.81 (1H, m), 2.12 (3H, s), 0.72 – 0.66 (2H, m), 0.58 – 0.53 (2H, m) |
| 46 | 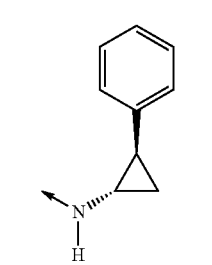 | 389 | 8.43 (1H, d), 7.89 – 7.83 (2H, m), 7.75 (1H, d), 7.49 (1H, d), 7.19 (1H, t), 7.15 – 7.10 (2H, m), 7.04 (1H, d), 6.83 (1H, d), 6.69 (1H, d), 4.55 (1H, dd), 4.44 (1H, dd), 2.88 – 2.81 (1H, m), 2.28 (3H, s), 2.11 (3H, s), 0.71 – 0.66 (2H, m), 0.58 – 0.53 (2H, m) |
| 47[a,b] | 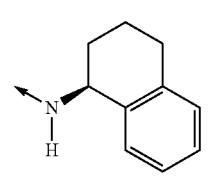 | 401 | 8.46 – 8.42 (1H, m), 7.86 (1H5 dd), 7.74 (1H, d), 7.70 (1H, d), 7.49 (1H, d), 7.30 – 7.24 (2H, m), 7.19 – 7.14 (3H, m), 6.86 (1H, d), 6.72 (1H, d), 3.04 – 2.98 (1H, m), 2.88 – 2.81 (1H, m), 2.11 (3H, s), 2.15 – 2.04 (1H, m), 1.52 – 1.42 (1H, m), 1.25 – 1.15 (1H, m), 0.72 – 0.66 (2H, m), 0.58 – 0.53 (2H, m) |
| 48 |  | 415 | 8.47 – 8.41 (1H, m), 7.87 (1H, dd), 7.80 7.76 (1H, m), 7.49 (1H, d), 7.25 – 7.09 (5H, m), 6.91 – 6.89 (1H, m), 6.77 – 6.74 (1H, m), 5.31 – 5.22 (1H, m), 2.89 – 2.69 (3H, m), 2.15 (1.5H, s), 2.13(1.51 – 1, s), 2.03 – 1.85 (3H, m), 1.82 – 1.71 (1H, m), 0.72 – 0.66 (2H, m), 0.59 – 0.53 (2H, m) |

TABLE 1-continued

| | | MS [M + H]+ | |
|---|---|---|---|
| Example | R | m/z | ¹H NMR δ (DMSO-d₆) |
| 49 | ✎NH (neopentyl-like) | 355 | 8.44 (1H, d), 7.87 (1H, dd), 7.76 (1H, d), 7.49 (1H, d), 6.98 (1H, t), 6.84 (1H, d), 6.68 (1H, d), 3.35 – 3.28 (1H, m), 3.14 (1H, dd), 2.89 – 2.81 (1H, m), 2.10 (3H, s), 0.91 (9H, s), 0.71 – 0.66 (2H, m), 0.58 – 0.53 (2H, m) |

Example 50

N-Cyclopropyl-4-methyl-3-[2-oxo-3-[[(2S)-2-phenylpropyl]amino]-1(2H)-pyrazinyl]benzamide A mixture of 3-(3,5-dibromo-2-oxo-2H-pyrazin-1-yl)-4-methyl-benzoic acid, methyl ester (Example 1b, 0.1 g), N,N-diisopropylethylamine (0.1 mL), (S)-2-phenyl-1-propylamine (0.05 mL) and tetrahydrofuran (1 mL) was stirred at room temperature overnight. Cyclopropylamine (0.2 mL) was added followed by the addition of cyclopentylmagnesium bromide (2M in diethyl ether, 0.8 mL). The mixture was stirred for 10 min., quenched with sat. NH₄Cl and extracted into ethyl acetate. The organic phase concentrated in vacuo. The residue was treated with ethanol (5 mL), wet 10% palladium on carbon (45 mg) was added followed by N,N-diisopropylethylamine (0.1 mL) and ammonium formate (0.4 g). The mixture was stirred under nitrogen atmosphere at 70° C. for 30 min. The mixture was filtered through a pad of Celite and the filtrate concentrated in vacuo. Purification by preparative HPLC (Gemini column, 0.1% ammonia:acetonitrile eluent) afforded the title compound as a solid (64 mg).

MS: APCI (+ve) 393 (M+H⁺).

¹H NMR δ(DMSO-d₆, 400 MHz) 8.42 (1H, t), 7.85 (1H, dd), 7.72 (1H, t), 7.47 (1H, d), 7.34-7.23 (4H, m), 7.23-7.13 (3H, m), 6.87 and 6.86 (1H, 2×d), 6.68 and 6.67 (1H, 2×d), 3.59-3.38 (2H, m), 3.25-3.14 (1H, m), 2.84 (1H, m), 2.08 and 2.06 (3H, 2×s), 1.22 (3H, d), 0.68 (2H, m), 0.55 (2H, m).

The following examples 51-99 (Table 2) were prepared from 3-(3,5-dibromo-2-oxo-2H-pyrazin-1-yl)-4-methyl-benzoic acid, methyl ester (Example 1b) and the corresponding amines using the general procedure described for Example 50.

Example 51

[[3-[[[4-[5-[(Cyclopropylamino)carbonyl]-2-methylphenyl]-3,4-dihydro-3-oxopyrazinyl]amino]methyl]phenyl]methyl]-carbamic acid, 1,1-dimethylethyl ester

Example 52

[[4-[[[4-[5-[(Cyclopropylamino)carbonyl]-2-methylphenyl]-3,4-dihydro-3-oxopyrazinyl]amino]methyl]phenyl]methyl]-carbamic acid, 1,1-dimethylethyl ester

Example 53

N-Cyclopropyl-4-methyl-3-[2-oxo-3-(3-phenyl-1-piperazinyl)-1(2H)-pyrazinyl]-benzamide

Example 54

N-Cyclopropyl-4-methyl-3-[2-oxo-3-(3-phenyl-1-pyrrolidinyl)-1(2H)-pyrazinyl]-benzamide

Example 55

N-Cyclopropyl-3-[3-[[(2R)-2-hydroxy-2-phenylethyl]amino]-2-oxo-1(2H)-pyrazinyl]-4-methyl-benzamide

Example 56

N-Cyclopropyl-3-[3-[[(2S)-2-hydroxy-2-phenylethyl]amino]-2-oxo-1(2H)-pyrazinyl]-4-methyl-benzamide

Example 57

N-Cyclopropyl-4-methyl-3-[2-oxo-3-[[(2R)-2-phenylpropyl]amino]-1(2H)-pyrazinyl]-benzamide

Example 58

N-Cyclopropyl-4-methyl-3-[2-oxo-3-[[(2S)-2-phenylpropyl]amino]-1(2H)-pyrazinyl]-benzamide

Example 59

N-Cyclopropyl-4-methyl-3-[2-oxo-3-[3-[4-[2-(1-pyrrolidinyl)ethoxy]phenyl]-1-piperidinyl]-1(2H)-pyrazinyl]-benzamide

Example 60

N-Cyclopropyl-4-methyl-3-[2-oxo-3-(3-phenyl-1-piperidinyl)-1(2H)-pyrazinyl]-benzamide

Example 61

N-Cyclopropyl-3-[3-[[2-(dimethylamino)-2-phenylethyl] amino]-2-oxo-1(2H)-pyrazinyl]-4-methyl-benzamide

Example 62

N-Cyclopropyl-3-[3-[[2-(4-fluorophenyl)-1,1-dimethyl-ethyl]amino]-2-oxo-1(2H)-pyrazinyl]-4-methyl-benzamide

Example 63

N-Cyclopropyl-4-methyl-3-[2-oxo-3-[[2-phenyl-2-(1-pyrrolidinyl)ethyl]amino]-1(2H)-pyrazinyl]-benzamide

Example 64

N-Cyclopropyl-3-[3-[(2,3-dihydro-1H-inden-2-yl)amino]-2-oxo-1(2H)-pyrazinyl]-4-methyl-benzamide

Example 65

N-Cyclopropyl-3-[3-[(1,1-dimethyl-2-phenylethyl)amino]-2-oxo-1(2H)-pyrazinyl]-4-methyl-benzamide

Example 66

N-Cyclopropyl-4-methyl-3-[3-[methyl(2-phenylethyl)amino]-2-oxo-1(2H)-pyrazinyl]benzamide

Example 67

N-Cyclopropyl-4-methyl-3-[2-oxo-3-(2-phenyl-4-morpholinyl)-1(2H)-pyrazinyl]-benzamide

Example 68

N-Cyclopropyl-3-[3-[[(2-hydroxyphenyl)methyl]amino]-2-oxo-1(2H)-pyrazinyl]-4-methyl-benzamide

Example 69

N-Cyclopropyl-3-[3-[[[3-[(cyclopropylamino)carbonyl] phenyl]methyl]amino]-2-oxo-1(2H)-pyrazinyl]-4-methyl-benzamide

Example 70

N-Cyclopropyl-3-[3-[[2-(4-hydroxyphenyl)ethyl]amino]-2-oxo-1(2H)-pyrazinyl]-4-methyl-benzamide

Example 71

N-Cyclopropyl-3-[3-[[2-(3-hydroxyphenyl)ethyl]amino]-2-oxo-1(2H)-pyrazinyl]-4-methyl-benzamide

Example 72

N-Cyclopropyl-4-methyl-3-[3-[[2-(2-methylphenyl)ethyl] amino]-2-oxo-1(2H)-pyrazinyl]-benzamide

Example 73

N-Cyclopropyl-4-methyl-3-[3-[[2-(3-methylphenyl)ethyl] amino]-2-oxo-1(2H)-pyrazinyl]-benzamide

Example 74

N-Cyclopropyl-4-methyl-3-[3-[[2-(4-methylphenyl)ethyl] amino]-2-oxo-1(2H)-pyrazinyl-benzamide

Example 75

N-Cyclopropyl-3-[3-[2-[(2-fluorophenyl)methyl]-1-pyrrolidinyl]-2-oxo-1(2H)-pyrazinyl]-4-methyl-benzamide

Example 76

N-Cyclopropyl-4-methyl-3-[2-oxo-3-(1-piperidinyl)-1(2H)-pyrazinyl]-benzamide

Example 77

N-Cyclopropyl-4-methyl-3-[3-[[3-(4-morpholinyl)-1-phenylpropyl]amino]-2-oxo-1(2H)-pyrazinyl]-benzamide

Example 78

N-Cyclopropyl-3-[3-[[(2-ethoxyphenyl)methyl]amino]-2-oxo-1(2H)-pyrazinyl]-4-methyl-benzamide

Example 79

N-Cyclopropyl-4-methyl-3-[2-oxo-3-[[[2-(trifluoromethyl) phenyl]methyl]amino]-1(2H)-pyrazinyl]-benzamide

Example 80

N-Cyclopropyl-3-[3-[[(1S)-2-hydroxy-1-phenylethyl] amino]-2-oxo-1(2H)-pyrazinyl]-4-methyl-benzamide

Example 81

N-Cyclopropyl-3-[3-[[(1R)-2-hydroxy-1-phenylethyl] amino]-2-oxo-1(2H)-pyrazinyl]-4-methyl-benzamide

Example 82

N-Cyclopropyl-β-[[4-[5-[(cyclopropylamino)carbonyl]-2-methylphenyl]-3,4-dihydro-3-oxopyrazinyl]amino]-benzenepropanamide

Example 83

N-Cyclopropyl-3-[3-[(3-hydroxy-1-phenylpropyl)amino]-2-oxo-1(2H)-pyrazinyl]-4-methyl-benzamide

Example 84

N-Cyclopropyl-4-methyl-3-[3-[[(1R)-1-(1-naphthalenyl) ethyl]amino]-2-oxo-1(2H)-pyrazinyl]-benzamide

Example 85

N-cyclopropyl-4-methyl-3-[2-oxo-3-[[(1S)-1-phenylpropyl] amino]-1(2H)-pyrazinyl]-benzamide

Example 86

N-Cyclopropyl-4-methyl-3-[2-oxo-3-(2-phenyl-1-pyrrolidinyl)-1(2H)-pyrazinyl]-benzamide

Example 87

(βR)-β-[[4-[5-[(Cyclopropylamino)carbonyl]-2-methylphenyl]-3,4-dihydro-3-oxopyrazinyl]amino]-benzenepropanoic acid, 1,1-dimethylethyl ester

Example 88

N-Cyclopropyl-3-[3-(cyclopropylamino)-2-oxo-1(2H)-pyrazinyl]-4-methyl-benzamide

Example 89

(βR)—N-cyclopropyl-β-[[4-[5-[(cyclopropylamino)carbonyl]-2-methylphenyl]-3,4-dihydro-3-oxopyrazinyl]amino-benzenepropanamide

Example 90

N-Cyclopropyl-4-methyl-3-[2-oxo-3-[[(tetrahydro-2H-pyran-4-yl)methyl]amino]-1(2H)-pyrazinyl]-benzamide

Example 91

N-Cyclopropyl-3-[3-[[(2,3-dihydro-1,4-benzodioxin-5-yl)methyl]amino]-2-oxo-1(2H)-pyrazinyl]-4-methyl-benzamide

Example 92

N-Cyclopropyl-3-[3-[[(2,3-dimethylphenyl)methyl]amino]-2-oxo-1(2H)-pyrazinyl]-4-methyl-benzamide

Example 93

N-Cyclopropyl-4-methyl-3-[2-oxo-3-[[[3-(trifluoromethyl)phenyl]methyl]amino]-1(2H)-pyrazinyl]-benzamide

Example 94

N-Cyclopropyl-4-methyl-3-[3-[2-(3-methylphenyl)-1-piperidinyl]-2-oxo-1(2H)-pyrazinyl]-benzamide

Example 95

N-Cyclopropyl-3-[3-[[(3,5-dimethylphenyl)methyl]amino]-2-oxo-1(2H)-pyrazinyl]-4-methyl-benzamide

Example 96

N-Cyclopropyl-4-methyl-3-[3-[2-(3-methylphenyl)-1-pyrrolidinyl]-2-oxo-1(2H)-pyrazinyl]-benzamide

Example 97

N-Cyclopropyl-3-[3-[2-(2-methoxyphenyl)-1-pyrrolidinyl]-2-oxo-1(2H)-pyrazinyl]-4-methyl-benzamide

Example 98

N-Cyclopropyl-3-[3-[[(2,5-dimethylphenyl)methyl]amino]-2-oxo-1(2H)-pyrazinyl]-4-methyl-benzamide

Example 99

3-[3-[[[3,5-Bis(trifluoromethyl)phenyl]methyl]amino]-2-oxo-1(2H)-pyrazinyl]-N-cyclopropyl-4-methyl-benzamide

TABLE 2

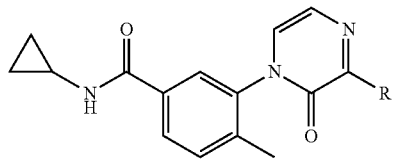

| Example | R | MS [M + H]+ m/z | 1H NMR δ (DMSO-d6) |
|---|---|---|---|
| 51 |  | 504 | 8.43 (1H, d), 7.87 (2H, m), 7.74 (1H, s), 7.49 (1H, d), 7.37(1H, t), 7.25 (1H, t), 7.19 (2H, m), 7.09 (1H, d), 6.82 (1H, d), 6.69 (1H, d), 4.57 (1H, dd), 4.46 (1H, dd), 4.10 (2H, d), 2.84 (1H, m), 2.12 (3H, s), 0.68 (2H, m), 0.55 (2H, m) |
| 52 |  | 504 | 8.43 (1H, d), 7.88 (2H, m), 7.75 (1H, s), 7.49 (1H, d), 7.35 (1H, m), 7.27 (2H, d), 7.17 (2H, d), 6.82 (1H, d), 6.69 (1H, d), 4.56 (1H, dd), 4.47 (1H, dd), 4.09 (1H, d), 2.85 (1H, m), 2.11 (3H, s), 0.67 (2H, m), 0.56 (2H, m) |
| 53a |  | 430 | 7.72 and 7.70 (1H, 2 × dd), 7.58 and 7.54 (1H, 2 × d), 7.44 (2H, m), 7.40 and 7.38 (1H, 2 × d), 7.33 – 7.23 (4H, m), 7.01 (1H, d), 6.57 (1H, d), 4.78 (1H, m), 3.98 (1H, d), 3.25-3.00 (3H, m), 2.93 – 2.79 (2H, m), 2.22 and 2.18 (3H, 2 × s), 0.86 (2H, m), 0.59 (2H, m) |

TABLE 2-continued

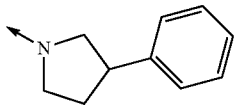

| Example | R | MS [M + H]+ m/z | ¹H NMR δ (DMSO-d₆) |
|---|---|---|---|
| 54 | 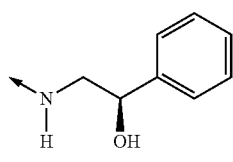 | 415 | 8.44 (1H, d), 7.84 (1H, dd), 7.71 (1H, t), 7.47 (1H, d), 7.36 – 7.28 (3H, m), 7.29 – 7.19 (2H, m), 6.88 (1H, d), 6.72 and 6.71(1H, 2 × d), 4.38 - 4.17 (1H, m), 4.08 – 3.91 (1H, m), 3.85 – 3.56 (2H, m), 3.42 (1H, m), 2.85 (1H, m), 2.35 – 2.20 (1H, m), 2.14 and 2.11 (3H, 2 × s), 1.98 (1H, m), 0.68 (2H, m), 0.56 (2H, m) |
| 55 | 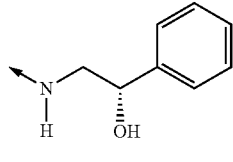 | 405 | 8.44 (1H, d), 7.86 (1H, dd), 7.73 (1H, s), 7.49 (1H, d), 7.42 – 7.31 (4H, m), 7.30 – 7.22 (1H, m), 7.08(1H, m), 6.86 and 6.85 (1H, 2 × d), 6.71 and 6.70 (1H, 2 × d), 5.62 (1H, s), 4.87 (1H, m), 3.61 (1H, m), 3.42 (1H, m), 2.84 (1H, m), 2.09 (3H, 2 × s), 0.69 (2H, m), 0.56 (2H, m) |
| 56 | 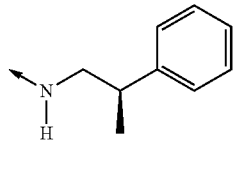 | 405 | 8.44 (1H, d), 7.86 (1H, dd), 7.73 (1H, s), 7.49 (1H, d), 7.42 – 7.31 (4H, m), 7.30 – 7.22 (1H, m), 7.08(1H, m), 6.86 and 6.85 (1H, 2 × d), 6.71 and 6.70 (1H, 2 × d), 5.62 (1H, s), 4.87 (1H, m), 3.61 (1H, m), 3.42 (1H, m), 2.84 (1H, m),2.09 (3H, 2 x s), 0.70 (2H, m), 0.55 (2H, m) |
| 57 | 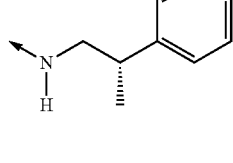 | 403 | 8.42 (1H, t), 7.85(1H, dd), 7.72 (1H, t,), 7.47 (1H, d), 7.34 – 7.23 (4H, m), 7.23 – 7.13 (2H, m), 6.87 and 6.86 (1H, 2 × d,),6.68 and 6.67(1H, 2 × d), 3.59 – 3.38 (2H, m), 3.25 – 3.14 (1H, m), 2.84 (1H, m), 2.08 and 2.06 (3H, 2 × s), 1.22 (3H, d), 0.68 (2H, m), 0.55 (2H, m) |
| 58[b] | 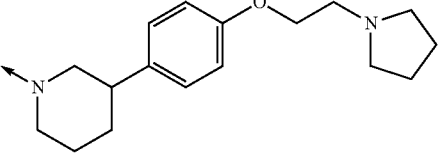 | 403 | 8.42 (1H, t), 7.85 (1H, dd), 7.72 (1H, t,), 7.47 (1H, d), 7.34 – 7.23 (4H, m), 7.23 – 7.13 (2H, m), 6.87 and 6.86 (1H, 2 × d,), 6.68 and 6.67 (1H, 2 × d), 3.59 – 3.38 (2H, m), 3.25 – 3.14 (1H, m), 2.84 (1H, m), 2.08 and 2.06 (3H, 2 × s), 1.22 (3H, d), 0.68 (2H, m), 0.55 (2H, m) |
| 59 | 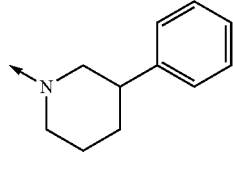 | 542 | 8.44 (1H, br), 7.85 (1H, dd), 7.73 and 7.71 (1H, 2 × d), 7.48 and 7.36 (1H, 2 × d), 7.17 (2H, dd), 6.99 (1H, d), 6.95 and 6.94 (1H, 2 x d), 6.87 (2H, dd), 4.69 (2H, m), 4.02 (2H, t), 2.92 – 2.69 (9H, m), 2.11 and 2.08 (3H, 2 × s), 1.97 – 1.87 (1H, m), 1.83– 1.58 (8H, m), 0.69 (2H, m), 0.56 (2H , m) |
| 60 |  | 429 | 8.43 (1H, br), 7.85 (1H, dd), 7.73 and 7.71 (1H, 2 × d), 7.48 and 7.36 (1H, 2 × d), 7.35 – 7.17 (5H, m), 7.00 (1H, d), 6.95 and 6.94 (1H, 2 × d), 4.72 (2H, m), 2.97 – 2.74 (4H, m), 2.11 and 2.08 (3H, s), 1.95 (1H, m), 1.84 – 1.59 (3H, m),0.69 (2H, m), 0.56 (2H, m) |

TABLE 2-continued

[Core structure: N-cyclopropyl-3-(3-R-2-oxo-pyrazin-1-yl)-4-methylbenzamide]

| Example | R | MS [M + H]+ m/z | 1H NMR δ (DMSO-d6) |
|---|---|---|---|
| 61 | -NH-CH2-CH(Ph)-N(CH3)2 | 432 | 8.43 (1H, d), 7.85 (1H, dd), 7.71 (1H, d), 7.48 (1H, d), 7.40 – 7.23 (5H, m), 6.86 (1H, d), 6.83 (1H, m), 6.69 (1H, d), 3.93 – 3.50 (3H, m), 2.83 (1H, m), 2.12 (6H, s), 2.07 (3H, s), 0.69 (2H, m), 0.54 (2H, m) |
| 62 | -NH-C(CH3)2-CH2-(4-F-C6H4) | 435 | 8.44 (1H, d,), 7.86(1H, dd), 7.75 (1H, d), 7.49 (1H, d), 7.14 – 7.03 (4H, m), 6.95 (1H, d), 6.78 (1H, d), 6.16 (1H, s), 3.28 (1H, d), 3.06 (1H, d), 2.85 (1H, m), 2.11 (3H, s), 1.44 (3H, s), 1.36 (3H, s), 0.69 (2H, m), 0.55 (2H, m) |
| 63 | -NH-CH2-CH(Ph)-pyrrolidin-1-yl | 458 | 8.43 (1H, t), 7.85 (1H, dd), 7.70 (1H, s), 7.47 (1H, dd), 7.36 – 7.18 (5H, m), 6.83 and 6.82 (1H, 2 × d), 6.72 (1H, m), 6.67 and 6.66 (1H, 2 × d), 3.81 (1H, m), 3.65 – 3.51 (2H, m), 2.83 (1H, m), 2.40 (2H, m), 2.06 and 2.04 (3H, 2 × s), 1.66 (4H, m), 0.68 (2H, m), 0.55 (2H, m) |
| 64 | -NH-(indan-2-yl) | 401 | 8.43 (1H, d), 7.86 (1H, d), 7.75 (1H, s), 7.49 (1H, d), 7.41 (1H, d), 7.30 – 7.07 (4H, m) 6.91 (1H, d), 6.73 (1H, d), 4.70 (1H, m), 3.27 – 3.18 (2H, m), 3.12 – 2.92 (2H, m), 2.85 (1H, m), 2.12 (3H, s), 0.69 (2H, m), 0.55 (2H, m) |
| 65 | -NH-C(CH3)2-CH2-Ph | 417 | 8.45 (1H, s), 7.87 (1H, d), 7.76 (1H, s), 7.49 (1H, d), 7.31 – 7.16 (3H, m), 7.09 (2H, d), 6.96 (1H, d), 6.77 (1H, d), 6.16 (1H, s), 3.04 (1H, d), 2.91 – 2.80 (1H, m), 2.11 (3H, s), 1.46 (3H, s), 1.37 (3H, s), 0.75 – 0.64 (2H, m), 0.62 – 0.50 (2H, m) |
| 66 | -N(CH3)-CH2-CH2-Ph | 403 | 8.45 (1H, d), 7.85 (1H, dd), 7.69 (1H, d), 7.47 (1H, d), 7.29 – 7.22 (2H, m), 7.22 – 7.14 (3H, m), 6.93 (1H, d), 6.79 (1H, d), 4.11 – 4.01 (1H, m), 3.99 – 3.89 (1H, m), 3.11 (3H, s), 2.91 – 2.80 (3H, m), 2.08 (3H, s), 0.74 – 0.65 (2H, m), 0.59 – 0.53 (2H, m) |
| 67 | -(2-phenylmorpholin-4-yl) | 431 | 8.44 (1H, t), 7.86 (1H, dd), 7.77 and 7.71 (1H, 2 × d), 7.49 and 7.47 (1H, 2 × d), 7.42 – 7.27 (5H, m), 7.05 – 7.01 (2H, s), 4.70 (1H, t), 4.61 (1H, dt), 4.57 – 4.48 (1H, dd), 4.05(1H, dd), 3.77 (1H, tt), 3.07 (1H, tt), 2.89 – 2.79 (2H, m), 2.12 and 2.09 (3H, 2 × s), 0.73 – 0.65 (2H, m), 0.60 – 0.52 (1H, m) |
| 68 | -NH-CH2-(2-OH-C6H4) | 391 | 9.93 (1H, s), 8.42 (1H, d), 7.86 (1H, dd), 7.78 – 7.71 (2H, m), 7.49 (1H, d), 7.13 (1H, dd), 7.09 (1H, dt), 6.84 (1H, d), 6.81 (1H, dd), 6.76 (1H, dt),6.72 (1H, d), 4.56 – 4.36 (2H, m), 2.89 – 2.79 (1H, m), 2.15 (3H, s), 0.73 – 0.64 (2H, m), 0.59 – 0.51 (2H, m) |

TABLE 2-continued

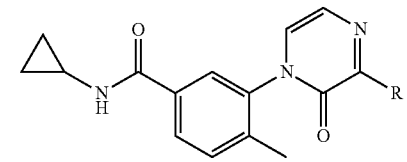

| Example | R | MS [M + H]+ m/z | ¹H NMR δ (DMSO-d₆) |
|---|---|---|---|
| 69 | 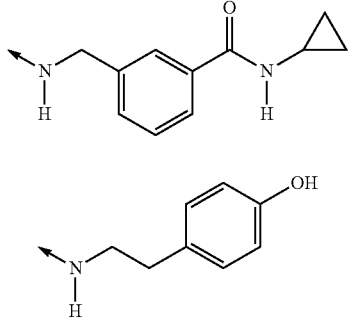 | 458 | 8.42 (2H, m), 7.99 (1H, t), 7.87 (1H, dd), 7.78 (1H, s), 7.75 (1H, d), 7.66 (1H, d), 7.49 (1H, d), 7.46 (1H, d), 7.37 (1H,t), 6.82 (1H, d), 6.71 (1H, d), 4.62 (1H, dd), 4.51 (1H, dd), 2.90 – 2.79 (2H, m), 2.16 (3H, s), 0.73 – 0.64 (4H, m), 0.60 – 0.52 (4H, m) |
| 70 | 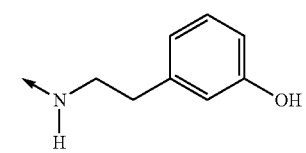 | 405 | 8.43 (1H, d), 7.86 (1H, dd), 7.73 (1H, d), 7.48 (1H, d), 7.27 (1H,t), 7.03 (2H, d), 6.87 (1H, d), 6.71 – 6.65 (3H, m), 3.58 – 3.41 (2H, m), 2.90 – 2.70 (3H, m), 2.10 (3H, s), 0.69 (2H, m), 0.55 (2H, m) |
| 71 | 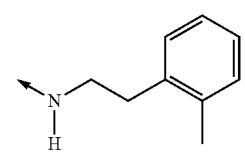 | 405 | 9.26 (1H, s), 8.43 (1H, d), 7.86 (1H, dd), 7.73 (1H, d), 7.48 (1H, d), 7.32(1H, t), 7.08 (1H,t), 6.88 (1H, d), 6.69 (1H, d), 6.67 – 6.63 (2H, m), 6.60 (1H, m), 3.52 (2H, m), 2.90 – 2.76 (3H, m), 2.10 (3H, s), 0.69 (2H, m), 0.55 (2H, m) |
| 72 | 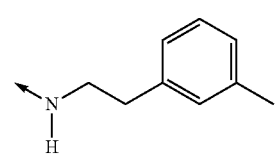 | 403 | 8.44 (1H, d), 7.86 (1H, dd), 7.74 (1H, d), 7.49 (1H, d), 7.43 (1H,t), 7.20 – 7.07 (4H, m), 6.88 (1H, d), 6.68 (1H, d), 3.59 – 3.44 (2H, m), 2.96 – 2.79 (3H, m), 2.33 (3H, s), 2.10 (3H, s), 0.69 (2H, m), 0.56 (2H, m) |
| 73 | 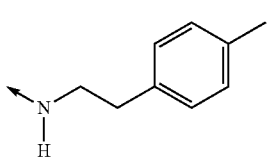 | 403 | 8.44 (1H, d), 7.86 (1H, dd), 7.73 (1H, d), 7.49 (1H, d), 7.34 (1H, t), 7.18 (1H, t), 7.03 (3H, m), 6.88 (1H, d), 6.69 (1H, d), 3.61 – 3.47 (2H, m), 2.93 – 2.78 (3H, m), 2.28 (3H, s), 2.10 (3H, s), 0.69 (2H, m), 0.55 (2H, m) |
| 74 | 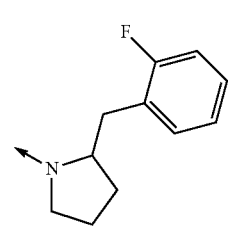 | 403 | 8.44 (1H, d), 7.86 (1H, dd), 7.73 (1H, d), 7.48 (1H, d), 7.30 (1H, t), 7.11 (4H, m), 6.88 (1H, d), 6.68 (1H, d), 3.62 – 3.45 (2H, m), 2.91 – 2.77 (3H, m), 2.26 (3H, s), 2.09 (3H, s), 0.69 (2H, m), 0.55 (2H, m) |
| 75 | 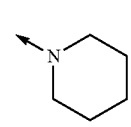 | 447 | 8.45 (1H, d), 7.86 (1H, m), 7.74 and 7.68 (1H, 2 × d), 7.48 (1H, d), 7.38 – 7.20 (2H, m), 7.18 – 7.06 (2H, m), 6.95 and 6.91 (1H, 2 × d), 6.76 and 6.71 (1H, 2 × d), 4.95(1H, br) 3.87 – 3.73 (1H, br), 3.70 – 3.56 (1H, br), 3.02 – 2.71 (3H, m), 2.13 and 2.11 (3H, 2 × s), 1.92 – 1.75 (3H, m), 1.69 – 1.60 (1H, m), 0.69 (2H, m), 0.56 (2H, m) |
| 76 |  | 353 | 8.43 (1H, d), 7.85 (1H, dd), 7.71 (1H, d), 7.47 (1H, d), 6.98 (1H, d), 6.92 (1H, d), 3.75 – 3.62 (4H, m), 2.85 (1H, m), 2.09 (3H, s), 1.66 – 1.50 (6H, m), 0.69 (2H, m), 0.56 (2H, m) |

TABLE 2-continued

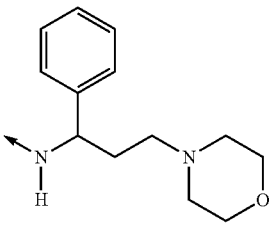

| Example | R | MS [M + H]+ m/z | ¹H NMR δ (DMSO-d₆) |
|---|---|---|---|
| 77 | 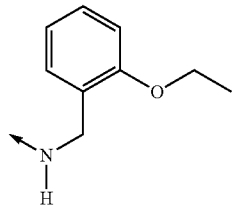 | 488 | 8.52 and 8.38 (1H, 2 × d), 8.45 and 8.41 (1H, 2 × d), 7.87 (1H, dd), 7.74 (1H, dd), 7.50 and 7.49 (1H, 2 × d), 7.40 – 7.16 (5H, m), 6.76 and 6.75 (1H, 2 × d), 6.66 (1H, d), 5.16 (1H, m), 3.73 – 3.51 (4H, m), 2.84 (1H, m), 2.44 – 2.18 (8H, m), 2.12 and 2.08 (3H, 2 × s), 0.69 (2H, m), 0.55 (2H, m) |
| 78 | 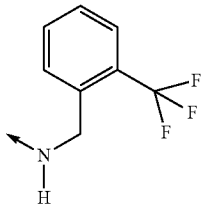 | 419 | 8.44 (1H, d), 7.87 (1H, dd), 7.76 (1H, d), 7.55 (1H, t), 7.49 (1H, d), 7.21 (1H, dt), 7.12 (1H, dd), 6.97 (1H, d), 6.88 (1H, dt), 6.82 (1H, d), 6.70 (1H, d), 4.61 – 4.44 (2H, m), 4.08 (2H, q), 2.85 (1H, m), 2.12 (3H, s), 1.36 (1H, t), 0.69 (2H, m), 0.55 (2H, m) |
| 79 | 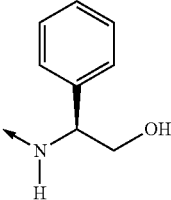 | 443 | 8.46 (1H, d), 7.99 (1H, t), 7.88 (1H, dd), 7.79 (1H, d), 7.73 (1H, d), 7.64 (1H, t), 7.51 (1H, d), 7.49 – 7.42 (2H, m), 6.80 (1H, d), 6.75 (1H, d), 4.80 (1H, d), 4.69 (1H, d), 2.86 (1H, m), 2.14 (3H, s), 0.70 (2H, m), 0.56 (2H, m) |
| 80 | 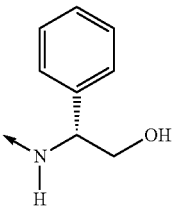 | 405 | 8.44 and 8.41 (1H, 2 × d), 7.87 (1H, dd), 7.75 and 7.73 (1H, 2 × d), 7.52 – 7.47 (1H, m), 7.46 – 7.28 (5H, m), 7.23 (1H, m), 6.79 and 6.77 (1H, 2 × d), 6.70 and 6.69 (1H, 2 × d), 5.02 (2H, m), 3.73 (2H, m), 2.85 (1H, m), 2.13 and 2.09(3H, 2 × s), 0.68 (2H, m), 0.55 (2H, m) |
| 81 | 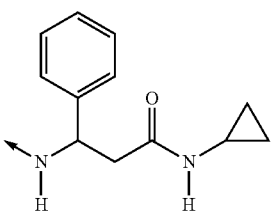 | 405 | 8.44 and 8.41 (1H, 2 × d), 7.87 (1H, dd), 7.75 and 7.73 (1H, 2 × d), 7.52 – 7.47 (1H, m), 7.46 – 7.28 (5H, m), 7.23 (1H, m), 6.79 and 6.77 (1H, 2 × d), 6.70 and 6.69 (1H, 2 × d), 5.02 (2H, m), 3.73 (2H, m), 2.85 (1H, m), 2.13 and 2.09(3H, 2 × s), 0.68 (2H, m), 0.55 (2H, m) |
| 82 | | 472 | 8.45 and 8.40 (1H, 2 × d), 7.96 – 7.88 (2H, m), 7.87 (1H, dd), 7.74 and 7.72 (1H, 2 × d), 7.49 and 7.48 (1H, 2 × d), 7.39 – 7.27 (4H, m), 7.25 – 7.19 (1H, m), 6.80 and 6.79 (1H, 2 × d), 6.69 and 6.69 (1H, 2 × d), 5.43 – 5.34 (1H, m), 2.89 – 2.80 (1H, m), 2.70 (1H, dd), 2.61 – 2.49 (1H, m), 2.13 and 2.08 (3H, 2 × s), 0.73 – 0.63 (2H, m), 0.59 – 0.50 (4H, m), 0.30 – 0.15 (2H, m) |

TABLE 2-continued

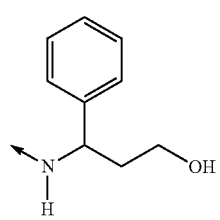

| Example | R | MS [M + H]+ m/z | ¹H NMR δ (DMSO-d₆) |
|---|---|---|---|
| 83 | 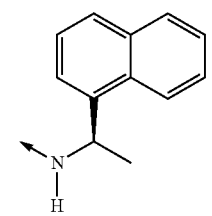 | 419 | 8.44 and 8.39 (1H, 2 × d), 7.90 – 7.77 (2H, m), 7.73 (1H, d), 7.49 and 7.48 (1H, 2 × d), 7.43 – 7.35 (2H, m), 7.35 – 7.26 (2H, m), 7.21 (1H, m), 6.77 (1H, d), 6.66 and 6.65 (1H, 2 × d), 5.18 (1H, m), 4.61 (1H, m), 3.48 – 3.35 (2H, m), 2.85 (1H, m), 2.13 and 2.07 (3H, 2 × s), 2.15– 1.87 (2H, m), 0.74 – 0.62 (2H, m), 0.61– 0.48 (2H, m) |
| 84 | 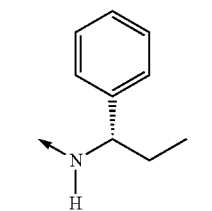 | 439 | 8.45 and 8.41 (1H, 2 × d), 8.23 (1H, m), 7.91 (1H, d), 7.84 (1H, d), 7.81 (1H, m), 7.78 – 7.69 (2H, m), 7.65 – 7.44 (5H, m), 6.78 and 6.75 (1H, 2 × d), 6.69 and 6.68 (1H, 2 × d), 5.95 (1H, m), 2.85 (1H, m), 2.14 and 2.08 (3H, 2 × s), 1.64 and 1.63 (3H, 2 × d), 0.68 (2H, m), 0.55 (2H, m) |
| 85 | 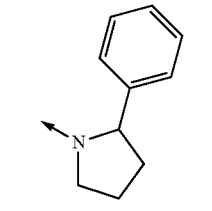 | 403 | 8.44 and 8.38 (1H, 2 × d), 7.86 (1H, d), 7.71 and 7.61(1H , 2 × s), 7.59 (1H, d), 7.49 (1H, m), 7.46 – 7.37 (2H, m), 7.31 (2H, t), 7.26 – 7.17 (1H, m), 6.80(1H, m), 6.67 (1H, m), 4.91 (1H, q), 2.84 (1H, m), 2.13 (3H, 2 × s), 2.04 – 1.90 (1H, m), 1.88 – 1.73 (1H, m), 0.86 (3H, t), 0.68 (2H, m), 0.55 (2H, m) |
| 86 | 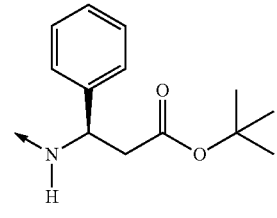 | 415 | 8.45 – 8.37 (1H, m), 7.84 – 7.77 (1H, m), 7.68 and 7.58 (1H, 2 × s), 7.44 and 7.36 (1H, 2 × d), 7.29 – 7.23 (3H, m), 7.19 – 7.06 (3H, m), 6.87 – 6.78 (1H, m), 6.71 and 6.68 (1H, d), 5.70 (1H, br), 4.10 (1H, br), 3.83 (1H, br), 2.83 (1H, m), 2.41 – 2.27 (1H, m), 2.1 (1H, s), 1.93 – 1.64 (6H, m), 0.68 (2H, m), 0.54 (2H, m) |
| 87 | 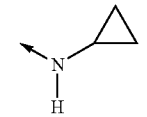 | 489 | 8.47 and 8.39 (1H, 2 × d), 7.90 – 7.78 (2H, m), 7.72 and 7.71 (1H, 2 × d), 7.51 – 7.41 (3H, m), 7.35 – 7.28 (2H, m), 7.26 – 7.20 (1H, m), 6.84 and 6.83 (1H, 2 × d), 6.71 and 6.70 (1H, 2 × d), 5.54 – 5.40 (1H, m), 3.02– 2.92 (1H, m), 2.89 – 2.77 (2H, m), 2.10 and 2.07 (3H, 2 × s), 1.28 and 1.27 (9H, 2 × s), 0.68 (2H, m), 0.54 (2H, m) |
| 88 |  | 325 | 8.43 (1H, d), 7.86 (1H, d), 7.73 (1H, s), 7.48 (1H, d), 7.40 (1H, d), 6.89 (1H, d), 6.72 (1H, d), 2.92 – 2.71 (2H, m), 2.10 (3H, s), 0.78 – 0.45 (8H, m) |

TABLE 2-continued
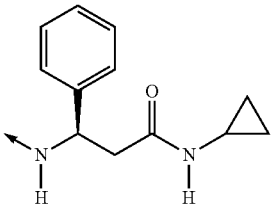
| Example | R | MS [M + H]+ m/z | 1H NMR δ (DMSO-d6) |
|---|---|---|---|
| 89 | 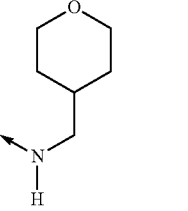 | 472 | 8.45 and 8.40 (1H, 2 × d), 7.96 – 7.88 (2H, m), 7.87 (1H, dd), 7.74 and 7.72 (1H, 2 × d), 7.49 and 7.48 (1H, 2 × d), 7.39 – 7.27 (4H, m), 7.25 – 7.19 (1H, m), 6.80 and 6.79 (1H, 2 xx d), 6.69 and 6.69 (1H, 2 × d), 5.43 – 5.34 (1H, m), 2.89– 2.80(1H, m), 2.70 (1H, dd),2.61 – 2.49 (1H, m), 2.13 and 2.08 (3H, 2 × s), 0.73 – 0.63 (2H, m), 0.59 – 0.50 (4H, m), 0.30 – 0.15 (2H, m) |
| 90 | 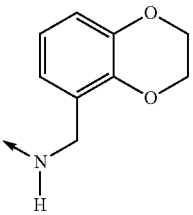 | 383 | 8.43 (1H, d), 7.86 (1H, dd), 7.74 (1H, d), 7.48 (1H, d), 7.40 (1H, t), 6.84 (1H, d), 6.66 (1H, d), 3.84 (2H, dd), 3.30 – 3.09 (4H, m), 2.84 (1H, m), 2.10 (3H, s), 2.01 – 1.82(1H, m), 1.57 (2H, d), 1.27 – 1.10 (2H, m), 0.69 (2H, m), 0.55 (2H, m) |
| 91 | 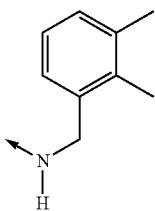 | 433 | 8.44 (1H, d), 7.87 (1H, dd), 7.77 (1H, d), 7.59 (1H,t), 7.50 (1H, d), 6.82 (1H, d), 6.77 – 6.65 (4H, m), 4.55 (1H, dd), 4.44 (1H, dd), 4.35 – 4.21 (4H, m), 2.85 (1H, m), 2.13 (3H, s),0.69 (2H, m), 0.56 (2H,m) |
| 92 | 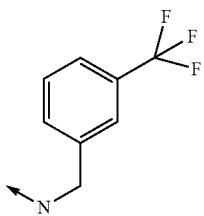 | 403 | 8.44 (1H, d), 7.87 (1H, dd), 7.76 (1H, d), 7.63 (1H, t), 7.49 (1H, d), 7.09 – 6.97 (3H, m), 6.82 (1H, d), 6.70 (1H, d), 4.58 (1H, dd), 4.47 (1H, dd), 2.85 (1H, m), 2.25 (3H, s), 2.20 (3H, s), 2.12 (3H, s), 0.69 (2H, m), 0.56 (2H, m) |
| 93 | 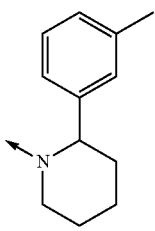 | 443 | 8.43 (1H, d), 8.10 (1H,t), 7.87 (1H, dd), 7.75 (1H, d), 7.72 – 7.52 (4H, m), 7.49 (1H, d),6.82(1H, d), 6.72 (1H, d), 4.66 (1H, dd), 4.56 (1H, dd), 2.85 (1H, m), 2.11 (3H, s), 0.69 (2H, m), 0.55 (2H, m) |
| 94 | | 443 | 8.44 (1H, d), 7.84 (1H, d), 7.75 and 7.71 (1H, 2 × s), 7.46 (1H, t), 7.27 – 6.90 (5H, m), 6.16 and 6.05 (1H, 2 × br s), 4.47 (1H, t), 2.98 (1H, m), 2.84 (1H, m), 2.38 – 2.22 (1H, m), 2.29 (3H, s), 2.13 and 2.02 (3H, 2 × s), 1.97 – 1.80 (1H, m), 1.72 – 1.37 (4H, m), 0.69 (2H, m), 0.56 (2H, m) |

TABLE 2-continued
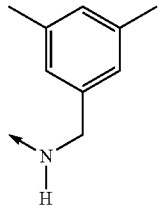
| Example | R | MS [M + H]⁺ m/z | ¹H NMR δ (DMSO-d₆) |
|---|---|---|---|
| 95 | 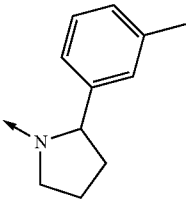 | 403 | 8.44 (1H, d), 7.86 (1H, dd), 7.79 (1H, t), 7.75 (1H, d), 7.49 (1H, d), 6.93 (2H, s), 6.86 (1H, s), 6.83 (1H, d), 6.69 (1H, d), 4.52 (1H, dd), 4.40 (1H, dd), 2.85 (1H, m), 2.25 (6H, d), 2.11 (3H, s), 0.69 (2H, m), 0.55 (2H, m) |
| 96 | 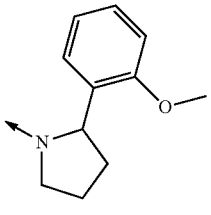 | 429 | 8.45 – 8.37 (1H, m), 7.80 (1H, m), 7.68 and 7.59 (1H, 2 × s), 7.44 and 7.37 (1H, 2 × d), 7.19 – 7.08 (1H, m), 7.01 – 6.76 (4H, m), 6.71 and 6.68 (1H, 2 × d), 5.81 – 5.55 (1H, br), 4.18 – 3.97 (1H, br), 3.93 – 3.72 (1H, br), 2.83 (1H, m), 2.29 – 2.21 (2H, m), 2.26 and 2.25 (3H, 2 × s), 2.08 (1H, s), 1.92 – 1.66 (4H, m), 0.67 (2H, m), 0.54 (2H, m) |
| 97 | 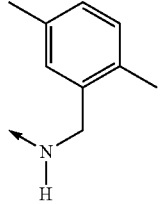 | 445 | 8.43 – 8.38 (1H, m), 7.84 – 7.77 (1H, m), 7.69 and 7.59 (1H, 2 × s), 7.44 and 7.36 (1H, 2 × d), 7.19 – 7.11 (1H, m), 6.94 (1H, d), 6.87 – 6.77 (3H, m), 6.68 and 6.66 (1H, 2 × d), 6.05 – 5.89 (1H, br), 4.21 – 4.05 (1H, br), 3.80 (1H, br), 3.80 and 3.79 (3H, 2 × s), 2.84 (1H, m), 2.30 – 2.13 (2H, m), 2.09 (1H.8), 1.93 – 1.81 (2H, m), 1.80 – 1.63 (4H, m), 0.67 (2H, m), 0.55 (2H, m) |
| 98 | 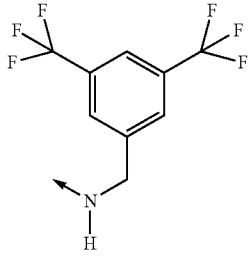 | 403 | 8.45 (1H, d), 7.87 (1H, dd), 7.98 (1H, s), 7.77 (1H, d), 7.64 (1H, t), 7.50 (1H, d), 7.08 – 7.01 (2H, m), 6.95 (1H, d), 6.83 (1H, d), 6.71 (1H, d), 4.53 (1H, dd), 4.42 (1H, dd), 2.85 (1H, m), 2.27 (3H, s), 2.22 (3H, s), 2.12 (3H, s), 0.69 (2H, m), 0.56 (2H, m) |
| 99 |  | 511 | 8.44 (1H, d), 8.20 (1H, t), 8.03 (2H, s), 7.87 (1H, dd), 7.76 (1H, d), 7.49 (1H, d), 6.82 (1H, d), 6.74 (1H, d), 4.80 – 4.57 (2H, m), 2.84 (1H, m), 2.10 (3H, s), 0.69 (2H, m), 0.55 (2H, m) |
a) ¹H NMR in CDCl₃
b) Also included as example

Example 100

N-Cyclopropyl-4-methyl-3-[2-oxo-3-[[[2-[2-(1-pyrrolidinyl)ethoxy]phenyl]methyl]amino]-1(2H)-pyrazinyl]-benzamide

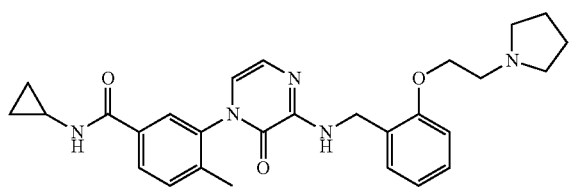

To a stirred solution of 3-(3,5-dibromo-2-oxo-2H-pyrazin-1-yl)-4-methyl-benzoic acid, methyl ester (Example 1b, 0.1 g) in tetrahydrofuran (2 mL) in a microwave vial was added triethylamine (38 µL) and 2-(aminomethyl)-phenol (34 mg). The reaction was stirred overnight before the solvent was removed. The residue was dissolved dry N,N-dimethylformamide (3 mL) and 1-(2-chloroethyl)-pyrrolidine hydrochloride (211 mg) and cesium carbonate (808 mg) were added. The reaction mixture was heated at 80° C. for 12 h. The volatiles were removed under reduced pressure. Ethyl acetate was added and the mixture washed with water and brine, then dried (MgSO$_4$), filtered and the solvent removed. Tetrahydrofuran (3 mL) was added to the vial followed by cyclopropylamine (0.15 mL) and cyclopentylmagnesium bromide (2M in diethyl ether, 1 mL) dropwise. After stirring for 30 minutes, ethanol (2 mL) was added followed by the addition of ammonium formate (0.3 g) and 10% palladium on carbon (30 mg). The reaction mixture was heated within a microwave for 60 minutes at 100° C. before being cooled to room temperature, filtered and washed with ethanol. The filtrate was concentrated in vacuo. Purification by preparative HPLC (Gemini column, 0.1% ammonia:acetonitrile eluent) afforded the title compound as a solid (33 mg).

MS: APCI (+ve) 488 (M+H$^+$).

$^1$H NMR δ(DMSO-d$_6$, 400 MHz) 8.44 (1H, d), 7.87 (1H, dd), 7.76 (1H, d), 7.53 (1H, t), 7.49 (1H, d), 7.24-7.18 (1H, m), 7.14-7.11 (1H, m), 6.99 (1H, d), 6.91-6.86 (1H, m), 6.81 (1H, d), 6.70 (1H, d), 4.57 (1H, dd), 4.48 (1H, dd), 4.12 (2H, t), 2.89-2.81 (3H, m), 2.59-2.53 (4H, m), 2.12 (3H, s), 1.71-1.65 (4H, m), 0.72-0.66 (2H, m), 0.58-0.53 (2H, m)

Example 101

N-Cyclopropyl-4-methyl-3-[2-oxo-3-[[(R)-phenyl-4-piperidinylmethyl]amino]-1(2H)-pyrazinyl]-benzamide, trifluoroacetate

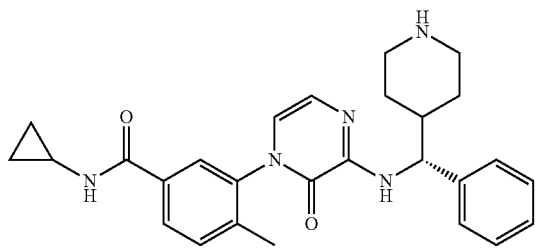

a) 4-[(R)-[[(R)-(1,1-Dimethylethyl)sulfinyl]amino]phenylmethyl]-1-piperidinecarboxylic acid, phenylmethyl ester A mixture of 4-formyl-piperidine-1-carboxylic acid, benzyl ester (0.96 g), (R)-2-methyl-2-propanesulfinamide (0.51 g), anhydrous copper(II) sulphate (1.5 g) and dichloromethane (20 mL) was stirred at room temperature for 48 h. Copper(II) sulphate was filtered off and the filtrate concentrated. The residue was treated with dry dichloromethane (15 mL) and cooled to −78° C. A solution of phenylmagnesium bromide in diethyl ether (3M, 4 mL) was added dropwise. The mixture was slowly warmed to 0° C., then quenched with sat. aqueous NH$_4$Cl solution. The mixture was stirred for 15 min and extracted into dichloromethane. The organic phase was dried (Na$_2$SO$_4$), filtered and concentrated in vacuo. The residue was purified (SiO$_2$ chromatography eluting with isohexane:ethyl acetate (0-100%)) to give the title compound (623 mg).

$^1$H NMR δ(CDCl$_3$, 400 MHz) 7.38-7.27 (8H, m), 7.22 (2H, m), 5.08 (2H, s), 4.29-4.13 (3H, m), 3.41 (1H, d), 2.87-2.58 (2H, m), 2.04 (1H, m), 1.88 (1H, m), 1.50 (1H, m), 1.23 (9H, s), 1.20-1.01 (2H, m).

b) 4-[(R)-Aminophenylmethyl]-1-piperidinecarboxylic acid, phenylmethyl ester A mixture of 4-[(R)-[[(R)-(1,1-dimethylethyl)sulfinyl]amino]phenylmethyl]-1-piperidinecarboxylic acid, phenylmethyl ester (0.59 g), methanol (5 mL) and hydrogen chloride in 1,4-dioxane (4M, 5 mL) was stirred at room temperature for 10 minutes then concentrated in vacuo. The residue was diluted in dichloromethane (2 mL) and triturated with diethyl ether to afford the subtitle compound as a solid (470 mg).

$^1$H NMR δ(DMSO-d$_6$, 400 MHz) 8.56 (2H, d), 7.51-7.26 (10H, m), 5.05 (2H, s), 4.13-4.01 (2H, m), 3.92 (1H, d), 2.90-2.59 (2H, m), 2.02 (1H, m), 1.92 (1H, m), 1.18 (2H, m), 1.00 (1H, m).

c) N-Cyclopropyl-4-methyl-3-[2-oxo-3-[[(R)-phenyl-4-piperidinylmethyl]amino]-1(2H)-pyrazinyl]-benzamide To a stirred solution of 3-(3,5-dibromo-2-oxo-2H-pyrazin-1-yl)-4-methyl-benzoic acid, methyl ester (Example 1b, 0.1 g) in tetrahydrofuran (1.5 mL) within a microwave vial was added N,N-diisopropylethylamine (130 µL) and 4-[(R)-aminophenylmethyl]-1-piperidinecarboxylic acid, phenylmethyl ester (98 mg). The reaction was heated at 110° C. for 60 minutes within a microwave. The reaction was cooled to room temperature before the addition of cyclopropylamine (0.13 mL) and cyclopentylmagnesium bromide (2M in diethyl ether, 1 mL) dropwise. After stirring for 30 minutes, ethanol (1 mL) was added followed by ethyl acetate. The solvent was washed with water, and brine, then dried (Na$_2$SO$_4$), filtered and the solvent removed. The product was dissolved in t-butanol (2 mL) followed by the addition of 1,4-cyclohexadiene (1 mL) and 10% Pd on carbon (30 mg). The reaction mixture was heated within a microwave at 120° C. for 30 minutes, cooled to room temperature, filtered and purified by preparative HPLC (Gemini column, 0.1% trifluoroacetic acid:acetonitrile eluent) to afford N-cyclopropyl-4-methyl-3-[2-oxo-3-[[(R)-phenyl-4-piperidinylmethyl]amino]-1(2H)-pyrazinyl]-benzamide (58 mg) and 4-[(R)-[[4-[5-[(cyclopropylamino)

carbonyl]-2-methylphenyl]-3,4-dihydro-3-oxopyrazinyl] amino]phenylmethyl]-1-piperidinecarboxylic acid, phenyl ester (19 mg).

MS: APCI (+ve) 458 (M+H⁺).

¹H NMR δ(DMSO-d₆, 400 MHz) 8.46 (0.5H, d), 8.36 (0.5H, d), 7.89-7.83 (2H, m), 7.71 (1H, dd), 7.51-7.43 (3H, m), 7.37-7.31 (2H, m), 7.28-7.23 (1H, m), 6.83-6.80 (1H, m), 6.72-6.68 (1H, m), 4.86-4.79 (1H, m), 3.37-3.29 (1H, m), 3.24-3.17 (1H, m), 2.89-2.70 (3H, m), 2.29-2.18 (1H, m), 2.13 (1.5H, s), 2.10-2.00 (1H, m), 2.04 (1.5H, s), 1.45-1.22 (4H, m), 0.72-0.63 (2H, m), 0.58-0.49 (2H, m).

Example 102

4-[(R)-[[4-[5-[(Cyclopropylamino)carbonyl]-2-methylphenyl]-3,4-dihydro-3-oxopyrazinyl]amino]phenylmethyl]-1-piperidinecarboxylic acid, phenylmethyl ester

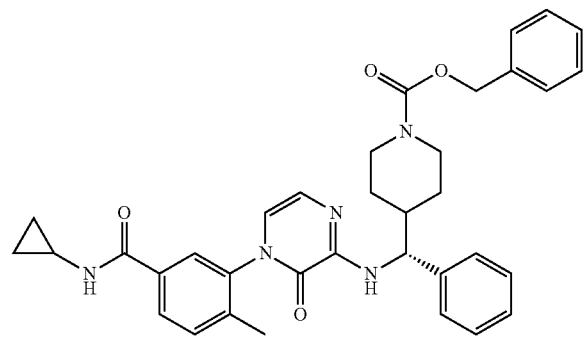

To a stirred solution of 3-(3,5-dibromo-2-oxo-2H-pyrazin-1-yl)-4-methyl-benzoic acid methyl ester (Example 1b, 0.1 g) in anhydrous THF (2 mL) within a microwave vial was added triethylamine (100 μL) and 4-[(R)-aminophenylmethyl]-1-piperidinecarboxylic acid phenylmethyl ester (Example 101b, 98 mg). The reaction was heated within a microwave at 120° C. for 60 minutes before cooling to room temperature and adding cyclopropylamine (150 μL) and cyclopentylmagnesium bromide (2M in diethyl ether, 0.75 mL) portionwise After stirring for 30 minutes, ethanol (2 mL) was added followed by the addition of ammonium formate (0.3 g) and 10% palladium on carbon (30 mg). The mixture was heated within a microwave for 180 minutes at 100° C. before being cooled to room temperature, filtered and washed with ethanol. The filtrate was concentrated in vacuo. Purification by preparative HPLC (Gemini column, 0.1% ammonia:acetonitrile eluent) afforded the title compound (19 mg).

MS: APCI (+ve) 592 (M+H⁺).

¹H NMR δ(DMSO-d₆, 400 MHz) 8.46 (0.5H, d), 8.36 (0.5H, d), 7.86-7.82 (1H, m), 7.80-7.71 (2H, m), 7.49-7.42 (3H, m), 7.36-7.29 (7H, m), 7.26-7.20 (1H, m), 6.81-6.78 (1H, m), 6.67-6.63 (1H, m), 5.50 (2H, s), 4.82-4.73 (1H, m), 4.12-4.0 (1H, m), 4.0-3.90 (1H, m), 2.90-2.75 (1H, m), 2.20-2.10 (1H, m), 2.13 (1.5H, s), 2.04 (1.5H, s), 2.00-1.88 (1H, m), 1.23-1.00 (4H, m), 0.7-0.64 (2H, m), 0.57-0.51 (2H, m).

Example 103

N-Cyclopropyl-4-methyl-3-[2-oxo-3-[[(S)-phenyl-4-piperidinylmethyl]amino]-1(2H)-pyrazinyl]-benzamide trifluoroacetate

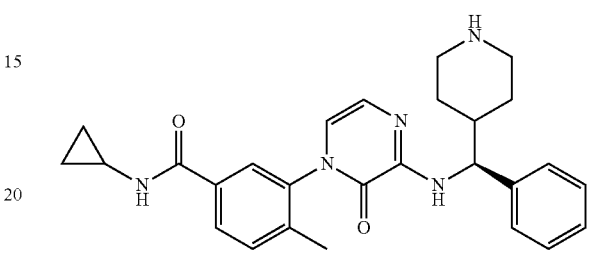

The title compound was prepared and purified in accordance with Example 101 using (S)-2-methyl-2-propanesulfinamide.

MS: APCI (+ve) 458 (M+H⁺).

¹H NMR δ(DMSO-d₆, 400 MHz) 8.46 (0.5H, d), 8.36 (0.5H, d), 7.91-7.84 (2H, m), 7.71 (1H, dd), 7.51-7.43 (3H, m), 7.37-7.30 (2H, m), 7.29-7.22 (1H, m), 6.82-6.80 (1H, m), 6.72-6.68 (1H, m), 4.86-4.80 (1H, m), 3.38-3.29 (1H, m), 3.25-3.17 (1H, m), 2.89-2.70 (3H, m), 2.30-2.18 (1H, m), 2.13 (1.5H, s), 2.04 (1.5H, s), 2.10-2.00 (1H, m), 1.43-1.21 (4H, m), 0.73-0.63 (2H, m), 0.58-0.49 (2H, m).

Example 104

3-[5-Cyano-2-oxo-3-[(phenylmethyl)amino]-1(2H)-pyrazinyl]-N-cyclopropyl-4-methyl-benzamide

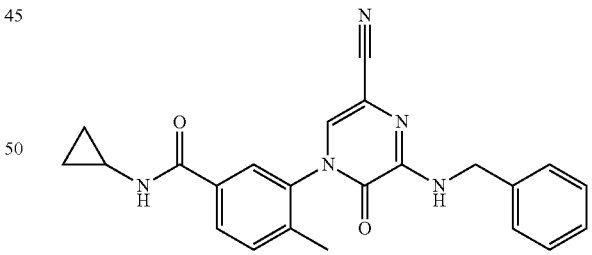

To a stirred solution of 3-(3,5-dibromo-2-oxo-2H-pyrazin-1-yl)-4-methyl-benzoic acid, methyl ester (Example 1b, 0.4 g) in tetrahydrofuran (2 mL) within a microwave vial was added N,N-diisopropylethylamine (330 μL) and benzenemethanamine (150 μL). The reaction was stirred overnight before the addition of cyclopropylamine (0.5 mL) and cyclopentylmagnesium bromide (2M in diethyl ether, 3 mL) dropwise. The reaction was stirred for 30 minutes before ethanol (2 mL) was added followed by ammonium chloride. The solution was extracted with ethyl acetate and the organics were washed with brine, dried (Na₂SO₄), filtered and the solvent removed to afford the amide as a solid (543 mg).

N,N-dimethylformamide (8 mL), tetrakis(triphenylphosphine)palladium(0) (50 mg) and zinc cyanide (421 mg) were added and the reaction was heated within a microwave at 170° C. for 10 minutes. The reaction was cooled to room temperature. Water was added and the mixture extracted with ethyl acetate. The pooled organics were washed with brine, dried (Na$_2$SO$_4$), filtered and the solvent removed to afford the title compound (570 mg).

MS: APCI (+ve) 400 (M+H$^+$).

$^1$H NMR δ(DMSO-d$_6$, 400 MHz) 8.50 (1H, t), 8.42 (1H, d), 7.87 (1H, dd), 7.81 (1H, d), 7.76 (1H, s), 7.50 (1H, d), 7.37-7.31 (4H, m), 7.29-7.23 (1H, m), 4.62-4.55 (1H, m), 4.52-4.44 (1H, m), 2.88-2.81 (1H, m), 2.14 (3H, s), 0.73-0.67 (2H, m), 0.58-0.53 (2H, m)

Example 105

N-Cyclopropyl-3-[5-[(dimethylamino)methyl]-2-oxo-3-[(phenylmethyl)amino]-1(2H)-pyrazinyl]-4-methyl-benzamide

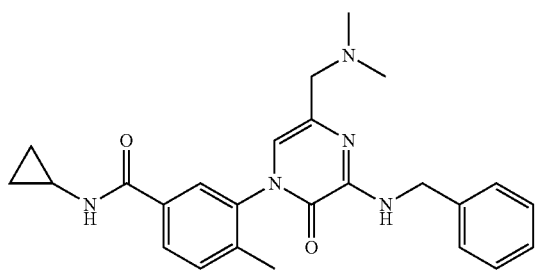

To a stirred solution of 3-[5-cyano-2-oxo-3-[(phenylmethyl)amino]-1(2H)-pyrazinyl]-N-cyclopropyl-4-methyl-benzamide (Example 104, 100 mg) in methanol (2 mL) was added cobalt(II) chloride (119 mg) followed by sodium borohydride (95 mg) portionwise. After 15 minutes 37% formaldehyde solution (0.5 mL) and sodium triacetoxyborohydride (150 mg) were added and the reaction stirred overnight. Water (5 mL) was added to the reaction and the mixture was extracted with dichloromethane. The pooled organics were washed with brine, dried (Na$_2$SO$_4$), filtered and the solvent removed. Purification by preparative HPLC (Gemini column, 0.1% ammonia:acetonitrile eluent) afforded the title compound (24 mg).

MS: APCI (+ve) 432 (M+H$^+$).

$^1$H NMR δ(DMSO-d$_6$, 400 MHz) 8.43 (1H, d), 7.88-7.81 (2H, m), 7.75 (1H, d), 7.48 (1H, d), 7.38-7.34 (2H, m), 7.33-7.28 (2H, m), 7.25-7.19 (1H, m), 6.56 (1H, s), 4.59 (1H, dd), 4.47 (1H, dd), 3.13 (2H, d), 2.88-2.80 (1H, m), 2.15 (6H, s), 2.11 (3H, s), 0.71-0.65 (2H, m), 0.57-0.53 (2H, m)

Example 106

4-[5-[(Cyclopropylamino)carbonyl]-2-methylphenyl]-4,5-dihydro-5-oxo-6-[(phenylmethyl)amino]-2-pyrazinecarboxamide

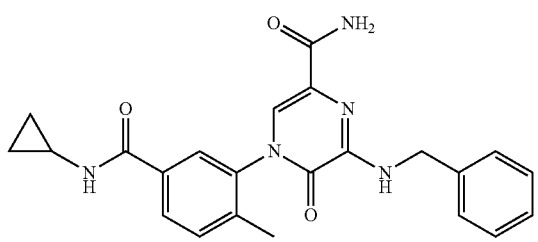

To a stirred solution of 3-[5-cyano-2-oxo-3-[(phenylmethyl)amino]-1(2H)-pyrazinyl]-N-cyclopropyl-4-methyl-benzamide (Example 104, 100 mg) in methanol (1 mL) was added conc. ammonia solution (1 mL) followed by 30% hydrogen peroxide solution (1 mL). After 12 h, water was added and the mixture was extracted with dichloromethane. The pooled organics were washed with brine, dried (MgSO$_4$), filtered and the solvent removed. Purification by preparative HPLC (Gemini column, 0.1% ammonia:acetonitrile eluent) afforded the title compound (31 mg).

MS: APCI (+ve) 418 (M+H$^+$).

$^1$H NMR δ(DMSO-d$_6$, 400 MHz) 8.44 (1H, d), 8.19 (1H, t), 7.86 (1H, dd), 7.77 (1H, d), 7.58 (1H, d), 7.49 (1H, d), 7.45-7.40 (3H, m), 7.32 (2H, td), 7.26-7.21 (2H, m), 4.72 (1H, dd), 4.57 (1H, dd), 2.88-2.80 (1H, m), 2.11 (3H, s), 0.71-0.66 (2H, m), 0.57-0.53 (2H, m).

Example 107

3-[5-Chloro-3-(4-methyl-1-piperazinyl)-2-oxo-1(2H)-pyrazinyl]-N-cyclopropyl-4-methyl-benzamide

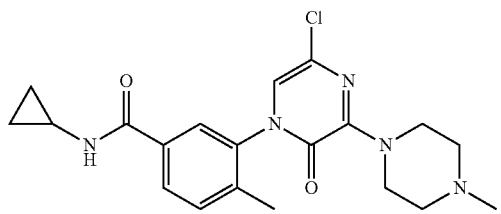

a) 3-(3,5-Dichloro-2-oxo-1(2H)-pyrazinyl)-4-methyl-benzoic acid, methyl ester To 3-[(cyanomethyl)amino]-4-methyl-benzoic acid, methyl ester (Example 1a, 1.2 g) was added 1,2-dichlorobenzene (20 mL) and oxalyl chloride (3 mL). The reaction was heated at 100° C. for four h before the volatiles were removed under reduced pressure. The residue was purified (SiO$_2$ chromatography eluting with dichloromethane) to afford the subtitle compound (800 mg).

MS: APCI (+ve) 313 (M+H$^+$).

b) 3-[5-Chloro-3-(4-methyl-1-piperazinyl)-2-oxo-1(2H)-pyrazinyl]-4-methyl-benzoic acid, methyl ester To a stirred solution of 3-(3,5-dichloro-2-oxo-1(2H)-pyrazinyl)-4-methyl-benzoic acid, methyl ester, (Example 107a, 250 mg) in acetonitrile (5 mL) was added 1-methyl-piperazine (0.2 mL). After 12 h, the reaction mixture was concentrated in vacuo. The residue was diluted with dichloromethane, washed with sat. aqueous NaHCO$_3$, dried (MgSO$_4$), filtered and the solvent removed to afford the subtitle compound.

MS: APCI (+ve) 377 (M+H$^+$).

c) 3-[5-Chloro-3-(4-methyl-1-piperazinyl)-2-oxo-1 (2H)-pyrazinyl]-N-cyclopropyl-4-methyl-benzamide To a stirred solution of 3-[5-chloro-3-(4-methyl-1-piperazinyl)-2-oxo-1(2H)-pyrazinyl]-4-methyl-benzoic acid, methyl ester (Example 107b) in tetrahydrofuran (6 mL) under nitrogen was added cyclopropylamine (0.15 mL) followed by iso-propylmagnesium chloride (2M in tetrahydrofuran, 0.8 mL), portionwise. After 1 h, sat. aqueous NH$_4$Cl was added and the mixture extracted into ethyl acetate. The combined organic extracts were washed with brine, dried (MgSO$_4$), filtered and the solvent removed in vacuo. Purification by preparative HPLC (Gemini column, 0.1% ammonia:acetonitrile eluent) afforded the title compound (35 mg).

MS: APCI (+ve) 402 (M+H$^+$).

$^1$H NMR $\delta$(DMSO-d$_6$, 400 MHz) 8.42 (1H, d), 7.84 (1H, dd), 7.73 (1H, d), 7.46 (1H, d), 7.18 (1H, s), 3.88-3.74 (4H, m), 2.88-2.80 (1H, m), 2.43-2.36 (4H, m), 2.19 (3H, s), 2.12 (3H, s), 0.72-0.66 (2H, m), 0.58-0.53 (2H, m).

Example 108

3-[5-Chloro-3-[[3-(dimethylamino)propyl]amino]-2-oxo-1(2H)-pyrazinyl]-N-cyclopropyl-4-methyl-benzamide

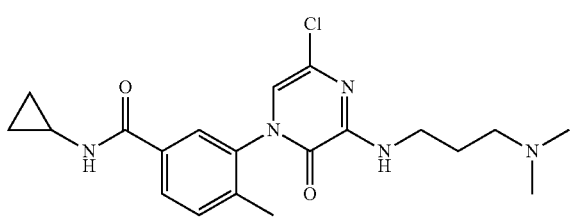

To a stirred solution of 3-(3,5-dichloro-2-oxo-1(2H)-pyrazinyl)-4-methyl-benzoic acid, methyl ester (Example 107a, 200 mg) in tetrahydrofuran (3 mL) was added N,N-dimethyl-1,3-propanediamine (90 μL) and the mixture was stirred at room temperature for 12 h. Cyclopropylamine (220 μL) was added followed by the addition of iso-propylmagnesium chloride (2M in tetrahydrofuran, 1 mL) portionwise. The reaction mixture was stirred for 60 minutes and iso-propylmagnesium chloride (2M in tetrahydrofuran, 1 mL) was added. The mixture was stirred for an additional 30 minutes and sat. aqueous NH$_4$Cl was added. The aqueous solution was extracted with ethyl acetate. The pooled organic was washed with brine and dried (MgSO$_4$), filtered and the solvent removed. Purification by preparative HPLC (Gemini column, 0.1% ammonia:acetonitrile eluent) gave the title compound (149 mg).

MS: APCI (+ve) 404 (M+H$^+$).

$^1$H NMR $\delta$(DMSO-d$_6$, 400 MHz) 8.43 (1H, d), 8.03 (1H, t), 7.85 (1H, dd), 7.76 (1H, d), 7.48 (1H, d), 6.89 (1H, s), 3.41-3.26 (2H, m), 2.89-2.81 (1H, m), 2.27 (2H, t), 2.14 (6H, s), 2.12 (3H, s), 1.71 (2H, quintet), 0.72-0.66 (2H, m), 0.58-0.53 (2H, m)

Example 109

3-[5-Chloro-2-oxo-3-[(phenylmethyl)amino]-1(2H)-pyrazinyl]-N-cyclopropyl-4-methyl-benzamide

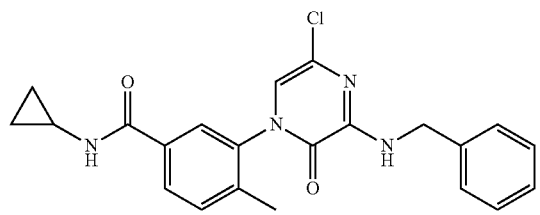

To a stirred solution of 3-(3,5-dibromo-2-oxo-2H-pyrazin-1-yl)-4-methyl-benzoic acid, methyl ester (Example 1b, 0.2 g) in tetrahydrofuran (3 mL) within a microwave vial was added triethylamine (76 μL) and benzylamine (64 mg). The reaction was stirred overnight before the addition of cyclopropylamine (0.22 mL) and iso-propylmagnesium chloride (2M in tetrahydrofuran, 1.5 mL) dropwise. After stirring for 30 minutes, ethanol (2 mL), formic acid (0.4 mL) and 10% palladium on carbon (30 mg) were added. The reaction mixture was heated within a microwave for 60 minutes at 110° C. before being cooled to room temperature, filtered and washed with ethanol. The filtrate was concentrated in vacuo. Purification by preparative HPLC (Gemini column, 0.1% ammonia:acetonitrile eluent) afforded the title compound (80 mg).

MS: APCI (+ve) 409 (M+H$^+$).

$^1$H NMR $\delta$(DMSO-d$_6$, 400 MHz) 8.47-8.39 (2H, m), 7.86 (1H, dd), 7.78 (1H, d), 7.48 (1H, d), 7.37-7.31 (4H, m), 7.28-7.22 (1H, m), 6.94 (1H, s), 4.52 (2H, ddd), 2.88-2.80 (1H, m), 2.13 (3H, s), 0.72-0.66 (2H, m), 0.57-0.53 (2H, m).

Example 110

3-[5-Chloro-2-oxo-3-[(2-phenylethyl)amino]-1(2H)-pyrazinyl]-N-cyclopropyl-4-methyl-benzamide

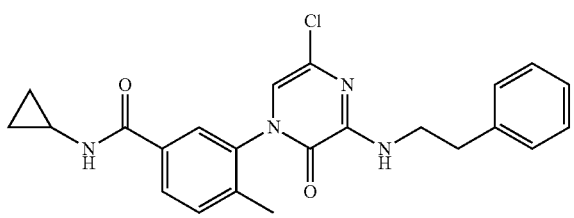

The title compound was prepared and purified in accordance to Example 109. MS: APCI (+ve) 423 (M+H$^+$).

$^1$H NMR $\delta$(DMSO-d$_6$, 300 MHz) 8.43 (1H, d), 7.94-7.82 (2H, m), 7.76 (1H, s), 7.48 (1H, d), 7.35-7.18 (5H, m), 6.92

(1H, d), 3.64-3.46 (2H, m), 2.96-2.80 (3H, m), 2.12 (3H, s), 0.74-0.63 (2H, m), 0.61-0.50 (2H, m).

Example 111

N-Methoxy-4-methyl-3-[3-[[[2-[(4-methyl-1-piperazinyl)methyl]phenyl]methyl]amino]-2-oxo-1(2H)-pyrazinyl]-benzamide

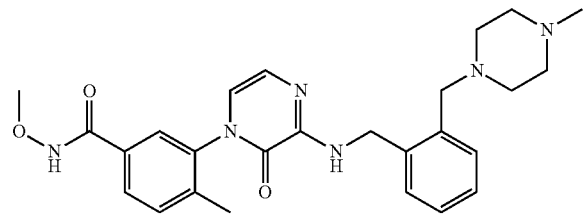

To a stirred solution of 3-(3,5-dibromo-2-oxo-2H-pyrazin-1-yl)-4-methyl-benzoic acid, methyl ester (Example 1b, 0.1 g) in tetrahydrofuran (2 mL) in a microwave vial was added triethylamine (250 µL) and 2-[(4-methyl-1-piperazinyl)methyl]-benzenemethanamine (90 mg). The reaction was stirred overnight before the addition of O-methylhydroxylamine hydrochloride (83 mg) and cyclopentylmagnesium bromide (2M in diethyl ether, 2 mL) dropwise. After stirring for 60 minutes, ethanol (2 mL) was added followed by the addition of ammonium formate (0.4 g) and 10% palladium on carbon (40 mg). The reaction mixture was heated within a microwave for 30 minutes at 100° C. before being cooled to room temperature, filtered and washed with ethanol. The filtrate was concentrated in vacuo. Purification by preparative HPLC (Gemini column, 0.1% trifluoroacetic acid:acetonitrile eluent) afforded the title compound (13 mg).

MS: APCI (+ve) 477 (M+H$^+$).

$^1$H NMR δ(DMSO-d$_6$, 400 MHz) 7.77 (1H, d), 7.67 (1H, s), 7.51 (1H, d), 7.41 (1H, d), 7.33-7.27 (3H, m), 6.90 (1H, d), 6.75 (1H, d), 4.72 (1H, d), 4.62 (1H, d), 3.80-3.69 (2H, m), 3.69 (3H, s), 3.44-3.25 (4H, m), 2.70 (3H, s), 2.50-2.35 (2H, m), 2.12 (3H, s).

Example 112

N-Methoxy-4-methyl-3-[3-[(1-methyl-1-phenylethyl)amino]-2-oxo-1(2H)-pyrazinyl]-benzamide

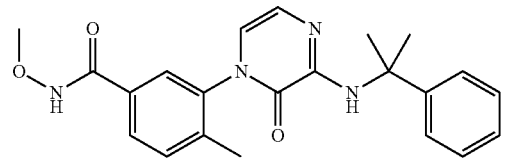

To a stirred solution of 3-(3,5-dibromo-2-oxo-2H-pyrazin-1-yl)-4-methyl-benzoic acid, methyl ester (Example 1b, 0.1 g) in tetrahydrofuran (1 mL) within a microwave vial was added triethylamine (38 µL) and α,α-dimethyl-benzenemethanamine (74 mg). The reaction was heated within a microwave for 120 minutes at 120° C. before being cooled to room temperature and the addition of O-methylhydroxylamine hydrochloride (83 mg) and cyclopentylmagnesium bromide (2M in diethyl ether, 2 mL) added dropwise. After stirring for 30 minutes, ethanol (2 mL) was added followed by the addition of ammonium formate (0.4 g) and 10% palladium on carbon (40 mg). The reaction mixture was heated within a microwave for 120 minutes at 80° C. before being cooled to room temperature, filtered and washed with ethanol. The filtrate was concentrated in vacuo. Purification by preparative HPLC (Gemini column, 0.1% ammonia:acetonitrile eluent) afforded the title compound as a solid (40 mg).

MS: APCI (+ve) 393 (M+H$^+$).

$^1$H NMR δ(DMSO-d$_6$, 400 MHz) 11.78 (1H, s), 7.79 (1H, dd), 7.67 (1H, s), 7.52 (1H, d), 7.41-7.37 (2H, m), 7.34-7.27 (2H, m), 7.21-7.16 (1H, m), 6.93 (1H, s), 6.67 (2H, s), 3.70 (3H, s), 2.13 (3H, s), 1.76 (3H, s), 1.73 (3H, s).

Example 113

N-Methoxy-4-methyl-3-[2-oxo-3-[[(1R)-1-phenylpropyl]amino]-1(2H)-pyrazinyl]-benzamide, trifluoroacetate

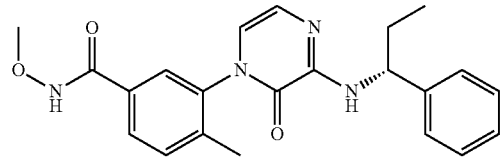

To a stirred solution of 3-(3,5-dibromo-2-oxo-2H-pyrazin-1-yl)-4-methyl-benzoic acid, methyl ester (Example 1b, 0.2 g) in tetrahydrofuran (2 mL) within a microwave vial was added triethylamine (80 µL) and α-ethyl-(αR)-benzenemethanamine (74 mg). The reaction was stirred for 12 h and ammonium formate (0.3 g), 10% palladium on carbon (30 mg) and ethanol (3 mL) were added. The reaction mixture was heated within a microwave for 30 minutes at 70° C. before being cooled to room temperature, filtered and washed with ethanol. The filtrate was concentrated in vacuo. The residue was treated with ethyl acetate and washed with water. The organic phase was concentrated and the residue taken up in tetrahydrofuran (5 mL) and O-methylhydroxylamine hydrochloride (166 mg) was added followed by dropwise addition of cyclopentylmagnesium bromide (2M in diethyl ether, 4 mL). After 30 min. sat. aqueous NH$_4$Cl was added and the mixture extracted with ethyl acetate. The organic phase was concentrated in vacuo. Purification by preparative HPLC (Gemini column, 0.1% trifluoroacetic acid:acetonitrile eluent) afforded the title compound as a solid (137 mg).

MS: APCI (+ve) 393 (M+H$^+$).

$^1$H NMR δ(DMSO-d$_6$, 400 MHz) 11.84-11.71 (1H, m), 7.78 (1H, d), 7.67 (1H, d), 7.52 (2H, t), 7.46-7.41 (2H, m), 7.35-7.30 (2H, m), 7.26-7.21 (1H, m), 6.82-6.79 (1H, m), 6.73-6.70 (1H, m), 4.90 (1H, q), 3.71 (1.5H, s), 3.68 (1.5H, s), 2.15 (1.5H, s), 2.09 (1.5H, s), 2.03-1.95 (1H, m), 1.90-1.78 (1H, m), 0.87 (3H, t).

Example 114

N-Cyclopropyl-4-methyl-3-(2-oxo-3-phenyl-1(2H)-pyrazinyl)-benzamide

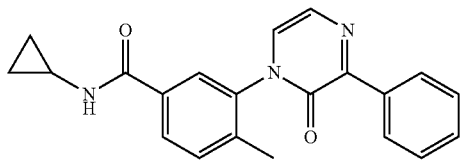

To a stirred solution of 3-(3,5-dibromo-2-oxo-2H-pyrazin-1-yl)-4-methyl-benzoic acid, methyl ester (Example 1b, 0.2 g) in tetrahydrofuran (2 mL) and water (1 mL) was added phenylboronic acid (61 mg), sodium carbonate (105 mg) and tetrakis(triphenylphosphine)palladium(0) (20 mg). The reagents were heated within a microwave at 120° C. for 30 minutes. The reaction was cooled to room temperature, phenylboronic acid (30 mg) added and then heated within a microwave at 80° C. for 40 minutes. The reaction was cooled to room temperature followed by the addition of ammonium formate (0.4 g), 10% palladium on carbon (30 mg), formic acid (0.2 mL) and ethanol (1 mL). The reaction mixture was heated within a microwave for 60 minutes at 100° C. before being cooled to room temperature. Water was added and the mixture extracted with ethyl acetate. The pooled organic were washed with water, dried ($Na_2SO_4$), filtered and concentrated. The product was taken up in tetrahydrofuran (4 mL) followed by the addition of cyclopropylamine (0.22 mL) and cyclopentylmagnesium bromide (2M in diethyl ether, 1.5 mL) dropwise. After stirring for 60 minutes, ethanol (2 mL) was added and the mixture was purified by preparative HPLC (Gemini column, 0.1% ammonia:acetonitrile eluent) to afford the title compound as a solid (20 mg).

MS: APCI (+ve) 346 (M+H[+]).

$^1$H NMR δ(DMSO-$d_6$, 400 MHz) 8.46 (1H, d), 8.30-8.24 (2H, m), 7.90 (1H, dd), 7.83 (1H, d), 7.66 (1H, d), 7.60 (1H, d), 7.53 (1H, d), 7.48-7.44 (3H, m), 2.89-2.82 (1H, m), 2.16 (3H, s), 0.72-0.67 (2H, m), 0.59-0.54 (2H, m).

Example 115

N-Ethyl-4-methyl-3-[2-oxo-3-[(phenylmethyl)amino]-1(2H)-pyrazinyl]-benzamide

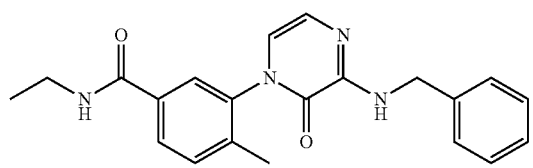

The title compound was prepared and purified in accordance to Example 1c using benzylamine and ethylamine (2M in tetrahydrofuran).

MS: APCI (+ve) 363 (M+H[+]).

$^1$H NMR δ(DMSO-$d_6$, 400 MHz) 8.47 (1H, t), 7.92 (1H, t), 7.88 (1H, dd), 7.77 (1H, d), 7.50 (1H, d), 7.36-7.29 (4H, m), 7.25-7.20 (1H, m), 6.83 (1H, d), 6.71 (1H, d), 4.59 (1H, dd), 4.49 (1H, dd), 3.30-3.24 (2H, m), 2.12 (3H, s), 1.11 (3H, t).

Example 116

N-Cyclopropyl-4-methyl-3-(2-oxo-3-phenoxy-1(2H)-pyrazinyl)-benzamide

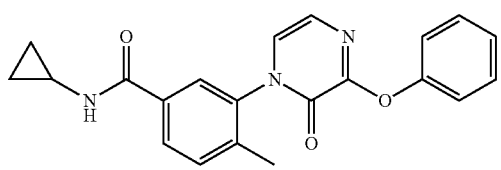

A mixture of 3-(3,5-dibromo-2-oxo-2H-pyrazin-1-yl)-4-methyl-benzoic acid, methyl ester (Example 1b, 204 mg), phenol (206 mg), N,N-diisopropylethylamine (0.3 mL) and tetrahydrofuran (1 mL) was heated within a microwave for 60 minutes at 140° C. before being cooled to room temperature. The mixture was transferred to a mixture of palladium on carbon (10%, 38 mg) and tetrahydrofuran (1 mL). 1,4-Cyclohexadiene (1 mL) was added and the mixture was heated under atmosphere of nitrogen within a microwave for 10 minutes at 90° C. before being cooled to room temperature. The mixture was filtered and concentrated. The residue was treated with tetrahydrofuran (10 mL), water (2 mL) and lithium hydroxide (193 mg). The mixture was stirred for 2 h, diluted with ethyl acetate, washed with 2M hydrochloric acid and water. The organic phase was dried ($Na_2SO_4$) and concentrated. The solid was washed with small amount of diethyl ether and treated with dichloromethane (3 mL) then N,N-dimethylformamide (1 drop) and oxalyl chloride (0.05 mL) were added. The mixture was stirred till solid disappeared and the solution of acid chloride was transferred to a solution of cyclopropylamine (0.3 mL) in dichloromethane (5 mL). The resulting mixture was stirred for 30 min. then diluted with ethyl acetate (50 mL). The mixture was washed with 2M hydrochloric acid and twice with water. The organic phase was dried ($Na_2SO_4$) and concentrated in vacuo. Purification by preparative HPLC (Gemini column, 0.1% ammonia:acetonitrile eluent) afforded the title compound as a solid (70 mg).

MS: APCI (+ve) 362 (M+H[+]).

$^1$H NMR δ(CDCl$_3$, 400 MHz) 7.74 (1H, dd), 7.65 (1H, d), 7.44 (3H, m), 7.27 (3H, m), 6.85 (1H, d), 6.80 (1H, d), 6.28 (1H, br s), 2.90 (1H, m), 2.28 (3H, s), 0.62 (2H, m), 0.88 (2H, m).

Example 117

N-Cyclopropyl-4-methyl-3-[2-oxo-3-(phenylthio)-1(2H)-pyrazinyl]-benzamide

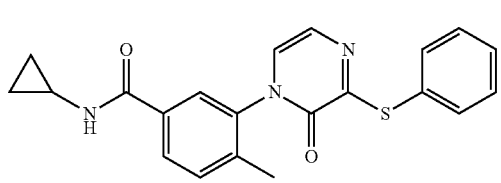

A mixture of N-cyclopropyl-4-methyl-3-(2-oxo-3-phenoxy-1(2H)-pyrazinyl)-benzamide (Example 116, 55 mg), benzenethiol (0.1 mL) and THF (1 mL) was heated under an atmosphere of nitrogen within a microwave for 90 minutes at 120° C. Purification by preparative HPLC (Gemini column, 0.1% ammonia:acetonitrile eluent) afforded the title compound as a solid (32 mg).

MS: APCI (+ve) 378 (M+H⁺).

¹H NMR δ(CDCl₃, 400 MHz) 7.74 (1H, dd), 7.61 (3H, m), 7.47 (3H, m), 7.41 (1H, d), 7.15 (1H, d), 6.81 (1H, d), 6.30 (1H, s), 2.88 (1H, m), 2.23 (3H, s), 0.86 (2H, m), 0.60 (2H, m).

Example 118

N-Cyclopropyl-4-methyl-3-[2-oxo-3-(phenylthio)-1 (2H)-pyrazinyl]-benzamide

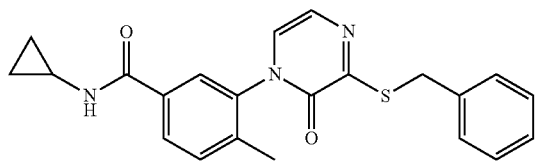

A solution of iso-propylmagnesium chloride (2M in tetrahydrofuran, 0.5 mL) was added to a stirred mixture of N-cyclopropyl-4-methyl-3-(2-oxo-3-phenoxy-1(2H)-pyrazinyl)-benzamide (Example 116, 45 mg), benzylthiol (0.2 mL) and tetrahydrofuran (0.5 mL) and the mixture was stirred at room temperature for 36 h. Solid NH₄Cl and water were added and the mixture extracted into ethyl acetate. The organic phase was dried (Na₂SO₄) and concentrated in vacuo. Purification by preparative HPLC (Gemini column, 0.1% ammonia:acetonitrile eluent) afforded the title compound as a solid (8 mg).

MS: APCI (+ve) 392 (M+H⁺).

¹H NMR δ(CDCl₃, 300 MHz) 7.72 (1H, d), 7.55 (1H, s), 7.35 (7H, m), 6.81 (1H, d), 6.31 (1H, s), 4.34 (2H, m), 2.86 (1H, m), 2.19 (3H, s), 0.83 (2H, m), 0.57 (2H, m).

Examples 119 and 120

N-Cyclopropyl-4-methyl-3-[3-(4-methyl-2-phenyl-1-piperazinyl)-2-oxo-1(2H)-pyrazinyl]-benzamide (Example 119) and 3-[5-bromo-3-(4-methyl-2-phenyl-1-piperazinyl)-2-oxo-1(2H)-pyrazinyl]-N-cyclopropyl-4-methyl-benzamide (Example 120)

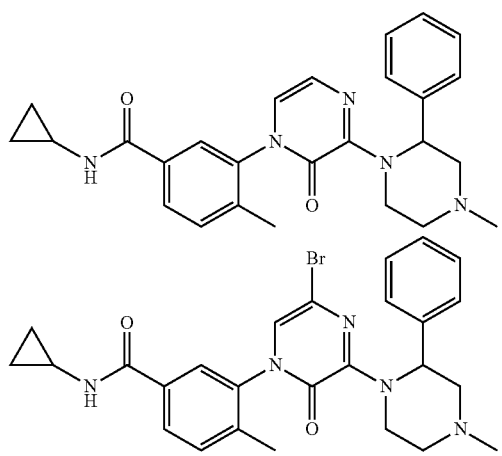

A mixture of 3-(3,5-dibromo-2-oxo-2H-pyrazin-1-yl)-4-methyl-benzoic acid, methyl ester (Example 1b, 115 mg), 1-methyl-3-phenyl-piperazine (77 mg), N,N-diisopropyl-ethylamine (0.1 mL) and tetrahydrofuran (1 mL) was heated within a microwave for 30 minutes at 100° C. before being cooled to room temperature. The mixture was transferred to a mixture of palladium on carbon (10%, 50 mg) and tetrahydrofuran (1 mL) and 1,4-cyclohexadiene (1 mL) was added. The mixture was heated under atmosphere of nitrogen within a microwave for 2.5 h at 120° C. An additional portion of palladium on carbon (50 mg) in tetrahydrofuran (1 mL) was added and the mixture was heated for 1 h at 120° C. After cooling, cyclopropylamine (0.3 mL) was added followed by dropwise addition of a solution of iso-propylmagnesium chloride (2M in tetrahydrofuran, 2.5 mL). The mixture was stirred for 10 min. and quenched with sat. aqueous NH₄Cl and extracted into ethyl acetate. The organic phase was dried (Na₂SO₄), filtered and concentrated. Purification by preparative HPLC (Gemini column, 0.1% ammonia:acetonitrile eluent) afforded N-cyclopropyl-4-methyl-3-(4-methyl-3'-oxo-2-phenyl-3,4,5,6-tetrahydro-2H,3'H-[1,2']bipyrazinyl-4'-yl)-benzamide (49 mg) and 3-(6'-Bromo-4-methyl-3'-oxo-2-phenyl-3,4,5,6-tetrahydro-2H,3'H-1-[1,2']bipyrazinyl-4'-yl)-N-cyclopropyl-4-methyl-benzamide (8 mg).

N-Cyclopropyl-4-methyl-3-[3-(4-methyl-2-phenyl-1-piperazinyl)-2-oxo-1(2H)-pyrazinyl]-benzamide MS: APCI (+ve) 444 (M+H⁺).

¹H NMR δ(DMSO-d₆, 400 MHz) 8.45 (1H, m), 7.88-7.83 (1H, m), 7.75 and 7.71 (1H, 2×d), 7.52-7.42 (3H, m), 7.37-7.28 (2H, m), 7.25-7.16 (1H, m), 6.98 (2H, s), 6.17 and 6.07 (1H, 2×br s), 3.27-3.10 (1H, m), 2.90-2.70 (2H, m), 2.48-2.37 (2H, m), 2.20 (3H, m), 2.15 (2H, m), 2.11 and 2.04 (3H, 2×s), 0.69 (2H, m), 0.55 (2H, m).

3-[5-Bromo-3-(4-methyl-2-phenyl-1-piperazinyl)-2-oxo-1(2H)-pyrazinyl]-N-cyclopropyl-4-methyl-benzamide MS: APCI (+ve) 522 (M+H⁺).

¹H NMR δ(DMSO-d₆, 400 MHz) 8.42 (1H, m), 7.85 (1H, m), 7.77 and 7.74 (1H, 2×d), 7.52-7.41 (3H, m), 7.37-7.28 (2H, m), 7.27-7.19 (2H, m), 6.28 and 6.16 (1H, 2×br s), 3.29 (3H, s), 3.18-3.03 (1H, m), 2.89-2.72 (2H, m), 2.48-2.36 (1H, m), 2.20 (3H, m), 2.15 and 2.07 (3H, 2×s), 0.69 (2H, m), 0.55 (2H, m).

Example 121

N-Cyclopropyl-3-[3-[[2-(dimethylamino)ethyl](phenylmethyl)amino]-2-oxo-1(2H)-pyrazinyl]-4-methyl-benzamide

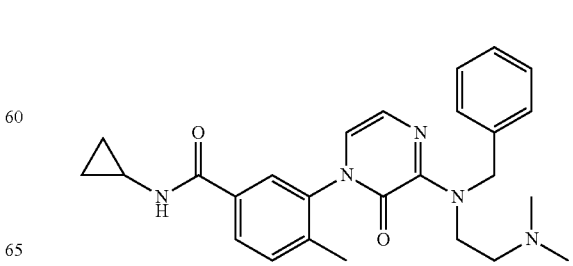

a) 3-[3-[[2-(Dimethylamino)ethyl](phenylmethyl) amino]-2-oxo-1(2H)-pyrazinyl]-4-methyl-benzoic acid, methyl ester A mixture of 3-(3,5-dibromo-2-oxo-2H-pyrazin-1-yl)-4-methyl-benzoic acid, methyl ester (Example 1b, 129 mg), W-benzyl-N,N-dimethylethylenediamine (0.1 mL), N,N-diisopropylethylamine (0.1 mL) and tetrahydrofuran (1 mL) was heated within a microwave for 15 minutes at 100° C. before being cooled to room temperature. The mixture was transferred to a mixture of palladium on carbon (10%, 50 mg) and tetrahydrofuran (1 mL) and 1,4-cyclohexadiene (1 mL) was added. The mixture was heated within a microwave for 60 minutes at 120° C. before being cooled to room temperature. The mixture was filtered and the filtrated concentrated in vacuo. Purification by preparative HPLC (Gemini column, 0.1% ammonia:acetonitrile eluent) afforded the title compound as a solid (50 mg).

$^1$H NMR δ(CDCl$_3$, 300 MHz) 8.00 (1H, dd), 7.90 (1H, d), 7.40 (1H, d), 7.35-7.17 (5H, m), 6.96 (1H, d), 6.50 (1H, d), 5.16 (1H, d), 4.97 (1H, d), 3.97-3.84 (4H, m), 3.90 (3H, m), 3.71 (1H, m), 2.55 (2H, m), 2.22 (6H, s), 2.20 (3H, s).

b) N-Cyclopropyl-3-[3-[[2-(dimethylamino)ethyl] (phenylmethyl)amino]-2-oxo-1(2H)-pyrazinyl]-4-methyl-benzamide A mixture of 3-{3-[benzyl-(2-dimethylamino-ethyl)-amino]-2-oxo-2H-pyrazin-1-yl}-4-methyl-benzoic acid, methyl ester (Example 121a, 50 mg), cyclopropylamine (1 mL) and water (0.5 mL) was stirred at room temperature for 10 days. Purification by preparative HPLC (Gemini column, 0.1% ammonia:acetonitrile eluent) afforded the title compound as a solid (10 mg).

MS: APCI (+ve) 446 (M+H$^+$).

$^1$H NMR δ(DMSO-d$_6$, 300 MHz) 8.52 (1H, s), 7.85 (1H, d), 7.74 (1H, s), 7.46 (1H, d), 7.38-7.19 (5H, m), 6.93 (1H, m), 6.86 (1H, m), 5.10 (1H, d), 4.84 (1H, d), 3.85 (1H, m), 3.58 (2H, m), 2.85 (1H, m), 2.10 (6H, s), 2.08 (3H, s), 0.69 (2H, m), 0.56 (2H, m).

Example 122

1-[3-[5-Bromo-2-oxo-3-[3-phenyl-4-[2-(1-pyrrolidinyl)ethyl]-1-piperazinyl]-1(2H)-pyrazinyl]-4-methyl-benzoyl]-pyrrolidine

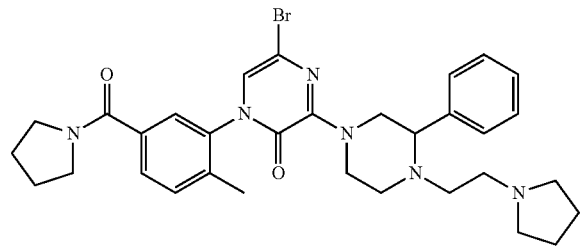

A mixture of 3-(3,5-dibromo-2-oxo-2H-pyrazin-1-yl)-4-methyl-benzoic acid, methyl ester (Example 1b, 200 mg), 2-phenylpiperazine (100 mg), N,N-diisopropylethylamine (0.1 mL) and tetrahydrofuran (1 mL) was stirred at room temperature for 2 h. 1,2-Dibromoethane (0.2 mL) was added and the mixture was heated within a microwave for 2 h at 120° C. The mixture was quenched with sat. aqueous NaHCO$_3$ and extracted with ethyl acetate. The organic phase was dried (Na$_2$SO$_4$), filtered and concentrated in vacuo. Pyrrolidine (0.4 mL) was added and the mixture was heated within a microwave for 15 min. at 100° C. After cooling the mixture was purified by preparative HPLC (Gemini column, 0.1% ammonia:acetonitrile eluent) to give the title compound (60 mg).

MS: APCI (+ve) 619 (M+H$^+$).

$^1$H NMR δ(DMSO-d$_6$, 400 MHz) 7.53 (1H, dd), 7.49 and 7.45 (1H, 2×d), 7.45-7.27 (6H, m), 7.22 (1H, d), 3.49-3.33 (8H, m), 3.18 (1H, m), 3.09 (1H, m), 2.83 (1H, m), 2.48-2.30 (6H, m), 2.24 (4H, m), 2.12 and 2.08 (3H, s), 1.83 (4H, m), 1.56 (4H, m), 2.06 (1H, m).

Further elution of the column gave 3-[5-bromo-2-oxo-3-[3-phenyl-4-[2-(1-pyrrolidinyl)ethyl]-1-piperazinyl]-1(2H)-pyrazinyl]-4-methyl-benzoic acid, methyl ester (50 mg) that was used in the next step (Example 123).

MS: APCI (+ve) 580 (M+H$^+$).

$^1$H NMR δ(DMSO-d$_6$, 400 MHz) 7.95 (1H, dd), 7.89 and 7.86 (1H, 2×d), 7.54 (1H, t), 7.41-7.26 (5H, m), 7.23 (1H, d), 3.86 and 3.84 (3H, 2×s), 3.39-3.27 (1H, m), 3.23-3.02 (2H, m), 2.83 (1H, m), 2.48-2.30 (6H, m), 2.24 (4H, m), 2.17 and 2.12 (3H, s), 2.06 (1H, m), 1.57 (4H, m).

Example 123

N-Cyclopropyl-4-methyl-3-[2-oxo-3-[3-phenyl-4-[2-(1-pyrrolidinyl)ethyl]-1-piperazinyl]-1(2H)-pyrazinyl]-benzamide

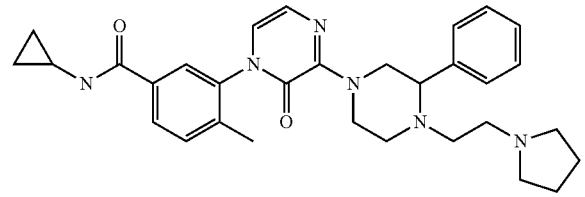

A mixture of 3-[5-bromo-2-oxo-3-[3-phenyl-4-[2-(1-pyrrolidinyl)ethyl]-1-piperazinyl]-1(2H)-pyrazinyl]-4-methyl-benzoic acid, methyl ester (50 mg), ammonium formate (322 mg), palladium 10% on carbon (22 mg), N,N-diisopropylethylamine (0.1 mL) and ethanol (2.5 mL) was heated under an atmosphere of nitrogen within a microwave for 30 min. at 70° C. The mixture was filtered and concentrated. Cyclopropylamine (0.3 mL) and water (0.5 mL) were added and the mixture was heated under atmosphere of nitrogen within a microwave for 5 h at 100° C. and concentrated in vacuo. Purification by preparative HPLC (Gemini column, 0.1% TFA:acetonitrile eluent) gave the title compound (30 mg).

MS: APCI (+ve) 527 (M+H$^+$).

$^1$H NMR δ(CDCl$_3$, 300 MHz) 8.04 and 7.88 (1H, d), 7.73 (1H, d), 7.64-7.33 (6H, m), 7.02 (1H, m), 6.64 (1H, m), 6.34 (1H, s), 5.06-4.65 (2H, m), 3.78 (1H, m), 3.58-2.64 (13H, m), 2.20 and 2.17 (3H, 2×s), 2.00 (4H, m), 0.86 (2H, m), 0.60 (2H, m).

Example 124

3-[3-[[[3-(Aminomethyl)phenyl]methyl]amino]-2-oxo-1(2H)-pyrazinyl]-N-cyclopropyl-4-methyl-benzamide

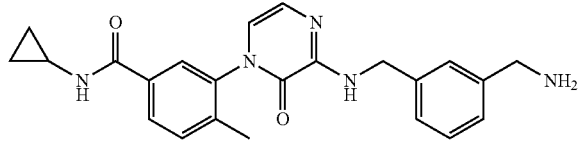

A mixture of [[3-[[[4-[5-[(cyclopropylamino)carbonyl]-2-methylphenyl]-3,4-dihydro-3-oxopyrazinyl]amino]methyl]phenyl]methyl]-carbamic acid, 1,1-dimethylethyl ester (Example 51, 90 mg), dichloromethane (2 mL) and trifluoroacetic acid (0.5 mL) was stirred at room temperature for 30 min. The mixture was concentrated in vacuo. Purification by preparative HPLC (Gemini column, 0.1% ammonia: acetonitrile eluent) afforded the title compound as a solid (22 mg).

MS: APCI (+ve) 404 (M+H$^+$)

$^1$H NMR δ(DMSO-d$_6$, 400 MHz) 8.43 (1H, d), 7.86 (2H, m), 7.75 (1H, s), 7.49 (1H, d), 7.29 (1H, s), 7.27-7.13 (3H, m), 6.83 (1H, d), 6.70 (1H, d), 4.58 (1H, dd), 4.47 (1H, dd), 3.69 (2H, s), 3.29 (2H, s), 2.84 (1H, m), 2.11 (3H, s), 0.68 (2H, m), 0.55 (2H, m).

Example 125

3-[3-[[[4-(Aminomethyl)phenyl]methyl]amino]-2-oxo-1(2H)-pyrazinyl]-N-cyclopropyl-4-methyl-benzamide

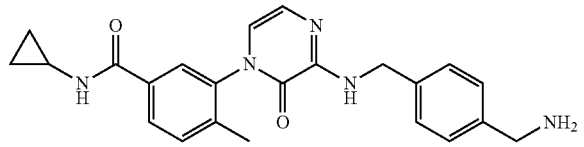

The title compound was prepared from Example 54 using the method described for Example 124.

MS: APCI (+ve) 404 (M+H$^+$).

$^1$H NMR δ(DMSO-d$_6$, 400 MHz) 8.43 (1H, d), 7.87 (2H, m), 7.75 (1H, s), 7.49 (1H, d), 7.26 (4H, s), 6.82 (1H, d), 6.69 (1H, d), 4.55 (1H, dd), 4.45 (1H, dd), 3.67 (2H, s), 2.84 (1H, m), 2.11 (3H, s), 0.69 (2H, m), 0.54 (2H, m).

Example 126 and Example 127

N-Methoxy-4-methyl-3-[2-oxo-3-(3-phenyl-1-piperazinyl)-1(2H)-pyrazinyl]-benzamide (Example 126) and 3-(3-cyclopentyl-2-oxo-1(2H)-pyrazinyl)-N-methoxy-4-methyl-benzamide (Example 127)

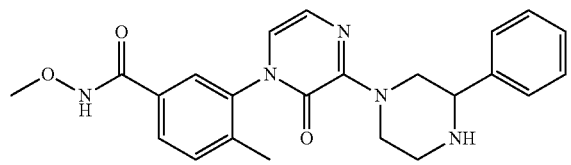

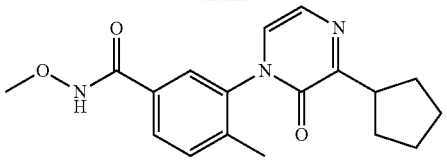

A mixture of 3-(3,5-dibromo-2-oxo-2H-pyrazin-1-yl)-4-methyl-benzoic acid, methyl ester (Example 1b, 0.21 g), N,N-diisopropylethylamine (0.2 mL), 2-phenylpiperazine (0.12 g) and tetrahydrofuran (1 mL) was stirred at room temperature for 2 h. Ethanol (3 mL) was added followed by wet 10% palladium on carbon (50 mg) and ammonium formate (0.45 g). The mixture was stirred under nitrogen atmosphere at 70° C. for 30 min. The mixture was filtered through a pad of Celite. The filtrate concentrated in vacuo. The residue was treated with O-methylhydroxylamine hydrochloride (180 mg) and tetrahydrofuran (1 mL) followed by addition of cyclopentylmagnesium bromide (2M in diethyl ether, 0.8 mL). The mixture was stirred for 10 min., quenched with sat. NH$_4$Cl and extracted into ethyl acetate. The organic phase was concentrated in vacuo. Purification by preparative HPLC (Gemini column, 0.1% TFA:acetonitrile eluent) afforded N-methoxy-4-methyl-3-[2-oxo-3-(3-phenyl-1-piperazinyl)-1(2H)-pyrazinyl]-benzamide trifluoroacetate (50 mg) and 3-(3-cyclopentyl-2-oxo-2H-pyrazin-1-yl)-N-methoxy-4-methyl-benzamide trifluoroacetate (67 mg).

N-Methoxy-4-methyl-3-[2-oxo-3-(3-phenyl-1-piperazinyl)-1(2H)-pyrazinyl]-benzamide, trifluoroacetate MS: APCI (+ve) 420 (M+H$^+$).

$^1$H NMR δ(DMSO-d$_6$, 400 MHz) 11.81 (1H, s), 7.77 (1H, dd), 7.66 and 7.63 (1H, 2×d), 7.54-7.46 (3H, m), 7.45-7.32 (3H, m), 7.08-7.03 (2H, m), 4.83-4.62 (2H, m), 4.24 (1H, s), 3.71 and 3.70 (3H, 2×s), 3.21-2.99 (4H, m), 2.13 and 2.10 (3H, 2×s).

3-(3-Cyclopentyl-2-oxo-2H-pyrazin-1-yl)-N-methoxy-4-methyl-benzamide, trifluoroacetate MS: APCI (+ve) 328 (M+H$^+$).

$^1$H NMR δ(DMSO-d$_6$, 400 MHz) 11.80 (1H, s), 7.79 (1H, dd), 7.67 (1H, d), 7.52 (1H, d), 7.44 (1H, d), 7.32 (1H, d), 3.88 (1H, s), 3.70 (3H, s), 3.49 (1H, quintet), 2.09 (3H, s), 2.00-1.86 (2H, m), 1.84-1.54 (6H, m).

Example 128

N-Cyclopropyl-4-methyl-3-[3-[[[2-(methylthio)phenyl]methyl]amino]-2-oxo-1(2H)-pyrazinyl]-benzamide

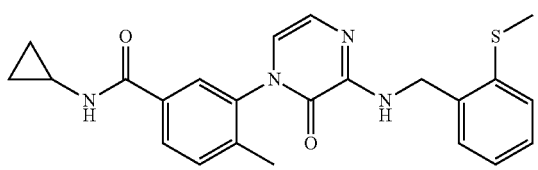

a) 4-Methyl-3-(2-oxo-3-phenoxy-1(2H)-pyrazinyl)-benzoic acid, methyl ester

A mixture of 3-(3,5-dibromo-2-oxo-2H-pyrazin-1-yl)-4-methyl-benzoic acid, methyl ester (Example 1b, 400 mg), phenol (400 mg), N,N-diisopropylethylamine (0.4 mL) and tetrahydrofuran (2 mL) was heated within a microwave for 3 h at 120° C. before being cooled to room temperature. The mixture was transferred to a mixture of palladium on carbon (10%, 38 mg) and tetrahydrofuran (1 mL). 1,4-Cyclohexadiene (2 mL) was added and the mixture was heated under atmosphere of nitrogen within a microwave for 15 minutes at 90° C. before being cooled to room temperature. The mixture was filtered and concentrated to give a crude product that was used in the next step without purification.

b) N-Cyclopropyl-4-methyl-3-[3-[[[2-(methylthio)phenyl]methyl]amino]-2-oxo-1(2H)-pyrazinyl]-benzamide A mixture of 4-methyl-3-(2-oxo-3-phenoxy-2H-pyrazin-1-yl)-benzoic acid, methyl ester (Example 128a, 111 mg), 2-(methylthio)-benzenemethanamine (100 mg) and tetrahydrofuran (1 mL) was heated within a microwave for 5 h at 120° C. before being cooled to room temperature. Cyclopropylamine (0.2 mL) was added followed by addition of cyclopentylmagnesium bromide (2M in diethyl ether, 0.8 mL). The mixture was stirred for 10 min., quenched with sat. NH$_4$Cl and extracted into ethyl acetate. The organic phase was concentrated in vacuo. Purification by preparative HPLC (Gemini column, 0.1% ammonia:acetonitrile eluent) afforded the title compound as a solid (39 mg).

MS: APCI (+ve) 421 (M+H$^+$).

$^1$H NMR δ(DMSO-d$_6$, 300 MHz) 8.45 (1H, d), 7.88 (1H, dd), 7.80-7.73 (2H, m), 7.50 (1H, d), 7.33-7.22 (2H, m), 7.19-7.08 (2H, m), 6.81 (1H, d), 6.72 (1H, d), 4.57 (1H, dd), 4.46 (1H, dd), 2.91-2.80 (1H, m), 2.51 (3H, s), 2.13 (3H, s), 0.70 (2H, m), 0.57 (2H, m).

Example 129

3-[3-[[(2-Chlorophenyl)methyl]amino]-2-oxo-1(2H)-pyrazinyl]-N-cyclopropyl-4-methyl-benzamide

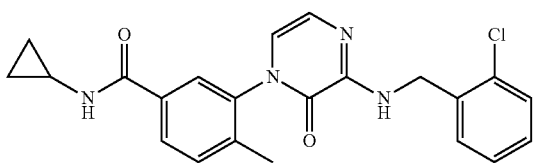

The title compound was prepared from of 4-methyl-3-(2-oxo-3-phenoxy-1(2H)-pyrazinyl)-benzoic acid, methyl ester (Example 128a) and 2-chlorobenzenemethanamine using the method described for Example 128.

MS: APCI (+ve) 409 (M+H$^+$).

$^1$H NMR δ(DMSO-d$_6$, 400 MHz) 8.45 (1H, d), 7.92 (1H, t), 7.88 (1H, dd), 7.78 (1H, d), 7.50 (1H, d), 7.45 (1H, m), 7.34-7.24 (3H, m), 6.81 (1H, d), 6.74 (1H, d), 4.65 (1H, dd), 4.55 (1H, dd), 2.86 (1H, m), 2.14 (3H, s), 0.70 (2H, m), 0.56 (2H, m).

Example 130

3-[3-[[(3-Chlorophenyl)methyl]amino]-2-oxo-1(2H)-pyrazinyl]-N-cyclopropyl-4-methyl-benzamide

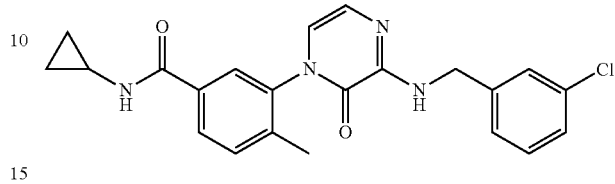

The title compound was prepared from 4-methyl-3-(2-oxo-3-phenoxy-1(2H)-pyrazinyl)-benzoic acid, methyl ester (Example 128a) and 3-chlorobenzenemethanamine using the method described for Example 128.

MS: APCI (+ve) 409 (M+H$^+$).

$^1$H NMR δ(DMSO-d$_6$, 400 MHz) 8.43 (1H, d), 8.03 (1H, t), 7.87 (1H, dd), 7.76 (1H, d), 7.49 (1H, d), 7.39-7.36 (1H, m), 7.34 (1H, d), 7.32-7.26 (2H, m), 6.82 (1H, d), 6.72 (1H, d), 4.58 (1H, dd), 4.48 (1H, dd), 2.85 (1H, m), 2.11 (3H, s), 0.69 (2H, m), 0.55 (2H, m).

Example 131

N-Cyclopropyl-4-methyl-3-[3-[[(1R)-3-(4-methyl-1-piperazinyl)-3-oxo-1-phenylpropyl]amino]-2-oxo-1(2H)-pyrazinyl]-benzamide

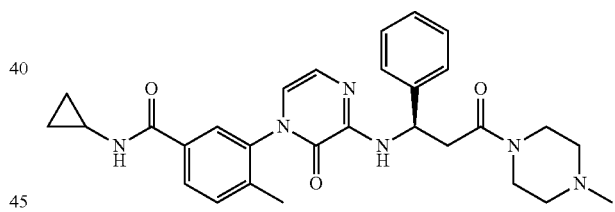

A solution of iso-propylmagnesium chloride (2M in tetrahydrofuran, 1.3 mL) was added to a stirred mixture of (□R)-□-[[4-[5-[(cyclopropylamino)carbonyl]-2-methylphenyl]-3,4-dihydro-3-oxopyrazinyl]amino]-benzenepropanoic acid, 1,1-dimethylethyl ester (Example 87, 100 mg), 1-methylpiperazine (0.2 mL) and tetrahydrofuran (2 mL). The reaction mixture was heated within a microwave for 20 min. at 60° C. before being cooled to room temperature and quenched with sat. aqueous NH$_4$Cl. The mixture was extracted into ethyl acetate. The organic phase was concentrated in vacuo. Purification by preparative HPLC (Gemini column, 0.1% ammonia:acetonitrile eluent) afforded the title compound as a solid (60 mg).

MS: APCI (+ve) 415 (M+H$^+$).

$^1$H NMR δ(DMSO-d$_6$, 400 MHz) 8.44 and 8.39 (1H, 2×d), 7.91-7.83 (2H, m), 7.74 and 7.72 (1H, 2×d), 7.49 and 7.48 (1H, 2×d), 7.43-7.36 (2H, m), 7.31 and 7.30 (2H, 2×t), 7.25-7.18 (1H, m), 6.797 and 6.794 (1H, 2×d), 6.683 and 6.679 (1H, 2×d), 5.47 (1H, m), 3.45-3.30 (8H, m), 3.19 (1H, dd), 2.88-2.80 (1H, m), 2.76 (1H, dd), 2.13, 2.11, 2.10, 2.08 (6H, 4×s), 0.68 (2H, m), 0.55 (2H, m).

Example 132

N-Methoxy-4-methyl-3-[2-oxo-3-(1-pyrrolidinyl)-1(2H)-pyrazinyl]-benzamide

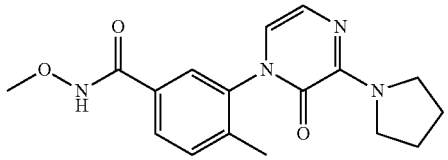

The title compound was prepared from 3-(3,5-dibromo-2-oxo-2H-pyrazin-1-yl)-4-methyl-benzoic acid, methyl ester using the method described in Example 126.

MS: APCI (+ve) 329 (M+H$^+$).

$^1$H NMR δ(DMSO-d$_6$, 400 MHz) 11.81 (1H, s), 7.76 (1H, d), 7.64 (1H, s), 7.50 (1H, d), 6.84 (1H, d), 6.78 (1H, d), 3.91-3.72 (4H, m), 3.70 (3H, s), 2.15 (3H, s), 1.96-1.82 (4H, m).

Example 133

N-Cyclopropyl-4-methyl-3-[2-oxo-3-[[2-[4-[2-(1-pyrrolidinyl)ethoxy]phenyl]ethyl]amino]-1(2H)-pyrazinyl]-benzamide

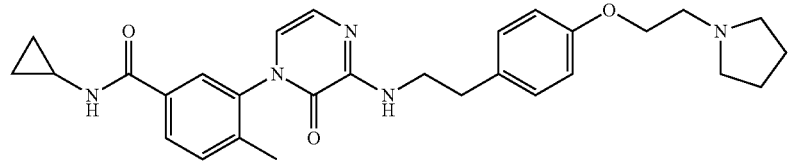

To a stirred solution of 3-(3,5-dibromo-2-oxo-2H-pyrazin-1-yl)-4-methyl-benzoic acid, methyl ester (Example 1b, 0.1 g) in tetrahydrofuran (2 mL) was added triethylamine (0.17 mL) and 4-(2-aminoethyl)-phenol (34 mg). The reaction mixture was stirred for 12 h and 1-(2-chloroethyl)-pyrrolidine hydrochloride (120 mg), cesium carbonate (646 mg) and N,N-dimethylformamide (2 mL) were added. The mixture was heated within a microwave at 130° C. for 100 minutes. The reaction mixture was cooled to room temperature and quenched with sat. NaHCO$_3$. The mixture was extracted with dichloromethane. The pooled organics were washed with water and brine, dried (Na$_2$SO$_4$), filtered and the solvent removed. The product was taken up in tetrahydrofuran (3 mL) followed by the addition of cyclopropylamine (0.15 mL) and cyclopentylmagnesium bromide (2M in diethyl ether, 0.75 mL) portionwise. The reaction mixture was stirred under nitrogen for 1 h before the addition of ethanol (2 mL), ammonium formate (300 mg) and 10% palladium on carbon (30 mg). The reaction mixture was heated within a microwave at 100° C. for 60 minutes, filtered and washed with ethanol. The filtrate was concentrated in vacuo. Purification by preparative HPLC (Gemini column, 0.1% ammonia:acetonitrile eluent) afforded the title compound (60 mg).

MS: APCI (+ve) 502 (M+H$^+$).

$^1$H NMR δ(DMSO-d$_6$, 400 MHz) 8.43 (1H, d), 7.86 (1H, dd), 7.73 (1H, d), 7.48 (1H, d), 7.29 (1H, t), 7.17-7.12 (2H, m), 6.89-6.84 (3H, m), 6.68 (1H, d), 4.02 (2H, t), 3.60-3.44 (2H, m), 2.88-2.78 (3H, m), 2.76 (2H, t), 2.54-2.46 (4H, m), 2.09 (3H, s), 1.71-1.65 (4H, m), 0.71-0.66 (2H, m), 0.58-0.53 (2H, m).

Example 134

N-Cyclopropyl-4-methyl-3-[3-[[1-methyl-1-[2-[2-(1-pyrrolidinyl)ethoxy]phenyl]ethyl]amino]-2-oxo-1(2H)-pyrazinyl]-benzamide

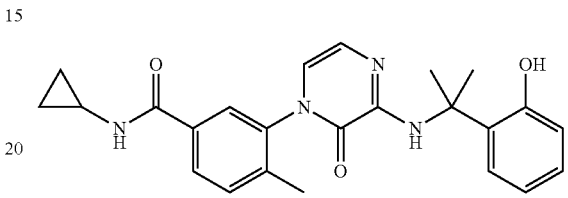

a) α,α-Dimethyl-2-(phenylmethoxy)-benzenemethanamine

A suspension of anhydrous cerium chloride (1.0 g) in anhydrous tetrahydrofuran (10 mL) under nitrogen was stirred for 30 minutes and then cooled to −78° C. A solution of methyl lithium in diethyl ether (1.6M, 3 mL) was added and the reaction mixture was stirred for 30 minutes. A solution of 2-(phenylmethoxy)-benzonitrile (0.3 g) in tetrahydrofuran (2 mL) was added. The reaction was stirred and gradually warmed to −10° C. then cooled to −78° C. and quenched with conc. ammonia solution. The mixture was stirred for 12 h then filtered and the solid washed with ethyl acetate. The organic phase was separated and the aqueous phase being extracted twice with ethyl acetate. The pooled organics were washed with water, brine then dried (Na$_2$SO$_4$), filtered and concentrated in vacuo. Purification using SCX chromatography afforded the subtitle compound (360 mg).

b) N-Cyclopropyl-3-[3-[[1-(2-hydroxyphenyl)-1-methylethyl]amino]-2-oxo-1(2H)-pyrazinyl]-4-methyl-benzamide To a stirred solution of 3-(3,5-dibromo-2-oxo-2H-pyrazin-1-yl)-4-methyl-benzoic acid methyl ester (Example 1b, 0.4 g) in tetrahydrofuran (3 mL) within a microwave vial was added N,N-diisopropylethylamine (200 μL) and α,α-dimethyl-2-(phenylmethoxy)-benzenemethanamine (360 mg). The reaction was heated in a microwave for 100 minutes at 120° C. The reaction mixture was cooled to room temperature and cyclopropylamine (0.5 mL) was added. A solution of cyclopentylmagnesium bromide (2M in diethyl ether, 3 mL) was added dropwise. The reaction mixture was stirred for 30 minutes. Ethanol (2 mL) and sat. aqueous NH$_4$Cl were added and the mixture extracted with ethyl acetate. The pooled organic were washed with brine, dried (Na$_2$SO$_4$), filtered and concentrated in vacuo. The residue was taken up in ethanol (3 mL) and ammonium formate (0.3 g) and 10% palladium on carbon (40 mg) were added. The reaction mixture was heated within a microwave for 30 minutes at 100° C. and then 90 minutes at 60° C. before being cooled to room temperature, then filtered and washed with ethanol. The filtrate was concentrated in vacuo. The residue was purified (SiO$_2$ chromatography eluting with iso-hexane:ethyl acetate) to afford the subtitle compound as a solid (330 mg).

MS: APCI (+ve) 419 (M+H$^+$).

$^1$H NMR δ(DMSO-d$_6$, 400 MHz) 9.50 (1H, s), 8.43 (1H, d), 7.86 (1H, dd), 7.73 (1H, d), 7.48 (1H, d), 7.24 (1H, dd), 7.06-7.01 (1H, m), 6.99-6.97 (1H, m), 6.79-6.72 (2H, m), 6.70 (1H, d), 6.64 (1H, d), 2.89-2.81 (1H, m), 2.10 (3H, s), 1.85 (3H, s), 1.82 (3H, s), 0.71-0.66 (2H, m), 0.57-0.53 (2H, m).

Example 135

N-Cyclopropyl-4-methyl-3-[3-[[1-methyl-1-[2-[2-(1-pyrrolidinyl)ethoxy]phenyl]ethyl]amino]-2-oxo-1(2H)-pyrazinyl]-benzamide

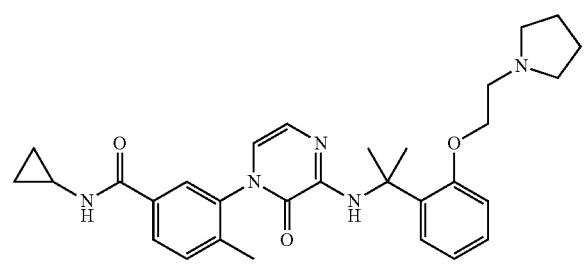

To a stirred solution of N-cyclopropyl-3-(3-(2-(2-hydroxyphenyl)propan-2-ylamino)-2-oxopyrazin-1(2H)-yl)-4-methylbenzamide (Example 134, 0.1 g) in N,N-dimethylformamide (3 mL), N-(2-chloroethyl)-pyrrolidine, hydrochloride (0.12 g) and cesium carbonate (0.47 g) were added. The reaction was stirred under nitrogen at 80° C. for 12 h. After 2 h additional batches of N-(2-chloroethyl)-pyrrolidine hydrochloride (0.12 g) and cesium carbonate (0.47 g) were added. The reaction mixture was stirred at 100° C. for 10 h and then at 90° C. for 10 h. Ethyl acetate was added and the mixture was washed with water and brine. The organic phase was dried (Na$_2$SO$_4$), filtered and concentrated in vacuo. Purification by preparative HPLC (Gemini column—acetonitrile/0.1% ammonia mobile phase) afforded the title compound as a solid (34 mg).

MS: APCI (+ve) 516 (M+H$^+$).

$^1$H NMR δ(DMSO-d$_6$, 400 MHz) 8.42 (1H, d), 7.86 (1H, dd), 7.72 (1H, d), 7.48 (1H, d), 7.32 (1H, dd), 7.21-7.16 (1H, m), 6.98 (1H, d), 6.92-6.86 (2H, m), 6.65 (1H, d), 6.62 (1H, d), 4.06-3.94 (2H, m), 2.88-2.80 (1H, m), 2.79 (2H, t), 2.52-2.43 (4H, m), 2.09 (3H, s), 1.83 (6H, s), 1.69-1.61 (4H, m), 0.72-0.66 (2H, m), 0.57-0.51 (2H, m).

Example 136

N-Cyclopropyl-3-[3-[[(1R,2R)-3-hydroxy-2-methyl-1-phenylpropyl]amino]-2-oxo-1(2H)-pyrazinyl]-4-methyl-benzamide

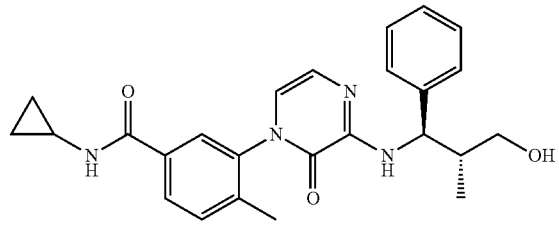

a) (2S)-3-[[(1,1-Dimethylethyl)diphenylsilyl]oxy]-N-methoxy-N,2-dimethyl-propanamide A solution of iso-propylmagnesium chloride (2M in tetrahydrofuran, 28 mL) was added dropwise to a stirred mixture of (2S)-3-(tert-butyl-diphenyl-silanyloxy)-2-methyl-propionic acid, methyl ester (Eur. J. Org. Chem. 2006, 3645, 7.5 g), O,N-dimethylhydroxylamine hydrochloride (2.55 g) and tetrahydrofuran (65 mL) at 0° C. After completion the mixture was quenched with sat. aqueous NH$_4$Cl and extracted into ethyl acetate. The organic phase was dried (Na$_2$SO$_4$), filtered and concentrated in vacuo to give the crude product as a solid (8.1 g).

$^1$H NMR δ(CDCl$_3$, 400 MHz) 7.72-7.62 (4H, m), 7.45-7.34 (6H, m), 3.93 (1H, dd), 3.66 (3H, s), 3.59 (1H, dd), 3.20 (3H, s), 3.26-3.14 (1H, m), 1.08 (3H, d), 1.03 (9H, s)

b) (R)—N-[(1R,2R)-3-[[(1,1-Dimethylethyl)diphenylsilyl]oxy]-2-methyl-1-phenylpropyl]-2-methyl-2-propanesulfinamide A solution of diisobutylaluminium hydride in tetrahydrofuran (1M, 50 mL) was added dropwise to a stirred solution of (2S)-3-[[(1,1-dimethylethyl)diphenylsilyl]oxy]-N-methoxy-N,2-dimethyl-propanamide (Example 136a, 6.2 g) in tetrahydrofuran (40 mL) at 0° C. The mixture was stirred for 30 minutes and poured onto a mixture of ethyl acetate (250 mL) and 2M hydrochloric acid (100 mL). The organic phase was washed with brine, dried (Na$_2$SO$_4$), filtered and concentrated in vacuo to give the crude aldehyde. Tetrahydrofuran (30 mL) was added followed by (R)-(+)-2-methyl-2-propanesulfinamide (2.6 g) and titanium ethoxide (10 mL). The mixture was stirred at room temperature for 90 min., then diluted with ethyl acetate (300 mL) and quenched with brine (100 mL). The mixture was stirred for 1 h. The organic phase was separated, dried (Na$_2$SO$_4$), filtered through a pad of Celite and concentrated in vacuo to give the crude sulfinimine, which was dissolved in dry dichloromethane (90 mL) and the solution was cooled to −50° C. A solution of phenylmagnesium bromide in diethyl ether (3M, 13 mL) was added dropwise and the reaction mixture was warmed up to 0° C. over 3 h, quenched with sat. aqueous NH$_4$Cl (150 mL) and extracted into dichloromethane. The organic phase was dried (Na$_2$SO$_4$), filtered and concentrated in vacuo. The residue was purified (SiO₂ chromatography eluting with iso-hexane: ethyl acetate (0-100%)) to give the subtitle compound (5.2 g).

¹H NMR δ(CDCl₃, 400 MHz) 7.66-7.62 (3H, m), 7.59-7.55 (3H, m), 7.45-7.22 (14H, m), 4.59 (1H, dd), 3.87 (1H, d), 3.55 (1H, dd), 3.40 (1H, dd), 2.23 (1H, m), 1.16 (9H, s), 1.06 (9H, s), 0.88 (3H, d).

c) 3-[3-[[(1R,2R)-3-Hydroxy-2-methyl-1-phenylpropyl]amino]-2-oxo-1(2H)-pyrazinyl]-4-methyl-benzoic acid, methyl ester A mixture of (R)—N-[(1R,2R)-3-[[(1,1-dimethylethyl)diphenylsilyl]oxy]-2-methyl-1-phenylpropyl]-2-methyl-2-propanesulfinamide (Example 136b, 5.2 g), methanol (25 mL) and a solution of hydrogen chloride in 1,4-dioxane (4M, 25 mL) was stirred at 50° C. for 7 h and left at room temperature for 70 h. The mixture was concentrated in vacuo and the residue was washed with ether to give the crude amine hydrochloride (2.0 g). 3-(3,5-Dibromo-2-oxo-2H-pyrazin-1-yl)-4-methyl-benzoic acid, methyl ester (Example 1b, 3.5 g) was added followed by N,N-diisopropylethylamine (4 mL) and tetrahydrofuran (50 mL). The mixture was stirred at 50° C. for 24 h. After cooling to room temperature, the mixture was diluted with ethyl acetate (200 mL) and washed with sat. aqueous NaHCO₃. The organic phase was dried (Na₂SO₄), filtered and concentrated in vacuo. Ethanol (50 mL) was added under nitrogen atmosphere followed by wet palladium on carbon (10%, 227 mg), ammonium formate (3 g) and N,N-diisopropylethylamine (2 mL). The mixture was stirred at 70° C. for 2 h, cooled to room temperature, filtered through a pad of Celite and concentrated in vacuo. The residue was diluted with ethyl acetate (200 mL) and washed with water. The organic phase was dried (Na₂SO₄), filtered and concentrated in vacuo to give the subtitle compound (3.5 g).

¹H NMR δ(DMSO-d₆, 400 MHz) 7.96 (1H, d), 7.91 and 7.88 (1H, 2×d), 7.84 and 7.79 (1H, 2×d), 7.58 and 7.56 (1H, 2×d), 7.43-7.36 (2H, m), 7.31 (2H, t), 7.25-7.19 (1H, m), 6.76 and 6.755 (1H, 2×d), 6.662 and 6.657 (1H, 2×d), 5.02 (1H, dd), 4.77 (1H, d), 3.86 and 3.84 (3H, 2×s), 3.22-3.14 (2H, m), 2.29-2.13 (1H, m), 2.16 and 2.09 (3H, 2×s), 0.87 (3H, d).

d) N-Cyclopropyl-3-[3-[[(1R,2R)-3-hydroxy-2-methyl-1-phenylpropyl]amino]-2-oxo-1(2H)-pyrazinyl]-4-methyl-benzamide A solution of iso-propylmagnesium chloride (2M in tetrahydrofuran, 5.5 mL) was added dropwise to a stirred mixture of 3-[3-[[(1R,2R)-3-hydroxy-2-methyl-1-phenylpropyl]amino]-2-oxo-1(2H)-pyrazinyl]-4-methyl-benzoic acid, methyl ester (Example 136c, 500 mg), cyclopropylamine (0.3 mL) and tetrahydrofuran (20 mL) at 0° C. After 15 min the reaction was quenched with sat. aqueous NH₄Cl and extracted into ethyl acetate. The organic phase was dried (Na₂SO₄), filtered and concentrated in vacuo to give a crude title product (525 mg). Purification by preparative HPLC (Gemini column, 0.1% ammonia:acetonitrile eluent) afforded the title compound.

MS: APCI (+ve) 433 (M+H⁺).

¹H NMR δ(DMSO-d₆, 400 MHz) 8.45 and 8.38 (1H, 2×d), 7.97-7.83 (2H, m), 7.75 and 7.70 (1H, 2×d), 7.49 and 7.47 (2H, 2×d), 7.44-7.20 (5H, m), 6.77 and 6.76 (1H, 2×d), 6.65 and 6.64 (1H, 2×d), 5.05-4.99 (1H, m), 4.80 and 4.74 (1H, 2×t), 3.23-3.12 (2H, m), 2.90-2.79 (1H, m), 2.30-2.13 (1H, m), 2.12 and 2.05 (3H, 2×s), 0.87 (3H, d), 0.72-0.63 (2H, m), 0.60-0.50 (2H, m).

Example 137

N-Cyclopropyl-3-[3-[[(1R,2R)-3-hydroxy-2-methyl-1-(1-naphthalenyl)propyl]amino]-2-oxo-1(2H)-pyrazinyl]-4-methyl-benzamide

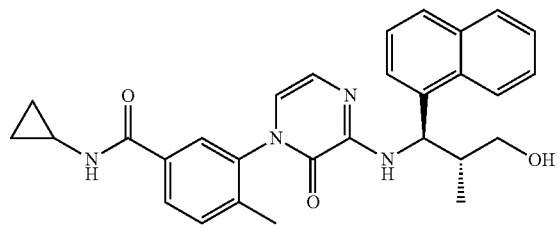

a) 3-[3-[[(1R,2R)-3-Hydroxy-2-methyl-1-(1-naphthalenyl)propyl]amino]-2-oxo-1(2H)-pyrazinyl]-4-methyl-benzoic acid, methyl ester The title compound was prepared from (2S)-3-[[(1,1-dimethylethyl)diphenylsilyl]oxy]-N-methoxy-N,2-dimethyl-propanamide (Example 136a) and 1-naphthalenylmagnesium bromide using methods described in the Example 136a and 136b.

¹H NMR δ(DMSO-d₆, 400 MHz) 8.34 and 8.33 (1H, 2×d), 8.05 (1H, d), 7.98 and 7.84 (1H, 2×d), 7.88 (1H, d), 7.80 (1H, t), 7.61 (1H, t), 7.56-7.37 (4H, m), 7.16 (1H, d), 6.90 (1H, d), 6.54-6.46 (1H, m), 6.45 and 6.44 (1H, 2×d), 3.93 and 3.88 (3H, 2×s), 3.71-3.63 (1H, m), 3.49-3.40 (1H, m), 2.55-2.38 (1H, m), 2.31 and 2.17 (3H, 2×s), 0.76 and 0.75 (3H, 2×d).

b) N-Cyclopropyl-3-[3-[[(1R,2R)-3-hydroxy-2-methyl-1-(1-naphthalenyl)propyl]amino]-2-oxo-1(2H)-pyrazinyl]-4-methyl-benzamide The title compound was prepared from 3-[3-((1R,2R)-3-hydroxy-2-methyl-1-naphthalen-1-yl-propylamino)-2-oxo-2H-pyrazin-1-yl]-4-methyl-benzoic acid, methyl ester (Example 137a) using the method described in the Example 136c.

MS: APCI (+ve) 483 (M+H⁺).

¹H NMR δ(DMSO-d₆, 400 MHz) 8.47-8.36 (2H, m), 7.95 (1H, d), 7.87 (1H, d), 7.82 (1H, d), 7.77 and 7.71 (1H, 2×d), 7.65-7.45 (6H, m), 6.73 and 6.72 (1H, 2×d), 6.67 and 6.67 (1H, 2×d), 6.08 (1H, dd), 4.87 and 4.83 (1H, 2×t), 3.35-3.26 (2H, m), 2.90-2.78 (1H, m), 2.41-2.30 (1H, m), 2.15 and 2.06 (3H, 2×s), 0.87 (3H, d), 0.73-0.63 (2H, m), 0.60-0.50 (2H, m).

Example 138

N-Cyclopropyl-4-methyl-3-[3-[[(1R,2S)-2-methyl-3-(4-morpholinyl)-1-phenylpropyl]amino]-2-oxo-1(2H)-pyrazinyl]-benzamide

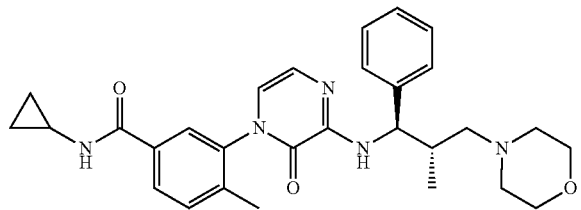

a) N-Cyclopropyl-4-methyl-3-[3-[[(1R,2R)-2-methyl-3-oxo-1-phenylpropyl]amino]-2-oxo-1(2H)-pyrazinyl]-benzamide A solution of Dess-Martin periodinane (600 mg) in dichloromethane (3 mL) was added dropwise to a solution of N-cyclopropyl-3-(3-((1R,2R)-3-hydroxy-2-methyl-1-phenylpropylamino)-2-oxopyrazin-1(2H)-yl)-4-methylbenzamide (Example 136, 405 mg) in dichloromethane (4 mL) at 25° C. The resulting mixture was stirred at 25° C. for 30 minutes. The reaction mixture was quenched with sat. aqueous $Na_2S_2O_3$ (7 mL) and sat. aqueous $NaHCO_3$. The mixture was stirred for 15 min. and extracted into dichloromethane. The organic phase was dried ($Na_2SO_4$), filtered and evaporated to afford crude product (475 mg) that was used in the next step without purification.

b) N-Cyclopropyl-4-methyl-3-[3-[[(1R,2S)-2-methyl-3-(4-morpholinyl)-1-phenylpropyl]amino]-2-oxo-1(2H)-pyrazinyl]-benzamide To a solution of N-cyclopropyl-4-methyl-3-[3-((1R,2R)-2-methyl-3-oxo-1-phenyl-propylamino)-2-oxo-2H-pyrazin-1-yl]-benzamide (Example 138a, 135 mg) in dichloromethane (4 mL) morpholine (0.2 mL) was added followed by sodium triacetoxyborohydride (70 mg). The reaction was stirred at room temperature for 17 h and quenched with sat. aqueous $NaHCO_3$. The mixture was stirred for 15 min. and extracted into dichloromethane. The organic phase was concentrated in vacuo. Purification by preparative HPLC (Gemini column, 0.1% ammonia:acetonitrile eluent) afforded the title compound (45 mg).

MS: APCI (+ve) 502 (M+H$^+$).

$^1$H NMR $\delta$(DMSO-d$_6$, 400 MHz) 9.23 and 9.08 (1H, 2×d), 8.45 and 8.41 (1H, 2×d), 7.87 (1H, dd), 7.74 and 7.70 (1H, 2×d), 7.49 and 7.48 (1H, 2×d), 7.38-7.21 (5H, m), 6.732 and 6.73 (1H, 2×d), 6.64 (1H, d), 5.07 (1H, dd), 3.79-3.58 (4H, m), 2.89-2.79 (1H, m), 2.37-2.21 (3H, m), 2.14 (1H, m), 2.11 and 2.06 (3H, 2×s), 2.02-1.94 (2H, m), 0.79 and 0.78 (3H, 2×d), 0.73-0.63 (2H, m), 0.59-0.51 (2H, m).

The following Examples 139-157 (Table 3) were prepared from the corresponding alcohols and amines using the general procedure described for Example 138b (in some reactions a mixture of diastereoisomers was obtained. Isomers were separated by preparative HPLC).

Example 139

N-Cyclopropyl-4-methyl-3-[3-[[(1R,2S)-2-methyl-3-(4-methyl-1-piperazinyl)-1-phenylpropyl]amino]-2-oxo-1(2H)-pyrazinyl]-benzamide

Example 140

3-[3-[[(1R,2S)-3-(4-Acetyl-1-piperazinyl)-2-methyl-1-phenylpropyl]amino]-2-oxo-1(2H)-pyrazinyl]-N-cyclopropyl-4-methyl-benzamide

Example 141

N-Cyclopropyl-4-methyl-3-[3-[[(1R,2S)-2-methyl-1-phenyl-3-(1-piperidinyl)propyl]amino]-2-oxo-1(2H)-pyrazinyl]-benzamide

Example 142

N-Cyclopropyl-4-methyl-3-[3-[[(1R,2S)-2-methyl-1-phenyl-3-(1-pyrrolidinyl)propyl]amino]-2-oxo-1(2H)-pyrazinyl]-benzamide

Example 143

N-Cyclopropyl-3-[3-[[(1R,2S)-3-(dimethylamino)-2-methyl-1-phenylpropyl]amino]-2-oxo-1(2H)-pyrazinyl]-4-methyl-benzamide

Example 144

N-Cyclopropyl-4-methyl-3-[3-[[(1R,2S)-2-methyl-1-(1-naphthalenyl)-3-(1-pyrrolidinyl)propyl]amino]-2-oxo-1(2H)-pyrazinyl]-benzamide

Example 145

N-Cyclopropyl-4-methyl-3-[3-[[(1R,2S)-2-methyl-3-(4-morpholinyl)-1-(1-naphthalenyl)propyl]amino]-2-oxo-1(2H)-pyrazinyl]-benzamide

Example 146

N-cyclopropyl-3-[3-[[(1R,2S)-3-(diethylamino)-2-methyl-1-phenylpropyl]amino]-2-oxo-1(2H)-pyrazinyl]-4-methyl-benzamide

Example 147

N-Cyclopropyl-3-[3-[[(1R,2S)-3-[(2R)-2-(methoxymethyl)-1-pyrrolidinyl]-2-methyl-1-phenylpropyl]amino]-2-oxo-1(2H)-pyrazinyl]-4-methyl-benzamide

Example 148

N-Cyclopropyl-3-[3-[[(1R,2R)-3-[(2R)-2-(methoxymethyl)-1-pyrrolidinyl]-2-methyl-1-phenylpropyl]amino]-2-oxo-1(2H)-pyrazinyl]-4-methyl-benzamide

Example 149

N-Cyclopropyl-3-[3-[[(1R,2S)-3-[(2S)-2-(methoxymethyl)-1-pyrrolidinyl]-2-methyl-1-phenylpropyl]amino]-2-oxo-1(2H)-pyrazinyl]-4-methyl-benzamide

Example 150

N-Cyclopropyl-3-[3-[[(1R,2R)-3-[(2S)-2-(methoxymethyl)-1-pyrrolidinyl]-2-methyl-1-phenylpropyl]amino]-2-oxo-1(2H)-pyrazinyl]-4-methyl-benzamide

Example 151

N-Cyclopropyl-3-[3-[[(1R,2S)-3-[4-(hydroxymethyl)-1-piperidinyl]-2-methyl-1-phenylpropyl]amino]-2-oxo-1(2H)-pyrazinyl]-4-methyl-benzamide

Example 152

N-Cyclopropyl-3-[3-[[(1R,2S)-3-(4-hydroxy-1-piperidinyl)-2-methyl-1-phenylpropyl]amino]-2-oxo-1(2H)-pyrazinyl]-4-methyl-benzamide

Example 153

N-Cyclopropyl-3-[3-[[(1R,2S)-3-[(1,1-dimethylethyl)amino]-2-methyl-1-phenylpropyl]amino]-2-oxo-1(2H)-pyrazinyl]-4-methyl-benzamide

Example 154

N-Cyclopropyl-3-[3-[[(1R,2S)-3-[(1,1-dimethylethyl)methylamino]-2-methyl-1-phenylpropyl]amino]-2-oxo-1(2H)-pyrazinyl]-4-methyl-benzamide

Example 155

N-Cyclopropyl-3-[3-[[(1R,2S)-3-[[2-(dimethylamino)ethyl]amino]-2-methyl-1-phenylpropyl]amino]-2-oxo-1(2H)-pyrazinyl]-4-methyl-benzamide

Example 156

N-Cyclopropyl-3-[3-[[(1R,2S)-3-[[2-(dimethylamino)ethyl]methylamino]-2-methyl-1-phenylpropyl]amino]-2-oxo-1(2H)-pyrazinyl]-4-methyl-benzamide

Example 157

N-Cyclopropyl-3-[3-[[(1R,2S)-3-[(2,2-dimethylpropyl)amino]-2-methyl-1-phenylpropyl]amino]-2-oxo-1(2H)-pyrazinyl]-4-methyl-benzamide

TABLE 3

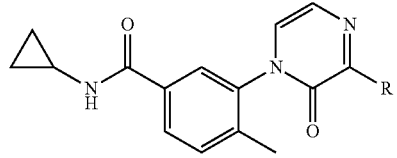

| Example | R | MS [M + H]+ m/z | $^1$H NMR δ (DMSO-$d_6$) |
|---|---|---|---|
| 139 | (phenyl-CH(NH-)-CH(CH₃)-CH₂-N(4-methylpiperazinyl)) | 515 | 8.78 and 8.69 (1H, 2 × d), 8.45 and 8.40 (1H, 2 × d), 7.86 (1H, dd), 7.74 and 7.70 (1H, 2 × d), 7.48 and 7.47 (1H, 2 × d), 7.38-7.29 (5H, m), 7.27-7.21 (2H, m), 6.75 and 6.74 (1H, 2 × d), 6.641 and 6.635 (1H, 2 × d), 5.03 (1H, m), 2.90-2.79 (1H, m), 2.46-2.29 (2H, m), 2.20-2.13 (8H, m), 2.11-2.06 (2H, m), 2.11 and 2.05 (3H, 2 × s), 1.93-1.83 (1H, m), 0.80 (3H, d), 0.73-0.63 (2H, m), 0.60-0.50 (2H, m) |
| 140 | (phenyl-CH(NH-)-CH(CH₃)-CH₂-N(4-acetylpiperazinyl)) | 543 | 9.32 and 9.17 (1H, 2 × d), 8.45 and 8.40 (1H, 2 × d), 7.86 (1H, dd), 7.74 and 7.70 (1H, 2 × d), 7.49 and 7.47 (1H, 2 × d), 7.38-7.21 (5H, m), 6.735 and 6.73 (1H, 2 × d), 6.64 (1H, d), 5.08 (1H, dd), 3.67-3.43 (5H, m), 2.90-2.78 (1H, m), 2.37-2.13 (5H, m), 2.11 and 2.05 (3H, 2 × s), 2.01-1.94 (1H, m), 1.96 and 1.955 (3H, 2 × s), 0.79 and 0.78 (3H, 2 × d), 0.72-0.64 (2H, m), 0.59-0.51 (2H, m) |
| 141 | (phenyl-CH(NH-)-CH(CH₃)-CH₂-N(piperidinyl)) | 500 | 9.32 and 9.21 (1H, 2 × d), 8.45 and 8.41 (1H, 2 × d), 7.87 (1H, dd), 7.74 and 7.71 (1H, 2 × d), 7.49 and 7.48 (1H, 2 × d), 7.38-7.20 (5H, m), 6.71 (1H, d), 6.62 (1H, d), 5.06 (1H, dd), 2.89-2.80 (1H, m), 2.58-2.41 (1H, m), 2.30-2.16 (2H, m), 2.16-2.02 (1H, m), 2.11 and 2.05 (3H, 2 × s), 1.95-1.86 (1H, m), 1.75-1.63 (2H, m), 1.64-1.51 (2H, m), 1.44-1.31 (2H, m), 0.77 and 0.76 (3H, 2 × d), 0.73-0.64 (2H, m), 0.60-0.51 (2H, m) |

TABLE 3-continued

| Example | R | MS [M + H]+ m/z | ¹H NMR δ (DMSO-d₆) |
|---|---|---|---|
| 142 | | 486 | 9.17 and 9.00 (1H, 2 × d), 8.45 and 8.40 (1H, 2 × d), 7.86 (1H, d), 7.74 and 7.69 (1H, 2 × d), 7.48 and 7.47 (1H, 2 × d), 7.38-7.28 (4H, m), 7.28-7.21 (1H, m), 6.73 and 6.72 (1H, 2 × d), 6.62 (1H, d), 5.10-5.02 (1H, m), 2.89-2.79 (2H, m), 2.61-2.30 (4H, m), 2.11 and 2.04 (3H, 2 × s), 2.05-1.99 (1H, m), 1.82-1.64 (4H, m), 0.83-0.76 (3H, m), 0.73-0.63 (3H, m), 0.60-0.50 (2H, m) |
| 143 | | 460 | 8.80 and 8.62 (1H, 2 × d), 8.45 and 8.40 (1H, 2 × d), 7.86 (1H, d), 7.74 and 7.70 (1H, 2 × d), 7.49 and 7.48 (1H, 2 × d), 7.37-7.20 (5H, m), 6.735 and 6.73 (1H, 2 × d), 6.63 (1H, d), 5.10-5.03 (1H, m), 2.89-2.80 (1H, m), 2.49-2.32 (2H, m), 2.15-2.04 (9H, m), 1.97-1.90 (1H, m), 0.81 and 0.79 (3H, 2 × d), 0.72-0.64 (2H, m), 0.59-0.51 (2H, m) |
| 144 | | 536 | 8.49 and 8.26 (1H, 2 × d), 8.46 and 8.41 (1H, 2 × d), 8.39 (1H, d), 7.94 (1H, dt), 7.86 (1H, d), 7.77 and 7.69 (1H, 2 × d), 7.63-7.45 (5H, m), 6.71 and 6.69 (1H, 2 × d), 6.64 and 6.63 (1H, 2 × d), 6.12 (1H, m), 2.59-2.38 (6H, m), 2.23-2.15 (1H, m), 2.13 and 2.04 (3H, 2 × s), 1.82-1.68 (4H, m), 0.82 and 0.80 (3H, 2 × d), 0.73-0.63 (2H, m), 0.60-0.50 (2H, m) |
| 145 | | 552 | 8.49-8.18 (3H, m), 7.95 and 7.87 (1H, 2 × d), 7.83 (1H, d), 7.77 and 7.70 (1H, 2 × d), 7.63-7.45 (5H, m), 6.71 and 6.70 (1H, 2 × d), 6.65 and 6.64 (1H, 2 × d), 6.21-6.11 (1H, m), 3.77-3.58 (5H, m), 2.91-2.78 (1H, m), 2.41-2.24 (5H, m), 2.16-2.07 (1H, m), 2.13 and 2.05 (3H, 2 × s), 0.80 and 0.78 (3H, 2 × d), 0.73-0.63 (2H, m), 0.59-0.50 (2H, m) |
| 146 | | 488 | 8.69 and 8.63 (1H, 2 × d), 8.45 and 8.41 (1H, 2 × d), 7.86 (1H, dd), 7.73 and 7.72 (1H, 2 × d), 7.49 and 7.48 (1H, 2 × d), 7.36-7.28 (4H, m), 7.27-7.19 (1H, m), 6.732 and 6.727 (1H, 2 × d), 6.64 (1H, d), 5.11-5.01 (1H, m), 2.90-2.79 (1H, m), 2.64-2.30 (5H, m), 2.28-2.13 (1H, m), 2.12-2.04 (1H, m), 2.10 and 2.05 (3H, 2 × s), 0.99-0.90 (6H, m), 0.81 (3H, t,), 0.73-0.64 (2H, m), 0.60-0.50 (2H, m) |

TABLE 3-continued

| Example | R | MS [M + H]+ m/z | 1H NMR δ (DMSO-d6) |
|---|---|---|---|
| 147 | | 530 | 9.00 and 8.97 (1H, 2 × d), 8.47 and 8.42 (1H, 2 × d), 7.86 and 7.72 (1H, 2 × d), 7.71 and 7.49 (1H, 2 × d), 7.38-7.30 (4H, m), 7.28-7.21 (1H, m), 6.72 and 6.71 (1H, 2 × d), 6.63 and 6.62 (1H, 2 × d), 5.20-5.11 (1H, m), 3.44-3.37 (1H, m), 3.27-3.19 (1H, m), 3.22 and 3.21 (3H, 2 × s), 2.92-2.80 (2H, m), 2.58-2.31 (3H, m), 2.16-2.04 (1H, m), 2.11 and 2.07 (3H, 2 × s), 2.00 (1H, d), 1.88-1.70 (2H, m), 1.69-1.57 (1H, m), 1.54-1.42 (1H, m), 0.74 (3H, d), 0.72-0.65 (2H, m), 0.59-0.52 (2H, m) |
| 148 | | 530 | 8.44 and 8.37 (1H, 2 × d), 8.31 and 8.13 (1H, 2 × d), 7.86 (1H, 2 × dt), 7.75 and 7.70 (1H, 2 × d), 7.48 and 7.47 (1H, 2 × d), 7.44-7.37 (2H, m), 7.35-7.28 (2H, m), 7.25-7.18 (1H, m), 6.77 and 6.75 (1H, 2 × d), 6.65 and 6.63 (1H, 2 × d), 4.80-4.70 (1H, m), 3.34-3.27 (1H, m), 3.20 and 3.20 (3H, 2 × s), 3.17-3.10 (1H, m), 3.06-2.99 (1H, m), 2.90-2.80 (1H, m), 2.66-2.54 (1H, m), 2.30-2.10 (2H, m), 2.12 and 2.05 (3H, 2 × s), 1.85-1.73 (1H, m), 1.70-1.58 (2H, m), 1.51-1.39 (1H, m), 0.744 and 0.734 (3H, 2 × d), 0.71-0.63 (2H, m), 0.59-0.50 (2H, m) |
| 149 | | 530 | 8.45 and 8.39 (1H, 2 × s), 8.18 and 7.94 (1H, 2 × d), 7.87 (1H, d), 7.76 and 7.70 (1H, 2 × s), 7.52-7.45 (1H, m), 7.43-7.29 (4H, m), 7.27-7.18 (1H, m), 6.81-6.74 (1H, m), 6.69-6.62 (1H, m), 4.98-4.87 (1H, m), 3.20 (3H, s), 3.18-3.08 (1H, m), 2.99-2.90 (1H, m), 2.89-2.80 (1H, m), 2.60-2.34 (4H, m), 2.21-1.96 (2H, m), 2.13 and 2.05 (3H, 2 × s), 1.86-1.71 (1H, m), 1.69-1.56 (2H, m), 1.53-1.40 (1H, m), 0.90 (3H, s), 0.74-0.64 (2H, m), 0.60-0.50 (2H, m) |
| 150 | | 530 | 9.02-8.95 (1H, m), 8.50-8.35 (1H, m), 7.90-7.83 (1H, m), 7.74-7.66 (1H, m), 7.53-7.44 (1H, m), 7.44-7.16 (5H, m), 6.76-6.58 (2H, m), 4.73 and 4.58 (1H, 2 × m), 3.43-3.31 (1H, m), 3.26-3.11 (4H, m), 3.08-2.97 (1H, m), 2.93-2.79 (1H, m), 2.6-2.4 (2H, m), 2.30-2.02 (5H, m), 1.88-1.59 (3H, m), 1.52-1.38 (1H, m), 0.78-0.62 (5H, m), 0.61-0.48 (2H, m) |
| 151 | | 530 | 9.08 and 8.87 (1H, 2 × d), 8.45 and 8.40 (1H, 2 × d), 7.86 (1H, dd), 7.74 and 7.70 (1H, 2 × d), 7.49 and 7.48 (1H, 2 × d), 7.37-7.21 (5H, m), 6.72 (1H, d), 6.62 (1H, d), 5.10-5.02 (1H, m), 4.36 (1H, t), 3.18 (2H, t), 3.14-3.00 (1H, m), 2.89-2.79 (1H, m), 2.78-2.69 (1H, m), 2.12 and 2.05 (3H, 2 × s), 1.96-1.84 (2H, m), 1.80-1.70 (1H, m), 1.69-1.54 (2H, m), 1.50-1.37 (1H, m), 1.36-1.21 (2H, m), 0.80 and 0.78 (3H, 2 × d), 0.72-0.64 (2H, m), 0.59-0.51 (2H, m) |

TABLE 3-continued

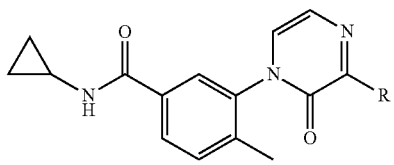

| Example | R | MS [M + H]⁺ m/z | ¹H NMR δ (DMSO-d₆) |
|---|---|---|---|
| 152 | | 516 | 9.18 and 9.06 (1H, 2 × d), 8.45 and 8.40 (1H, 2 × d), 7.86 (1H, dd), 7.74 and 7.70 (1H, 2 × d), 7.49 and 7.47 (1H, 2 × d), 7.38-7.21 (5H, m), 6.72 (1H, d), 6.62 (1H, d), 5.06 (1H, dd), 4.49 (1H, d), 3.52-3.41 (1H, m), 2.93-2.78 (2H, m), 2.62-2.37 (2H, m), 2.25-2.00 (1H, m), 2.11 and 2.05 (3H, 2 × s), 1.98-1.45 (6H, m), 0.78 and 0.77 (3H, 2 × d), 0.72-0.64 (2H, m), 0.59-0.51 (2H, m) |
| 153 | | 488 | 9.14 and 9.09 (1H, 2 × d), 8.45 and 8.40 (1H, 2 × d), 7.86 (1H, d), 7.72 (1H, d), 7.48 and 7.48 (1H, 2 × d), 7.40-7.27 (4H, m), 7.26-7.19 (1H, m), 6.74-6.68 (1H, m), 6.63-6.58 (1H, m), 5.11-5.02 (1H, m), 2.89-2.79 (1H, m), 2.40-2.27 (2H, m), 2.25-2.13 (1H, m), 2.10 and 2.06 (3H, 2 × s), 1.01 (9H, s), 0.83 and 0.82 (3H, 2 × d), 0.72-0.64 (2H, m), 0.59-0.51 (2H, m) |
| 154 | | 502 | 8.47 and 8.41 (1H, 2 × d), 8.08, 7.83 and 7.87 (2H, 3 × d), 7.75 and 7.73 (1H, 2 × s), 7.49 and 7.48 (1H, 2 × d), 7.38-7.28 (4H, m), 7.26-7.18 (1H, m), 6.75 (1H, d), 6.66 and 6.65 (1H, 2 × d), 5.14 and 5.05 (1H, 2 × dd), 2.90-2.79 (1H, m), 2.41-2.20 (2H, m), 2.14, 2.11, 2.09 and 2.07 (6H, 4 × s), 2.04-1.95 (1H, m), 0.96 and 0.94 (9H, 2 × s), 0.84 and 0.81 (3H, 2 × d), 0.73-0.64 (2H, m), 0.59-0.51 (2H, m) |
| 155 | | 503 | 8.69 and 8.54 (1H, 2 × d), 8.44 and 8.38 (1H, 2 × d), 7.86 (1H, d), 7.74 and 7.70 (1H, 2 × d), 7.49 and 7.47 (2 × d, J = 7.9 Hz, 1H), 7.41-7.28 (4H, m), 7.26-7.19 (1H, m), 6.75 and 6.74 (1H, 2 × d), 6.63 and 6.62 (1H, 2 × d), 5.03 (1H, dd), 2.90-2.78 (1H, m), 2.42-2.22 (7H, m), 2.12 and 2.05 (3H, 2 × s), 2.09 (6H, s), 0.84 (3H, d), 0.73-0.64 (2H, m), 0.59-0.50 (2H, m) |
| 156 | | 517 | 8.59 and 8.54 (1H, 2 × d), 8.46 and 8.40 (1H, 2 × d), 7.87 (1H, d), 7.74 and 7.72 (1H, 2 × d), 7.50 and 7.48 (1H, 2 × d), 7.40-7.29 (5H, m), 7.28-7.20 (1H, m), 6.751 and 6.747 (1H, 2 × d), 6.65 (1H, d), 5.11-5.03 (1H, m), 2.90-2.80 (1H, m), 2.45-2.28 (6H, m), 2.20, 2.18, 2.13, 2.11, 2.10, and 2.07 (12H, 6 × s), 2.04-1.96 (1H, m), 0.81 (3H, d), 0.74-0.64 (2H, m), 0.59-0.51 (2H, m) |
| 157 | | 502 | 8.48-8.36 (2H, m), 7.86 (1H, dd), 7.74 and 7.70 (1H, 2 × d), 7.49 and 7. (1H, 2 × d), 7.40-7.28 (4H, m), 7.26-7.18 (1H, m), 6.74 (1H, d), 6.63 and 6.62 (1H, 2 × d), 5.11-5.03 (1H, m), 2.91-2.78 (1H, m), 2.41-2.02 (5H, m), 2.11 and 2.05 (3H, 2 × s), 0.88 (9H, s), 0.85 (3H, d), 0.74-0.63 (2H, m), 0.59-0.50 (2H, m) |

Example 158

N-Methoxy-4-methyl-3-[3-[[(1R,2S)-2-methyl-1-(1-naphthalenyl)-3-(1-pyrrolidinyl)propyl]amino]-2-oxo-1(2H)-pyrazinyl]-benzamide

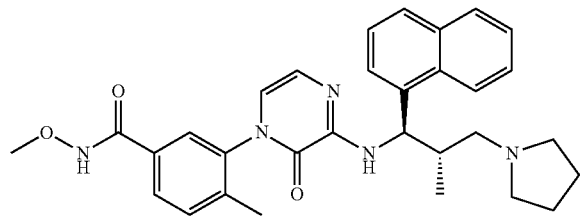

a) 4-Methyl-3-[3-[[(1R,2R)-2-methyl-1-(1-naphthalenyl)-3-oxopropyl]amino]-2-oxo-1(2H)-pyrazinyl]-benzoic acid, methyl ester The subtitle compound was prepared from 3-[3-[[(1R,2R)-3-hydroxy-2-methyl-1-(1-naphthalenyl)propyl]amino]-2-oxo-1(2H)-pyrazinyl]-4-methyl-benzoic acid, methyl ester (Example 137a) using the method described in Example 138a.

b) 4-Methyl-3-[3-[[(1R,2S)-2-methyl-1-(1-naphthalenyl)-3-(1-pyrrolidinyl)propyl]amino]-2-oxo-1(2H)-pyrazinyl]-benzoic acid, methyl ester The subtitle compound was prepared from 4-methyl-3-[3-[[(1R,2R)-2-methyl-1-(1-naphthalenyl)-3-oxopropyl]amino]-2-oxo-1(2H)-pyrazinyl]-benzoic acid, methyl ester (Example 158a) using the method described in the Example 138b.

MS: APCI (+ve) 511 (M+H$^+$).

$^1$H NMR $\delta$(DMSO-d$_6$, 400 MHz) 8.53-8.21 (2H, m), 8.03-7.75 (4H, m), 7.66-7.43 (6H, m), 6.75-6.57 (2H, m), 6.19-6.04 (1H, m), 3.87 and 3.84 (3H, s), 2.50-2.39 (6H, m), 2.29-2.18 (1H, m), 2.17 and 2.08 (3H, 2×s), 2.50-2.39 (6H, m), 1.82-1.68 (4H, m), 0.82 and 0.80 (3H, 2×d).

c) N-Methoxy-4-methyl-3-[3-[[(1R,2S)-2-methyl-1-(1-naphthalenyl)-3-(1-pyrrolidinyl)propyl]amino]-2-oxo-1(2H)-pyrazinyl]-benzamide A solution of iso-propylmagnesium chloride (2M in diethyl ether, 1.2 mL) was added dropwise to a stirred mixture of 4-methyl-3-[3-[[(1R,2S)-2-methyl-1-(1-naphthalenyl)-3-(1-pyrrolidinyl)propyl]amino]-2-oxo-1(2H)-pyrazinyl]-benzoic acid, methyl ester (Example 158b, 90 mg), O-methylhydroxylamine hydrochloride (65 mg) and tetrahydrofuran (2 mL) at room temperature. After 15 min the reaction was quenched with sat. aqueous NH$_4$Cl and extracted into ethyl acetate. The organic phase was dried (Na$_2$SO$_4$), filtered and concentrated in vacuo. Purification by preparative HPLC (Gemini column, 0.1% ammonia:acetonitrile eluent) afforded the title compound as a solid (65 mg).

MS: APCI (+ve) 526 (M+H$^+$).

$^1$H NMR $\delta$(DMSO-d$_6$, 400 MHz) 11.81 and 11.75 (1H, 2×s), 8.40 (1H, dd), 8.57-8.18 (1H, m), 7.95 (1H, d), 7.83 (1H, d), 7.79 (1H, dd), 7.70-7.48 (6H, m), 6.72 and 6.70 (1H, 2×d), 6.66-6.63 (1H, m), 6.16-6.06 (1H, m), 3.71 and 3.68 (3H, 2×s), 2.64-2.40 (4H, br), 2.27-2.11 (1H, br), 2.14 and 2.05 (3H, 2×s), 1.82-1.68 (4H, br), 0.89-0.77 (3H, br).

The following Examples 159-161 (Table 4) were prepared from corresponding alcohols (Examples 136c or 137a) and amines using the method described for Example 158.

Example 159

N-Methoxy-4-methyl-3-[3-[[(1R,2S)-2-methyl-1-phenyl-3-(1-pyrrolidinyl)propyl]amino]-2-oxo-1(2H)-pyrazinyl]-benzamide

Example 160

N-Methoxy-4-methyl-3-[3-[[(1R,2S)-2-methyl-3-(4-morpholinyl)-1-phenylpropyl]amino]-2-oxo-1(2H)-pyrazinyl]-benzamide

Example 161

N-Methoxy-4-methyl-3-[3-[[(1R,2S)-2-methyl-3-(4-morpholinyl)-1-(1-naphthalenyl)propyl]amino]-2-oxo-1(2H)-pyrazinyl]-benzamide

TABLE 4

| Example | R | MS [M + H]$^+$ m/z | $^1$H NMR $\delta$ (DMSO-d$_6$) |
|---|---|---|---|
| 159 | (structure) | 476 | 11.84 and 11.76 (1H, 2 × s), 9.46-9.29 (1H, m), 7.79 (1H, d), 7.69 and 7.64 (1H, 2 × s), 7.60-7.22 (5H, m), 6.84 and 6.83 (1H, 2 × d), 6.76 and 6.75 (1H, 2 × d), 5.23-5.09 (1H, m), 3.71 and 3.68 (3H, 2 × s), 3.64-3.48 (2H, m), 3.19-2.77 (3H, m), 2.65-2.54 (1H, m), 2.16 and 2.08 (3H, 2 × s), 2.01-1.78 (5H, m), 1.06 and 1.05 (3H, 2 × d) |

TABLE 4-continued

| | | MS [M + H]+ | |
|---|---|---|---|
| Example | R | m/z | ¹H NMR δ (DMSO-d₆) |
| 160 | | 492 | 9.24 and 9.09 (1H, 2 × d), 7.79 (1H, d), 7.65 and 7.61 (1H, 2 × d), 7.52 and 7.51 (1H, 2 × d), 7.38-7.21 (6H, m), 6.73 (1H, d), 6.643 and 6.639 (1H, 2 × d), 5.07 (1H, dd), 3.81-3.59 (4H, m), 3.71 and 3.69 (3H, 2 × s), 2.35-2.22 (3H, m), 2.21-2.09 (1H, m), 2.12 and 2.07 (3H, 2 × s), 1.98 (1H, dd), 0.79 and 0.78 (3H, 2 × d) |
| 161 | | 542 | 11.81 and 11.75 (1H, 2 × s), 8.49-8.18 (2H, m), 7.95 (1H, d), 7.83 (1H, d), 7.79 (1H, dd), 7.70-7.48 (6H, m), 6.72 and 6.70 (1H, 2 × d), 6.65 and 6.645 (1H, 2 × d), 6.21-6.13 (1H, m), 3.75-3.60 (4H, m), 3.71 and (3H, 2 × s), 2.61-2.42 (4H, m), 2.42-2.26 (2H, m), 2.14 and 2.06 (3H, 2 × s), 2.07 (1H, m), 0.80 and 0.78 (3H, 2 × d) |

Example 162

3-[3-[[(1R,2R)-3-Hydroxy-2-methyl-1-phenylpropyl]amino]-2-oxo-1(2H)-pyrazinyl]-N-methoxy-4-methyl-benzamide, trifluoroacetate

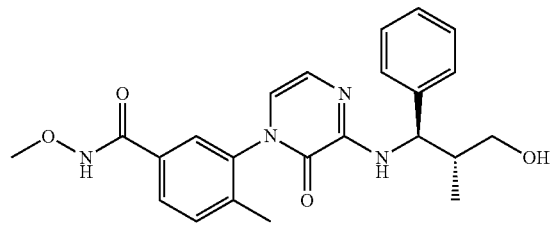

A solution of iso-propylmagnesium chloride (2M in tetrahydrofuran, 5.5 mL) was added dropwise to a stirred mixture of 3-[3-((1R,2R)-3-hydroxy-2-methyl-1-phenyl-propylamino)-2-oxo-2H-pyrazin-1-yl]-4-methyl-benzoic acid, methyl ester (Example 136c, 374 mg), O-methylhydroxylamine hydrochloride (200 mg) and tetrahydrofuran (5 mL) at 0° C. After 15 min the reaction was quenched with sat. aqueous NH₄Cl and extracted into ethyl acetate. The organic phase was dried (Na₂SO₄), filtered and concentrated in vacuo to give a crude title product (392 mg). Purification by preparative HPLC (Gemini column, 0.1% TFA:acetonitrile eluent) afforded the title compound.

MS: APCI (+ve) 423 (M+H⁺)

¹H NMR δ(DMSO-d₆, 400 MHz) 11.77 (1H, m), 7.78 (1H, d), 7.68 and 7.62 (1H, 2×s), 7.51 (1H, t), 7.42 (2H, t), 7.33 (2H, t), 7.24 (1H, t), 6.80-6.75 (1H, m), 6.71-6.66 (1H, m), 5.04-4.97 (1H, m), 3.71 and 3.68 (3H, 2×s), 3.23-3.12 (2H, m), 2.31-2.20 (1H, m), 2.14 and 2.07 (3H, 2×s), 0.88 (3H, d).

Example 163

N-Cyclopropyl-4-methyl-3-[3-[[1-methyl-1-[2-[2-(methylamino)ethoxy]phenyl]ethyl]amino]-2-oxo-1(2H)-pyrazinyl]-benzamide

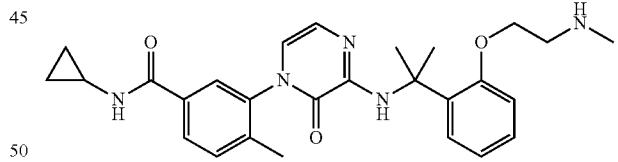

Potassium carbonate (330 mg) and 1-bromo-2-chloroethane (0.2 mL) were added to a stirred solution of N-cyclopropyl-3-(3-(2-(2-hydroxyphenyl)propan-2-ylamino)-2-oxopyrazin-1(2H)-yl)-4-methylbenzamide (Example 134, 0.1 g) in acetonitrile (5 mL). The reaction mixture was stirred under nitrogen at 83° C. for 16 h then concentrated in vacuo. The residue was treated with water and extracted into dichloromethane. The organic phase was washed with brine, dried (Na₂SO₄), filtered and concentrated in vacuo. The residue (120 mg) was treated with 33% methylamine in ethanol (3 mL) and heated within a microwave at 100° C. for 60 minutes. The mixture was concentrated in vacuo. Purification by preparative HPLC (Gemini column, 0.1% ammonia:acetonitrile eluent) afforded the title compound as a solid (65 mg).

MS: APCI (+ve) 476 (M+H⁺).

¹H NMR δ (DMSO-d₆, 400 MHz) 8.43 (1H, d), 7.86 (1H, dd), 7.72 (1H, d), 7.48 (1H, d), 7.35 (1H, dd), 7.22-7.17 (1H, m), 6.97 (1H, d), 6.94-6.85 (2H, m), 6.67 (1H, d), 6.63 (1H, d), 4.04-3.92 (2H, m), 2.89-2.80 (3H, m), 2.28 (3H, s), 2.09 (3H, s), 1.83 (6H, s), 0.71-0.66 (2H, m), 0.57-0.52 (2H, m).

Example 164

N-Cyclopropyl-4-methyl-3-[3-[[1-methyl-1-[2-[3-(methylamino)propoxy]phenyl]ethyl]amino]-2-oxo-1(2H)-pyrazinyl]-benzamide

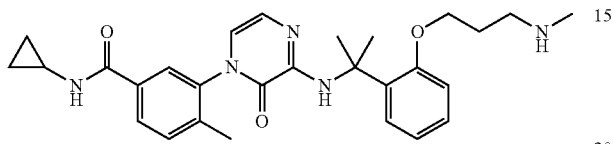

The title compound was prepared from N-cyclopropyl-3-(3-(2-(2-hydroxyphenyl)propan-2-ylamino)-2-oxopyrazin-1(2H)-yl)-4-methylbenzamide (Example 134) and 1-bromo-3-chloropropane using the method described for Example 163.
MS: APCI (+ve) 490 (M+H⁺).
¹H NMR δ (DMSO-d₆, 400 MHz) 8.43 (1H, d), 7.86 (1H, dd), 7.73 (1H, d), 7.48 (1H, d), 7.35 (1H, dd), 7.23-7.17 (1H, m), 6.98-6.88 (3H, m), 6.67 (1H, d), 6.64 (1H, d), 4.05-3.93 (2H, m), 2.88-2.39 (2H, m), 2.34 (3H, s), 2.10 (3H, s), 2.00-1.91 (2H, m), 1.85 (3H, s), 1.83 (3H, s), 0.72-0.67 (2H, m), 0.57-0.53 (2H, m).

Example 165

N-Cyclopropyl-4-methyl-3-[2-oxo-3-[[(1R)-1-[2-[2-(1-pyrrolidinyl)ethoxy]phenyl]propyl]amino]-1(2H)-pyrazinyl]-benzamide

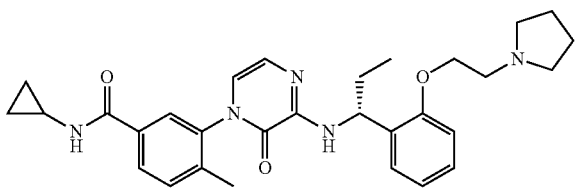

a) (S)-2-Methyl-N-[(1R)-1-[2-(2-hydroxyethoxy)phenyl]propyl]-2-propanesulfinamide and (S)-2-methyl-N-[(1S)-1-[2-(2-hydroxyethoxy)phenyl]propyl]-2-propanesulfinamide (S)-2-Methyl-2-propanesulfinamide (398 mg) and anhydrous copper (II) sulphate (1.15 g) were added to a stirred solution of 2-(2-hydroxyethoxy)-benzaldehyde (0.5 g) in dichloromethane (15 mL). The reaction mixture was stirred for 72 h then filtered and concentrated in vacuo. The residue was treated with dichloromethane (15 mL) and cooled to −78° C. A solution of ethylmagnesium chloride in tetrahydrofuran (2M, 4.5 mL) was added dropwise. The mixture was stirred at −78° C. for 1 h and allowed to warm to −10° C. over two h, then was quenched with saturated NH₄Cl solution. The mixture was extracted with dichloromethane. The pooled organics were washed with brine, dried (Na₂SO₄), filtered and concentrated in vacuo. Purification (SiO₂ chromatography eluting with 1:1 ethyl acetate/iso-hexane) afforded both sub-title compounds.

(S)-2-Methyl-N-[(1R)-1-[2-(2-hydroxyethoxy)phenyl]propyl]-2-propanesulfinamide (330 mg)

¹H NMR δ(DMSO-d₆, 400 MHz) 7.29 (1H, dd), 7.20-7.15 (1H, m), 6.96-6.88 (2H, m), 5.17 (1H, d), 4.90 (1H, t), 4.53 (1H, d), 4.04-3.93 (2H, m), 3.73 (2H, q), 1.86-1.67 (2H, m), 1.05 (9H, s), 0.82 (3H, t).

(S)-2-Methyl-N-[(1S)-1-[2-(2-hydroxyethoxy)phenyl]propyl]-2-propanesulfinamide (360 mg)

¹H NMR δ(DMSO-d₆, 400 MHz) 7.32 (1H, dd), 7.21-7.16 (1H, m), 6.97-6.87 (2H, m), 5.35 (1H, d), 4.92 (1H, t), 4.43-4.37 (1H, m), 4.06-3.95 (2H, m), 3.73 (2H, q), 1.81-1.62 (2H, m), 1.11 (9H, s), 0.82 (3H, t).

b) N-Cyclopropyl-3-[3-[[(1R)-1-[2-(2-hydroxyethoxy)phenyl]propyl]amino]-2-oxo-1(2H)-pyrazinyl]-4-methyl-benzamide A mixture of (S)-2-methyl-N-[(1R)-1-[2-(2-hydroxyethoxy)phenyl]propyl]-2-propanesulfinamide (Example 165a, 330 mg), methanol (10 mL) and a solution of hydrogen chloride in 1,4-dioxane (4M, 4 mL) was stirred at room temperature for 17 h. The mixture was concentrated in vacuo. The residue was treated with 3-(3,5-dibromo-2-oxo-2H-pyrazin-1-yl)-4-methyl-benzoic acid, methyl ester (Example 1b, 400 mg), triethylamine (0.92 mL) and tetrahydrofuran (5 mL). The mixture was stirred at room temperature for 5 days before the addition of cyclopropylamine (0.5 mL) and cyclopentyl-magnesium bromide (2M in diethyl ether, 5 mL) dropwise. The mixture was stirred for 15 min., quenched with saturated NH₄Cl solution and extracted into ethyl acetate. The pooled organics were washed with brine, dried (Na₂SO₄), filtered and concentrated in vacuo. The residue was treated with ethanol (5 mL) was added followed by the addition of ammonium formate (0.42 g) and 10% palladium on carbon (60 mg). The reaction mixture was heated within a microwave for 2 h at 100° C. before being cooled to room temperature, filtered and washed with ethanol. The filtrate was concentrated in vacuo. The residue was treated with dichloromethane and washed with brine, dried (Na₂SO₄), filtered and concentrated in vacuo to give the crude product (410 mg) that was used in the next step without purification.

c) N-Cyclopropyl-4-methyl-3-[2-oxo-3-[[(1R)-1-[2-[2-(1-pyrrolidinyl)ethoxy]phenyl]propyl]amino]-1(2H)-pyrazinyl]-benzamide Methanesulfonyl chloride (0.21 mL) was added to a stirred solution of N-cyclopropyl-3-[3-[[(1R)-1-[2-(2-hydroxyethoxy)phenyl]propyl]amino]-2-oxo-1(2H)-pyrazinyl]-4-methyl-benzamide (410 mg) and triethylamine (0.5 mL) in dichloromethane (10 mL) at 0° C. The mixture was stirred for 1 h at 0° C. and 1 h at room temperature. Water was added and the organic phase was separated, (Na₂SO₄), filtered and concentrated in vacuo. The residue was treated with dichloromethane (10 mL) and pyrrolidine (0.73 mL) and the mixture was stirred at room temperature for 24 h. The mixture was concentrated in vacu. Purification by preparative HPLC (Gemini column, 0.1% ammonia:acetonitrile eluent) afforded the title compound as a solid (147 mg).
MS: APCI (+ve) 516 (M+H⁺).

$^1$H NMR δ(DMSO-d$_6$, 400 MHz) 8.44 (0.5H, d), 8.40 (0.5H, d), 7.88-7.84 (1H, m), 7.77 (0.5H, d), 7.71 (0.5H, d), 7.51-7.46 (1H, m), 7.40-7.35 (1H, m), 7.31-7.25 (1H, m), 7.23-7.17 (1H, m), 7.03-6.98 (1H, m), 6.92-6.86 (1H, m), 6.81-6.78 (1H, m), 6.69-6.65 (1H, m), 5.26-5.19 (1H, m), 4.15-4.08 (2H, m), 2.88-2.80 (3H, m), 2.60-2.52 (4H, m), 2.13 (1.5H, s), 2.07 (1.5H. s), 1.90-1.79 (2H, m), 1.71-1.65 (4H, m), 0.89-0.82 (3H, m), 0.72-0.64 (2H, m), 0.58-0.51 (2H, m).

Example 166

N-Cyclopropyl-4-methyl-3-[2-oxo-3-[[(1S)-1-[2-[2-(1-pyrrolidinyl)ethoxy]phenyl]propyl]amino]-1(2H)-pyrazinyl]-benzamide

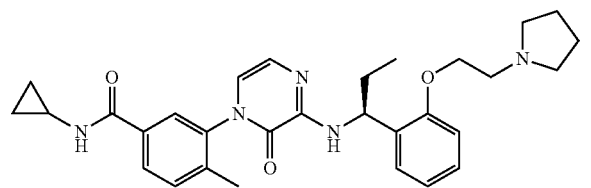

The title compound was prepared from (S)-2-methyl-N-[(1S)-1-[2-(2-hydroxyethoxy)phenyl]propyl]-2-propane-sulfinamide (Example 165a) using the method described for Example 165b and 165c.

MS: APCI (+ve) 516 (M+H$^+$).

$^1$H NMR δ(DMSO-d$_6$, 400 MHz) 8.44 (0.5H, d), 8.40 (0.5H, d), 7.88-7.84 (1H, m), 7.77 (0.5H, d), 7.71 (0.5H, d), 7.51-7.46 (1H, m), 7.40-7.35 (1H, m), 7.31-7.25 (1H, m), 7.23-7.17 (1H, m), 7.03-6.98 (1H, m), 6.92-6.86 (1H, m), 6.80 (1H, t), 6.67 (1H, dd), 5.26-5.18 (1H, m), 4.16-4.08 (2H, m), 2.89-2.79 (3H, m), 2.61-2.52 (4H, m), 2.13 (1.5H, s), 2.07 (1.5H, s), 1.90-1.78 (2H, m), 1.72-1.64 (4H, m), 0.89-0.82 (3H, m), 0.72-0.64 (2H, m), 0.59-0.51 (2H, m).

Example 167

N-Cyclopropyl-4-methyl-3-[3-[[1-[2-[2-(methylamino)ethoxy]phenyl]cyclopropyl]amino]-2-oxo-1(2H)-pyrazinyl]-benzamide

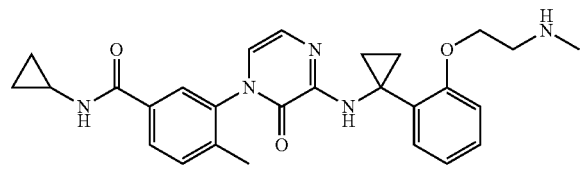

a) 1-(2-(Benzyloxy)phenyl)cyclopropanamine

Titanium(IV) isopropoxide (1.62 mL) was added to a stirred solution of 2-(benzyloxy)benzonitrile (1.05 g) in diethyl ether (25 mL) cooled to −78° C. under N$_2$ followed by the dropwise addition of ethylmagnesium bromide (3.67 mL of a 3M solution in diethylether). The resulting mixture was stirred at −78° C. for 10 min and then warmed to rt over 1 h. Boron trifluoride diethyl etherate (1.27 mL) was added dropwise and the mixture was stirred for 1 h. The reaction was quenched with 1M HCl (30 mL). Diethyl ether (30 mL) was added and the organic layer separated. To the aqueous layer was added aqueous 10% NaOH (50 mL) and diethyl ether and this was filtered through celite to remove solids (which were washed with further diethyl ether). This mixture was extracted with diethyl ether (2×70 mL) and dichloromethane (70 mL). All the organic layers were combined, dried (Na$_2$SO$_4$) and the solvents removed in vacuo. The residue was dissolved in dichloromethane and loaded on to an 10 g SCX cartridge. The impurities were washed through with methanol (50 mL) and discarded. Elution with 7N methanolic ammonia (25 mL) and evaporation in vacuo gave the subtitle compound as a brown oil (0.625 g).

$^1$H NMR δ(CDCl$_3$) 7.47 (d, 2H), 7.40 (t, 2H), 7.33 (t, 1H), 7.26-7.20 (m, 2H), 6.95 (d, 1H), 6.90 (td, 1H), 5.18 (s, 2H), 1.07 (dd, 2H), 0.89 (dd, 3H).

b) Methyl 3-(3-(1-(2-(benzyloxy)phenyl)cyclopropylamino)-5-bromo-2-oxopyrazin-1(2H)-yl)-4-methyl benzoate To 3-(3,5-dibromo-2-oxo-2H-pyrazin-1-yl)-4-methylbenzoic acid, methyl ester (Example 1b, 0.7 g) in THF (3 mL) was added 1-(2-(Benzyloxy)phenyl)cyclopropanamine (Example 167a, 0.625 g) and N,N-diisopropylamine (0.43 mL) and the reaction heated within a CEM Discover microwave at 120° C. for 80 min within a sealed 10 mL microwave vial. After cooling to rt, the organics were washed with water, dried (Na$_2$SO$_4$), filtered and the crude product purified (SiO$_2$ chromatography eluting with 50-100% dichloromethane in iso-hexane) to afford the subtitle product as an orange foam (0.62 g).

$^1$H NMR δ (DMSO-d$_6$) 7.94 (dd, 1H), 7.85 (d, 1H), 7.55-7.51 (m, 5H), 7.35 (t, 2H), 7.29 (t, 1H), 7.20 (td, 1H), 7.03 (d, 1H), 7.01 (s, 1H), 6.89 (td, 1H), 5.22 (s, 2H), 3.83 (s, 3H), 2.12 (s, 3H), 1.27-1.08 (m, 4H).

c) Methyl 3-(3-(1-(2-hydroxyphenyl)cyclopropylamino)-2-oxopyrazin-1(2H)-yl)-4-methyl benzoate To Methyl 3-(3-(1-(2-(benzyloxy)phenyl)cyclopropylamino)-5-bromo-2-oxopyrazin-1(2H)-yl)-4-methylbenzoate (Example 167b, 543 mg) in ethanol (15 mL) was added ammonium formate (855 mg) and 10% Pd/C (103 mg) and the reaction was heated at 75° C. for 1 h. The mixture was filtered through celite and the solids washed with ethanol. The filtrate was collected and the volatiles removed in vacuo to give a pale yellow solid. dichloromethane and water were added and the organic layer separated. The aqueous layer was further extracted with dichloromethane and ethyl acetate. The combined organic extracts were dried (Na$_2$SO$_4$) and the solvent removed in vacuo to give the subtitle product an off white foam (331 mg).

$^1$H NMR δ (DMSO-d$_6$) 11.26 (s, 1H), 8.45 (s, 1H), 7.95 (d, 1H), 7.85 (s, 1H), 7.56 (d, 1H), 7.45 (d, 1H), 7.11 (t, 1H), 6.88 (d, 1H), 6.80-6.73 (m, 3H), 3.84 (s, 3H), 3.31 (s, 2H), 2.12 (s, 3H), 1.11-1.03 (m, 2H), 1.30-1.22 (m, 2H).

d) N-Cyclopropyl-3-(3-(1-(2-hydroxyphenyl)cyclopropylamino)-2-oxopyrazin-1(2H)-yl)-4-methylbenzamide To cyclopropylamine (0.60 mL, 8.46 mmol) and Methyl 3-(3-(1-(2-hydroxyphenyl)cyclopropylamino)-2-oxopyrazin-1(2H)-yl)-4-methylbenzoate (Example 167c, 0.331 g)

in THF (5 mL) at rt was added isopropylmagnesium chloride (0.85 mL of a 2M solution in THF) dropwise. The reaction was stirred for 1 h and then further isopropylmagnesium chloride (0.85 mL of 2M solution in THF) was added and the reaction stirred for 16 h. Water and 2M aqueous HCl were cautiously added and the aqueous layer extracted with dichloromethane (2×). The combined organics were dried ($Na_2SO_4$) and the solvent removed in vacuo to give the subtitle product as a yellow solid (0.342 g).

$^1$H NMR δ (DMSO-$d_6$) 11.15 (s, 1H), 8.47 (s, 1H), 8.36 (d, 1H), 7.85 (dd, 1H), 7.71 (d, 1H), 7.47 (d, 1H), 7.46 (dd, 1H), 7.11 (dt, 1H), 6.89 (d, 1H), 6.80-6.73 (m, 3H), 2.87-2.79 (m, 1H), 2.09 (s, 3H), 1.30-1.21 (m, 2H), 1.14-1.04 (m, 2H), 0.70-0.64 (m, 2H), 0.55-0.51 (m, 2H).

e) 3-(3-(1-(2-(2-Chloroethoxy)phenyl)cyclopropylamino)-2-oxopyrazin-1(2H)-yl)-N-cyclopropyl-4-methylbenzamide To N-Cyclopropyl-3-(3-(1-(2-hydroxyphenyl)cyclopropylamino)-2-oxopyrazin-1(2H)-yl)-4-methylbenzamide (Example 167d, 0.34 g) in acetonitrile (5 mL) under nitrogen was added potassium carbonate (1.13 g) followed by 1-bromo-2-chloroethane (1.35 mL) and the reaction heated at 95° C. for 15 h. After cooling to rt the mixture was filtered through celite, and the solid cake washed with further acetonitrile. The filtrates were collected and the solvents removed in vacuo to give the subtitle product as a brown-orange solid (0.373 g).

$^1$H NMR δ (DMSO-$d_6$) 8.35 (d, 1H), 7.84 (dd, 1H), 7.67 (d, 1H), 7.52 (dd, 1H), 7.46 (d, 1H), 7.25 (s, 1H), 7.21 (dt, 1H), 6.97 (d, 1H), 6.90 (t, 1H), 6.87 (d, 1H), 6.71 (d, 1H), 4.31 (t, 2H), 4.00 (t, 2H), 2.86-2.78 (m, 1H), 2.05 (s, 3H), 1.26-1.06 (m, 4H), 0.69-0.64 (m, 2H), 0.55-0.50 (m, 2H).

f) N-Cyclopropyl-4-methyl-3-(3-(1-(2-(2-(methylamino)ethoxy)phenyl)cyclopropylamino)-2-oxopyrazin-1(2H)-yl)benzamide To 3-(3-(1-(2-(2-Chloroethoxy)phenyl)cyclopropylamino)-2-oxopyrazin-1(2H)-yl)-N-cyclopropyl-4-methylbenzamide (Example 167e, 100 mg) in a 10 mL microwave vial was added methylamine (2 mL of a 33% solution in ethanol). This was sealed and heated within a CEM Discover microwave for 30 min at 100° C. The volatiles were removed in vacuo and the residue taken up in methanol and purified by preparative HPLC (ACE column, 0.1% TFA:acetonitrile eluent) afforded the title compound. This was dissolved in acetonitrile and filtered through SCX resin eluting with acetonitrile and methanol (discarded) followed by 7N $NH_3$ in methanol. The basic fractions were collected and the volatiles were removed in vacuo. Trituration with diethyl ether afforded the title product as a white solid (46 mg).

MS: APCI (+ve) 474 (M+H)$^+$.

$^1$H NMR δ (DMSO-$d_6$) 8.35 (d, 1H), 7.84 (dd, 1H), 7.68 (d, 1H), 7.53-7.49 (m, 2H), 7.46 (d, 1H), 7.19 (td, 1H), 6.96 (d, 1H), 6.86 (t, 1H), 6.86 (d, 1H), 6.69 (d, 1H), 4.08 (t, 2H), 2.95 (t, 2H), 2.86-2.79 (m, 1H), 2.39 (s, 3H), 2.06 (s, 3H), 1.20-1.01 (m, 4H), 0.69-0.64 (m, 2H), 0.55-0.50 (m, 2H).

Example 168

N-Cyclopropyl-4-methyl-3-[3-[[1-[2-[2-(ethylamino)ethoxy]phenyl]cyclopropyl]amino]-2-oxo-1(2H)-pyrazinyl]-benzamide

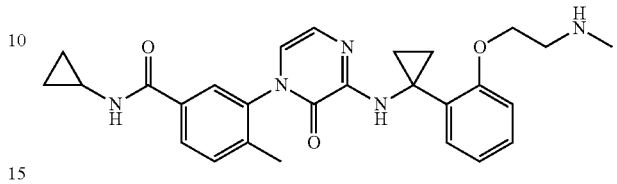

The title product was prepared from 3-(3-(1-(2-(2-chloroethoxy)phenyl)cyclopropylamino)-2-oxopyrazin-1(2H)-yl)-N-cyclopropyl-4-methylbenzamide (Example 167e) and ethylamine (70% in water) in ethanol as co-solvent using a similar method to that described for example 167f.

MS: APCI (+ve) 488 (M+H)$^+$.

$^1$H NMR δ (DMSO-$d_6$) 8.35 (d, 1H), 7.84 (d, 1H), 7.68 (s, 1H), 7.50-7.41 (m, 3H), 7.19 (t, 1H), 6.95 (d, 1H), 6.88-6.83 (m, 2H), 6.70 (d, 1H), 4.05 (t, 2H), 2.94 (t, 2H), 2.88-2.77 (m, 1H), 2.62 (q, 2H), 2.06 (s, 3H), 1.22-0.97 (m, 4H), 0.99 (t, 3H), 0.70-0.64 (m, 2H), 0.54-0.49 (m, 2H).

Example 169

N-Cyclopropyl-3-fluoro-4-methyl-5-[3-[[1-methyl-1-[2-[2-(methylamino)ethoxy]phenyl]ethyl]amino]-2-oxo-1(2H)-pyrazinyl]-benzamide

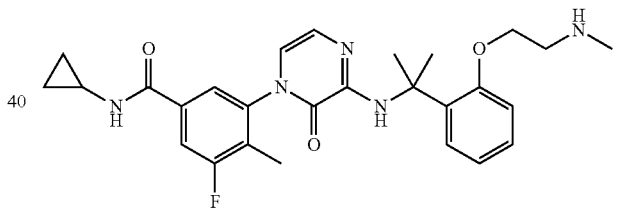

a) 3-Fluoro-4-methyl-5-nitro-benzoic acid, ethyl ester

To ethyl 3-amino-4-methyl-5-nitrobenzoate (J. Chem. Soc. 1960, 672-6; 5 g) solid at 0° C. was added ice cooled 48% aqueous tetrafluoroboric acid (35 mL) slowly (exotherm) and the mixture stirred for 5 min. Sodium nitrite (1.69 g) was added and the mixture stirred for 1 h then further tetrafluoroboric acid (15 mL) was added. After 1 h the precipitate was filtered off (caution—potentially explosive), washed with water and diethyl ether to afford a solid (1.27 g). This was diluted with solid sand and heated at 130° C. for 1 h (gas evolution observed). After cooling to rt, dichloromethane (30 mL) was added and the solids filtered off. The filtrate was collected and the solvent removed in vacuo to afford the crude product an oil. This was combined with the crude product from an identical reaction carried out on 1/5 scale and purified ($SiO_2$ chromatography eluting with iso-hexane) to afford the subtitle product as an yellow solid (1.43 g).

$^1$H NMR δ ($CDCl_3$) 8.37 (s, 1H), 7.94 (dd, 1H), 4.43 (q, 2H), 2.53 (d, 3H), 1.42 (t, 3H).

b) 3-Amino-5-fluoro-4-methyl-benzoic acid, ethyl ester

3-Fluoro-4-methyl-5-nitro-benzoic acid, ethyl ester (Example 169a, 1.43 g) in ethanol (30 mL) was pumped continuously through a Pd/C cartridge for 4 h under an atmosphere of hydrogen. The solvents were removed to give the subtitle product (1.20 g) as a solid.

$^1$H NMR δ (CDCl$_3$) 7.15 (s, 1H), 7.13 (d, 1H), 4.34 (q, 2H), 3.81 (s, 2H), 2.10 (d, 3H), 1.37 (t, 3H).

c) 3-[(Cyanomethyl)amino]-5-fluoro-4-methyl-benzoic acid, ethyl ester

To a stirred solution of 3-amino-5-fluoro-4-methyl-benzoic acid, ethyl ester (Example 169b, 1.2 g) in THF (10 mL) at room temperature was added N-ethyldiisopropylamine (1.28 mL) followed by bromoacetonitrile (0.51 mL) and the reaction was heated at reflux for 14 h. Additional bromoacetonitrile (0.21 mL) was added and the mixture was heated at reflux for 6 h. Further bromoacetonitrile (0.21 mL) was added and heating was continued for a further 12 h. After cooling to room temperature the reaction was concentrated. Aqueous HCl (30 mL, 1N) and ethyl acetate (30 mL) were added. The layers were separated and the organic fraction was dried (Na$_2$SO$_4$), filtered and concentrated to give the subtitle product (1.43 g) as a solid.

$^1$H NMR δ (CDCl$_3$) 7.30 (d, 1H), 7.17 (s, 1H), 4.38 (q, 2H), 4.24 (s, 2H), 4.03 (s, 1H), 2.12 (s, 3H), 1.40 (t, 3H).

d) 3-(3,5-Dibromo-2-oxo-1(2H)-pyrazinyl)-5-fluoro-4-methyl-benzoic acid, ethyl ester To a stirred suspension of 3-[(cyanomethyl)amino]-5-fluoro-4-methyl-benzoic acid, ethyl ester (Example 169c, 1.43 g) in dichloromethane (13 mL) under nitrogen at room temperature was added DMF (0.04 mL) and oxalyl bromide (1.70 mL) dropwise over 5 min. After stirring at room temperature for 6 h further oxalyl bromide (0.85 mL) and DMF (0.04 mL) were added and the reaction stirred for 14 h. The mixture was concentrated in vacuo (caution: volatiles contain oxalyl bromide). The residue was purified (SiO$_2$ chromatography eluting with dichloromethane) to afford the subtitle product (1.23 g).

$^1$H NMR δ (DMSO-d$_6$) 8.11 (s, 1H), 7.93 (s, 1H), 7.84 (dd, 1H), 4.34 (q, 2H), 2.10 (d, 3H), 1.32 (t, 3H).

e) 3-[5-Bromo-3-[[1-methyl-1-[2-(phenylmethoxy)phenyl]ethyl]amino]-2-oxo-1(2H)-pyrazinyl]-5-fluoro-4-methyl-benzoic acid, ethyl ester 3-(3,5-Dibromo-2-oxo-1(2H)-pyrazinyl)-5-fluoro-4-methyl-benzoic acid, ethyl ester (Example 169d, 1.137 g, 2.62 mmol) was dissolved in dioxane (10 mL). α,α-Dimethyl-2-(phenylmethoxy)-benzenemethanamine (Example 134a, 0.63 g) and N-ethyldiisopropylamine (0.67 mL, 3.93 mmol) were added under nitrogen and the resulting solution was stirred at 100° C. for 10 h. The reaction mixture was diluted with water (50 mL), and extracted with ethyl acetate (100 mL×2). The combined organics were dried (MgSO$_4$), filtered and evaporated to afford the crude product. This was purified by (SiO$_2$ chromatography eluting with dichloromethane) to afford the subtitle product (1.55 g).

MS: APCI (+ve) 595 (M+H)$^+$.

f) 3-[5-Bromo-3-[[1-methyl-1-[2-(phenylmethoxy)phenyl]ethyl]amino]-2-oxo-1(2H)-pyrazinyl]-N-cyclopropyl-5-fluoro-4-methyl-benzamide Cyclopropylamine (1.86 mL) was added to 3-[5-bromo-3-[[1-methyl-1-[2-(phenylmethoxy)phenyl]ethyl]amino]-2-oxo-1(2H)-pyrazinyl]-5-fluoro-4-methyl-benzoic acid, ethyl ester (Example 169e, 1.6 g) in THF (24 mL) under nitrogen at room temperature and isopropylmagnesium chloride (5.28 mL of a 2M solution in THF) was then added dropwise over 10 min. The resulting solution was stirred at 75° C. for 16 h. After cooling to room temperature, the solution was acidified with 2M HCl and extracted into dichloromethane. The organic fractions were concentrated in vacuo to give the subtitle compound (0.7 g).

$^1$H NMR δ (DMSO-d$_6$) 8.51 (d, 1H), 7.74 (d, 1H), 7.67 (s, 1H), 7.43 (dd, 2H), 7.37-7.29 (m, 4H), 7.26-7.21 (m, 1H), 7.15 (s, 1H), 7.08 (d, 1H), 6.99 (s, 1H), 6.95 (t, 1H), 5.13 (s, 2H), 2.90-2.81 (m, 1H), 1.97 (d, 3H), 1.84 (s, 6H), 0.76-0.67 (m, 2H), 0.58-0.53 (m, 2H).

MS: APCI (+ve) 605 (M+H)$^+$.

g) N-Cyclopropyl-3-fluoro-5-[3-[[1-(2-hydroxyphenyl)-1-methylethyl]amino]-2-oxo-1(2H)-pyrazinyl]-4-methyl-benzamide The title product was prepared from 3-[5-bromo-3-[[1-methyl-1-[2-(phenylmethoxy)phenyl]ethyl]amino]-2-oxo-1(2H)-pyrazinyl]-N-cyclopropyl-5-fluoro-4-methyl-benzamide (Example 169f, 0.7 g) using a similar hydrogenation method to that described for example 167c.

MS: APCI (+ve) 437 (M+H)$^+$.

h) 3-[3-[[1-[2-(2-Chloroethoxy)phenyl]-1-methylethyl]amino]-2-oxo-1(2H)-pyrazinyl]-N-cyclopropyl-5-fluoro-4-methyl-benzamide The title product was prepared from N-cyclopropyl-3-fluoro-5-[3-[[1-(2-hydroxyphenyl)-1-methylethyl]amino]-2-oxo-1(2H)-pyrazinyl]-4-methyl-benzamide (Example 169g, 0.33 g) and 1-bromo-2-chloroethane using a similar method to that described for example 167e.

MS: APCI (+ve) 500 (M+H)$^+$.

i) N-Cyclopropyl-3-fluoro-4-methyl-5-[3-[[1-methyl-1-[2-[2-(methylamino)ethoxy]phenyl]ethyl]amino]-2-oxo-1(2H)-pyrazinyl]-benzamide The title product was prepared from 3-[3-[[1-[2-(2-chloroethoxy)phenyl]-1-methylethyl]amino]-2-oxo-1(2H)-pyrazinyl]-N-cyclopropyl-5-fluoro-4-methyl-benzamide (Example 169h) and methylamine using a similar method to that described for example 167f. Purification was by RPHPLC (0.2% ammonia/MeCN gradient on a Phenominex column).

$^1$H NMR δ (DMSO-d$_6$) 8.52 (d, 1H), 7.75 (d, 1H), 7.64 (s, 1H), 7.34 (d, 1H), 7.34 (dd, 1H), 7.19 (t, 1H), 6.98-6.87 (m, 3H), 6.68 (s, 2H), 4.03-3.89 (m, 2H), 2.90-2.79 (m, 3H), 2.26 (s, 3H), 1.99 (d, 3H), 1.83 (s, 6H), 0.73-0.67 (m, 2H), 0.58-0.52 (m, 2H).

MS: APCI (+ve) 494 (M+H)$^+$.

The following Examples 170-197 (Table 5) were prepared from the corresponding alcohol (Example 136d) and amines using the methods described for Example 138.

Example 170

N-Cyclopropyl-4-methyl-3-[3-[[(1R,2S)-2-methyl-3-(4-methyl-1-piperidinyl)-1-phenylpropyl]amino]-2-oxo-1(2H)-pyrazinyl]-benzamide

Example 171

N-Cyclopropyl-4-methyl-3-[3-[[(1R,2S)-2-methyl-3-[4-(1-methylethyl)-1-piperazinyl]-1-phenylpropyl]amino]-2-oxo-1(2H)-pyrazinyl]-benzamide

Example 172

N-Cyclopropyl-4-methyl-3-[3-[[(1R,2S)-2-methyl-1-phenyl-3-(1-piperazinyl)propyl]amino]-2-oxo-1(2H)-pyrazinyl]-benzamide

Example 173

N-Cyclopropyl-3-[3-[[(1R,2S)-3-(hexahydro-4-methyl-1H-1,4-diazepin-1-yl)-2-methyl-1-phenylpropyl]amino]-2-oxo-1(2H)-pyrazinyl]-4-methyl-benzamide

Example 174

N-Cyclopropyl-3-[3-[[(1R,2S)-3-(4-fluoro-1-piperidinyl)-2-methyl-1-phenylpropyl]amino]-2-oxo-1(2H)-pyrazinyl]-4-methyl-benzamide

Example 175

N-Cyclopropyl-3-[3-[[(1R,2S)-3-(4,4-difluoro-1-piperidinyl)-2-methyl-1-phenylpropyl]amino]-2-oxo-1(2H)-pyrazinyl]-4-methyl-benzamide

Example 176

N-Cyclopropyl-3-[3-[[(1R,2S)-3-[4-(dimethylamino)-1-piperidinyl]-2-methyl-1-phenylpropyl]amino]-2-oxo-1(2H)-pyrazinyl]-4-methyl-benzamide

Example 177

N-Cyclopropyl-4-methyl-3-[3-[[(1R,2S)-2-methyl-1-phenyl-3-[4-(trifluoromethyl)-1-piperidinyl]propyl]amino]-2-oxo-1(2H)-pyrazinyl]-benzamide

Example 178

N-Cyclopropyl-4-methyl-3-[3-[[(1R,2S)-2-methyl-3-(3-oxo-1-piperazinyl)-1-phenylpropyl]amino]-2-oxo-1(2H)-pyrazinyl]-benzamide

Example 179

N-Cyclopropyl-3-[3-[[(1R,2S)-3-(1,4-dioxa-8-azaspiro[4.5]dec-8-yl)-2-methyl-1-s phenylpropyl]amino]-2-oxo-1(2H)-pyrazinyl]-4-methyl-benzamide

Example 180

N-Cyclopropyl-4-methyl-3-[3-[[(1R,2S)-2-methyl-3-[(3R)-3-methyl-1-piperazinyl]-1-phenylpropyl]amino]-2-oxo-1(2H)-pyrazinyl]-benzamide

Example 181

N-Cyclopropyl-4-methyl-3-[3-[[(1R,2S)-2-methyl-3-[(3S)-3-methyl-1-piperazinyl]-1-phenylpropyl]amino]-2-oxo-1(2H)-pyrazinyl]-benzamide

Example 182

N-Cyclopropyl-4-methyl-3-[3-[[(1R,2S)-2-methyl-3-[(2-methylpropyl)amino]-1-phenylpropyl]amino]-2-oxo-1(2H)-pyrazinyl]-benzamide

Example 183

N-Cyclopropyl-3-[3-[[(1R,2S)-3-(cyclopropylamino)-2-methyl-1-phenylpropyl]amino]-2-oxo-1(2H)-pyrazinyl]-4-methyl-benzamide

Example 184

N-Cyclopropyl-4-methyl-3-[3-[[(1R,2S)-2-methyl-3-[(2R)-2-methyl-1-pyrrolidinyl]-1-phenylpropyl]amino]-2-oxo-1(2H)-pyrazinyl]-benzamide

Example 185

N-Cyclopropyl-3-[3-[[(1R,2S)-3-[(3S)-3-hydroxy-1-piperidinyl]-2-methyl-1-phenylpropyl]amino]-2-oxo-1(2H)-pyrazinyl]-4-methyl-benzamide

Example 186

N-Cyclopropyl-3-[3-[[(1R,2S)-3-[(3R)-3-hydroxy-1-piperidinyl]-2-methyl-1-phenylpropyl]amino]-2-oxo-1(2H)-pyrazinyl]-4-methyl-benzamide

Example 187

N-Cyclopropyl-4-methyl-3-[3-[[(1R,2S)-2-methyl-3-[(2R)-2-methyl-1-piperazinyl]-1-phenylpropyl]amino]-2-oxo-1(2H)-pyrazinyl]-benzamide

Example 188

N-Cyclopropyl-3-[3-[[(1R,2S)-3-(2,7-diazaspiro[3.5]non-7-yl)-2-methyl-1-phenylpropyl]amino]-2-oxo-1(2H)-pyrazinyl]-4-methyl-benzamide

Example 189

N-Cyclopropyl-4-methyl-3-[3-[[(1R,2S)-2-methyl-1-phenyl-3-(4-s thiomorpholinyl)propyl]amino]-2-oxo-1(2H)-pyrazinyl]-benzamide

Example 190

N-Cyclopropyl-3-[3-[[(1R,2S)-3-[(3S)-3-hydroxy-1-pyrrolidinyl]-2-methyl-1-phenylpropyl]amino]-2-oxo-1(2H)-pyrazinyl]-4-methyl-benzamide

Example 191

N-Cyclopropyl-4-methyl-3-[3-[[(1R,2S)-2-methyl-1-phenyl-3-[4-(tetrahydro-1,1-dioxido-3-thienyl)-1-piperazinyl]propyl]amino]-2-oxo-1(2H)-pyrazinyl]-benzamide Example 192

1-[(2S,3R)-3-[[4-[5-[(cyclopropylamino)carbonyl]-2-methylphenyl]-3,4-dihydro-3-oxopyrazinyl]amino]-2-methyl-3-phenylpropyl]-4-piperidinecarboxamide Example 193

N-Cyclopropyl-3-[3-[[(1R,2S)-3-[(2-hydroxy-1,1-dimethylethyl)amino]-2-methyl-1-phenylpropyl]amino]-2-oxo-1(2H)-pyrazinyl]-4-methyl-benzamide Example 194

N-Cyclopropyl-3-[3-[[(1R,2S)-3-[(3R,5S)-3,5-dimethyl-1-piperazinyl]-2-methyl-1-phenylpropyl]amino]-2-oxo-1(2H)-pyrazinyl]-4-methyl-benzamide Example 195

N-Cyclopropyl-4-methyl-3-[3-[[(1R,2S)-2-methyl-1-phenyl-3-(4-piperidinylamino)propyl]amino]-2-oxo-1(2H)-pyrazinyl]-benzamide Example 196

N-Cyclopropyl-4-methyl-3-[3-[[(1R,2S)-2-methyl-3-(5-methyl-2,5-diazabicyclo[2.2.1]hept-2-yl)-1-phenylpropyl]amino]-2-oxo-1(2H)-pyrazinyl]-benzamide Example 197

N-Cyclopropyl-3-[3-[[(1R,2S)-3-(2,2-dimethyl-1-pyrrolidinyl)-2-methyl-1-phenylpropyl]amino]-2-oxo-1(2H)-pyrazinyl]-4-methyl-benzamide

TABLE 5

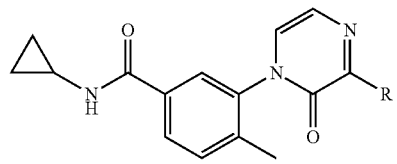

| Example | R | MS [M + H]+ m/z | 1H NMR δ (DMSO-d6 or as indicated) |
|---|---|---|---|
| 170 |  | 514 | 9.09 and 8.87 (1H, 2 × d), 8.45 and 8.40 (1H, 2 × d), 7.88-7.84 (1H, m), 7.74 and 7.70 (1H, 2 × d), 7.49 and 7.48 (1H, 2 × d), 7.37-7.20 (5H, m), 6.72 (1H, d), 6.62 (1H, d), 5.10-5.03 (1H, m), 3.10-2.96 (1H, m), 2.89-2.79 (1H, m), 2.75-2.66 (1H, m), 2.53-2.40 (1H, m), 2.16-2.02 (1H, m), 2.12 and 2.06 (3H, s), 1.96-1.84 (2H, m), 1.81-1.72 (1H, m), 1.63-1.42 (3H, m), 1.39-1.25 (2H, m), 0.85 (3H, d), 0.79 and 0.78 (3H, 2 × d), 0.72-0.64 (2H, m), 0.59-0.51 (2H, m) |
| 171 |  | 543 | 8.90 and 8.65 (1H, 2 × d), 8.44 and 8.39 (1H, 2 × d), 7.88-7.82 (1H, dt), 7.74 and 7.69 (1H, 2 × d), 7.48 and 7.47 (1H, 2 × d), 7.37-7.21 (5H, m), 6.73 (1H, d), 6.64 and 6.63 (1H, d), 5.10-5.02 (1H, m), 2.89-2.79 (1H, m), 2.64-2.19 (7H, m), 2.36-2.20 (2H, br m), 2.17-2.03 (1H, m), 2.13 and 2.06 (3H, 2 × s), 1.98-1.90 (1H, m), 0.92 (6H, d), 0.81 and 0.79 (3H, 2 × d), 0.72-0.64 (2H, m), 0.59-0.50 (2H, m) |
| 172 |  | 501 | 9.32 and 9.19 (1H, 2 × d), 8.45 and 8.41 (1H, 2 × d), 7.86 (1H, dd), 7.74 and 7.70 (1H, 2 × d), 7.49 and 7.48 (1H, 2 × d), 7.39-7.20 (5H, m), 6.72 and 6.71 (1H, 2 × d), 6.62 (1H, d), 5.07 (1H, dd), 2.91-2.69 (m, 5H), 2.25-2.04 (3H, m), 2.11 and 2.05 (3H, 2 × s), 1.95-1.88 (1H, m), 0.78 and 0.76 (3H, 2 × d), 0.72-0.64 (2H, m), 0.59-0.51 (2H, m) |

TABLE 5-continued

| Example | R | MS [M + H]+ m/z | 1H NMR δ (DMSO-d6 or as indicated) |
|---------|---|-----------------|-------------------------------------|
| 173 | | 506 | 8.89 and 8.72 (1H, 2 × d), 8.45 and 8.40 (1H, 2 × d), 7.86 (1H, dd), 7.74 and 7.71 (1H, 2 × d), 7.49 and 7.48 (1H, 2 × d), 7.38-7.20 (5H, m), 6.735 and 6.73 (1H, 2 × d), 6.63 (1H, d), 5.13-5.04 (1H, m), 2.90-2.79 (1H, m), 2.75-2.50 (7H, m), 2.43-2.31 (2H, m), 2.27-2.04 (2H, m), 2.22 (3H, s), 2.12 and 2.06 (3H, 2 × s), 1.84-1.71 (2H, m), 0.79 and 0.77 (3H, 2 × d), 0.72-0.65 (2H, m), 0.59-0.51 (2H, m) |
| 174 | | 518 | 9.31 and 9.19 (1H, 2 × d), 8.45 and 8.40 (1H, 2 × d), 7.86 (1H, d), 7.74 and 7.70 (1H, 2 × d), 7.49 and 7.48 (1H, 2 × d), 7.39-7.21 (5H, m), 6.72 (1H, d), 6.63 (1H, d), 5.10-5.04 (1H, m), 4.71 (1H, d), 2.91-2.78 (1H, m), 2.73-1.71 (11H, m), 2.11 and 2.05 (3H, s), 0.78 and 0.77 (3H, 2 × d), 0.72-0.64 (2H, m), 0.59-0.51 (2H, m) |
| 175 | | 536 | 9.25 and 9.08 (1H, 2 × d), 8.45 and 8.40 (1H, 2 × d), 7.86 (1H, d), 7.74 and 7.70 (1H, 2 × d), 7.49 and 7.48 (1H, 2 × d), 7.39-7.22 (5H, m), 6.74 (1H, d), 6.64 (1H, d), 5.11-5.04 (1H, m), 2.89-2.79 (1H, m), 2.76-1.95 (11H, m), 2.11 and 2.05 (3H, 2 × s), 0.79 and 0.78 (3H, 2 × d), 0.73-0.64 (2H, m), 0.59-0.51 (2H, m) |
| 176 | | 543 | 9.21 and 9.01 (1H, d), 8.44 and 8.39 (1H, 2 × d), 7.88-7.82 (1H, m), 7.74 and 7.69 (1H, 2 × d), 7.48 and 7.46 (1H, 2 × d), 7.38-7.20 (5H, m), 6.72 (1H, d), 6.63 (1H, d), 5.10-5.02 (1H, m), 3.16-3.01 (1H, m), 2.89-2.71 (m, 2H), 2.12, 2.10, 2.10 and 2.06 (9H, 4 × s), 2.19-1.49 (10H, m), 0.78 and 0.77 (3H, 2 × d), 0.71-0.64 (2H, m), 0.59-0.51 (2H, m) |
| 177 | | 568 | 8.95 and 8.67 (1H, 2 × d), 8.44 and 8.39 (1H, 2 × d), 7.85 (1H, dd), 7.74 and 7.69 (1H, 2 × d), 7.48 and 7.47 (1H, 2 × d), 7.38-7.21 (5H, m), 6.73 (1H, d), 6.64 (1H, d), 5.11-5.01 (1H, m), 3.23-3.08 (1H, m), 2.89-2.78 (2H, m), 2.57-1.54 (10H, m), 2.12 and 2.06 (3H, 2 × s), 0.82 and 0.79 (3H, 2 × d), 0.72-0.64 (2H, m), 0.59-0.50 (2H, m) |

TABLE 5-continued

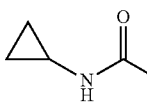

| Example | R | MS [M + H]+ m/z | 1H NMR δ (DMSO-d6 or as indicated) |
|---|---|---|---|
| 178 | 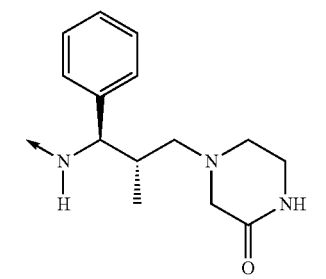 | 515 | 8.69 and 8.53 (1H, 2 × d), 8.46 and 8.40 (1H, 2 × d), 7.85 (1H, d), 7.75-7.68 (2H, m), 7.48 and 7.47 (1H, 2 × d), 7.39-7.22 (5H, m), 6.75 and 6.74 (1H, 2 × d), 6.65 and 6.64 (1H, 2 × d), 5.11-5.03 (1H, m), 3.46-3.34 (1H, m), 3.21-3.10 (1H, m), 3.00-2.70 (4H, m), 2.44-2.29 (1H, m), 2.22-2.09 (1H, m), 2.11 and 2.04 (3H, 2 × s), 2.08-2.00 (1H, m), 0.83 and 0.82 (3H, 2 × d), 0.72-0.64 (2H, m), 0.59-0.51 (2H, m) |
| 179 | 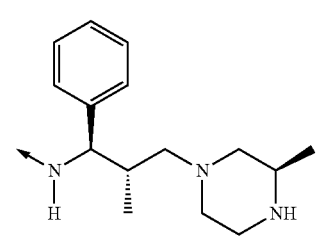 | 558 | 9.34 and 9.22 (1H, 2 × d), 8.45 and 8.41 (1H, 2 × d), 7.87 (1H, dd), 7.73 and 7.70 (1H, 2 × d), 7.49 and 7.48 (1H, 2 × d), 7.38-7.21 (5H, m), 6.715 and 6.713 (1H, 2 × d), 6.62 (1H, d), 5.07 (1H, dd), 3.82 (4H, d), 2.89-2.78 (1H, m), 2.71-2.54 (1H, m), 2.42-2.25 (2H, m), 2.23-2.08 (1H, m), 2.11 and 2.05 (3H, 2 × s), 1.98-1.91 (1H, m), 1.88-1.77 (3H, m), 1.75-1.64 (3H, m), 0.77 and 0.76 (3H, 2 × d), 0.72-0.64 (2H, m), 0.59-0.51 (2H, m) |
| 180 | 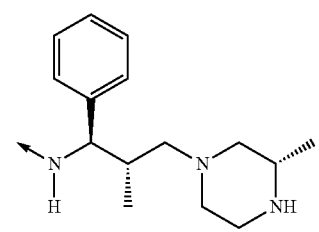 | 515 | 9.30 and 9.20 (1H, 2 × d), 8.45 and 8.41 (1H, 2 × d), 7.86 (1H, dd), 7.74 and 7.69 (1H, 2 × d), 7.49 and 7.48 (1H, 2 × d), 7.38-7.20 (5H, m), 6.715 and 6.711 (1H, 2 × d), 6.62 (1H, d), 5.10-5.02 (1H, m), 3.08-2.71 (4H, m), 2.64-2.55 (1H, m), 2.19-2.08 (1H, m), 2.11 and 2.05 (3H, 2 × s), 1.94-1.78 (4H, m), 1.46-1.36 (1H, m), 0.88 and 0.87 (3H, 2 × d), 0.78 and 0.76 (3H, 2 × d), 0.72-0.64 (2H, m), 0.58-0.51 (2H, m) |
| 181 | 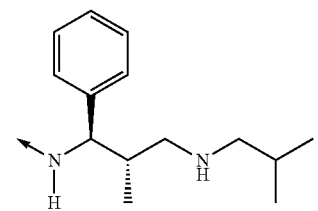 | 515 | 9.30 and 9.20 (1H, 2 × d), 8.45 and 8.41 (1H, 2 × d), 7.86 (1H, dd), 7.74 and 7.69 (1H, 2 × d), 7.49 and 7.48 (1H, 2 × d), 7.38-7.20 (5H, m), 6.715 and 6.711 (1H, 2 × d), 6.62 (1H, d), 5.10-5.02 (1H, m), 3.08-2.71 (4H, m), 2.64-2.55 (1H, m), 2.19-2.08 (1H, m), 2.11 and 2.05 (3H, 2 × s), 1.94-1.8 (3H, m), 1.46-1.36 (1H, m), 1.46-1.36 (1H, m), 0.88 and 0.87 (3H, 2 × d), 0.78 and 0.76 (3H, 2 × d), 0.72-0.64 (2H, m), 0.58-0.51 (2H, m) |
| 182 | | 488 | 8.61 and 8.52 (1H, 2 × d), 8.45 and 8.39 (1H, 2 × d), 7.86 (1H, dd), 7.74 and 7.70 (1H, 2 × d), 7.49 and 7.47 (1H, 2 × d), 7.40-7.19 (5H, m), 6.74 and 6.73 (1H, 2 × d), 6.63 and 6.62 (1H, 2 × d), 5.09-5.02 (1H, m), 2.91-2.78 (1H, m), 2.35-2.13 (5H, m), 2.11 and 2.05 (3H, 2 × s), 1.81-1.59 (2H, m), 0.90-0.81 (9H, m), 0.73-0.63 (2H, m), 0.59-0.50 (2H, m) |

TABLE 5-continued

| Example | R | MS [M + H]+ m/z | 1H NMR δ (DMSO-d6 or as indicated) |
|---|---|---|---|
| 183 | | 472 | 8.46 and 8.39 (1H, 2 × d), 7.86 (1H, 2 × d), 7.75 and 7.70 (1H, 2 × d), 7.49 and 7.48 (1H, 2 × d), 7.46-7.21 (5H, m), 6.78 and 6.77 (1H, 2 × d), 6.68 and 6.67 (1H, 2 × d), 5.09-5.01 (1H, m), 2.90-2.79 (1H, m), 2.67-2.57 (1H, m), 2.53-2.2 (3H, m), 2.13 and 2.06 (3H, 2 × s), 0.99-0.89 (3H, m), 0.74-0.63 (2H, m), 0.61-0.41 (6H, m) |
| 184 | | 500 | 8.46-8.36 (m, 1H), 8.29-8.07 (m, 1H), 7.88-7.83 (m, 1H), 7.76-7.68 (m, 1H), 7.50-7.45 (m, 1H), 7.41-7.35 (m, 2H), 7.34-7.30 (m, 2H), 7.24-7.20 (m, 1H), 6.78-6.74 (m, 1H), 6.66-6.62 (m, 1H), 4.96-4.88 (m, 1H), 2.94-2.88 (m, 1H), 2.87-2.79 (m, 1H), 2.40-2.20 (m, 3H), 2.08 (d, 3H), 2.03-1.98 (m, 1H), 1.97-1.91 (m, 1H), 1.90-1.78 (m, 1H), 1.68-1.55 (m, 2H), 1.34-1.25 (m, 1H), 0.95 (t, 3H), 0.92-0.89 (m, 3H), 0.72-0.64 (m, 2H), 0.58-0.50 (m, 2H) |
| 185 | | 516 | 9.39-9.30 (m, 1H), 8.44 (dd, 1H), 7.87 (d, 1H), 7.72 (d, 1H), 7.49 (t, 1H), 7.36-7.31 (m, 2H), 7.29-7.22 (m, 3H), 6.74-6.71 (m, 1H), 6.64-6.61 (m, 1H), 5.08-5.04 (m, 1H), 4.52 (t, 1H), 3.80-3.71 (m, 1H), 3.08-2.91 (m, 1H), 2.88-2.80 (m, 1H), 2.55-2.45 (m, 2H), 2.21-2.13 (m, 1H), 2.08 (d, 3H), 2.03-1.96 (m, 1H), 1.95-1.89 (m, 1H), 1.79-1.71 (m, 1H), 1.71-1.63 (m, 2H), 1.63-1.54 (m, 1H), 1.15-1.05 (m, 1H), 0.79-0.74 (m, 3H), 0.72-0.65 (m, 2H), 0.58-0.51 (m, 2H) |
| 186 | | 516 | 9.26 (dd, 1H), 8.47-8.39 (m, 1H), 7.87 (d, 1H), 7.72 (d, 1H), 7.51-7.45 (m, 1H), 7.38-7.31 (m, 2H), 7.31-7.22 (m, 3H), 6.72 (d, 1H), 6.62 (d, 1H), 5.08-5.02 (m, 1H), 3.70-3.59 (m, 1H), 2.99-2.91 (m, 1H), 2.89-2.73 (m, 2H), 2.19-2.07 (m, 1H), 2.07 (d, 3H), 1.98-1.92 (m, 1H), 1.85-1.63 (m, 4H), 1.61-1.49 (m, 1H), 1.10-0.97 (m, 1H), 0.80-0.73 (m, 3H), 0.72-0.64 (m, 2H), 0.60-0.51 (m, 2H) |
| 187 | | 515 | 8.47-8.38 (m, 1H), 7.88-7.84 (m, 1H), 7.76-7.70 (m, 1H), 7.51-7.46 (m, 1H), 7.36-7.28 (m, 4H), 7.27-7.20 (m, 1H), 6.75-6.72 (m, 1H), 6.65-6.62 (m, 1H), 5.05-4.98 (m, 1H), 2.90-2.78 (m, 3H), 2.69-2.62 (m, 1H), 2.47-2.31 (m, 4H), 2.27-2.16 (m, 2H), 2.06 (d, 3H), 1.96-1.82 (m, 1H), 0.92-0.87 (m, 3H), 0.86-0.80 (m, 3H), 0.72-0.64 (m, 2H), 0.59-0.51 (m, 2H) |

TABLE 5-continued
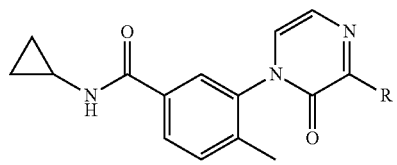
| Example | R | MS [M + H]+ m/z | 1H NMR δ (DMSO-d6 or as indicated) |
|---|---|---|---|
| 188 | | 541 | 9.05-8.57 (m, 2H), 8.51-8.36 (m, 1H), 7.89-7.84 (m, 1H), 7.76-7.69 (m, 1H), 7.66-7.20 (m, 7H), 7.11-6.94 (m, 1H), 6.86-6.72 (m, 2H), 5.20-5.04 (m, 1H), 3.73 (s, 4H), 3.05-2.60 (m, 4H), 2.18-2.04 (m, 5H), 2.03-1.79 (m, 3H), 1.10-0.97 (m, 2H), 0.75-0.63 (m, 2H), 0.59-0.49 (m, 2H) |
| 189 | | 518 | δ (CD3OD) 7.86-7.80 (m, 1H), 7.76-7.67 (m, 1H), 7.52-7.36 (m, 5H), 7.34-7.28 (m, 1H), 6.94 (dd, 1H), 6.71 (dd, 1H), 5.34-5.26 (m, 1H), 3.72-3.34 (m, 3H), 3.20-3.10 (m, 2H), 3.09-2.89 (m, 4H), 2.87-2.73 (m, 2H), 2.19 (d, 3H), 1.08-0.99 (m, 3H), 0.83-0.75 (m, 2H), 0.65-0.55 (m, 2H) |
| 190 | | 502 | 9.18 (m, 1H), 8.43 (m, 1H), 7.86 (dd, 1H), 7.72 (dd, 1H), 7.49 (d, 1H), 7.37-7.28 (m, 4H), 7.27-7.22 (m, 1H), 6.74 (dd, 1H), 6.63 (dd, 1H), 5.04 (m, 1H), 4.60-4.55 (m, 1H), 4.27-4.18 (m, 1H), 2.90-2.79 (m, 2H), 2.69-2.59 (m, 2H), 2.48-2.42 (m, 1H), 2.41-2.31 (m, 2H), 2.28-2.21 (m, 1H), 2.13-1.97 (m, 5H), 1.62-1.53 (m, 1H), 0.78 (d, 3H), 0.72-0.64 (m, 2H), 0.59-0.51 (m, 2H) |
| 191 | | 619 | δ (CD3OD) 7.87-7.81 (m, 1H), 7.72-7.65 (m, 1H), 7.51-7.45 (m, 1H), 7.34-7.27 (m, 4H), 7.26-7.22 (m, 1H), 6.76-6.73 (m, 1H), 6.54-6.51 (m, 1H), 5.12-5.07 (m, 1H), 3.26-3.11 (m, 2H), 3.07-2.94 (m, 2H), 2.87-2.60 (m, 7H), 2.59-2.24 (m, 6H), 2.22-2.12 (m, 3H), 2.10-1.96 (m, 2H), 0.87-0.82 (m, 3H), 0.81-0.74 (m, 2H), 0.64-0.57 (m, 2H) |
| 192 | | 543 | 8.78-8.56 (m, 1H), 8.45-8.36 (m, 1H), 7.84-7.80 (m, 1H), 7.71-7.65 (m, 1H), 7.47-7.42 (m, 1H), 7.34-7.25 (m, 4H), 7.24-7.18 (m, 1H), 7.11-7.07 (m, 1H), 6.72-6.70 (m, 1H), 6.64-6.58 (m, 2H), 5.06-5.01 (m, 1H), 3.05-2.94 (m, 1H), 2.86-2.76 (m, 1H), 2.75-2.62 (m, 1H), 2.46-2.34 (m, 1H), 2.11-1.96 (m, 5H), 1.94-1.84 (m, 2H), 1.83-1.73 (m, 2H), 1.72-1.60 (m, 3H), 0.82-0.74 (m, 3H), 0.69-0.61 (m, 2H), 0.56-0.48 (m, 2H) |

TABLE 5-continued
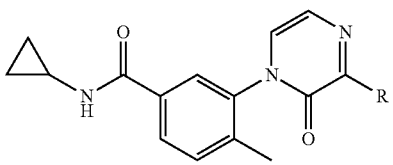
| Example | R | MS [M + H]+ m/z | 1H NMR δ (DMSO-d6 or as indicated) |
|---|---|---|---|
| 193 | 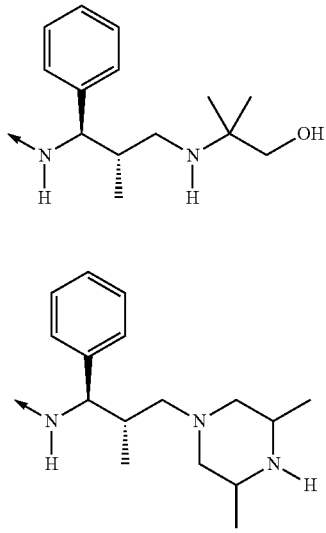 | 504 | 9.09-8.94 (m, 1H), 8.45-8.36 (m, 1H), 7.86-7.82 (m, 1H), 7.72-7.68 (m, 1H), 7.48-7.43 (m, 1H), 7.36-7.26 (m, 4H), 7.23-7.17 (m, 1H), 6.71-6.68 (m, 1H), 6.60-6.57 (m, 1H), 5.07-5.01 (m, 1H), 4.53-4.41 (m, 1H), 3.30-3.29 (m, 2H), 2.85-2.78 (m, 1H), 2.35-2.28 (m, 2H), 2.21-2.11 (m, 1H), 2.09-2.02 (m, 3H), 0.91-0.89 (m, 3H), 0.89-0.87 (m, 3H), 0.82-0.78 (m, 3H), 0.70-0.62 (m, 2H), 0.56-0.49 (m, 2H) |
| 194 | | 529 | 9.44-8.84 (m, 1H), 8.41 (d, 1H), 8.24-8.13 (m, 1H), 7.86 (dd, 1H), 7.72 (dd, 1H), 7.51-7.47 (m, 1H), 7.39-7.22 (m, 4H), 7.03 (d, 1H), 6.76 (dd, 1H), 6.67 (d, 1H), 5.12-5.06 (m, 1H), 3.46-3.26 (m, 3H), 3.02-2.95 (m, 1H), 2.89-2.79 (m, 1H), 2.35-2.22 (m, 1H), 2.14-1.98 (m, 4H), 1.90-1.81 (m, 1H), 1.26-1.12 (m, 6H), 0.79-0.74 (m, 3H), 0.73-0.65 (m, 2H), 0.58-0.51 (m, 2H) |
| 195 | 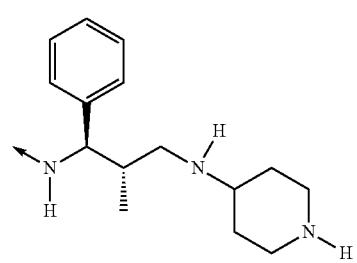 | 515 | δ (CD3OD) 7.87-7.81 (m, 1H), 7.72 (d, J = 26.7 Hz, 1H), 7.52-7.46 (m, 1H), 7.45-7.34 (m, 4H), 7.31-7.26 (m, 1H), 6.94-6.88 (m, 1H), 6.69-6.64 (m, 1H), 5.32-5.21 (m, 1H), 3.55-3.46 (m, 2H), 3.23-2.99 (m, 3H), 2.92-2.78 (m, 3H), 2.59-2.44 (m, 1H), 2.31-2.13 (m, 5H), 1.91-1.75 (m, 2H), 1.04-0.96 (m, 3H), 0.83-0.74 (m, 2H), 0.66-0.57 (m, 2H) |
| 196 | 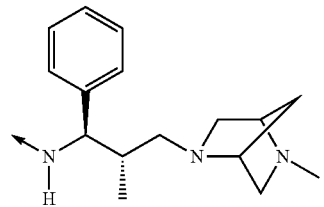 | 527 | 9.61-9.15 (m, 1H), 8.46-8.39 (m, 1H), 7.84 (dd, 1H), 7.74-7.62 (m, 1H), 7.48-7.43 (m, 1H), 7.36-7.15 (m, 5H), 6.70-6.67 (m, 1H), 6.61-6.56 (m, 1H), 5.06-4.86 (m, 1H), 3.19-3.16 (m, 1H), 3.09-3.02 (m, 1H), 2.90-2.56 (m, 5H), 2.45-2.37 (m, 1H), 2.37-2.31 (m, 1H), 2.20-2.19 (m, 3H), 2.05 (d, J = 20.5 Hz, 3H), 1.82-1.67 (m, 1H), 1.60-1.51 (m, 1H), 0.98-0.92 (m, 1H), 0.77-0.73 (m, 2H), 0.70-0.62 (m, 2H), 0.57-0.49 (m, 2H) |
| 197 | 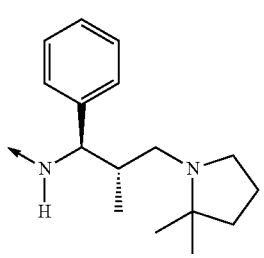 | 514 | 9.06-8.52 (m, 1H), 8.46-8.33 (m, 1H), 7.86-7.81 (m, 1H), 7.72-7.63 (m, 1H), 7.48-7.43 (m, 1H), 7.38-7.24 (m, 4H), 7.24-7.15 (m, 1H), 6.71-6.64 (m, 1H), 6.62-6.56 (m, 1H), 5.15-4.50 (m, 1H), 2.87-2.77 (m, 1H), 2.45-2.35 (m, 2H), 2.35-2.20 (m, 1H), 2.08-2.01 (m, 4H), 2.00-1.92 (m, 1H), 1.74-1.57 (m, 3H), 1.56-1.46 (m, 1H), 1.03-0.62 (m, 11H), 0.57-0.48 (m, 2H) |

Example 198

N-Cyclopropyl-3-[3-[[1-[2-[2-(ethylamino)ethoxy]phenyl]-1-methylethyl]amino]-2-oxo-1(2H)-pyrazinyl]-4-methyl-benzamide

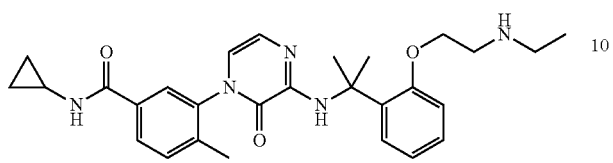

a) 3,3-Dimethyl-2(3H)-benzofuranone

A solution of benzofuran-2(3H)-one (20 g) dissolved in DMF (250 mL) was treated with iodomethane (33.4 mL) at 0° C. before adding potassium carbonate (134 g) portionwise over a period of 10 minutes under nitrogen. The resulting suspension was stirred at 25° C. for 3 days. The mixture was filtered and the solids washed with ethyl acetate. The filtrate was diluted with 2M hydrochloric acid, extracted with ethyl acetate. The organic was dried (MgSO$_4$), filtered and evaporated to afford crude product. The crude product was purified (SiO$_2$ chromatography eluting with 30% dichloromethane in iso-hexane). Pure fractions were evaporated to dryness to afford the subtitle compound (19.70 g).

$^1$H NMR δ (CDCl$_3$) 7.32-7.08 (m, 4H), 1.53 (s, 6H).

b) 2-Hydroxy-α,α-dimethyl-benzeneacetamide 3,3-Dimethylbenzofuran-2(3H)-one (Example 198a, 19.7 g) was dissolved in 7N ammonia in methanol (50 mL) under nitrogen. The resulting solution was stirred at 25° C. for 16 h. The reaction mixture was evaporated to afford crude product. The solid was triturated with diethyl ether and filtered to give the subtitle compound (15.34 g).

$^1$H NMR δ (DMSO-d$_6$) 7.18 (d, 1H), 7.07-7.00 (m, 1H), 6.78-6.71 (m, 2H), 6.63 (s, 1H), 6.38 (s, 1H), 3.35 (s, 1H), 1.43 (s, 6H).

c) α,α-Dimethyl-2-(phenylmethoxy)-benzeneacetamide

A solution of 2-hydroxy-α,α-dimethyl-benzeneacetamide (Example 198b, 15.34 g) dissolved in DMF (150 mL) was treated with potassium carbonate (11.83 g) and benzyl bromide (10.18 mL) under nitrogen. The resulting mixture was stirred at 25° C. for 16 h. The reaction mixture was diluted with water (500 mL) and stirred for 30 min. The solid was filtered off and washed with water and dried in vacuo to afford the subtitle compound (19.45 g).

MS: APCI (+ve) 270 (M+H)$^+$ d) α,α-Dimethyl-2-(phenylmethoxy)-benzenemethanamine

A solution of α,α-dimethyl-2-(phenylmethoxy)-benzeneacetamide (Example 198c, 19.45 g) dissolved in acetonitrile (200 mL) and water (200 mL) was treated with (Bis(trifluoroacetoxy)iodo)benzene (31.1 g) under nitrogen. The resulting solution was stirred at 20° C. for 60 h. The reaction mixture was diluted with water (300 mL), and extracted with diethyl ether. The aqueous layer was basified at 0° C. with 2M NaOH solution and extracted with ethyl acetate. The organic was dried (MgSO$_4$), filtered and evaporated to afford the subtitle compound (13.26 g).

$^1$H NMR δ (DMSO-d$_6$) 7.54-7.29 (m, 6H), 7.22-7.13 (m, 1H), 7.07 (d, 1H), 6.93-6.84 (m, 1H), 5.20 (s, 2H), 2.21 (s, 2H), 1.46 (s, 6H).

e) 3-[3-[[1-[2-(2-Chloroethoxy)phenyl]-1-methylethyl]amino]-2-oxo-1(2H)-pyrazinyl]-N-cyclopropyl-4-methyl-benzamide The subtitle compound was prepared by using α,α-dimethyl-2-(phenylmethoxy)-benzenemethanamine (Example 198d) using the methods described in example 134 to give N-cyclopropyl-4-methyl-3-[3-[[1-methyl-1-[2-[2-(1-pyrrolidinyl)ethoxy]phenyl]ethyl]amino]-2-oxo-1(2H)-pyrazinyl]-benzamide which was alkylated with 1-bromo-2-chloroethane as described in example 167e to afford the subtitle product.

MS: APCI (+ve) 481 (M+H)$^+$.

f) N-Cyclopropyl-3-[3-[[1-[2-[2-(ethylamino)ethoxy]phenyl]-1-methylethyl]amino]-2-oxo-1(2H)-pyrazinyl]-4-methyl-benzamide The title compound was prepared from 3-[3-[[1-[2-(2-chloroethoxy)phenyl]-1-methylethyl]amino]-2-oxo-1(2H)-pyrazinyl]-N-cyclopropyl-4-methyl-benzamide (Example 198e) and 70% ethylamine in water using the method of example 167f.

MS: APCI (+ve) 490 (M+H)$^+$.

$^1$H NMR δ (DMSO-d$_6$) 8.42 (d, 1H), 7.85 (d, 1H), 7.74 (s, 1H), 7.47 (d, 1H), 7.34 (d, 1H), 7.23-7.14 (m, 1H), 6.99-6.87 (m, 3H), 6.69-6.59 (m, 2H), 4.01-3.89 (m, 2H), 2.90-2.78 (m, 3H), 2.54-2.44 (m, 2H), 2.06 (s, 3H), 1.80 (s, 6H), 0.92-0.78 (m, 3H), 0.73-0.64 (m, 2H), 0.59-0.50 (m, 2H).

The following examples 199-213 (Table 6) were prepared in a similar manner to Example 198.

Example 199

N-Cyclopropyl-4-methyl-3-[3-[[1-methyl-1-[2-[2-(1-piperazinyl)ethoxy]phenyl]ethyl]amino]-2-oxo-1(2H)-pyrazinyl]-benzamide

Example 200

N-Cyclopropyl-3-[3-[[1-[2-[2-(diethylamino)ethoxy]phenyl]-1-methylethyl]amino]-2-oxo-1(2H)-pyrazinyl]-4-methyl-benzamide

Example 201

N-Cyclopropyl-4-methyl-3-[3-[[1-methyl-1-[2-[2-(1-piperidinyl)ethoxy]phenyl]ethyl]amino]-2-oxo-1(2H)-pyrazinyl]-benzamide

Example 202

N-Cyclopropyl-4-methyl-3-[3-[[1-methyl-1-[2-[2-(4-methyl-1-piperazinyl)ethoxy]phenyl]ethyl]amino]-2-oxo-1(2H)-pyrazinyl]-benzamide

Example 203

N-Cyclopropyl-4-methyl-3-[3-[[1-methyl-1-[2-[2-(4-morpholinyl)ethoxy]phenyl]ethyl]amino]-2-oxo-1(2H)-pyrazinyl]-benzamide

Example 204

N-Cyclopropyl-4-methyl-3-[3-[[1-methyl-1-[2-[4-(methylamino)butoxy]phenyl]ethyl]amino]-2-oxo-1(2H)-pyrazinyl]-benzamide

Example 205

N-Cyclopropyl-4-methyl-3-[3-[[1-methyl-1-[2-[4-[(2,2,2-trifluoroethyl)amino]butoxy]phenyl]ethyl]amino]-2-oxo-1(2H)-pyrazinyl]-benzamide

Example 206

N-Cyclopropyl-4-methyl-3-[3-[[1-methyl-1-[2-[4-(4-methyl-1-piperazinyl)butoxy]phenyl]ethyl]amino]-2-oxo-1(2H)-pyrazinyl]-benzamide

Example 207

N-Cyclopropyl-4-methyl-3-[3-[[1-methyl-1-[2-[3-[(2,2,2-trifluoroethyl)amino]propoxy]phenyl]ethyl]amino]-2-oxo-1(2H)-pyrazinyl]-benzamide

Example 208

N-Cyclopropyl-4-methyl-3-[3-[[1-methyl-1-[2-[3-(4-methyl-1-piperazinyl)propoxy]phenyl]ethyl]amino]-2-oxo-1(2H)-pyrazinyl]-benzamide

Example 209

N-Cyclopropyl-4-methyl-3-[3-[[1-methyl-1-[2-[1-methyl-2-(4-methyl-1-piperazinyl)ethoxy]phenyl]ethyl]amino]-2-oxo-1(2H)-pyrazinyl]-benzamide

Example 210

N-Cyclopropyl-3-[3-[[1-[2-[2-[(2-methoxyethyl)amino]ethoxy]phenyl]-1-methylethyl]amino]-2-oxo-1(2H)-pyrazinyl]-4-methyl-benzamide

Example 211

N-Cyclopropyl-3-[3-[[1-[2-[2-[(2-hydroxyethyl)amino]ethoxy]phenyl]-1-methylethyl]amino]-2-oxo-1(2H)-pyrazinyl]-4-methyl-benzamide

Example 212

N-Cyclopropyl-4-methyl-3-[3-[[1-methyl-1-[2-[2-[(1-methylethyl)amino]ethoxy]phenyl]ethyl]amino]-2-oxo-1(2H)-pyrazinyl]-benzamide

Example 213

N-Cyclopropyl-3-[3-[[1-[2-[2-[[(2S)-2-hydroxypropyl]amino]ethoxy]phenyl]-1-methylethyl]amino]-2-oxo-1(2H)-pyrazinyl]-4-methyl-6-benzamide

TABLE 6

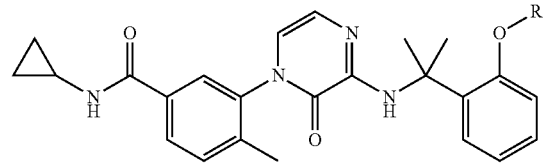

| Example | R | MS [M + H]+ m/z | 1H NMR δ (DMSO-d6) |
|---|---|---|---|
| 199 | ![piperazine-propyl] | 531 | 8.43 (d, 1H), 7.85 (d, 1H), 7.75 (s, 1H), 7.47 (d, 1H), 7.32 (d, 1H), 7.22-7.14 (m, 1H), 6.99-6.83 (m, 3H), 6.68-6.58 (m, 2H), 4.06-3.91 (m, 2H), 2.90-2.78 (m, 1H), 2.69-2.58 (m, 6H), 2.39-2.28 (m, 4H), 2.11 (s, 3H), 1.87 (s, 6H), 0.73-0.63 (m, 2H), 0.60-0.50 (m, 2H) |
| 200 | ![diethylamino-propyl] | 517 | 8.47-8.38 (m, 1H), 7.91-7.81 (m, 1H), 7.77 (s, 1H), 7.45 (d, 1H), 7.32 (d, 1H), 7.23-7.13 (m, 1H), 7.02-6.92 (m, 1H), 6.93-6.83 (m, 2H), 6.68-6.58 (m, 2H), 3.98-3.85 (m, 2H), 2.86-2.70 (m, 3H), 2.53-2.46 (m, 4H), 2.11 (s, 3H), 1.87 (s, 6H), 0.92 (t, 6H), 0.72-0.65 (m, 2H), 0.59-0.52 (m, 2H) |

TABLE 6-continued

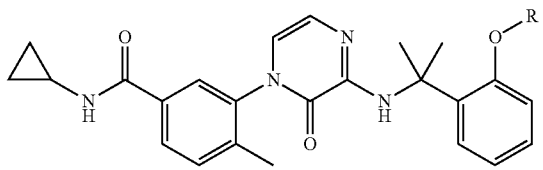

| Example | R | MS [M + H]+ m/z | 1H NMR δ (DMSO-d6) |
|---|---|---|---|
| 201 | piperidinyl-propyl | 530 | 8.43 (d, 1H), 7.86 (d, 1H), 7.77 (s, 1H), 7.48 (d, 1H), 7.32 (d, 1H), 7.22-7.14 (m, 1H), 7.00-6.84 (m, 3H), 6.68-6.57 (m, 2H), 4.06-3.90 (m, 2H), 2.89-2.78 (m, 1H), 2.70-2.58 (m, 2H), 2.44-2.32 (m, 4H), 2.02 (s, 3H), 1.79 (s, 6H), 1.52-1.28 (m, 6H), 0.74-0.64 (m, 2H), 0.60-0.51 (m, 2H) |
| 202 | 4-methylpiperazinyl-propyl | 545 | 8.44-8.36 (m, 1H), 7.84 (d, 1H), 7.73 (s, 1H), 7.46 (d, 1H), 7.30 (d, 1H), 7.19-7.12 (m, 1H), 6.97-6.84 (m, 3H), 6.67-6.56 (m, 2H), 4.00-3.89 (m, 2H), 2.87-2.76 (m, 1H), 2.69-2.58 (m, 2H), 2.45-2.17 (m, 8H), 2.13-2.03 (m, 6H), 1.76 (s, 6H), 0.68-0.62 (m, 2H), 0.56-0.49 (m, 2H) |
| 203 | morpholinyl-propyl | 532 | 8.44 (d, 1H), 7.88 (d, 1H), 7.76 (s, 1H), 7.50 (d, 1H), 7.34 (d, 1H), 7.23-7.17 (m, 1H), 7.01-6.85 (m, 3H), 6.69-6.60 (m, 2H), 4.06-3.97 (m, 2H), 3.58-3.49 (m, 4H), 2.90-2.81 (m, 1H), 2.72-2.63 (m, 2H), 2.47-2.40 (m, 4H), 2.13 (s, 3H), 1.88 (s, 6H), 0.73-0.66 (m, 2H), 0.60-0.53 (m, 2H) |
| 204 | methylamino-pentyl | 504 | 8.53-8.44 (m, 1H), 7.89 (d, 1H), 7.78 (s, 1H), 7.53 (d, 1H), 7.35 (d, 1H), 7.20 (t, 1H), 7.01-6.86 (m, 3H), 6.74-6.59 (m, 2H), 4.01-3.86 (m, 2H), 2.94-2.81 (m, 1H), 2.50-2.43 (m, 2H), 2.26 (s, 3H), 2.15 (s, 3H), 1.91 (s, 6H), 1.80-1.70 (m, 2H), 1.61-1.51 (m, 2H), 0.75-0.65 (m, 2H), 0.61-0.51 (m, 2H) |
| 205 | (2,2,2-trifluoroethyl)amino-pentyl | 572 | 8.48-8.39 (m, 1H), 7.87 (d, 1H), 7.76 (s, 1H), 7.48 (d, 1H), 7.31 (d, 1H), 7.23-7.11 (m, 2H), 6.99-6.85 (m, 3H), 6.71-6.57 (m, 2H), 4.00-3.86 (m, 2H), 3.27-3.14 (m, 2H), 2.90-2.77 (m, 1H), 2.69-2.56 (m, 2H), 2.01 (s, 3H), 1.78 (s, 6H), 1.78-1.68 (m, 2H), 1.61-1.51 (m, 2H), 0.74-0.64 (m, 2H), 0.58-0.48 (m, 2H) |

TABLE 6-continued
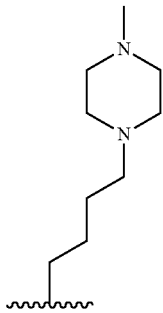
| Example | R | MS [M + H]+ m/z | $^1$H NMR δ (DMSO-$d_6$) |
|---|---|---|---|
| 206 | 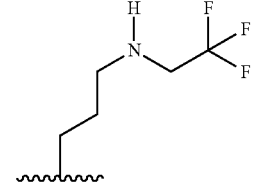 | 573 | 8.50-8.42 (m, 1H), 7.89 (d, 1H), 7.79 (s, 1H), 7.55-7.46 (m, 1H), 7.34 (d, 1H), 7.25-7.17 (m, 1H), 7.02-6.87 (m, 3H), 6.75-6.60 (m, 2H), 4.03-3.88 (m, 2H), 2.94-2.79 (m, 1H), 2.36-2.21 (m, 10H), 2.17-2.09 (m, 6H), 1.89-1.82 (m, 6H), 1.79-1.72 (m, 2H), 1.62-1.52 (m, 2H), 0.75-0.65 (m, 2H), 0.62-0.53 (m, 2H) |
| 207 | 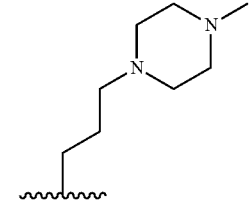 | 558 | 8.48-8.38 (m, 1H), 7.86 (d, 1H), 7.78 (s, 1H), 7.48 (d, 1H), 7.32 (d, 1H), 7.23-7.12 (m, 1H), 6.97-6.87 (m, 3H), 6.71-6.60 (m, 2H), 4.02-3.91 (m, 2H), 3.20-3.10 (m, 2H), 2.89-2.70 (m, 3H), 2.39-2.29 (m, 1H), 2.13 (s, 3H), 1.79 (s, 7H), 0.74-0.63 (m, 2H), 0.58-0.47 (m, 2H) |
| 208 | 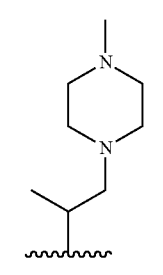 | 559 | 8.44-8.37 (m, 1H), 7.85 (d, 1H), 7.76 (s, 1H), 7.48 (d, 1H), 7.34 (d, 1H), 7.23-7.16 (m, 1H), 6.99-6.85 (m, 3H), 6.73-6.59 (m, 2H), 4.02-3.85 (m, 2H), 2.92-2.78 (m, 1H), 2.45-2.16 (m, 10H), 2.15-2.05 (m, 6H), 1.91-1.81 (m, 8H), 0.73-0.63 (m, 2H), 0.58-0.48 (m, 2H) |
| 209 | 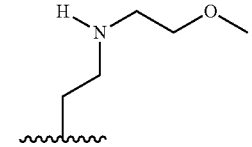 | 559 | 8.45-8.40 (m, 1H), 7.86 (dd, 1H), 7.71-7.67 (m, 1H), 7.50-7.47 (m, 1H), 7.34-7.31 (m, 1H), 7.16-7.16 (m, 1H), 6.99 (s, 1H), 6.87-6.85 (m, 2H), 6.64 (ddd, 2H), 4.67-4.63 (m, 1H), 2.84 (d, 2H), 2.36-2.25 (m, 6H), 2.11 (t, 6H), 2.08 (s, 2H), 1.86 (d, 3H), 1.79 (d, 3H), 1.12 (dd, 3H), 0.69 (dd, 2H), 0.56-0.54 (m, 2H) |
| 210 | 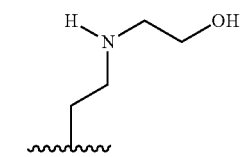 | 520 | 8.47 (s, 1H), 7.89 (d, 1H), 7.80 (s, 1H), 7.48 (d, 1H), 7.34 (d, 1H), 7.23-7.14 (m, 1H), 6.98-6.87 (m, 3H), 6.65 (d, 2H), 4.04-3.89 (m, 2H), 3.34-3.26 (m, 2H), 3.19 (s, 3H), 2.92-2.82 (m, 3H), 2.71-2.60 (m, 2H), 2.15 (s, 3H), 1.89 (s, 6H), 0.74-0.63 (m, 2H), 0.60-0.49 (m, 2H) |
| 211 | H-N-OH | 506 | 8.45-8.39 (m, 1H), 7.86 (d, 1H), 7.75 (s, 1H), 7.48 (d, 1H), 7.31 (d, 1H), 7.22-7.16 (m, 1H), 6.99-6.85 (m, 3H), 6.69-6.59 (m, 2H), 4.40-4.29 (m, 1H), 4.01-3.90 (m, 2H), 3.45-3.35 (m, 2H), 2.93-2.83 (m, 3H), 2.65-2.54 (m, 2H), 2.13 (s, 3H), 1.83 (d, 6H), 0.74-0.63 (m, 2H), 0.61-0.50 (m, 2H) |

TABLE 6-continued

| Example | R | MS [M + H]+ m/z | ¹H NMR δ (DMSO-d₆) |
|---|---|---|---|
| 212 | | 504 | 8.44-8.40 (m, 1H), 7.85 (d, 1H), 7.74 (s, 1H), 7.47 (d, 1H), 7.34 (d, 1H), 7.22-7.17 (m, 1H), 6.99-6.87 (m, 3H), 6.69-6.60 (m, 2H), 4.02-3.89 (m, 2H), 2.90-2.80 (m, 3H), 2.73-2.65 (m, 1H), 2.12 (s, 3H), 1.87-1.80 (m, 6H). 0.89 (d, 6H), 0.72-0.66 (m, 2H), 0.57-0.52 (m, 2H) |
| 213 | | 520 | 8.48 (s, 1H), 7.87 (d, 1H), 7.79 (s, 1H), 7.48 (d, 1H), 7.34 (d, 1H), 7.24-7.14 (m, 1H), 7.00-6.85 (m, 3H), 6.64 (d, 2H), 4.40-4.26 (m, 1H), 4.03-3.89 (m, 2H), 3.67-3.53 (m, 1H), 2.95-2.81 (m, 3H), 2.47-2.39 (m, 2H), 2.12 (s, 3H), 1.87 (s, 6H), 0.97 (d, 3H), 0.73-0.64 (m, 2H), 0.59-0.51 (m, 2H) |

Example 214

N-Cyclopropyl-4-methyl-3-[3-[[1-methyl-1-[2-(4-piperidinylmethoxy)phenyl]ethyl]amino]-2-oxo-1(2H)-pyrazinyl]-benzamide

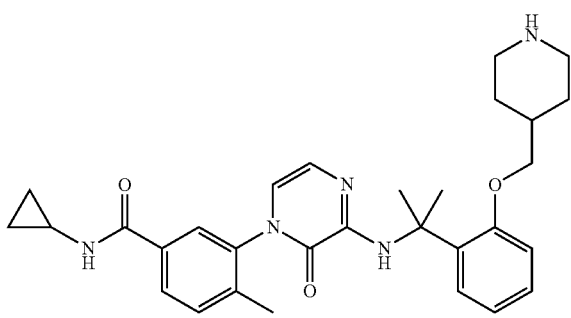

N-Cyclopropyl-3-(3-(2-(2-hydroxyphenyl)propan-2-ylamino)-2-oxopyrazin-1(2H)-yl)-4-methylbenzamide (Example 134, 0.172 g), potassium carbonate (0.114 g) and tert-butyl 4-(bromomethyl)piperidine-1-carboxylate (0.114 g) were stirred together in acetonitrile (10 mL) at reflux overnight. The cooled reaction mixture was evaporated to dryness and the residue partitioned between ethyl acetate (20 mL) and water (20 mL). The separated aqueous layer was further extracted into ethyl acetate (2×20 mL), the combined organics were dried (MgSO₄) and evaporated. The residue was dissolved in dichloromethane (10 mL) and treated with trifluoroacetic acid (1 ml), after stirring at room temperature for 1 h, the solvent was evaporated to leave the crude product. Purification by preparative HPLC (Gemini column—acetonitrile/0.2% ammonia mobile phase) afforded the title compound as a solid (50 mg).

MS: APCI (+ve) 516 (M+H)⁺.

¹H NMR δ (DMSO-d₆) 8.44 (s, 1H), 7.86 (d, 1H), 7.72 (s, 1H), 7.49 (d, 1H), 7.32 (d, 1H), 7.19 (t, 1H), 6.96 (d, 1H), 6.89 (t, 1H), 6.81 (s, 1H), 6.64 (q, 2H), 3.80-3.69 (m, 2H), 2.95-2.78 (m, 2H), 2.46-2.33 (m, 2H), 2.10 (s, 3H), 1.83 (s, 6H), 1.74-1.62 (m, 2H), 1.25-1.01 (m, 4H), 0.76-0.45 (m, 4H).

The following examples 215-219 (Table 7) were prepared in a similar manner to Example 214.

Example 215

N-Cyclopropyl-4-methyl-3-[3-[[1-[2-(3-azetidinyloxy)phenyl]-1-methylethyl]amino]-2-oxo-1(2H)-pyrazinyl]-benzamide

Example 216

N-Cyclopropyl-4-methyl-3-[3-[[1-methyl-1-[2-(3-pyrrolidinyloxy)phenyl]ethyl]amino]-2-oxo-1(2H)-pyrazinyl]-benzamide

Example 217

N-Cyclopropyl-4-methyl-3-[3-[[1-methyl-1-[2-[2-(4-piperidinyl)ethoxy]phenyl]ethyl]amino]-2-oxo-1(2H)-pyrazinyl]-benzamide

Example 218

N-Cyclopropyl-4-methyl-3-[3-[[1-methyl-1-[2-(3-piperidinylmethoxy)phenyl]ethyl]amino]-2-oxo-1(2H)-pyrazinyl]-benzamide

Example 219

N-Cyclopropyl-4-methyl-3-[3-[[1-methyl-1-[2-(4-piperidinyloxy)phenyl]ethyl]amino]-2-oxo-1(2H)-pyrazinyl]-benzamide

TABLE 7

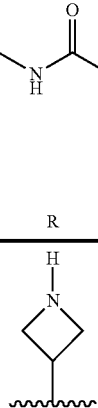

| Example | R | MS [M + H]+ m/z | 1H NMR δ (DMSO-d6) |
|---|---|---|---|
| 215 | 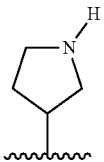 | 474 | 8.49-8.41 (m, 1H), 7.87 (d, 1H), 7.76 (s, 1H), 7.48 (d, 1H), 7.34 (d, 1H), 7.18-7.12 (m, 1H), 6.93-6.87 (m, 2H), 6.67-6.61 (m, 3H), 4.95-4.89 (m, 1H), 3.73-3.64 (m, 2H), 3.50-3.36 (m, 3H), 2.88-2.79 (m, 1H), 2.14 (s, 3H), 1.88 (s, 6H), 0.73-0.64 (m, 2H), 0.59-0.50 (m, 2H) |
| 216 | 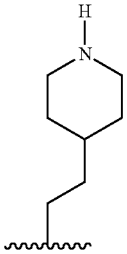 | 488 | 8.55-8.42 (m, 1H), 7.93-7.80 (m, 1H), 7.69 (d, 1H), 7.48 (d, 1H), 7.35 (d, 1H), 7.22-7.13 (m, 1H), 6.93-6.85 (m, 3H), 6.68-6.60 (m, 2H), 4.89-4.80 (m, 1H), 3.03-2.59 (m, 4H), 2.05 (s, 3H), 2.05-1.92 (m, 1H), 1.87-1.57 (m, 8H), 0.74-0.64 (m, 2H), 0.58-0.48 (m, 2H) |
| 217 | 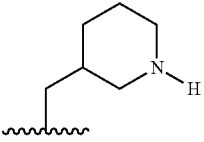 | 530 | 8.49-8.42 (m, 1H), 7.89-7.82 (m, 1H), 7.71 (s, 1H), 7.48-7.42 (m, 1H), 7.31 (d, 1H), 7.20-7.14 (m, 1H), 6.96 (d, 1H), 6.89-6.83 (m, 2H), 6.67-6.56 (m, 2H), 3.98-3.87 (m, 2H), 2.88-2.77 (m, 3H), 2.37-2.27 (m, 2H), 2.10 (s, 3H), 1.84 (s, 6H), 1.65-1.47 (m, 6H), 1.05-0.88 (m, 2H), 0.70-0.61 (m, 2H), 0.57-0.48 (m, 2H) |
| 218 | 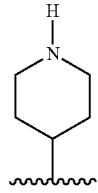 | 516 | 8.48-8.40 (m, 1H), 7.87 (d, 1H), 7.76 (s, 1H), 7.49 (d, 1H), 7.31 (d, 1H), 7.22-7.14 (m, 1H), 7.02-6.94 (m, 1H), 6.92-6.80 (m, 2H), 6.71-6.59 (m, 2H), 3.85-3.69 (m, 2H), 3.05-2.99 (m, 1H), 2.89-2.73 (m, 2H), 2.44-2.27 (m, 4H), 2.13 (s, 3H), 1.92-1.85 (m, 1H), 1.86 (s, 6H), 1.56-1.50 (m, 1H), 1.37-1.14 (m, 2H), 0.72-0.65 (m, 2H), 0.58-0.51 (m, 2H) |
| 219 | 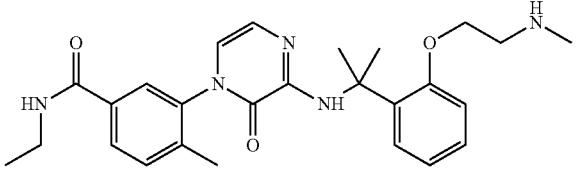 | 502 | 8.46-8.41 (m, 1H), 7.86 (d, 1H), 7.73 (s, 1H), 7.49 (d, 1H), 7.34 (d, 1H), 7.18-7.12 (m, 1H), 6.97 (d, 1H), 6.88-6.83 (m, 2H), 6.69-6.60 (m, 2H), 4.48-4.40 (m, 1H), 2.94-2.80 (m, 3H), 2.59-2.52 (m, 2H), 2.12 (s, 3H), 1.87 (s, 8H), 1.50-1.38 (m, 2H), 0.72-0.65 (m, 2H), 0.58-0.51 (m, 2H) |

Example 220

N-Ethyl-4-methyl-3-[3-[[1-methyl-1-[2-[2-(methylamino) ethoxy]phenyl]ethyl]amino]-2-oxo-1(2H)-pyrazinyl]-benzamide

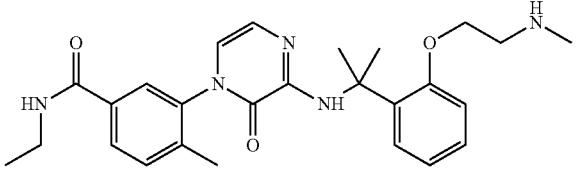

a) 3-[5-Bromo-3-[[1-methyl-1-[2-(phenylmethoxy)phenyl] ethyl]amino]-2-oxo-1(2H)-pyrazinyl]-4-methyl-benzoic acid methyl ester A solution of α,α-dimethyl-2-(phenylmethoxy)-benzenemethanamine (Example 198d, 1.5 g) dissolved in dioxane (52.2 mL) was treated with methyl 3-(3,5-dibromo-2-oxopyrazin-1(2H)-yl)-4-methylbenzoate (Example 1b, 2.499 g) and N-ethyldiisopropylamine (1.083 mL) under nitrogen. The resulting solution was stirred at 100° C. for 10 h. After cooling to room temperature, the reaction mixture was diluted with water (50 mL), and extracted with ethyl acetate (100 mL×2). The organic was dried (MgSO4), filtered and evaporated. The crude product was triturated with 50% diethyl ether in iso-hexane for 3 h. The solid was filtered off to afford the subtitle compound (2.405 g).

MS: APCI (+ve) 563 (M+H)+.

b) 3-[3-[[1-(2-Hydroxyphenyl)-1-methylethyl]amino]-2-oxo-1(2H)-pyrazinyl]-4-methyl-benzoic acid methyl ester To 3-[5-bromo-3-[[1-methyl-1-[2-(phenylmethoxy)phenyl]ethyl]amino]-2-oxo-1(2H)-pyrazinyl]-4-methyl-benzoic acid, methyl ester (Example 220a, 2 g) in ethanol (50 mL) was added ammonium formate (3.14 g) and 10% Pd/C (0.378 g) and the reaction heated at 75° C. for 1 h. The reaction was filtered through celite and the filtrate concentrated in vacuo. The reaction mixture was diluted with water (250 mL) and extracted with dichloromethane (250 mL). The organic layer was dried (MgSO$_4$), filtered and concentrated in vacuo to give the subtitle compound (1.410 g).

MS: APCI (+ve) 394 (M+H)+.

c) 4-Methyl-3-[3-[[1-methyl-1-[2-[2-[methyl[(phenylmethoxy)carbonyl]amino]ethoxy]phenyl]ethyl]amino]-2-oxo-1(2H)-pyrazinyl]-benzoic acid methyl ester To 3-[3-[[1-(2-Hydroxyphenyl)-1-methylethyl]amino]-2-oxo-1(2H)-pyrazinyl]-4-methyl-benzoic acid methyl ester (Example 220b, 2.495 g) in acetonitrile (150 mL) was added potassium carbonate (1.753 g) followed by benzyl 2-chloroethyl(methyl)carbamate (J. Med. Chem., 1992, 35 (17), 3246, 1.660 g) and the reaction heated at 85° C. for 72 h under nitrogen. Further benzyl 2-chloroethyl(methyl)carbamate (0.58 g) and potassium carbonate (0.35 g) were added and the reaction stirred for 2 days. The reaction mixture was cooled, evaporated to dryness and the residue partitioned between water and dichloromethane and the organic layer separated. The aqueous was further extracted with dichloromethane (2×) and the combined organics dried (Na$_2$SO$_4$) and evaporated. Purification (SiO$_2$ chromatography eluting with 40-100% ethyl acetate) gave the subtitle product (1.97 g).

$^1$H NMR δ (DMSO-d$_6$) 7.96 (d, 1H), 7.82 (s, 1H), 7.56 (d, 1H), 7.32 (s, 5H), 7.20-7.16 (m, 1H), 6.91 (t, 3H), 6.65 (d, 2H), 5.05 (s, 2H), 4.09-3.99 (m, 3H), 3.84 (s, 2H), 2.92 (d, 3H), 2.13 (s, 3H), 1.99 (d, 2H), 1.80 (s, 6H)

d) 4-Methyl-3-[3-[[1-methyl-1-[2-[2-[methyl[(phenylmethoxy)carbonyl]amino]ethoxy]phenyl]ethyl]amino]-2-oxo-1(2H)-pyrazinyl]-benzoic acid To 4-Methyl-3-[3-[[1-methyl-1-[2-[2-[methyl[(phenylmethoxy)carbonyl]amino]ethoxy]phenyl]ethyl]amino]-2-oxo-1(2H)-pyrazinyl]-benzoic acid methyl ester (Example 220c, 1.97 g) in THF (11 mL) was added lithium hydroxide monohydrate (0.424 g) in water (5.5 mL) (sonicated suspension) and the reaction stirred for 16 h at room temperature. Water was added and the solution acidified with 2M hydrochloric acid and then extracted with ethyl acetate. The organic layer was dried (MgSO$_4$) and evaporated. Trituration with diethyl ether/iso-hexane afforded the subtitle compound (1.790 g).

MS: APCI (+ve) 571 (M+H)+.

$^1$H NMR δ (DMSO-d$_6$) 7.95 (d, 1H), 7.79 (s, 1H), 7.54 (d, 1H), 7.32 (s, 6H), 7.19 (d, 1H), 7.00-6.89 (m, 3H), 6.66 (s, 2H), 5.05 (s, 2H), 4.06 (d, 2H), 3.64 (s, 2H), 2.92 (d, 3H), 2.12 (s, 3H), 1.80 (s, 6H).

e) [2-[2-[1-[[4-[5-[(Ethylamino)carbonyl]-2-methylphenyl]-3,4-dihydro-3-oxopyrazinyl]amino]-1-methylethyl]phenoxy]ethyl]methyl-carbamic acid phenylmethyl ester To 4-methyl-3-[3-[[1-methyl-1-[2-[2-[methyl[(phenylmethoxy)carbonyl]amino]ethoxy]phenyl]ethyl]amino]-2-oxo-1(2H)-pyrazinyl]-benzoic acid (Example 220d, 0.14 g) in DMF (3 mL) were added O-benzotriazol-1-yl-N,N,N',N'-tetramethyluronium tetrafluoroborate (0.158 g) followed by N-ethyldiisopropylamine (0.212 mL) and the reaction stirred for 15 min before ethylamine (0.032 mL) was added and the reaction stirred for 3 h. The reaction was diluted with water and the aqueous layer extracted with ethyl acetate. The combined organics were dried (Na$_2$SO$_4$) and solvents removed in vacuo to give the subtitle product (1.10 g).

MS: APCI (+ve) 598 (M+H)+.

f) N-Ethyl-4-methyl-3-[3-[[1-methyl-1-[2-[2-(methylamino)ethoxy]phenyl]ethyl]amino]-2-oxo-1(2H)-pyrazinyl]-benzamide To [2-[2-[1-[[4-[5-[(ethylamino)carbonyl]-2-methylphenyl]-3,4-dihydro-3-oxopyrazinyl]amino]-1-methylethyl]phenoxy]ethyl]methyl-carbamic acid phenylmethyl ester (Example 220d, 1.10 g) was added ethanol (10 mL) and this was pumped through a Pd/C cartridge at 1 mL/min under max H$_2$ at 50° C. on an H-Cube hydrogenator. The solvents were removed in vacuo and the residue then taken up in acetonitrile. Purification by preparative HPLC (ACE column, 0.2% TFA:acetonitrile eluent) followed by treatment with SCX resin (eluting with methanol (discarded) followed by 7N NH$_3$ in methanol and collected the basic fractions) and trituration with diethyl ether afforded the title product (2 mg).

MS: APCI (+ve) 464 (M+H)+.

$^1$H NMR δ (DMSO-d$_6$) 8.49 (s, 1H), 7.88 (d, 1H), 7.76 (s, 1H), 7.49 (d, 1H), 7.36 (d, 1H), 7.20 (t, 1H), 6.95 (m, 3H), 6.67 (d, 1H), 6.63 (d, 1H), 4.05-3.98 (m, 2H), 3.28 (t, 2H), 2.96 (d, 2H), 2.33 (s, 3H), 2.10 (s, 3H), 1.85 (s, 3H), 1.82 (s, 3H), 1.11 (t, 3H)

The following examples 221-229 (Table 8) were prepared in a similar manner to Example 220:

Example 221

1-[4-Methyl-3-[3-[[1-methyl-1-[2-[2-(methylamino)ethoxy]phenyl]ethyl]amino]-2-oxo-1(2H)-pyrazinyl]benzoyl]-azetidine

Example 222

N-Ethoxy-4-methyl-3-[3-[[1-methyl-1-[2-[2-(methylamino)ethoxy]phenyl]ethyl]amino]-2-oxo-1(2H)-pyrazinyl]-benzamide

Example 223

4-Methyl-N-(1-methylethyl)-3-[3-[[1-methyl-1-[2-[2-(methylamino)ethoxy]phenyl]ethyl]amino]-2-oxo-1(2H)-pyrazinyl]-benzamide

Example 224

N-Cyclobutyl-4-methyl-3-[3-[[1-methyl-1-[2-[2-(methylamino)ethoxy]phenyl]ethyl]amino]-2-oxo-1(2H)-pyrazinyl]-benzamide

Example 225

N-(2-Fluoroethyl)-4-methyl-3-[3-[[1-methyl-1-[2-[2-(methylamino)ethoxy]phenyl]ethyl]amino]-2-oxo-1(2H)-pyrazinyl]-benzamide

Example 226

4-Methyl-3-[3-[[1-methyl-1-[2-[2-(methylamino)ethoxy]phenyl]ethyl]amino]-2-oxo-1(2H)-pyrazinyl]-N-(2-methylpropyl)-benzamide

Example 227

4-Methyl-N-(1-methylcyclopropyl)-3-[3-[[1-methyl-1-[2-[2-(methylamino)ethoxy]phenyl]ethyl]amino]-2-oxo-1(2H)-pyrazinyl]-benzamide

Example 228

N-(2-Hydroxyethyl)-4-methyl-3-[3-[[1-methyl-1-[2-[2-(methylamino)ethoxy]phenyl]ethyl]amino]-2-oxo-1(2H)-pyrazinyl]-benzamide

Example 229

4-Methyl-3-[3-[[1-methyl-1-[2-[2-(methylamino)ethoxy]phenyl]ethyl]amino]-2-oxo-1(2H)-pyrazinyl]-benzamide

TABLE 8

| Example | R | MS [M + H]+ m/z | $^1$H NMR δ (DMSO-d$_6$) |
|---|---|---|---|
| 221 | azetidinyl | 476 | 7.64 (d, 1H), 7.48 (d, 2H), 7.35 (d, 1H), 7.19 (t, 1H), 6.98-6.88 (m, 3H), 6.62 (ddd, 2H), 4.33 (d, 2H), 4.06-3.93 (m, 3H), 3.44 (q, 2H), 2.83 (t, 2H), 2.27-2.25 (m, 3H), 2.11-2.06 (m, 3H), 1.83 (s, 6H), 1.06 (td, 2H) |
| 222 | H-N-O-ethyl | 480 | 7.78 (d, 1H), 7.71 (s, 1H), 7.52 (d, 1H), 7.42 (d, 1H), 7.26 (m, 1H), 7.24 (t, 1H), 7.01-6.96 (m, 2H), 6.70 (d, 1H), 6.63 (d, 1H), 4.26-4.09 (m, 2H), 3.92 (q, 2H), 3.40-3.23 (m, 2H), 2.52 (s, 3H), 2.11 (s, 3H), 1.89 (s, 3H), 1.80 (s, 3H), 1.21 (t, 3H) |
| 223 | H-N-isopropyl | 478 | 8.23 (d, 1H), 7.89 (dd, 1H), 7.81 (d, 1H), 7.49 (d, 1H), 7.38 (dd, 1H), 7.22 (dd, 1H), 7.12 (s, 1H), 7.00-6.93 (m, 3H), 6.67 (dd, 2H), 4.15-4.06 (m, 2H), 2.44 (s, 3H), 2.44 (s, 2H), 2.11 (s, 3H), 1.84 (d, 6H), 1.15 (d, 6H) |
| 224 | H-N-cyclobutyl | 490 | 8.64 (d, 1H), 7.90 (dd, 1H), 7.82 (s, 1H), 7.49 (d, 1H), 7.40 (dd, 1H), 7.23 (dd, 2H), 6.98 (q, 2H), 6.67 (dd, 2H), 4.41 (d, 1H), 4.21-4.15 (m, 2H), 3.40-3.26 (m, 2H), 2.53 (s, 3H), 2.21 (m, 2H), 2.11 (s, 3H), 2.05 (t, 2H), 1.88 (s, 6H), 1.72-1.61 (m, 2H) |
| 225 | H-N-CH$_2$CH$_2$F | 482 | 8.73 (s, 1H), 7.92-7.82 (m, 2H), 7.53-7.37 (m, 2H), 7.17 (d, 2H), 6.97 (s, 2H), 6.66 (s, 2H), 4.61 (s, 1H), 4.45 (s, 1H), 4.10 (s, 2H), 3.56 (d, 2H), 3.17 (s, 2H), 2.44 (s, 3H), 2.12 (s, 3H), 1.84 (d, 6H) |
| 226 | H-N-isobutyl | 492 | 8.47 (s, 1H), 7.90-7.87 (m, 1H), 7.75 (s, 1H), 7.49 (d, 1H), 7.34 (d, 1H), 7.19 (m, 1H), 6.98-6.91 (m, 3H), 6.68-6.63 (m, 2H), 4.09-3.91 (m, 1H), 3.18 (s, 2H), 3.16 (s, 2H), 2.84-2.82 (m, 2H), 2.09 (d, 3H), 1.99 (s, 3H), 1.83 (s, 6H), 1.20-1.09 (m, 6H) |

TABLE 8-continued

| Example | R | MS [M + H]+ m/z | 1H NMR δ (DMSO-d6) |
|---|---|---|---|
| 227 | ![structure] | 490 | 8.66 (s, 1H), 7.85 (dd, 1H), 7.71 (s, 1H), 7.47 (d, 1H), 7.34 (dd, 1H), 7.22-7.16 (m, 1H), 6.98-6.87 (m, 3H), 6.64 (dd, 2H), 3.96 (dtd, 2H), 2.83 (t, 2H), 2.26 (s, 3H), 2.09 (s, 3H), 1.83 (s, 6H), 1.35 (s, 3H), 0.73-0.70 (m, 2H), 0.61-0.57 (m, 2H) |
| 228 | ![structure] | 480 | 8.47 (s, 1H), 7.92 (s, 1H), 7.76 (s, 1H), 7.54 (s, 1H), 7.33 (s, 1H), 7.19 (s, 1H), 6.90 (s, 3H), 6.64 (s, 2H), 3.96 (s, 2H), 3.49 (s, 2H), 3.31-3.31 (m, 2H), 2.83 (s, 2H), 2.26 (s, 3H), 2.10 (s, 3H), 1.83 (s, 6H) |
| 229 | ![structure] | 436 | 7.98 (s, 1H), 7.90 (dd, 1H), 7.76 (d, 1H), 7.49 (d, 1H), 7.41 (s, 1H), 7.34 (dd, 1H), 7.19 (t, 1H), 6.96 (d, 1H), 6.90 (t, 2H), 6.65 (q, 2H), 3.96 (ddd, 2H), 2.83 (t, 2H), 2.26 (s, 3H), 2.10 (s, 3H), 1.83 (d, 6H) |

Example 230

N-Cyclopropyl-3-[3-[[1-[2-[2-[[(2S)-2-hydroxypropyl]amino]ethoxy]phenyl]cyclopropyl]amino]-2-oxo-1(2H)-pyrazinyl]-4-methyl-benzamide

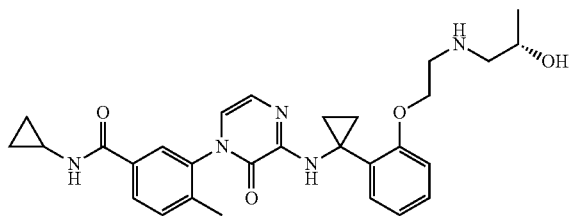

3-(3-(1-(2-(2-Chloroethoxy)phenyl)cyclopropylamino)-2-oxopyrazin-1(2H)-yl)-N-cyclopropyl-4-methylbenzamide (Example 167e, 100 mg) and (S)-(+)-1-amino-2-propanol (0.247 mL) were stirred together in dioxane (3 mL) in a sealed tube at 100° C. for 24 h. Purification of the cooled solution by preparative HPLC (Xbridge column—acetonitrile/0.2% ammonia mobile phase) afforded the title compound (60 mg).

MS: APCI (+ve) 518 (M+H)+.

1H NMR δ (DMSO-d6) 8.36 (d, 1H), 7.85 (d, 1H), 7.68 (s, 1H), 7.53-7.43 (m, 2H), 7.39-7.35 (m, 1H), 7.20 (t, 1H), 6.96 (d, 1H), 6.90-6.81 (m, 2H), 6.70 (d, 1H), 4.41 (s, 1H), 4.06 (t, 2H), 3.69 (s, 1H), 2.96 (t, 2H), 2.89-2.75 (m, 1H), 2.55-2.52 (m, 2H), 2.06 (s, 3H), 1.24-1.12 (m, 4H), 1.02 (d, 3H), 0.71-0.62 (m, 2H), 0.56-0.48 (m, 2H).

The following examples 231-249 (Table 9) were prepared in a similar manner to Example 230:

Example 231

N-Cyclopropyl-3-[3-[[1-[2-[2-[(2-methoxyethyl)amino]ethoxy]phenyl]cyclopropyl]amino]-2-oxo-1(2H)-pyrazinyl]-4-methyl-benzamide

Example 232

N-Cyclopropyl-3-[3-[[1-[2-[2-[4-(2-hydroxyethyl)-1-piperazinyl]ethoxy]phenyl]cyclopropyl]amino]-2-oxo-1(2H)-pyrazinyl]-4-methyl-benzamide

Example 233

N-Cyclopropyl-3-[3-[[1-[2-[2-[(2-hydroxyethyl)amino]ethoxy]phenyl]cyclopropyl]amino]-2-oxo-1(2H)-pyrazinyl]-4-methyl-benzamide

Example 234

N-Cyclopropyl-4-methyl-3-[3-[[1-[2-[2-[(1-methylethyl)amino]ethoxy]phenyl]cyclopropyl]amino]-2-oxo-1(2H)-pyrazinyl]-benzamide

Example 235

N-Cyclopropyl-3-[3-[[1-[2-[2-(hexahydro-4-methyl-1H-1,4-diazepin-1-yl)ethoxy]phenyl]cyclopropyl]amino]-2-oxo-1(2H)-pyrazinyl]-4-methyl-benzamide

Example 236

N-Cyclopropyl-3-[3-[[1-[2-[2-[(3R)-3-hydroxy-1-pyrrolidinyl]ethoxy]phenyl]cyclopropyl]amino]-2-oxo-1(2H)-pyrazinyl]-4-methyl-benzamide

Example 237

N-Cyclopropyl-3-[3-[[1-[2-[2-(dimethylamino)ethoxy]phenyl]cyclopropyl]amino]-2-oxo-1(2H)-pyrazinyl]-4-methyl-benzamide

Example 238

N-Cyclopropyl-4-methyl-3-[2-oxo-3-[[1-[2-[2-(1-pyrrolidinyl)ethoxy]phenyl]cyclopropyl]amino]-1(2H)-pyrazinyl]-benzamide

Example 239

N-Cyclopropyl-3-[3-[[1-[2-[2-[(2S)-2-(hydroxymethyl)-1-pyrrolidinyl]ethoxy]phenyl]cyclopropyl]amino]-2-oxo-1(2H)-pyrazinyl]-4-methyl-benzamide

Example 240

N-Cyclopropyl-4-methyl-3-[2-oxo-3-[[1-[2-[2-[(2,2,2-s trifluoroethyl)amino]ethoxy]phenyl]cyclopropyl]amino]-1(2H)-pyrazinyl]-benzamide

Example 241

N-Cyclopropyl-3-[3-[[1-[2-[2-(ethylmethylamino)ethoxy]phenyl]cyclopropyl]amino]-2-oxo-1(2H)-pyrazinyl]-4-methyl-benzamide

Example 242

N-Cyclopropyl-3-[3-[[1-[2-[2-[(3-hydroxy-2,2-dimethylpropyl)amino]ethoxy]phenyl]cyclopropyl]amino]-2-oxo-1(2H)-pyrazinyl]-4-methyl-benzamide

Example 243

N-Cyclopropyl-4-methyl-3-[2-oxo-3-[[1-[2-[2-(1-piperazinyl)ethoxy]phenyl]cyclopropyl]amino]-1(2H)-pyrazinyl]-benzamide

Example 244

N-Cyclopropyl-3-[3-[[1-[2-[2-(3,3-difluoro-1-pyrrolidinyl)ethoxy]phenyl]cyclopropyl]amino]-2-oxo-1(2H)-pyrazinyl]-4-methyl-benzamide

Example 245

N-Cyclopropyl-3-[3-[[1-[2-[2-[(2-fluoroethyl)amino]ethoxy]phenyl]cyclopropyl]amino]-2-oxo-1(2H)-pyrazinyl]-4-methyl-benzamide

Example 246

N-Cyclopropyl-4-methyl-3-[3-[[1-[2-[2-[(1-methylpropyl)amino]ethoxy]phenyl]cyclopropyl]amino]-2-oxo-1(2H)-pyrazinyl]-benzamide

Example 247

N-Cyclopropyl-4-methyl-3-[3-[[1-[2-[2-[(2R)-2-methyl-1-pyrrolidinyl]ethoxy]phenyl]cyclopropyl]amino]-2-oxo-1(2H)-pyrazinyl]-benzamide

Example 248

3-[3-[[1-[2-[2-(cyclobutylamino)ethoxy]phenyl]cyclopropyl]amino]-2-oxo-1(2H)-pyrazinyl]-N-Cyclopropyl-4-methyl-benzamide

Example 249

N-Cyclopropyl-3-[3-[[1-[2-[2-[[(1R)-2-hydroxy-1-methylethyl]amino]ethoxy]phenyl]cyclopropyl]amino]-2-oxo-1(2H)-pyrazinyl]-4-methyl-benzamide

Example 250

N-Cyclopropyl-3-[3-[[1-[2-[2-[(3-hydroxypropyl)amino]ethoxy]phenyl]cyclopropyl]amino]-2-oxo-1(2H)-pyrazinyl]-4-methyl-benzamide

Example 251

3-[3-[[1-[2-(2-aminoethoxy)phenyl]cyclopropyl]amino]-2-oxo-1(2H)-pyrazinyl]-N-cyclopropyl-4-methyl-benzamide

TABLE 9

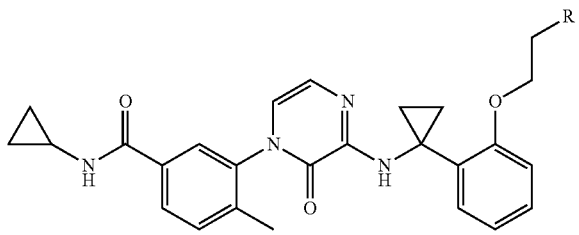

| Example | R | MS [M+H]+ m/z | 1H NMR δ (DMSO-d6 unless indicated) |
|---|---|---|---|
| 231 | 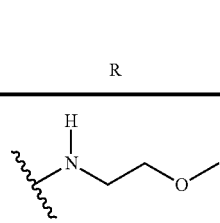 | 518 | 8.37-8.32 (1H, m), 7.84 (1H, d), 7.68 (1H, s), 7.47 (2H, t), 7.36 (1H, s), 7.19 (1H, t), 6.95 (1H, d), 6.90-6.81 (3H, m), 6.70 (1H, d), 4.06 (2H, t), 3.38 (2H, t), 3.18 (3H, s), 2.99-2.91 (1H, m), 2.87-2.69 (2H, m), 2.06 (3H, s), 1.27-1.10 (6H, m), 0.73-0.61 (2H, m), 0.56-0.46 (2H, m) |

TABLE 9-continued

| Example | R | MS [M + H]+ m/z | ¹H NMR δ (DMSO-d₆ unless indicated) |
|---|---|---|---|
| 232 | piperazinyl-CH₂CH₂OH | 573 | δ (CD₃OD) 7.81 (dd, 1H), 7.61 (d, 1H), 7.55 (dd, 1H), 7.44 (d, 1H), 7.22-7.17 (m, 1H), 6.92 (d, 1H), 6.89-6.83 (m, 2H), 6.56 (d, 1H), 4.19 (t, 2H), 3.61 (t, 2H), 2.92 (t, 2H), 2.84-2.76 (m, 1H), 2.76-2.65 (m, 4H), 2.63-2.52 (m, 4H), 2.48 (t, 2H), 2.11 (s, 3H), 1.29-1.15 (m, 3H), 1.14-1.08 (m, 1H), 0.79-0.72 (m, 2H), 0.61-0.55 (m, 2H). |
| 233 | NH-CH₂CH₂OH | 504 | 8.35 (1H, d), 7.84 (1H, dd), 7.67 (1H, d), 7.52-7.43 (2H, m), 7.38 (1H, s), 7.23-7.15 (1H, m), 6.96 (1H, d), 6.89-6.82 (2H, m), 6.70 (1H, d), 4.42 (1H, t), 4.06 (2H, t), 2.96 (2H, t), 2.88-2.75 (1H, m), 2.67 (2H, t), 2.06 (3H, s), 1.22-0.98 (6H, m), 0.71-0.61 (2H, m), 0.57-0.47 (2H, m) |
| 234 | NH-iPr | 502 | 8.35 (d, 1H), 7.84 (d, 1H), 7.68 (s, 1H), 7.48 (t, 2H), 7.35 (s, 1H), 7.20 (t, 1H), 6.96 (d, 1H), 6.89-6.82 (m, 3H), 6.71 (d, 1H), 4.05 (t, 2H), 2.94 (t, 2H), 2.87-2.70 (m, 2H), 2.06 (s, 3H), 1.29-1.11 (m, 2H), 0.98 (d, 6H), 0.88-0.79 (m, 2H), 0.71-0.61 (m, 2H), 0.56-0.46 (m, 2H) |
| 235 | 4-methyl-1,4-diazepan-1-yl | 557 | δ (CD₃OD) 7.79 (dd, 1H), 7.59 (d, 1H), 7.52 (dd, 1H), 7.42 (d, 1H), 7.20-7.14 (m, 1H), 6.92-6.80 (m, 2H), 6.54 (d, 1H), 4.12 (t, 2H), 3.02 (t, 2H), 2.93-2.87 (m, 4H), 2.82-2.74 (m, 1H), 2.69-2.62 (m, 4H), 2.27 (s, 3H), 2.08 (s, 3H), 1.85-1.78 (m, 2H), 1.32-1.05 (m, 5H), 0.89-0.81 (m, 1H), 0.77-0.70 (m, 2H), 0.59-0.52 (m, 2H) |
| 236 | (3R)-3-hydroxypyrrolidin-1-yl | 530 | δ (CD₃OD) 7.80 (dd, 1H), 7.59 (s, 1H), 7.54 (dd, 1H), 7.43 (d, 1H), 7.21-7.15 (m, 1H), 6.91 (d, 1H), 6.88-6.82 (m, 2H), 6.55 (dd, 1H), 4.35-4.29 (m, 1H), 4.15 (t, 2H), 3.04-2.85 (m, 4H), 2.82-2.75 (m, 1H), 2.70-2.63 (m, 2H), 2.17-2.06 (m, 4H), 1.74-1.64 (m, 1H), 1.26-1.15 (m, 2H), 1.15-1.08 (m, 1H), 0.95-0.81 (m, 1H), 0.78-0.71 (m, 2H), 0.59-0.54 (m, 2H) |
| 237 | N(CH₃)₂ | 488 | δ (CD₃OD) 7.80 (d, 1H), 7.62-7.53 (m, 2H), 7.46-7.39 (m, 1H), 7.22-7.14 (m, 1H), 6.95-6.82 (m, 2H), 6.57-6.50 (m, 1H), 4.19-4.10 (m, 2H), 3.32-3.25 (m, 2H), 2.91-2.84 (m, 2H), 2.82-2.74 (m, 1H), 2.41-2.34 (m, 6H), 2.12-2.05 (m, 3H), 1.32-1.07 (m, 4H), 0.78-0.71 (m, 2H), 0.60-0.52 (m, 2H) |

TABLE 9-continued

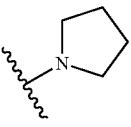

| Example | R | MS [M + H]+ m/z | 1H NMR δ (DMSO-d6 unless indicated) |
|---|---|---|---|
| 238 | 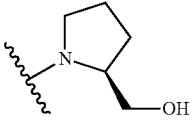 | 514 | δ (CD3OD) 7.80 (dd, 1H), 7.59 (d, 1H), 7.54 (dd, 1H), 7.43 (d, 1H), 7.21-7.16 (m, 1H), 6.92 (d, 1H), 6.88-6.82 (m, 2H), 6.54 (d, 1H), 4.17 (t, 2H), 3.01 (t, 2H), 2.83-2.76 (m, 1H), 2.75-2.68 (m, 3H), 2.09 (s, 3H), 1.83-1.77 (m, 4H), 1.25-1.15 (m, 3H), 1.15-1.08 (m, 1H), 0.90-0.81 (m, 1H), 0.78-0.71 (m, 2H), 0.59-0.54 (m, 2H) |
| 239 | 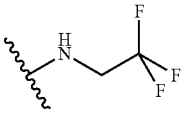 | 544 | δ (CD3OD) 7.83 (d, 1H), 7.63 (s, 1H), 7.56 (d, 1H), 7.46 (d, 1H), 7.21 (t, 1H), 6.94 (d, 1H), 6.91-6.84 (m, 2H), 6.58 (d, 1H), 4.20-4.14 (m, 2H), 3.62-3.48 (m, 2H), 3.43-3.35 (m, 2H), 2.92-2.79 (m, 2H), 2.74-2.66 (m, 1H), 2.54-2.43 (m, 1H), 2.12 (s, 3H), 1.99-1.87 (m, 1H), 1.82-1.73 (m, 2H), 1.70-1.60 (m, 1H), 1.32-1.08 (m, 4H), 0.92-0.84 (m, 1H), 0.81-0.74 (m, 2H), 0.63-0.57 (m, 2H) |
| 240 | 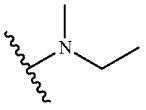 | 542 | δ (CD3OD) 7.91-7.86 (m, 1H), 7.76-7.71 (m, 1H), 7.70-7.65 (m, 1H), 7.57-7.51 (m, 1H), 7.42-7.35 (m, 1H), 7.14-7.09 (m, 1H), 7.08-7.03 (m, 1H), 6.97-6.92 (m, 1H), 6.88-6.83 (m, 1H), 4.40-4.33 (m, 2H), 3.80-3.71 (m, 2H), 3.57-3.52 (m, 1H), 3.51-3.46 (m, 2H), 3.25-3.21 (m, 1H), 2.93-2.85 (m, 1H), 2.26 (s, 3H), 1.58-1.52 (m, 1H), 1.52-1.44 (m, 2H), 1.41-1.34 (m, 1H), 1.28-1.21 (m, 1H), 0.89-0.83 (m, 2H), 0.70-0.64 (m, 2H) |
| 241 | 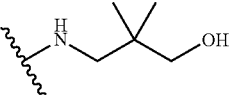 | 502 | δ (CD3OD) 7.81 (d, 1H), 7.68-7.58 (m, 2H), 7.46 (d, 1H), 7.34-7.27 (m, 1H), 7.05 (d, 1H), 6.99 (t, 1H), 6.87 (d, 1H), 6.77-6.72 (m, 1H), 4.47-4.40 (m, 2H), 3.77-3.59 (m, 2H), 3.50-3.43 (m, 1H), 2.93 (s, 3H), 2.85-2.76 (m, 1H), 2.16 (s, 3H), 1.53-1.11 (m, 9H), 0.78 (d, 2H), 0.62-0.55 (m, 2H) |
| 242 | 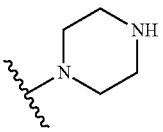 | 546 | δ (CD3OD) 7.90 (d, 1H), 7.79 (s, 1H), 7.70 (d, 1H), 7.56 (d, 1H), 7.45-7.39 (m, 1H), 7.16 (d, 1H), 7.10 (t, 1H), 6.95-6.91 (m, 2H), 4.50 (s, 2H), 3.70-3.58 (m, 2H), 3.58-3.55 (m, 2H), 3.21 (s, 2H), 2.93-2.86 (m, 1H), 2.30 (s, 3H), 1.72-1.65 (m, 1H), 1.64-1.58 (m, 1H), 1.57-1.50 (m, 1H), 1.43-1.34 (m, 1H), 1.05 (s, 6H), 0.86 (d, 2H), 0.72-0.66 (m, 2H) |
| 243 | | 529 | δ (CD3OD) 7.80 (dd, 1H), 7.60 (d, 1H), 7.54 (dd, 1H), 7.43 (d, 1H), 7.22-7.16 (m, 1H), 6.91 (d, 1H), 6.89-6.82 (m, 2H), 6.56 (d, 1H), 4.18 (t, 2H), 2.90 (t, 2H), 2.85 (t, 3H), 2.82-2.76 (m, 1H), 2.66-2.59 (m, 4H), 2.10 (s, 3H), 1.25-1.08 (m, 6H), 0.90-0.81 (m, 2H), 0.79-0.72 (m, 2H), 0.60-0.55 (m, 2H) |

TABLE 9-continued

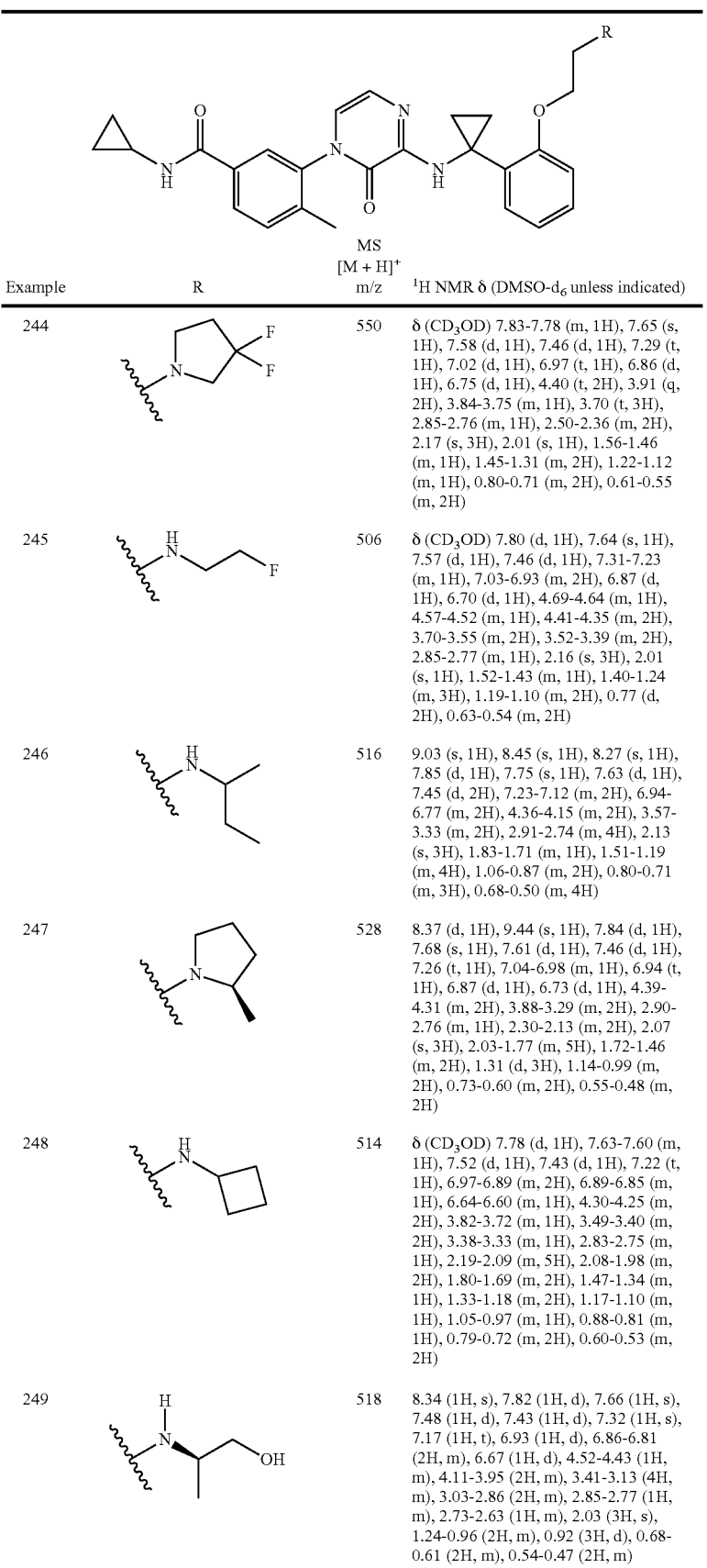

| Example | R | MS [M + H]+ m/z | 1H NMR δ (DMSO-d6 unless indicated) |
|---|---|---|---|
| 244 | (3,3-difluoropyrrolidinyl) | 550 | δ (CD3OD) 7.83-7.78 (m, 1H), 7.65 (s, 1H), 7.58 (d, 1H), 7.46 (d, 1H), 7.29 (t, 1H), 7.02 (d, 1H), 6.97 (t, 1H), 6.86 (d, 1H), 6.75 (d, 1H), 4.40 (t, 2H), 3.91 (q, 2H), 3.84-3.75 (m, 1H), 3.70 (t, 3H), 2.85-2.76 (m, 1H), 2.50-2.36 (m, 2H), 2.17 (s, 3H), 2.01 (s, 1H), 1.56-1.46 (m, 1H), 1.45-1.31 (m, 2H), 1.22-1.12 (m, 1H), 0.80-0.71 (m, 2H), 0.61-0.55 (m, 2H) |
| 245 | NH-CH2CH2-F | 506 | δ (CD3OD) 7.80 (d, 1H), 7.64 (s, 1H), 7.57 (d, 1H), 7.46 (d, 1H), 7.31-7.23 (m, 1H), 7.03-6.93 (m, 2H), 6.87 (d, 1H), 6.70 (d, 1H), 4.69-4.64 (m, 1H), 4.57-4.52 (m, 1H), 4.41-4.35 (m, 2H), 3.70-3.55 (m, 2H), 3.52-3.39 (m, 2H), 2.85-2.77 (m, 1H), 2.16 (s, 3H), 2.01 (s, 1H), 1.52-1.43 (m, 1H), 1.40-1.24 (m, 3H), 1.19-1.10 (m, 2H), 0.77 (d, 2H), 0.63-0.54 (m, 2H) |
| 246 | NH-sec-butyl | 516 | 9.03 (s, 1H), 8.45 (s, 1H), 8.27 (s, 1H), 7.85 (d, 1H), 7.75 (s, 1H), 7.63 (d, 1H), 7.45 (d, 2H), 7.23-7.12 (m, 2H), 6.94-6.77 (m, 2H), 4.36-4.15 (m, 2H), 3.57-3.33 (m, 2H), 2.91-2.74 (m, 4H), 2.13 (s, 3H), 1.83-1.71 (m, 1H), 1.51-1.19 (m, 4H), 1.06-0.87 (m, 2H), 0.80-0.71 (m, 3H), 0.68-0.50 (m, 4H) |
| 247 | (2-methylpyrrolidinyl) | 528 | 8.37 (d, 1H), 9.44 (s, 1H), 7.84 (d, 1H), 7.68 (s, 1H), 7.61 (d, 1H), 7.46 (d, 1H), 7.26 (t, 1H), 7.04-6.98 (m, 1H), 6.94 (t, 1H), 6.87 (d, 1H), 6.73 (d, 1H), 4.39-4.31 (m, 2H), 3.88-3.29 (m, 2H), 2.90-2.76 (m, 1H), 2.30-2.13 (m, 2H), 2.07 (s, 3H), 2.03-1.77 (m, 5H), 1.72-1.46 (m, 2H), 1.31 (d, 3H), 1.14-0.99 (m, 2H), 0.73-0.60 (m, 2H), 0.55-0.48 (m, 2H) |
| 248 | NH-cyclobutyl | 514 | δ (CD3OD) 7.78 (d, 1H), 7.63-7.60 (m, 1H), 7.52 (d, 1H), 7.43 (d, 1H), 7.22 (t, 1H), 6.97-6.89 (m, 2H), 6.89-6.85 (m, 1H), 6.64-6.60 (m, 1H), 4.30-4.25 (m, 2H), 3.82-3.72 (m, 1H), 3.49-3.40 (m, 2H), 3.38-3.33 (m, 1H), 2.83-2.75 (m, 1H), 2.19-2.09 (m, 5H), 2.08-1.98 (m, 2H), 1.80-1.69 (m, 2H), 1.47-1.34 (m, 1H), 1.33-1.18 (m, 2H), 1.17-1.10 (m, 1H), 1.05-0.97 (m, 1H), 0.88-0.81 (m, 1H), 0.79-0.72 (m, 2H), 0.60-0.53 (m, 2H) |
| 249 | NH-CH(CH3)-CH2OH | 518 | 8.34 (1H, s), 7.82 (1H, d), 7.66 (1H, s), 7.48 (1H, d), 7.43 (1H, d), 7.32 (1H, s), 7.17 (1H, t), 6.93 (1H, d), 6.86-6.81 (2H, m), 6.67 (1H, d), 4.52-4.43 (1H, m), 4.11-3.95 (2H, m), 3.41-3.13 (4H, m), 3.03-2.86 (2H, m), 2.85-2.77 (1H, m), 2.73-2.63 (1H, m), 2.03 (3H, s), 1.24-0.96 (2H, m), 0.92 (3H, d), 0.68-0.61 (2H, m), 0.54-0.47 (2H, m) |

TABLE 9-continued

| Example | R | MS [M + H]+ m/z | 1H NMR δ (DMSO-d6 unless indicated) |
|---|---|---|---|
| 250 | ⤳N(H)CH2CH2CH2OH | 518 | 8.35 (d, 1H), 7.84 (dd, 1H), 7.67 (d, 1H), 7.50 (dd, 1H), 7.46 (d, 1H), 7.41 (s, 1H), 7.19 (td, 1H), 6.95 (d, 1H), 6.88-6.83 (m, 2H), 6.69 (d, 1H), 4.05 (t, 2H), 3.44 (t, 2H), 2.93 (t, 2H), 2.82 (octet, 1H), 2.66 (t, 2H), 2.06 (s, 3H), 1.56 (quintet, 2H), 1.23-1.13 (m, 3H), 1.06-1.01 (m, 1H), 0.69-0.64 (m, 2H), 0.54-0.50 (m, 2H) |
| 251 | ⤳NH2 | 460 | 8.33 (d, 1H), 7.82 (dd, 1H), 7.65 (d, 1H), 7.47 (dd, 1H), 7.44-7.42 (m, 2H), 7.17 (td, 1H), 6.91 (d, 1H), 6.84-6.81 (m, 2H), 6.67 (d, 1H), 3.94 (t, 2H), 2.91 (t, 2H), 2.80 (octet, 1H), 2.03 (s, 3H), 1.21-1.14 (m, 3H), 1.03-1.00 (m, 1H), 0.66-0.62 (m, 2H), 0.52-0.48 (m, 2H) |

Example 252

N-Cyclopropyl-3-[3-[[1-[2-[2-(ethylamino)ethoxy]phenyl]-1-methylethyl]amino]-2-oxo-1(2H)-pyrazinyl]-5-fluoro-4-methyl-benzamide

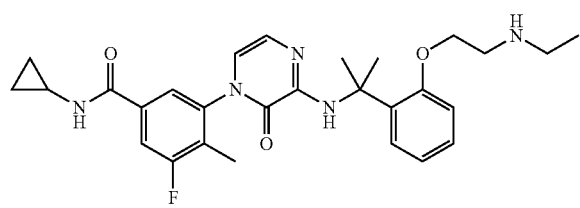

a) 2-Chloro-5-fluoro-4-methyl-benzoic acid methyl ester

To a solution of 1-bromo-2-chloro-5-fluoro-4-methylbenzene (70 g) dissolved in ethyl acetate (400 mL) was added N,N-diisopropylethylamine (161 mL), dichloro[1,1'-bis(diphenylphosphino)ferrocene]palladium(II) dichloromethane adduct (5.15 g) and methanol (120 mL). The resulting mixture was stirred at 90° C. for 24 h under carbon monoxide (4 bar) in a 1.5 L autoclave. Further dichloro[1,1'-bis(diphenylphosphino)ferrocene]palladium(II) dichloromethane adduct (2.57 g) was added and the reaction heated at 90° C. for a further 3 h. The cooled reaction mixture was evaporated to dryness and the residue purified by silica chromatography, eluting with 50% dichloromethane in iso-hexane to give the subtitle compound (57.7 g).

1H NMR δ (DMSO-d6) 7.64-7.50 (m, 2H), 3.90 (s, 3H), 2.31 (s, 3H).

b) 2-Chloro-5-fluoro-4-methyl-benzoic acid

A solution of 2-chloro-5-fluoro-4-methyl-benzoic acid methyl ester (Example 252a, 57.77 g) in methanol (400 mL) was treated with sodium hydroxide 2 M solution (285 mL) under nitrogen. The resulting mixture was stirred at 25° C. for 1 h. The reaction mixture was extracted with diethyl ether (discarded) and the aqueous layer diluted with 2 M hydrochloric acid (250 mL). The reaction mixture was extracted with ethyl acetate (500 mL). The combined organics were dried (MgSO4), filtered and evaporated to afford the subtitle compound (51.6 g).

1H NMR δ (DMSO-d6) 13.66 (s, 1H), 7.68-7.39 (m, 2H), 2.36 (s, 3H).

c) 2-Chloro-5-fluoro-4-methyl-3-nitro-benzoic acid

A solution of 2-chloro-5-fluoro-4-methylbenzoic acid (Example 252b, 51.57 g) dissolved in conc sulfuric acid (143 mL) was treated with potassium nitrate (32.4 g) portionwise over 10 min at 0° C. under nitrogen. The resulting mixture was allowed to warm to room temperature before stirring at 50° C. for 1 h. The reaction mixture was quenched with ice water and the precipitate was collected and dried in vacuo to afford the subtitle compound (65.5 g).

1H NMR δ (DMSO-d6) 7.94 (d, 1H), 2.26 (s, 3H).

d) 2-Chloro-5-fluoro-4-methyl-3-nitro-benzoic acid methyl ester

A solution of chlorotrimethylsilane (200 mL) in methanol (300 mL) was treated with 2-chloro-5-fluoro-4-methyl-3-nitrobenzoic acid (Example 252c, 65.5 g) portionwise under nitrogen. The resulting solution was stirred at 20° C. for 16 h. Further chlorotrimethylsilane (100 mL) was added and the reaction heated at 50° C. for 6 h. The reaction mixture was evaporated to afford crude product which was diluted with water and extracted with ethyl acetate (300 mL). The organic extract was dried (MgSO₄), filtered and evaporated to afford the subtitle compound (53.4 g).

¹H NMR δ (DMSO-d₆) 7.99 (d, 1H), 4.00 (s, 3H), 2.35 (s, 3H).

e) 3-Amino-5-fluoro-4-methyl-benzoic acid methyl ester

2-Chloro-5-fluoro-4-methyl-3-nitro-benzoic acid methyl ester (Example 252d, 53 g), 5% Pd/C (9 g) and ammonium formate (80 g) were stirred together in ethanol (500 mL) at 75° C. for 32 h. The reaction was filtered through celite and filtrate evaporated to a solid. This solid residue was dissolved in dichloromethane, washed with water. The separated aqueous layer was further extracted with dichloromethane (3×100 mL) and the combined organics dried (MgSO4) and evaporated. Analysis showed significant unreacted starting material. The reaction was repeated by new 5% P/C (9 g) and ammonium formate (80 g) together in ethanol (500 mL) and heating at 75° C. for 20 h. Further 5% Pd/C (9 g) and ammonium formate (80 g) were added and heating continued for 10 h. The mixture was filtered through celite and the filter cake was washed with further ethanol. The combined filtrates were evaporated, the residue dissolved in dichloromethane, washed with water. The separated aqueous layer was further extracted with dichloromethane (3×100 mL) and the combined organics dried (MgSO₄) and evaporated to afford the subtitle compound (34.7 g).

¹H NMR δ (CDCl₃) 7.15 (s, 1H), 7.12 (dd, 1H), 3.88 (s, 3H), 2.10 (d, 3H).

f) 3-[(Cyanomethyl)amino]-5-fluoro-4-methyl-benzoic acid, methyl ester

To a stirred solution of 3-amino-5-fluoro-4-methyl-benzoic acid methyl ester (Example 252e, 34.7 g) in THF (300 mL) at room temperature was added N,N-diisopropylethylamine (61.2 mL) followed by bromoacetonitrile (24.41 mL). The mixture was heated at reflux for 16 h, further bromoacetonitrile (4.8 mL) and N,N-diisopropylethylamine (12.5 mL) were added and heating was continued for 6 h. The reaction was cooled to room temperature and concentrated. 1N HCl (600 mL) and dichloromethane (800 mL) were added. This gave some solid precipitate which did not dissolve. Water (300 mL) was added to help identify layers. The lower organic layer containing solid and a bit of water was separated and this organic fraction was washed with 1M HCl/brine (400 mL of 1:1 mixture) before being dried (MgSO₄). A second drying (Na₂SO₄) was needed. After the drying agent was filtered off (washed through with 400 ml dichloromethane) the filtrate was concentrated (~60 g). This was azeotroped with toluene (400 mL) and final solvent removal gave subtitle compound (39.4 g).

¹H NMR δ (CDCl₃) 7.30 (d, 1H), 7.17 (s, 1H), 4.24 (d, 2H), 4.15-3.99 (m, 1H), 3.92 (s, 3H), 2.12 (s, 3H).

g) 3-(3,5-Dibromo-2-oxo-2H-pyrazin-1-yl)-5-fluoro-4-methyl-benzoic acid, methyl ester To a stirred solution of oxalyl bromide (49.9 mL) in dichloromethane (600 mL) at 0° C. under nitrogen was added 3-[(cyanomethyl)amino]-5-fluoro-4-methyl-benzoic acid methyl ester (Example 252f, 39.4 g) over 15 min. The mixture was allowed to warm to room temperature and stirred for 30 min then DMF (0.275 mL) was added and the mixture heated for 16 h at reflux. After cooling to 0° C., water (200 mL) was added over 15 min (caution) then the organic layer was separated, dried (MgSO₄) and evaporated. The residue was purified (SiO₂ chromatography eluting with dichloromethane) to afford the subtitle product (48.5 g).

¹H NMR δ (DMSO-d₆) 8.11 (s, 1H), 7.94 (s, 1H), 7.85 (dd, 1.5 Hz, 1H), 3.88 (s, 3H), 2.11 (d, 3H)

h) 3-[5-Bromo-3-[[1-methyl-1-[2-(phenylmethoxy)phenyl]ethyl]amino]-2-oxo-1(2H)-pyrazinyl]-5-fluoro-4-methyl-benzoic acid, methyl ester A solution of α,α-dimethyl-2-(phenylmethoxy)-benzenemethanamine (Example 198d, 5.25 g) dissolved in dioxane (40 mL) was treated with 3-(3,5-dibromo-2-oxo-2H-pyrazin-1-yl)-5-fluoro-4-methyl-benzoic acid, methyl ester (Example 252g, 9.14 g) and N,N-diisopropylethylamine (5.59 mL) under nitrogen. The resulting solution was stirred at 100° C. for 10 h. The reaction mixture was diluted with water (50 mL), and extracted with ethyl acetate (100 mL×2). The organic was dried (MgSO₄), filtered and evaporated. The crude product was purified (SiO₂ chromatography eluting with 20% ethyl acetate in iso-hexane) to afford the subtitle product (10.50 g).

MS: APCI (+ve) 580 (M+H)⁺.

i) 3-[5-Bromo-3-[[1-methyl-1-[2-(phenylmethoxy)phenyl]ethyl]amino]-2-oxo-1(2H)-pyrazinyl]-N-cyclopropyl-5-fluoro-4-methyl-benzamide A solution of 3-[5-bromo-3-[[1-methyl-1-[2-(phenylmethoxy)phenyl]ethyl]amino]-2-oxo-1(2H)-pyrazinyl]-5-fluoro-4-methyl-benzoic acid, methyl ester (Example 252h, 10.50 g) dissolved in THF (100 mL) was treated with cyclopropylamine (7.61 mL). Isopropylmagnesium chloride (45.2 mL of a 2.0M solution in THF) was added dropwise over 10 min under nitrogen. The resulting solution was stirred at 25° C. for 1 h. The reaction mixture was diluted with saturated ammonium chloride solution (300 mL) and extracted with ethyl acetate (×3). The organic was dried (MgSO₄), filtered and evaporated. The crude product was triturated with diethyl ether and filtered to afford the subtitle compound (9.86 g).

¹H NMR δ (DMSO-d₆) 8.54-8.47 (m, 1H), 7.78-7.64 (m, 2H), 7.46-6.91 (m, 10H), 5.15 (s, 2H), 4.08-3.98 (m, 1H), 2.01-1.93 (m, 3H), 1.87 (s, 6H), 0.74-0.67 (m, 2H), 0.59-0.52 (m, 2H).

j) N-Cyclopropyl-3-fluoro-5-[3-[[1-(2-hydroxyphenyl)-1-methylethyl]amino]-2-oxo-1(2H)-pyrazinyl]-4-methyl-benzamide To 3-[5-bromo-3-[[1-methyl-1-[2-(phenylmethoxy)phenyl]ethyl]amino]-2-oxo-1(2H)-pyrazinyl]-N-cyclopropyl-5-fluoro-4-methyl-benzamide (Example 252i, 9.84 g) was added 10% Pd/C (1.729 g) and ammonium formate (14.35 g). The reaction was heated at 75° C. for 2 h then filtered through celite and washed with ethanol. The filtrate was collected and the volatiles removed in vacuo and the resulting crude product was taken up in dichloromethane and washed with water. The organic layer dried (MgSO₄) and the solvent removed in vacuo and the residue triturated with diethyl ether to afford subtitle product (7.08 g).

¹H NMR δ (DMSO-d₆) 9.56-9.46 (m, H), 8.58-8.48 (m, 1H), 7.76 (d, 1H), 7.71 (s, 1H), 7.24 (d, 1H), 7.07-6.97 (m, 2H), 6.81-6.65 (m, 4H), 2.90-2.77 (m, 1H), 2.03 (s, 3H), 1.87-1.80 (m, 6H), 0.74-0.67 (m, 2H), 0.63-0.53 (m, 2H).

k) 3-[3-[[1-[2-(2-Chloroethoxy)phenyl]-1-methyl-ethyl]amino]-2-oxo-1(2H)-pyrazinyl]-N-cyclopropyl-5-fluoro-4-methyl-benzamide A solution of N-cyclopropyl-3-fluoro-5-[3-[[1-(2-hydroxyphenyl)-1-methylethyl]amino]-2-oxo-1(2H)-pyrazinyl]-4-methyl-benzamide (Example 252j, 7.08 g) dissolved in acetonitrile (150 mL) was treated with potassium carbonate (22.42 g) and 1-bromo-2-chloroethane (13.50 mL) under nitrogen. The resulting suspension was stirred at 83° C. for 10 h. The reaction mixture was evaporated to dryness, diluted with water (300 mL), and extracted with dichloromethane. The organic layer was dried (MgSO₄) and evaporated. The crude product was triturated with 50% diethyl ether in iso-hexane to afford subtitle compound (7.58 g).

¹H NMR δ (DMSO-d₆) δ 8.57-8.48 (m, 1H), 7.76 (d, 1H), 7.68 (s, 1H), 7.37-7.31 (m, 1H), 7.25-7.17 (m, 1H), 6.98-6.90 (m, 3H), 6.70 (s, 2H), 4.26-4.15 (m, 2H), 4.01-3.90 (m, 2H), 3.43-3.35 (m, 1H), 2.03 (s, 3H), 1.90 (s, 6H), 0.74-0.66 (m, 2H), 0.60-0.52 (m, 2H).

l) N-Cyclopropyl-3-[3-[[1-[2-[2-(ethylamino)ethoxy]phenyl]-1-methylethyl]amino]-2-oxo-1(2H)-pyrazinyl]-5-fluoro-4-methyl-benzamide A suspension of 3-[3-[[1-[2-(2-chloroethoxy)phenyl]-1-methylethyl]amino]-2-oxo-1(2H)-pyrazinyl]-N-cyclopropyl-5-fluoro-4-methyl-benzamide (Example 252k, 0.5 g) dissolved in 1,4-dioxane (2 mL) was treated with 70% ethylamine (2 mL) in a sealed tube. The resulting mixture was stirred at 100° C. for 1 h in a microwave (100 W). Evaporation and purification by preparative HPLC (Waters X-Terra column using a 95-5% gradient of aqueous 0.2% ammonia in acetonitrile as eluent) gave the title compound (0.255 g).

MS: APCI (+ve) 508 (M+H)⁺.

¹H NMR δ (DMSO-d₆) 8.57 (s, 1H), 7.75 (d, 2H), 7.69 (s, 1H), 7.40-7.29 (m, 1H), 7.24-7.13 (m, 1H), 6.98-6.86 (m, 3H), 6.73-6.62 (m, 2H), 4.10-3.88 (m, 2H), 3.42-3.24 (m, 1H), 2.91-2.79 (m, 2H), 2.04 (s, 3H), 1.89 (s, 6H), 0.92-0.80 (m, 5H), 0.76-0.64 (m, 2H), 0.61-0.48 (m, 2H).

The following examples 253-258 (Table 10) were prepared in a similar manner to Example 252.

Example 253

N-Cyclopropyl-3-fluoro-5-[3-[[1-[2-[2-[(2-hydroxyethyl)amino]ethoxy]phenyl]-1-methylethyl]amino]-2-oxo-1(2H)-pyrazinyl]-4-methyl-benzamide

Example 254

N-Cyclopropyl-3-fluoro-4-methyl-5-[3-[[1-methyl-1-[2-[2-[(1-methylethyl)amino]ethoxy]phenyl]ethyl]amino]-2-oxo-1(2H)-pyrazinyl]-benzamide

Example 255

N-Cyclopropyl-3-fluoro-5-[3-[[1-[2-[2-[(2-methoxyethyl)amino]ethoxy]phenyl]-1-methylethyl]amino]-2-oxo-1(2H)-pyrazinyl]-4-methyl-benzamide

Example 256

N-Cyclopropyl-3-fluoro-5-[3-[[1-[2-[2-[[(2R)-2-hydroxypropyl]amino]ethoxy]phenyl]-1-methylethyl]amino]-2-oxo-1(2H)-pyrazinyl]-4-methyl-benzamide

Example 257

N-Cyclopropyl-3-fluoro-5-[3-[[1-[2-[2-[(2-hydroxy-2-methylpropyl)amino]ethoxy]phenyl]-1-methylethyl]amino]-2-oxo-1(2H)-pyrazinyl]-4-methyl-benzamide

Example 258

N-Cyclopropyl-3-fluoro-5-[3-[[1-[2-[2-[[(2S)-2-hydroxypropyl]amino]ethoxy]phenyl]-1-methylethyl]amino]-2-oxo-1(2H)-pyrazinyl]-4-methyl-benzamide

TABLE 10

| Example | R | MS [M + H]⁺ m/z | ¹H NMR δ (DMSO-d₆) |
|---|---|---|---|
| 253 | ![H-N-CH₂-CH₂-OH] | 524 | 8.57-8.44 (m, 1H), 7.81-7.68 (m, 1H), 7.68 (s, 1H), 7.37-7.27 (m, 1H), 7.23-7.13 (m, 1H), 7.00-6.83 (m, 3H), 6.71-6.59 (m, 2H), 4.44-4.31 (m, 1H), 4.01-3.88 (m, 2H), 3.46-3.33 (m, 2H), 2.93-2.80 (m, 3H), 2.65-2.52 (m, 2H), 2.04 (s, 3H), 1.88 (s, 6H), 0.76-0.64 (m, 2H), 0.60-0.48 (m, 2H) |

TABLE 10-continued
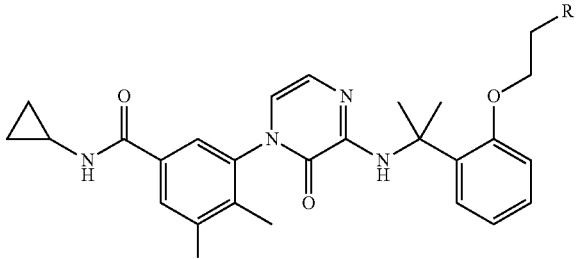
| Example | R | MS [M + H]+ m/z | 1H NMR δ (DMSO-d6) |
|---|---|---|---|
| 254 | 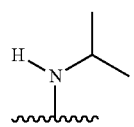 | 522 | 8.57-8.48 (m, 1H), 7.76 (d, 1H), 7.70-7.61 (m, 2H), 7.38-7.31 (m, 1H), 7.23-7.15 (m, 1H), 7.02-6.86 (m, 3H), 6.74-6.64 (m, 2H), 4.03-3.87 (m, 2H), 2.95-2.79 (m, 3H), 2.77-2.61 (m, 1H), 2.05-1.93 (m, 3H), 1.90-1.78 (m, 6H), 0.96-0.85 (m, 6H), 0.77-0.65 (m, 2H), 0.61-0.50 (m, 2H) |
| 255 | 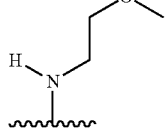 | 538 | 8.54-8.45 (m, 1H), 7.79-7.69 (m, 1H), 7.68-7.58 (m, 1H), 7.37-7.27 (m, 1H), 7.22-7.13 (m, 1H), 6.99-6.83 (m, 3H), 6.72-6.60 (m, 2H), 4.03-3.88 (m, 2H), 3.38-3.28 (m, 2H), 3.20-3.10 (m, 3H), 2.91-2.81 (m, 3H), 2.70-2.60 (m, 2H), 2.05 (s, 3H), 1.88 (s, 6H), 0.76-0.66 (m, 2H), 0.59-0.49 (m, 2H) |
| 256 | 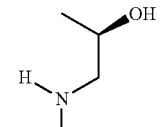 | 538 | 8.55-8.49 (m, 1H), 7.75 (d, 1H), 7.67 (s, 1H), 7.32 (d, 1H), 7.22-7.16 (m, 1H), 6.99-6.86 (m, 3H), 6.71-6.64 (m, 2H), 4.37-4.30 (m, 1H), 4.02-3.89 (m, 2H), 3.63-3.56 (m, 1H), 2.90-2.83 (m, 3H), 2.43 (d, 2H), 1.96 (s, 3H), 1.87-1.81 (m, 6H), 0.97 (d, 3H), 0.72-0.66 (m, 2H), 0.59-0.53 (m, 2H) |
| 257 | 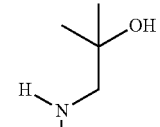 | 552 | 8.55-8.48 (m, 1H), 7.74 (d, 1H), 7.61 (s, 1H), 7.33 (d, 1H), 7.24-7.15 (m, 1H), 7.01-6.84 (m, 3H), 6.72-6.62 (m, 2H), 4.05 (s, 1H), 4.03-3.90 (m, 2H), 2.95-2.82 (m, 3H), 2.39 (s, 2H), 1.96 (s, 3H), 1.81 (s, 6H), 1.01 (s, 6H), 0.73-0.67 (m, 2H), 0.58-0.53 (m, 2H) |
| 258 | 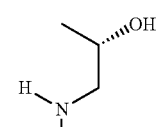 | 538 | 8.56-8.46 (m, 1H), 7.76 (d, 1H), 7.62 (s, 1H), 7.32 (d, 1H), 7.22-7.15 (m, 1H), 6.97-6.86 (m, 3H), 6.70-6.65 (m, 2H), 4.37-4.33 (m, 1H), 4.02-3.90 (m, 2H), 3.63-3.55 (m, 1H), 2.91-2.82 (m, 3H), 2.43 (d, 2H), 2.02 (s, 3H), 1.85-1.80 (m, 6H), 0.97 (d, 3H), 0.72-0.66 (m, 2H), 0.58-0.53 (m, 2H) |

Example 259

N-Cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide

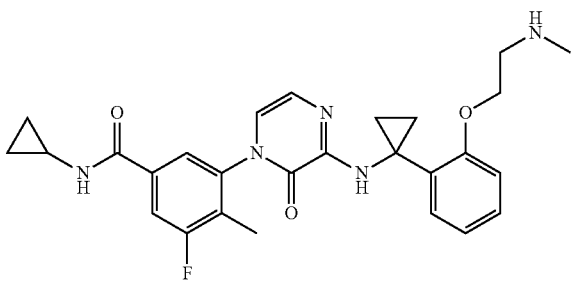

a) 3-[5-bromo-2-oxo-3-[[1-[2-(phenylmethoxy)phenyl]cyclopropyl]amino]-1(2H)-pyrazinyl]-5-fluoro-4-methyl-benzoic acid, methyl ester A solution of 1-(2-(benzyloxy)phenyl)cyclopropanamine (Example 167a, 5 g) in dioxane (200 mL) was treated with 3-(3,5-dibromo-2-oxo-2H-pyrazin-1-yl)-5-fluoro-4-methyl-benzoic acid, methyl ester (Example 252g, 7.5 g) and N-ethyldiisopropylamine (5.36 mL) under nitrogen. The resulting solution was stirred at 100° C. for 8 h. The cooled reaction mixture was diluted with 2M HCl (300 mL), and extracted with ether (3×300 mL). The combined organics were dried (MgSO$_4$), filtered and evaporated to afford crude product. Purification (SiO$_2$ chromatography eluting with 20% ethyl acetate in iso-hexane) gave the subtitle compound. (9.20 g).

$^1$H NMR δ (DMSO-d$_6$) 7.82-7.76 (m, 2H), 7.59-7.49 (m, 3H), 7.41-7.26 (m, 3H), 7.24-7.15 (m, 1H), 7.06-6.98 (m, 2H), 6.89 (t, 1H), 5.22 (s, 1H), 3.85 (s, 2H), 3.31 (s, 3H), 2.03 (d, 3H), 1.25-1.07 (m, 4H).

b) 3-Fluoro-5-[3-[[1-(2-hydroxyphenyl)cyclopropyl]amino]-2-oxo-1(2H)-pyrazinyl]-4-methyl-benzoic acid, methyl ester To 3-[5-bromo-2-oxo-3-[[1-[2-(phenylmethoxy)phenyl]cyclopropyl]amino]-1(2H)-pyrazinyl]-5-fluoro-4-methyl-benzoic acid, methyl ester (Example 259a, 9.2 g) in ethanol (400 mL) was added ammonium formate (14.04 g) and 10% Pd/C (1.693 g). The reaction was heated at 75° C. for 1 h, filtered through celite washing the celite with further warm ethanol (100 mL) followed by dichloromethane (2000 mL) and the combined filtrates were evaporated, diluted with dichloromethane (1000 mL) and washed with water, dried (MgSO$_4$) and evaporated to give the subtitle compound (6.16 g).

$^1$H NMR δ (DMSO-d$_6$) 11.23 (s, 1H), 7.85-7.73 (m, 2H), 7.48-7.42 (m, 1H), 7.16-7.04 (m, 1H), 6.91-6.86 (m, 1H), 6.83-6.67 (m, 3H), 5.75 (s, 1H), 3.85 (s, 3H), 2.03 (s, 3H), 1.32-1.16 (m, 2H), 1.12-1.01 (m, 2H).

c) N-Cyclopropyl-3-fluoro-5-[3-[[1-(2-hydroxyphenyl)cyclopropyl]amino]-2-oxo-1(2H)-pyrazinyl]-4-methyl-benzamide Isopropylmagnesium chloride (30.1 ml of a 2M solution in THF) was added over 20 min to a solution of cyclopropylamine (10.61 mL) and 3-fluoro-5-[3-[[1-(2-hydroxyphenyl)cyclopropyl]amino]-2-oxo-1(2H)-pyrazinyl]-4-methyl-benzoic acid methyl ester (Example 259b, 6.16 g) in tetrahydrofuran (200 mL) and the reaction stirred at room temperature under nitrogen for 1 h. Water (100 mL) and 2M HCl (200 mL) were cautiously added and the aqueous layer extracted with dichloromethane (3×200 mL) and the combined organic extracts dried (MgSO$_4$) and the solvent removed to give the subtitle compound (5.00 g).

$^1$H NMR δ (DMSO-d$_6$) 11.14 (s, 1H), 8.52 (s, 1H), 8.46 (d, 1H), 7.74 (dd, 1H), 7.64 (s, 1H), 7.46 (dd, 1H), 7.13-7.08 (m, 1H), 6.91 (d, 1H), 6.82-6.72 (m, 3H), 2.88-2.78 (m, 1H), 1.99 (d, 3H), 1.30-1.20 (m, 2H), 0.88-0.79 (m, 2H), 0.70-0.63 (m, 2H), 0.55-0.50 (m, 2H).

d) 3-[3-[[1-[2-(2-chloroethoxy)phenyl]cyclopropyl]amino]-2-oxo-1(2H)-pyrazinyl]-N-cyclopropyl-5-fluoro-4-methyl-benzamide N-Cyclopropyl-3-fluoro-5-[3-[[1-(2-hydroxyphenyl)cyclopropyl]amino]-2-oxo-1(2H)-pyrazinyl]-4-methyl-benzamide (Example 259c 5 g), 1-bromo-2-chloroethane (9.58 mL) and cesium carbonate (37.5 g) were stirred together in acetonitrile (200 mL) at 80° C. under nitrogen for 16 h. The cooled reaction mixture was evaporated to dryness, diluted with water (500 mL) and extracted with dichloromethane (3×300 mL). The combined organics were dried (MgSO$_4$), filtered and evaporated. The residue was triturated with 1:1 iso-hexane:diethyl ether to give the subtitle compound (4.60 g).

$^1$H NMR δ (DMSO-d$_6$) 8.45 (d, 1H), 7.72 (d, 1H), 7.60 (s, 1H), 7.51 (d, 1H), 7.27 (s, 1H), 7.24-7.16 (m, 1H), 7.00-6.84 (m, 2H), 6.75 (d, 1H), 4.30 (t, 2H), 4.00 (t, 2H), 2.93-2.77 (m, 1H), 1.95 (s, 3H), 1.31-1.02 (m, 4H), 0.75-0.62 (m, 2H), 0.58-0.47 (m, 2H).

e) N-Cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide 3-[3-[[1-[2-(2-chloroethoxy)phenyl]cyclopropyl]amino]-2-oxo-1(2H)-pyrazinyl]-N-cyclopropyl-5-fluoro-4-methyl-benzamide (Example 259d 0.5 g) and 40% methylamine in water (0.697 mL) were heated at 100° C. in dioxane (8 mL) in a sealed tube for 24 h. Purification of the cooled solution by preparative HPLC (Xbridge column—acetonitrile/0.2% ammonia mobile phase) gave the title compound (270 mg).

MS: APCI (+ve) 492 (M+H)$^+$.

$^1$H NMR δ (DMSO-d$_6$) 8.45 (1H, d), 7.73 (1H, d), 7.60 (1H, s), 7.52-7.47 (2H, m), 7.23-7.15 (1H, m), 6.95 (1H, d), 6.89-6.82 (2H, m), 6.73 (1H, d), 4.05 (2H, t), 2.89 (2H, t), 2.85-2.77 (1H, m), 2.35 (3H, s), 1.96 (3H, d), 1.25-0.97 (4H, m), 0.73-0.62 (2H, m), 0.57-0.48 (2H, m).

Example 260

N-Cyclopropyl-3-fluoro-5-[3-[[1-[2-[2-[(2-hydroxyethyl)amino]ethoxy]phenyl]cyclopropyl]amino]-2-oxo-1(2H)-pyrazinyl]-4-methyl-benzamide

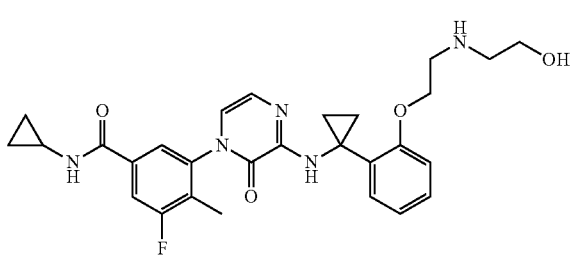

3-[3-[[1-[2-(2-chloroethoxy)phenyl]cyclopropyl]amino]-2-oxo-1(2H)-pyrazinyl]-N-cyclopropyl-5-fluoro-4-methyl-benzamide (Example 259d, 5 g) and ethanolamine (6.1 mL) were heated at 100° C. in dioxane (20 mL) in a sealed tube for 16 h. Purification of the cooled solution by preparative HPLC (Xterra column, eluting with a gradient of acetonitrile in 0.2% (v/v) aqueous ammonia) gave the title product (2.95 g) after solvent removal and trituration with isohexane/diethyl ether (1:1 80 mL)

MS: APCI (+ve) 522 (M+H)$^+$.

$^1$H NMR δ (DMSO-d$_6$) 8.46 (1H, d), 7.73 (1H, d), 7.61 (1H, s), 7.51 (1H, d), 7.43 (1H, s), 7.19 (1H, t), 6.95 (1H, d), 6.92-6.80 (2H, m), 6.74 (1H, d), 4.44 (1H, s), 4.06 (2H, t), 3.51-3.43 (2H, m), 3.42-3.30 (1H, m), 2.97 (2H, t), 2.90-2.77 (1H, m), 2.69 (2H, t), 1.97 (3H, s), 1.27-1.01 (4H, m), 0.75-0.63 (2H, m), 0.57-0.50 (2H, m).

The following examples 261-265 (Table 11) were prepared in a similar manner to Examples 259 and 260:

Example 261

N-Cyclopropyl-3-fluoro-5-[3-[[1-[2-[2-[(2-methoxyethyl)amino]ethoxy]phenyl]cyclopropyl]amino]-2-oxo-1(2H)-pyrazinyl]-4-methyl-benzamide

Example 262

N-Cyclopropyl-3-[3-[[1-[2-[2-(ethylamino)ethoxy]phenyl]cyclopropyl]amino]-2-oxo-1(2H)-pyrazinyl]-5-fluoro-4-methyl-benzamide

Example 263

N-Cyclopropyl-3-fluoro-5-[3-[[1-[2-[2-[[(2S)-2-hydroxypropyl]amino]ethoxy]phenyl]cyclopropyl]amino]-2-oxo-1(2H)-pyrazinyl]-4-methyl-benzamide

Example 264

N-Cyclopropyl-3-fluoro-4-methyl-5-[3-[[1-[2-[2-[(1-methylethyl)amino]ethoxy]phenyl]cyclopropyl]amino]-2-oxo-1(2H)-pyrazinyl]-benzamide

Example 265

N-Cyclopropyl-3-fluoro-5-[3-[[1-[2-[2-[[(2R)-2-hydroxypropyl]amino]ethoxy]phenyl]cyclopropyl]amino]-2-oxo-1(2H)-pyrazinyl]-4-methyl-benzamide

TABLE 11

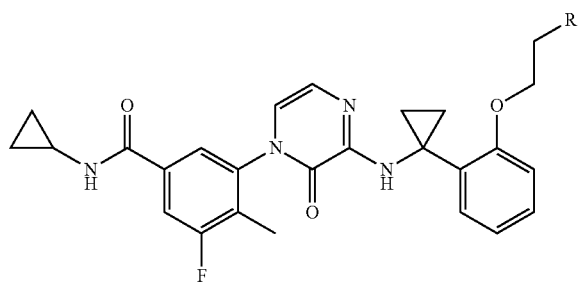

| Example | R | MS [M + H]$^+$ m/z | $^1$H NMR δ (DMSO-d$_6$) |
|---|---|---|---|
| 261 | ~~~N(H)CH$_2$CH$_2$OCH$_3$ | 536 | 8.47 (1H, d), 7.75 (1H, d), 7.63 (1H, s), 7.51 (1H, d), 7.42 (1H, s), 7.20 (1H, t), 6.96 (1H, d), 6.92-6.83 (2H, m), 6.75 (1H, d), 4.07 (2H, t), 3.40 (3H, t), 3.00-2.94 (2H, m), 2.90-2.81 (1H, m), 2.76 (2H, t), 1.98 (3H, s), 1.20 (3H, s), 1.13-0.78 (4H, m), 0.74-0.64 (2H, m), 0.60-0.49 (2H, m) |
| 262 | ~~~N(H)CH$_2$CH$_3$ | 506 | 8.45 (1H, d), 7.73 (1H, d), 7.61 (1H, s), 7.52-7.42 (2H, m), 7.19 (1H, t), 6.95 (1H, d), 6.91-6.81 (2H, m), 6.74 (1H, d), 4.05 (2H, t), 2.94 (2H, t), 2.89-2.78 (1H, m), 2.63 (2H, q), 1.97 (3H, s), 1.25-1.08 (4H, m), 1.00 (3H, t), 0.72-0.63 (2H, m), 0.57-0.51 (2H, m) |

TABLE 11-continued

[Structure shown: cyclopropyl-NH-C(=O)-benzene (with F and methyl substituents) linked to pyrazinone-NH-C(cyclopropyl)(2-substituted phenyl)-O-CH2CH2-R]

| Example | R | MS [M + H]+ m/z | $^1$H NMR δ (DMSO-d$_6$) |
|---|---|---|---|
| 263 | [structure: -NH-CH2-CH(OH)-CH3] | 536 | 8.44 (1H, d), 7.72 (1H, dd), 7.60 (1H, s), 7.49 (1H, dd), 7.39 (1H, d), 7.22-7.17 (1H, m), 6.96 (1H, d), 6.89-6.83 (2H, m), 6.73 (1H, d), 4.41-4.38 (1H, m), 4.10-4.02 (2H, m), 3.72-3.63 (1H, m), 2.98-2.91 (2H, m), 2.86-2.76 (1H, m), 1.96 (3H, s), 1.25-1.13 (4H, m), 1.02 (3H, dd), 0.88-0.80 (2H, m), 0.71-0.64 (2H, m), 0.56-0.49 (2H, m) |
| 264 | [structure: -NH-CH(CH3)2] | 520 | 8.44 (1H, d), 7.72 (1H, dd), 7.60 (1H, s), 7.49 (1H, dd), 7.37 (1H, s), 7.23-7.15 (1H, m), 6.95 (1H, d), 6.89-6.82 (2H, m), 6.74 (1H, d), 4.04 (2H, t), 2.94 (2H, t), 2.88-2.73 (2H, m), 1.96 (3H, d), 1.20-1.16 (2H, m), 0.98 (6H, d), 0.87-0.80 (2H, m), 0.72-0.63 (2H, m), 0.57-0.49 (2H, m) |
| 265 | [structure: -NH-CH2-CH(OH)-CH3] | 536 | 8.42 (1H, s), 7.74-7.63 (1H, m), 7.61-7.54 (1H, m), 7.51-7.34 (2H, m), 7.20-7.07 (1H, m), 6.96-6.76 (2H, m), 6.74-6.66 (1H, m), 4.45-4.32 (1H, m), 4.08-3.95 (2H, m), 3.72-3.56 (1H, m), 3.41-3.21 (1H, m), 3.02-2.71 (6H, m), 1.93 (3H, s), 1.27-0.88 (6H, m), 0.73-0.36 (4H, m) |

Example 266

N-Cyclopropyl-3-[3-[[1-[2-[2-(ethylamino)ethoxy]phenyl]-1-methylethyl]amino]-2-oxo-1(2H)-pyrazinyl]-4-methyl-benzamide

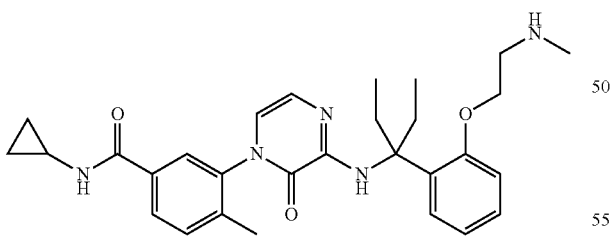

a) 3,3-Diethyl-2(3H)-benzofuranone

Benzofuran-2(3H)-one (2 g) in DMF (3.5 mL) was added dropwise to 60% sodium hydride (1.252 g) in DMF (10 mL) at 0° C. and after 20 min, ethyl iodide (5.18 mL) was added dropwise and the reaction warmed to room temperature and stirred for 20 h. The solids were filtered off and washed with ethyl acetate. The filtrate was acidified with 2M hydrochloric acid, and then extracted with ethyl acetate. The combined organic layers were dried (MgSO$_4$) and concentrated in vacuo. The crude product was purified (SiO$_2$ chromatography eluting with 20% diethyl ether in iso-hexane) to afford the subtitle product (1.14 g).

$^1$H NMR δ (DMSO-d$_6$) 7.41-7.34 (m, 2H), 7.27-7.22 (m, 2H), 1.90 (dseptet, 4H), 0.58 (t, 6H).

b) α,α-Diethyl-2-hydroxy-benzeneacetamide

7N Ammonia in methanol (10 mL) was added to 3,3-diethyl-2(3H)-benzofuranone (Example 266a, 1.14 g) and the reaction stirred at room temperature for 16 h. 880 Ammonia (20 mL) was added and the mixture stirred for 5 h. The reaction mixture was diluted with water and extracted with ethyl acetate. The organic layer was dried (MgSO$_4$), filtered and evaporated to afford crude product (1.21 g).

$^1$H NMR δ(CDCl$_3$) 7.47-7.44 (m, 1H), 7.40-7.35 (m, 1H), 7.00-6.93 (m, 2H), 5.10 (s, 2H), 2.19 (dt, 2H), 1.93 (dt, 2H), 0.73 (t, 6H).

c) α,α-Diethyl-2-(phenylmethoxy)-benzeneacetamide

A solution of α,α-diethyl-2-hydroxy-benzeneacetamide (Example 266b, 1.21 g) in DMF (9.93 mL) was treated with potassium carbonate (0.807 g) and benzyl bromide (0.694 mL) under nitrogen. The resulting mixture was stirred at room temperature for 16 h. The reaction mixture was diluted with water and extracted with ethyl acetate. The organic layer was dried (MgSO₄), filtered and evaporated. The crude product was purified (SiO₂ chromatography eluting with 30-100% ethyl acetate in iso-hexane) to afford the subtitle product (0.77 g).

MS: APCI (+ve) 298 (M+H)⁺.

d) α,α-diethyl-2-(phenylmethoxy)-benzenemethanamine

A solution of α,α-diethyl-2-(phenylmethoxy)-benzeneacetamide (Example 266c, 0.77 g) in acetonitrile (6 mL) and water (6 mL) was treated with (bis(trifluoroacetoxy)iodo)benzene (1.113 g) under nitrogen and the reaction stirred at room temperature for 16 h. Further (bis(trifluoroacetoxy)iodo)benzene (1.0 g) was added and the reaction stirred for 3 h. The reaction mixture was diluted with water and extracted with ethyl acetate. The organic layer was dried (MgSO₄), filtered and evaporated. The crude product was purified on SCX resin eluting with methanol (discarded) followed by 7N NH₃ in methanol. The basic fractions were collected and the volatiles were removed in vacuo to afford subtitle compound (0.83 g).

¹H NMR δ (CDCl₃) 7.43-7.34 (m, 7H), 6.98-6.94 (m, 4H), 5.12 (s, 2H), 2.13 (dt, 4H), 0.74 (t, 6H).

e) 3-[3-[[1-[2-(2-Chloroethoxy)phenyl]-1-ethylpropyl]amino]-2-oxo-1(2H)-pyrazinyl]-N-cyclopropyl-4-methyl-benzamide α,α-Diethyl-2-(phenylmethoxy)-benzenemethanamine (Example 266d) was converted to N-cyclopropyl-3-[3-[[1-ethyl-1-(2-hydroxyphenyl)propyl]amino]-2-oxo-1(2H)-pyrazinyl]-4-methyl-benzamide using the method described in Example 134. This phenol was alkylated with 1-bromo-2-chloroethane as described in example 167e to afford the subtitle product.

MS: APCI (+ve) 509 (M+H)⁺.

f) N-Cyclopropyl-3-[3-[[1-[2-[2-(ethylamino)ethoxy]phenyl]-1-methylethyl]amino]-2-oxo-1(2H)-pyrazinyl]-4-methyl-benzamide The title compound was prepared from 3-[3-[[1-[2-(2-Chloroethoxy)phenyl]-1-ethylpropyl]amino]-2-oxo-1(2H)-pyrazinyl]-N-cyclopropyl-4-methyl-benzamide (Example 266e) using the method of example 167f.

MS: APCI (+ve) 504 (M+H)⁺.

¹H NMR δ (DMSO-d₆) 8.48-8.42 (m, 1H), 7.87 (d, 1H), 7.78 (s, 1H), 7.48 (d, 1H), 7.29 (d, 1H), 7.23-7.16 (m, 1H), 7.01-6.88 (m, 3H), 6.67-6.61 (m, 2H), 4.01-3.89 (m, 2H), 2.89-2.76 (m, 3H), 2.47-2.27 (m, 4H), 2.26 (s, 3H), 2.11 (s, 3H), 0.71-0.61 (m, 8H), 0.57-0.52 (m, 2H).

Example 267

N-Cyclopropyl-3-[3-[[1-ethyl-1-[2-[2-(ethylamino)ethoxy]phenyl]propyl]amino]-2-oxo-1(2H)-pyrazinyl]-4-methyl-benzamide

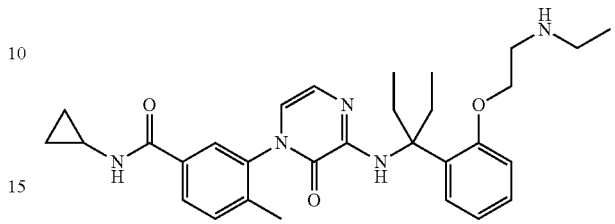

The title compound was prepared from 3-[3-[[1-[2-(2-chloroethoxy)phenyl]-1-ethylpropyl]amino]-2-oxo-1(2H)-pyrazinyl]-N-cyclopropyl-4-methyl-benzamide (Example 266e) using the method described in Example 167f but using 70% ethylamine in water.

MS: APCI (+ve) 518 (M+H)⁺.

¹H NMR δ (DMSO-d₆) 8.44 (d, 1H), 7.86 (d, 1H), 7.77 (s, 1H), 7.49 (d, 1H), 7.28 (d, 1H), 7.23-7.16 (m, 1H), 7.00-6.89 (m, 3H), 6.70-6.58 (m, 2H), 4.00-3.89 (m, 2H), 2.90-2.78 (m, 3H), 2.54-2.25 (m, 6H), 2.11 (s, 3H), 0.89 (t, 3H), 0.70-0.62 (m, 8H), 0.59-0.51 (m, 2H).

Example 268

N-Cyclopropyl-4-methyl-3-[3-[[1-[2-[2-(methylamino)ethoxy]phenyl]cyclobutyl]amino]-2-oxo-1(2H)-pyrazinyl]-benzamide

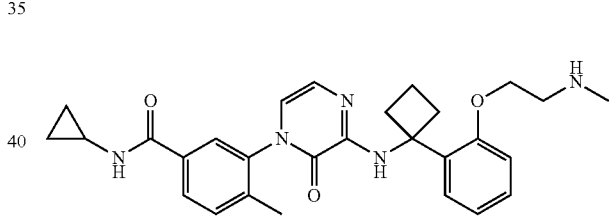

a) 1-(2-Methoxyphenyl)cyclobutanecarboxamide

To 1-(2-methoxyphenyl)cyclobutanecarbonitrile (4.29 g) was added sulfuric acid (20 mL, 95-98%)/water (20 mL) and the reaction warmed to 60° C. After 1 h the solution was warmed to 80° C. and heating was continued for 3 h. The reaction was cooled to room temperature and stirred for 16 h. Heating was resumed and after 1 h acetic acid (10 mL) was added. The temperature was increased to 90° C. and heating was continued for 1.75 h. The reaction was cooled to room temperature and then poured onto ~300 ml of ice and extracted with ethyl acetate. The organic layer was dried (Na₂SO₄) and the solvent removed in vacuo to afford the subtitle product (4.19 g).

¹H NMR δ (CDCl₃) 8.44 (s, 2H), 7.27 (td, 1H), 7.23 (dd, 1H), 6.99 (td, 1H), 6.90 (d, 1H), 3.83 (s, 3H), 2.87-2.77 (m, 2H), 2.51-2.41 (m, 2H), 2.24-2.11 (m, 1H), 1.88-1.77 (m, 1H).

b) 1-(2-(Benzyloxy)phenyl)cyclobutanecarboxamide

To 1-(2-methoxyphenyl)cyclobutanecarboxamide (Example 268a, 4.19 g) at 0° C. in dichloromethane (20 mL) was added boron tribromide (40.8 mL, 1 M in dichloromethane) and the reaction warmed to room temperature over 3 h. It was poured into ice, extracted with dichloromethane (×3) and the combined organics were dried (MgSO$_4$) and the solvent was removed in vacuo to give crude 1-(2-hydroxyphenyl)cyclobutanecarboxamide (2.96 g). This was dissolved in DMF (20 mL) and potassium carbonate (2.14 g) and benzyl bromide (1.84 mL) were added and the reaction stirred for 16 h. Water and ethyl acetate were added and the organic layer separated. The aqueous layer was extracted further with ethyl acetate. The combined organics were washed with water (×3), brine, dried (Na$_2$SO$_4$) and the solvent was removed in vacuo. The residue was purified (SiO$_2$ chromatography eluting with 5-50% ethyl acetate in iso-hexane) to afford the subtitle product (1.98 g).

$^1$H NMR δ (CDCl$_3$) 7.43-7.21 (m, 7H), 7.02-6.95 (m, 2H), 5.73 (s, 1H), 5.10 (s, 2H), 5.04 (s, 1H), 2.88-2.78 (m, 2H), 2.55-2.44 (m, 2H), 2.16 (sextet, 1H), 1.88-1.74 (m, 1H).

c) 1-(2-(Benzyloxy)phenyl)cyclobutanamine

A solution of 1-(2-(benzyloxy)phenyl)cyclobutanecarboxamide (Example 268b 1.984 g) dissolved in acetonitrile (16 mL) and water (16 mL) under nitrogen was treated with [bis(trifluoroacetoxy)iodo]benzene (4.55 g). The resulting solution was stirred at room temperature for 16 h. The reaction mixture was diluted with water, extracted with diethyl ether. The aqueous layer was separated, basified to pH13 with aqueous 1N NaOH and extracted with ethyl acetate. The combined diethyl ether/ethyl acetate organic extracts were dried (MgSO$_4$), filtered and the solvent was removed in vacuo. The residue was dissolved in dichloromethane and loaded on to an SCX cartridge. The impurities were washed through with ethyl acetate then methanol and discarded. Elution with 7N methanolic ammonia and evaporation in vacuo gave the subtitle product (1.164 g).

$^1$H NMR δ (CDCl$_3$) 7.46-7.29 (m, 5H), 7.19 (t, 2H), 6.96-6.91 (m, 2H), 5.10 (s, 2H), 2.62-2.42 (m, 2H), 2.28-2.06 (m, 3H), 1.85-1.63 (m, 1H).

d) Methyl 3-(3-(1-(2-(benzyloxy)phenyl)cyclobutylamino)-5-bromo-2-oxopyrazin-1(2H)-yl)-4-methylbenzoate To 3-(3,5-dibromo-2-oxo-2H-pyrazin-1-yl)-4-methylbenzoic acid, methyl ester (Example 1b, 1.083 g) in dioxane (6 mL) was added 1-(2-(benzyloxy)phenyl)cyclobutanamine (Example 268c, 1.16 g) and N,N-diisopropylethylamine (0.76 mL) and the reaction heated at 100° C. for 16 h. After cooling to room temperature, the reaction mixture was diluted with ethyl acetate and water, and the organic layer was separated, dried (MgSO$_4$), filtered and the crude product purified (SiO$_2$ chromatography eluting with 20-50% ethyl acetate in iso-hexane) to afford the subtitle product (1.46 g).

$^1$H NMR δ (DMSO-d$_6$) 7.95 (dd, 1H), 7.86 (d, 1H), 7.58-7.40 (m, 4H), 7.38-7.28 (m, 4H), 7.20 (td, 1H), 7.02 (d, 1H), 6.97-6.91 (m, 1H), 6.95 (s, 1H), 5.13 (s, 2H), 3.84 (s, 3H), 2.73-2.57 (m, 4H), 2.13 (s, 3H), 2.09-1.94 (m, 1H), 1.80-1.65 (m, 1H).

e) 3-(3-(1-(2-(Benzyloxy)phenyl)cyclobutylamino)-5-bromo-2-oxopyrazin-1(2H)-yl)-N-cyclopropyl-4-methyl benzamide A solution of methyl 3-(3-(1-(2-(benzyloxy)phenyl)cyclobutylamino)-5-bromo-2-oxopyrazin-1(2H)-yl)-4-methylbenzoate (Example 268d, 1.46 g) in THF (40 mL) under nitrogen was treated with cyclopropylamine (0.88 mL) followed by isopropylmagnesium chloride (3.81 mL, 2.0 M in THF) dropwise over 10 min. The reaction was stirred at room temperature for 1 h then diluted with saturated aqueous ammonium chloride solution (300 mL) and extracted with ethyl acetate (×3). The combined organics were dried (MgSO$_4$), filtered and evaporated to afford the subtitle product (1.537 g).

MS: APCI (+ve) 599 (M+H)$^+$.

f) N-Cyclopropyl-3-(3-(1-(2-hydroxyphenyl)cyclobutylamino)-2-oxopyrazin-1(2H)-yl)-4-methyl benzamide To 3-(3-(1-(2-(benzyloxy)phenyl)cyclobutylamino)-5-bromo-2-oxopyrazin-1(2H)-yl)-N-cyclopropyl-4-methylbenzamide (Example 268e, 1.537 g) in ethanol (16 mL) was added ammonium formate (2.263 g) and 5% Pd/C (0.546 g) and the reaction heated at 75° C. for 1 h. The mixture was filtered through celite and the solid washed through with ethanol and dichloromethane. The filtrate was collected and the volatiles removed in vacuo. The residue was purified (SiO$_2$ chromatography eluting with 0-30% diethyl ether in dichloromethane) to afford the subtitle product (0.874 g).

MS: APCI (+ve) 431 (M+H)$^+$.

g) 3-(3-(1-(2-(2-Chloroethoxy)phenyl)cyclobutylamino)-2-oxopyrazin-1(2H)-yl)-N-cyclopropyl-4-methylbenzamide To N-cyclopropyl-3-(3-(1-(2-hydroxyphenyl)cyclobutylamino)-2-oxopyrazin-1(2H)-yl)-4-methylbenzamide (Example 268f, 0.874 g) in acetonitrile (17 mL) was added 1-bromo-2-chloroethane (1.68 mL) and cesium carbonate (6.61 g) and the reaction heated at 90° C. for 18 h. Ethyl acetate and water were added and the organic layer separated, washed with water, brine, dried (MgSO$_4$), filtered and the solvent removed in vacuo. Purification (SiO$_2$ chromatography eluting with 50-70% ethyl acetate/iso-hexane) gave the subtitle product (304 mg). The drying agent was re-washed with dichloromethane (2×50 mL) and the solvent removed to afford further subtitle product (472 mg).

MS: APCI (+ve) 493 (M+H)$^+$.

h) N-Cyclopropyl-4-methyl-3-[3-[[1-[2-[2-(methylamino)ethoxy]phenyl]cyclobutyl]amino]-2-oxo-1(2H)-pyrazinyl]-benzamide The title product was prepared from 3-(3-(1-(2-(2-chloroethoxy)phenyl)cyclobutylamino)-2-oxopyrazin-1(2H)-yl)-N-cyclopropyl-4-methylbenzamide (Example 268g) and methylamine using a similar method to that described for example 167f.

MS: APCI (+ve) 488 (M+H)$^+$.

$^1$H NMR δ (DMSO-d$_6$) 8.37 (d, 1H), 7.85 (d, 1H), 7.69 (s, 1H), 7.48 (t, 2H), 7.24 (s, 1H), 7.18 (t, 1H), 6.96-6.88 (m, 2H), 6.73 (d, 1H), 6.62 (d, 1H), 3.99 (t, 2H), 2.87 (t, 2H), 2.89-2.78 (m, 1H), 2.74-2.55 (m, 4H), 2.33 (s, 3H), 2.07 (s, 3H), 2.11-1.97 (m, 1H), 1.86-1.64 (m, 1H), 0.72-0.62 (m, 2H), 0.57-0.48 (m, 2H).

Example 269

N-Cyclopropyl-3-[3-[[1-[2-[2-(ethylamino)ethoxy]phenyl]cyclobutyl]amino]-2-oxo-1(2H)-pyrazinyl]-4-methyl-benzamide

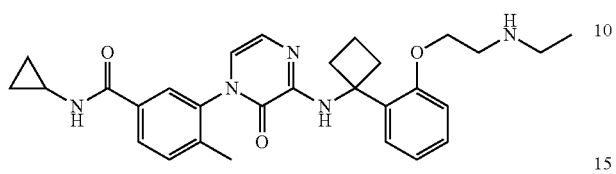

The title product was prepared from 3-(3-(1-(2-(2-chloroethoxy)phenyl)cyclobutylamino)-2-oxopyrazin-1(2H)-yl)-N-cyclopropyl-4-methylbenzamide (Example 268g) and ethylamine using a similar method to that described for example 167f.

MS: APCI (+ve) 502 (M+H)$^+$.

$^1$H NMR δ (DMSO-d$_6$) 8.36 (d, 1H), 7.85 (dd, 1H), 7.69 (d, 1H), 7.51-7.45 (m, 2H), 7.20-7.16 (m, 2H), 6.96-6.88 (m, 2H), 6.74 (d, 1H), 6.63 (d, 1H), 3.98 (t, 2H), 2.89 (t, 2H), 2.85-2.80 (m, 1H), 2.69 (t, 3H), 2.60-2.54 (m, 2H), 2.50 (d, 2H), 2.06 (s, 4H), 1.80-1.71 (m, 1H), 0.96 (t, 3H), 0.69-0.64 (m, 2H), 0.54-0.51 (m, 2H)

Example 270

N-Cyclopropyl-3-[3-[[1-[2-[2-[(2-hydroxyethyl)amino]ethoxy]phenyl]cyclobutyl]amino]-2-oxo-1(2H)-pyrazinyl]-4-methyl-benzamide

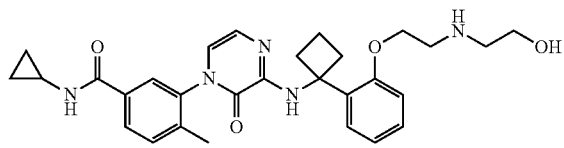

The title product was prepared from 3-(3-(1-(2-(2-chloroethoxy)phenyl)cyclobutylamino)-2-oxopyrazin-1(2H)-yl)-N-cyclopropyl-4-methylbenzamide (Example 268g) and ethanolamine using a similar method to that described for example 167f.

MS: APCI (+ve) 518 (M+H)$^+$.

$^1$H NMR δ (DMSO-d$_6$) 8.37 (d, 1H), 7.84 (d, 1H), 7.69 (s, 1H), 7.49 (q, 2H), 7.31 (s, 1H), 7.19 (t, 1H), 6.93 (q, 2H), 6.73 (d, 1H), 6.62 (d, 1H), 4.07 (s, 2H), 3.49 (s, 2H), 3.09 (s, 2H), 2.70 (s, 7H), 2.08 (s, 5H), 0.67 (d, 2H), 0.53 (d, 2H)

Example 271

N-Cyclopropyl-4-methyl-3-[3-[[1-[2-[2-[(1-methylethyl)amino]ethoxy]phenyl]cyclobutyl]amino]-2-oxo-1(2H)-pyrazinyl]-benzamide

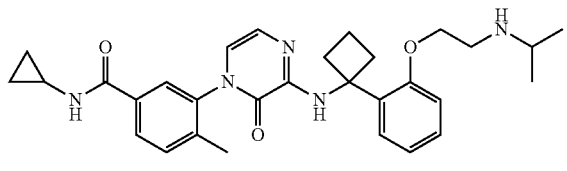

The title product was prepared from 3-(3-(1-(2-(2-chloroethoxy)phenyl)cyclobutylamino)-2-oxopyrazin-1(2H)-yl-N-cyclopropyl-4-methylbenzamide (Example 268g) and isopropylamine using a similar method to that described for example 167f.

MS: APCI (+ve) 516 (M+H)$^+$.

$^1$H NMR δ (DMSO-d$_6$) 8.37 (s, 1H), 7.84 (d, 1H), 7.69 (s, 1H), 7.49 (q, 2H), 7.27 (s, 1H), 7.19 (t, 1H), 6.98-6.89 (m, 2H), 6.83 (s, 1H), 6.63 (s, 1H), 4.05 (s, 2H), 3.05-2.96 (m, 3H), 2.83-2.83 (m, 1H), 2.71 (s, 4H), 2.08 (s, 3H), 1.84-1.69 (m, 2H), 1.02 (s, 6H), 0.67 (d, 2H), 0.53 (d, 2H)

Example 272

N-Cyclopropyl-3-[3-[[(1R,2R)-3-hydroxy-1-(2-methylphenyl)-2-methylpropyl]amino]-2-oxo-1(2H)-pyrazinyl]-4-methyl-benzamide

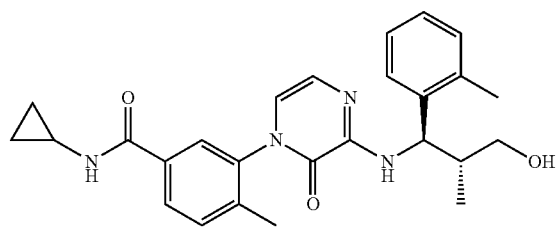

a) N-[(1R,2R)-3-[[(1,1-dimethylethyl)diphenylsilyl]oxy]-2-methyl-1-(2-methylphenyl)propyl]-2-methyl-2-propanesulfinamide The title compound was prepared from (2S)-3-[[(1,1-dimethylethyl)diphenylsilyl]oxy]-N-methoxy-N,2-dimethylpropanamide (Example 136a) and o-tolylmagnesium chloride using methods described in the Example 136b.

$^1$H NMR δ (CDCl$_3$) 7.63-7.58 (2H, m), 7.53-7.48 (2H, m), 7.42-7.27 (6H, m), 7.19-7.10 (4H, m), 4.86 (1H, dd), 3.59 (1H, d), 3.53 (1H, dd), 3.42 (1H, dd), 2.38 (3H, s), 2.14-2.04 (1H, m), 1.14 (9H, s), 1.03 (9H, s), 0.91 (3H, d).

b) 3-[3-[[(1R,2R)-3-hydroxy-2-methyl-1-(2-methylphenyl)propyl]amino]-2-oxo-1(2H)-pyrazinyl]-4-methyl-benzoic acid methyl ester The title compound was prepared from N-[(1R,2R)-3-[[(1,1-dimethylethyl)diphenylsilyl]oxy]-2-methyl-1-(2-methylphenyl)propyl]-2-methyl-2-propanesulfinamide (Example 272a) using the method described in the Example 136c.

¹H NMR δ (DMSO-d₆) 7.96 (2H, d), 7.85 (s, 1H), 7.80 (1H, s), 7.61-7.48 (3H, m), 7.30 (2H, d), 7.23 (2H, t), 7.01 (2H, d), 6.91 (2H, t), 6.79 (2H, d), 6.68 and 6.67 (2H, 2×d), 5.37 (1H, q), 4.66-4.59 (1H, m), 3.88-3.76 (4H, m), 3.29-3.12 (2H, m), 2.24-2.10 (1H, m), 2.16 and 2.09 (3H, 2×s), 0.86 (3H, d).

c) N-Cyclopropyl-3-[3-[[(1R,2R)-3-hydroxy-1-(2-methylphenyl)-2-methylpropyl]amino]-2-oxo-1(2H)-pyrazinyl]-4-methyl-benzamide The title compound was prepared from 3-[3-[[(1R,2R)-3-hydroxy-2-methyl-1-(2-methylphenyl)propyl]amino]-2-oxo-1(2H)-pyrazinyl]-4-methyl-benzoic acid, methyl ester (Example 272b) using the method described in the Example 136d.

MS: APCI (+ve) 447 (M+H⁺).

¹H NMR δ (DMSO-d₆) 8.45 and 8.36 (1H, 2×d), 7.89-7.82 (1H, m), 7.78-7.61 (2H, m), 7.55-7.44 (2H, m), 7.20-7.05 (3H, m), 6.82-6.76 (1H, m), 6.67-6.61 (1H, m), 5.26 (1H, t), 4.71-4.60 (1H, 2×t), 3.29-3.05 (2H, m), 2.93-2.76 (1H, m), 2.56-2.46 (3H, overlapped with DMSO), 2.28-2.13 (1H, m), 2.13 and 2.04 (3H, 2×s), 0.98-0.91 (3H, m), 0.74-0.48 (4H, m).

Example 273

N-Cyclopropyl-3-[3-[[(1R,2R)-3-hydroxy-1-(3-methylphenyl)-2-methylpropyl]amino]-2-oxo-1(2H)-pyrazinyl]-4-methyl-benzamide

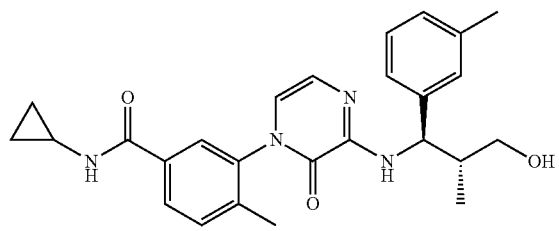

a) N-[(1R,2R)-3-[[(1,1-Dimethylethyl)diphenylsilyl]oxy]-2-methyl-1-(3-methylphenyl)propyl]-2-methyl-2-propanesulfinamide The title compound was prepared from (2S)-3-[[(1,1-dimethylethyl)diphenylsilyl]oxy]-N-methoxy-N,2-dimethylpropanamide (Example 136a) and m-tolylmagnesium chloride using methods described in the Example 136b.

¹H NMR δ (CDCl₃) 7.67-7.61 (2H, m), 7.59-7.53 (2H, m), 7.46-7.30 (6H, m), 7.20 (1H, t), 7.11-7.02 (3H, m), 4.53 (1H, dd), 3.83 (1H, d), 3.54 (1H, dd), 3.39 (1H, dd), 2.33 (3H, s), 2.26-2.14 (1H, m), 1.17 (9H, s), 1.06 (9H, s), 0.90 (3H, d).

b) N-Cyclopropyl-3-[3-[[(1R,2R)-3-hydroxy-1-(3-methylphenyl)-2-methylpropyl]amino]-2-oxo-1(2H)-pyrazinyl]-4-methyl-benzamide The title compound was prepared from N-[(1R,2R)-3-[[(1,1-dimethylethyl)diphenylsilyl]oxy]-2-methyl-1-(3-methylphenyl)propyl]-2-methyl-2-propanesulfinamide (Example 273a) using methods described in the Example 136c and 136d MS: APCI (+ve) 447 (M+H⁺).

¹H NMR δ (DMSO-d₆) 8.44 and 8.38 (1H, 2×d), 7.91-7.79 (2H, m), 7.75 and 7.69 (1H, 2×d), 7.49 and 7.47 (1H, 2×d), 7.24-7.13 (3H, m), 7.07-7.00 (1H, m), 6.78 and 6.77 (1H, 2×d), 6.65 and 6.64 (1H, 2×d), 5.03-4.95 (1H, m), 4.78 and 4.72 (1H, 2×t), 3.23-3.11 (2H, m), 2.90-2.78 (1H, m), 2.30 (3H, s), 2.26-2.14 (1H, m), 2.12 and 2.06 (3H, 2×s), 0.86 (3H, d), 0.72-0.63 (2H, m), 0.59-0.50 (2H, m).

Example 274

N-Cyclopropyl-3-[3-[[(1R,2R)-3-hydroxy-1-(2-methoxyphenyl)-2-methylpropyl]amino]-2-oxo-1(2H)-pyrazinyl]-4-methyl-benzamide

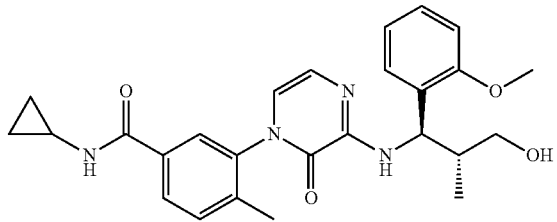

a) N-[(1R,2R)-3-[[(1,1-Dimethylethyl)diphenylsilyl]oxy]-1-(2-methoxyphenyl)-2-methylpropyl]-2-methyl-2-propanesulfinamide The title compound was prepared from (2S)-3-[[(1,1-dimethylethyl)diphenylsilyl]oxy]-N-methoxy-N,2-dimethylpropanamide (Example 136a) and 2-methoxyphenylmagnesium bromide using methods described in the Example 136b.

¹H NMR δ (CDCl₃) 7.62-7.58 (2H, m), 7.53-7.49 (2H, m), 7.41-7.25 (6H, m), 7.20-7.16 (2H, m), 6.88 (1H, dt), 6.82 (1H, d), 4.58 (1H, dd), 4.34 (1H, d), 3.76 (3H, s), 3.45 (1H, dd), 3.33 (1H, dd), 2.25-2.13 (1H, m), 1.17 (9H, s), 1.03 (9H, s), 0.96 (3H, d).

b) 3-[3-[[(1R,2R)-3-Hydroxy-2-methyl-1-(2-methoxyphenyl)propyl]amino]-2-oxo-1(2H)-pyrazinyl]-4-methyl-benzoic acid, methyl ester The title compound was prepared from N-[(1R,2R)-3-[[(1,1-dimethylethyl)diphenylsilyl]oxy]-2-methyl-1-(2-methoxyphenyl)propyl]-2-methyl-2-propanesulfinamide (Example 274a) using the method described in the Example 136c.

¹H NMR δ (DMSO-d₆) 7.96 (1H, d), 7.85 and 7.80 (1H, s), 7.61-7.48 (2H, m), 7.30 (1H, d), 7.23 (1H, t), 7.01 (1H, d), 6.91 (1H, m), 6.79 (1H, d), 6.68 and 6.67 (1H, 2×d), 5.37 (1H, q), 4.63 (1H, q), 3.90-3.80 (6H, m), 3.29-3.12 (2H, m), 2.24-2.10 (1H, m), 2.16 and 2.09 (3H, 2×s), 0.86 (3H, d).

c) N-Cyclopropyl-3-[3-[[(1R,2R)-3-hydroxy-1-(2-methoxyphenyl)-2-methylpropyl]amino]-2-oxo-1(2H)-pyrazinyl]-4-methyl-benzamide The title compound was prepared from 3-[3-[[(1R,2R)-3-hydroxy-2-methyl-1-(2-methoxyphenyl)propyl]amino]-2-oxo-1(2H)-pyrazinyl]-4-methyl-benzoic acid, methyl ester (Example 274b) using the method described in the Example 136d.

MS: APCI (+ve) 463 (M+H⁺).

¹H NMR δ (DMSO-d₆) 8.44 and 8.38 (1H, 2×d), 7.86 (1H, m), 7.76 and 7.69 (1H, 2×d), 7.56-7.45 (2H, m), 7.31 and 7.27 (1H, 2×dd), 7.23 (1H, m), 7.03-6.99 (1H, m), 6.94-6.87 (1H, m), 6.80 and 6.80 (1H, 2×d), 6.67 and 6.66 (1H, 2×d), 5.41-5.32 (1H, m), 4.67-4.59 (1H, m), 3.830 and 3.825 (3H, 2×s), 3.27-3.22 (1H, m), 3.21-3.12 (1H, m), 2.90-2.78 (1H, m), 2.25-2.14 (1H, m), 2.13 and 2.05 (3H, 2×s), 0.87 and 0.85 (3H, 2×d), 0.72-0.63 (2H, m), 0.59-0.50 (2H, m).

Example 275

N-Cyclopropyl-3-[3-[[(1R,2S)-1-(2-methylphenyl)-2-methyl-3-(1-pyrrolidinyl)propyl]amino]-2-oxo-1(2H)-pyrazinyl]-4-methyl-benzamide

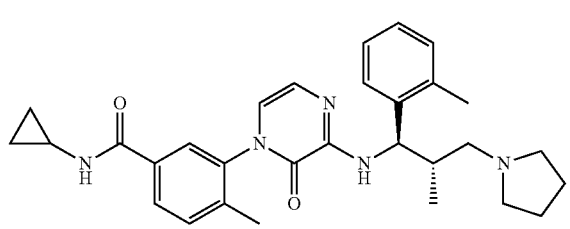

The title compound was prepared from N-cyclopropyl-3-[3-[[(1R,2R)-3-hydroxy-1-(2-methylphenyl)-2-methylpropyl]amino]-2-oxo-1(2H)-pyrazinyl]-4-methyl-benzamide (Example 272) using methods described in the Example 138a and 138b.

MS: APCI (+ve) 500 (M+H⁺).

¹H NMR δ (DMSO-d₆) 8.57 and 8.39 (1H, 2×d), 8.45 and 8.37 (1H, 2×d), 7.88-7.83 (1H, m), 7.74 and 7.67 (1H, 2×d), 7.48 (1H, t), 7.41 and 7.37 (1H, 2×d), 7.22-7.08 (3H, m), 6.77 and 6.76 (1H, 2×d), 6.62 and 6.61 (1H, 2×d), 5.34-5.26 (1H, m), 2.89-2.77 (1H, m), 2.48 (3H, s), 2.49-2.33 (6H, m), 2.21-2.12 (1H, m), 2.11 and 2.02 (3H, 2×s), 1.75-1.64 (4H, m), 0.85 and 0.84 (3H, 2×d), 0.72-0.63 (2H, m), 0.59-0.49 (2H, m).

Example 276

N-Cyclopropyl-3-[3-[[(1R,2S)-1-(3-methylphenyl)-2-methyl-3-(1-pyrrolidinyl)propyl]amino]-2-oxo-1(2H)-pyrazinyl]-4-methyl-benzamide

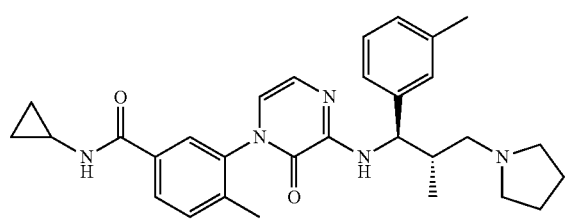

The title compound was prepared from N-cyclopropyl-3-[3-[[(1R,2R)-3-hydroxy-1-(3-methylphenyl)-2-methylpropyl]amino]-2-oxo-1(2H)-pyrazinyl]-4-methyl-benzamide (Example 273) using methods described in the Example 138a and 138b. MS: APCI (+ve) 500 (M+H⁺).

¹H NMR δ (DMSO-d₆) 9.11 and 8.93 (1H, 2×d), 8.45 and 8.41 (1H, 2×d), 7.89-7.83 (1H, m), 7.74 and 7.69 (1H, 2×d), 7.48 and 7.47 (1H, 2×d), 7.22 (1H, t), 7.14-7.02 (3H, m), 6.74 and 6.73 (1H, 2×d), 6.62 (1H, d), 5.07-4.99 (1H, m), 2.89-2.79 (1H, m), 2.61-2.28 (6H, m), 2.31 (3H, s), 2.11 and 2.05 (3H, s), 2.06-1.97 (1H, m), 1.82-1.65 (4H, m), 0.79 and 0.78 (3H, 2×d), 0.73-0.64 (2H, m), 0.59-0.50 (2H, m).

Example 277

N-Cyclopropyl-3-[3-[[(1R,2S)-1-(2-methoxyphenyl)-2-methyl-3-(1-pyrrolidinyl)propyl]amino]-2-oxo-1(2H)-pyrazinyl]-4-methyl-benzamide

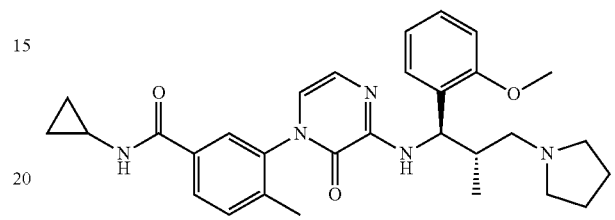

The title compound was prepared from N-cyclopropyl-3-[3-[[(1R,2R)-3-hydroxy-1-(2-methoxyphenyl)-2-methylpropyl]amino]-2-oxo-1(2H)-pyrazinyl]-4-methyl-benzamide (Example 274) using methods described in the Example 138a and 138b.

MS: APCI (+ve) 516 (M+H⁺).

¹H NMR δ (DMSO-d₆) 8.49 and 8.31 (1H, 2×d), 8.45 and 8.40 (1H, 2×d), 7.86 (1H, dt), 7.75 and 7.69 (1H, 2×d), 7.48 and 7.47 (1H, 2×d), 7.23 (2H, t), 7.01 (1H, d), 6.93 (1H, t), 6.77 and 6.76 (1H, 2×d), 6.632 and 6.628 (1H, 2×d), 5.59-5.50 (1H, m), 3.82 (3H, s), 2.90-2.78 (1H, m), 2.59-2.31 (6H, m), 2.11 and 2.04 (3H, 2×s), 2.14-2.03 (1H, m), 1.79-1.61 (4H, m), 0.78 (3H, d), 0.74-0.63 (2H, m), 0.60-0.49 (2H, m).

Example 278

N-Cyclopropyl-3-[3-[[1-[5-fluoro-2-[2-(methylamino)ethoxy]phenyl]cyclopropyl]amino]-2-oxo-1(2H)-pyrazinyl]-4-methyl-benzamide

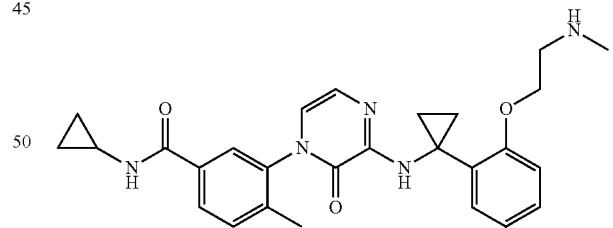

a) 1-[5-Fluoro-2-(phenylmethoxy)phenyl]-cyclopropanamine

Ethylmagnesium bromide, (35.2 ml of a 3M solution in diethyl ether) was added as a slow stream to a mechanically stirred mixture of tetraisopropyl orthotitanate (16.37 mL) and 2-(benzyloxy)-5-fluorobenzonitrile (12 g) in diethyl ether (400 mL) cooled to −78° C. The resulting solution was stirred at −78° C. for 15 min and then warmed to room temperature over 1.5 h. Boron trifluoride etherate (13.38 mL) was added and the mixture was stirred for 30 min. The reaction was quenched with 1 M HCl (400 ml) and the aqueous layer was separated. The diethyl ether layer was further extracted into 1M HCl (2×200 mL). The combined aqueous layers were cooled in an ice bath and basified with 1M aqueous NaOH solution. The resulting precipitate was filtered through celite washing the pad extensively with water (200 mL), dichloromethane (4×200 mL) then dichloromethane/MeOH (90:10, 300 mL). The combined filtrates were separated and the aqueous layer further extracted into dichloromethane (2×200 mL). The combined organics were dried ($MgSO_4$) and evaporated and residue purified by SCX resin (eluting with methanol followed by 10% 880 ammonia in methanol). The basic fractions were evaporated to give the subtitle compound (3.4 g).

$^1$H NMR δ ($CDCl_3$) 7.49-7.44 (2H, m), 7.42-7.36 (2H, m), 7.36-7.29 (1H, m), 6.99-6.92 (1H, m), 6.88-6.82 (2H, m), 5.13 (2H, s), 2.13 (2H, s), 1.00-0.95 (2H, m), 0.86-0.82 (2H, m).

b) 3-[5-Bromo-3-[[1-[5-fluoro-2-(phenylmethoxy)phenyl]cyclopropyl]amino]-2-oxo-1(2H)-pyrazinyl]-4-methyl-benzoic acid methyl ester A solution of 1-[5-fluoro-2-(phenylmethoxy)phenyl]-cyclopropanamine (Example 278a, 1.7 g) in dioxane (200 mL) was treated with 3-(3,5-dibromo-2-oxo-2H-pyrazin-1-yl)-4-methyl-benzoic acid, methyl ester (Example 1b, 1.99 g) and N-ethyldiisopropylamine (1.7 ml,) under nitrogen. The resulting solution was stirred at 100° C. for 8 h. The cooled reaction mixture was diluted with 2M HCl (300 mL), and extracted with diethyl ether (3×300 mL). The combined organics were dried ($MgSO_4$) filtered and evaporated to afford crude product. Trituration with iso-hexane gave the subtitle compound (2.89 g).

$^1$H NMR δ (DMSO-$d_6$) 7.98-7.91 (1H, m), 7.87 (1H, s), 7.62 (1H, s), 7.56-7.24 (6H, m), 7.05-6.98 (3H, m), 3.85 (3H, s), 3.58-3.55 (2H, m), 2.13 (3H, s), 1.32-1.05 (4H, m).

c) 3-[3-[[1-(5-fluoro-2-hydroxyphenyl)cyclopropyl]amino]-2-oxo-1(2H)-pyrazinyl]-4-methyl-benzoic acid methyl ester To 3-[5-bromo-3-[[1-[5-fluoro-2-(phenylmethoxy)phenyl]cyclopropyl]amino]-2-oxo-1(2H)-pyrazinyl]-4-methyl-benzoic acid, methyl ester (Example 278b, 2.8 g) in ethanol (200 mL) was added ammonium formate (5.0 g) and 10% Pd/C (1.0 g). The reaction was heated at 75° C. for 1 h, filtered through celite washing the celite with warm ethanol (100 mL) followed by dichloromethane (2000 mL). The combined filtrates were evaporated, diluted with dichloromethane (1000 mL) and washed with water, dried ($MgSO_4$) and evaporated to give the subtitle compound (1.2 g)

$^1$H NMR δ (DMSO-$d_6$) 11.12 (1H, s), 8.43 (1H, s), 7.96 (1H, dd), 7.85 (1H, d), 7.56 (1H, d), 7.23 (1H, dd), 6.98-6.91 (1H, m), 6.83 (2H, dd), 6.77-6.72 (1H, m), 3.84 (3H, s), 2.12 (3H, s), 1.28-1.24 (2H, m), 1.18-1.07 (2H, m).

d) N-cyclopropyl-3-[3-[[1-(5-fluoro-2-hydroxyphenyl)cyclopropyl]amino]-2-oxo-1(2H)-pyrazinyl]-4-methyl-benzamide Isopropylmagnesium chloride (5.86 mL of a 2M solution in THF) was added over 20 min to a solution of cyclopropylamine (2.066 mL) and 3-[3-[[1-(5-fluoro-2-hydroxyphenyl)cyclopropyl]amino]-2-oxo-1(2H)-pyrazinyl]-4-methyl-benzoic acid methyl ester (Example 278c, 1.2 g) in THF (200 mL) at room temperature under nitrogen. The reaction mixture was stirred for 1 h. Water and 2M HCl were cautiously added and the aqueous layer extracted with dichloromethane (3×200 mL), dried ($MgSO_4$) and the solvent removed to give the subtitle compound (1.22 g)

$^1$H NMR δ (DMSO-$d_6$) 8.58-8.48 (1H, m), 8.41-8.35 (1H, m), 7.86 (1H, d), 7.72 (1H, s), 7.48 (1H, d), 7.28-7.21 (1H, m), 7.05-6.86 (2H, m), 6.83-6.72 (2H, m), 3.65-3.57 (2H, m), 2.89-2.78 (1H, m), 2.10 (3H, s), 1.80-1.72 (2H, m), 0.73-0.63 (2H, m), 0.58-0.49 (2H, m).

e) 3-[3-[[1-[2-(2-chloroethoxy)-5-fluorophenyl]cyclopropyl]amino]-2-oxo-1(2H)-pyrazinyl]-N-cyclopropyl-4-methyl-benzamide N-Cyclopropyl-3-[3-[[1-(5-fluoro-2-hydroxyphenyl)cyclopropyl]amino]-2-oxo-1(2H)-pyrazinyl]-4-methyl-benzamide (Example 278d 1.22 g), 1-bromo-2-chloroethane (2.4 mL) and cesium carbonate (9.15 g) were stirred together in acetonitrile (100 mL) at 80° C. under nitrogen for 16 h. The cooled reaction mixture was evaporated to dryness, diluted with water (200 mL) and extracted with dichloromethane (3×100 mL). The combined organics were dried ($MgSO_4$), filtered and evaporated. The residue was triturated with 1:1 iso-hexane:diethyl ether to give the subtitle compound (1.13 g)

$^1$H NMR δ (DMSO-$d_6$) 8.37 (1H, d), 7.84 (1H, dd), 7.69 (1H, d), 7.46 (1H, d), 7.33-7.27 (2H, m), 7.08-6.95 (2H, m), 6.89 (1H, d), 6.73 (1H, d), 4.29 (2H, t), 3.99 (2H, t), 2.89-2.76 (1H, m), 2.06 (3H, s), 0.71-0.60 (2H, m), 0.57-0.48 (2H, m).

f) N-Cyclopropyl-3-[3-[[1-[5-fluoro-2-[2-(methylamino)ethoxy]phenyl]cyclopropyl]amino]-2-oxo-1(2H)-pyrazinyl]-4-methyl-benzamide 3-[3-[[1-[2-(2-chloroethoxy)-5-fluorophenyl]cyclopropyl]amino]-2-oxo-1(2H)-pyrazinyl]-N-cyclopropyl-4-methyl-benzamide (Example 278e, 0.25 g) and 40% methylamine in water (1 mL) were stirred together at 100° C. in dioxane (8 mL) in a sealed tube for 24 h. Purification of the cooled solution by preparative HPLC (Xbridge column—acetonitrile/0.2% ammonia mobile phase) gave the title compound (110 mg).

MS: APCI (+ve) 492 (M+H)$^+$.

$^1$H NMR δ (DMSO-$d_6$) 8.37 (1H, d), 7.85 (1H, d), 7.69 (1H, s), 7.58 (1H, s), 7.46 (1H, d), 7.30 (1H, dd), 7.06-6.91 (2H, m), 6.88 (1H, d), 6.71 (1H, d), 4.03 (2H, t), 2.90-2.79 (3H, m), 2.34 (3H, s), 2.06 (3H, s), 1.25-1.06 (4H, m), 0.70-0.62 (2H, m), 0.57-0.50 (2H, m)

The following examples 279-280 were prepared in a similar manner to Example 278:

Example 279

N-Cyclopropyl-3-[3-[[1-[5-fluoro-2-[2-[(2-hydroxyethyl)amino]ethoxy]phenyl]cyclopropyl]amino]-2-oxo-1(2H)-pyrazinyl]-4-methyl-benzamide

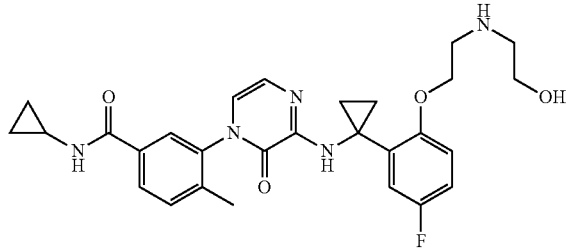

MS: APCI (+ve) 522 (M+H)$^+$.

$^1$H NMR δ (DMSO-d$_6$) 8.37 (1H, d), 7.85 (1H, dd), 7.69 (1H, d), 7.49 (1H, s), 7.46 (1H, d), 7.29 (1H, dd), 7.05-6.93 (2H, m), 6.89 (1H, d), 6.72 (1H, d), 4.45-4.40 (1H, m), 4.03 (2H, t), 3.46 (2H, q), 2.94 (2H, t), 2.88-2.78 (1H, m), 2.67 (2H, t), 2.06 (3H, s), 1.26-1.07 (4H, m), 0.71-0.62 (2H, m), 0.56-0.49 (2H, m).

Example 280

N-Cyclopropyl-3-[3-[[1-[2-[2-(ethylamino)ethoxy]-5-fluorophenyl]cyclopropyl]amino]-2-oxo-1(2H)-pyrazinyl]-4-methyl-benzamide

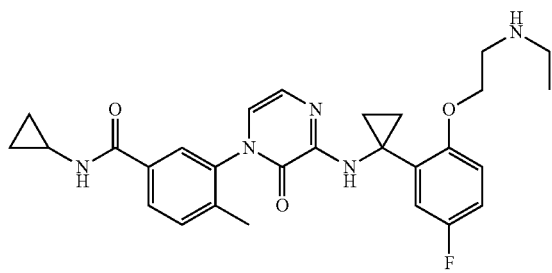

MS: APCI (+ve) 506 (M+H)$^+$.

$^1$H NMR δ (DMSO-d$_6$) 8.37 (1H, d), 7.85 (1H, dd), 7.69 (1H, d), 7.52 (1H, s), 7.46 (1H, d), 7.29 (1H, dd), 7.05-6.93 (2H, m), 6.88 (1H, d), 6.72 (1H, d), 4.03 (2H, t), 2.92 (2H, t), 2.88-2.79 (1H, m), 2.61 (2H, q), 2.06 (3H, s), 1.26-1.06 (4H, m), 0.99 (3H, t), 0.70-0.63 (2H, m), 0.55-0.49 (2H, m)

Example 281

N-Cyclopropyl-3-fluoro-5-{3-[(1-{5-fluoro-2-[2-(methylamino)ethoxy]phenyl}cyclopropyl)amino]-2-oxopyrazin-1(2H)-yl}-4-methylbenzamide

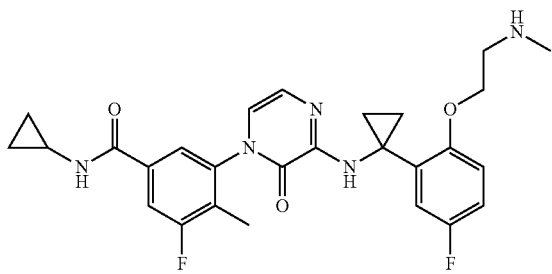

a) Methyl 3-[3-({1-[2-(benzyloxy)-5-fluorophenyl]cyclopropyl}amino)-5-bromo-2-oxopyrazin-1(2H)-yl]-5-fluoro-4-methylbenzoate The subtitle compound was prepared from 1-(2-(benzyloxy)-5-fluorophenyl)cyclopropanamine (Example 278a) and methyl 3-(3,5-dibromo-2-oxopyrazin-1(2H)-yl)-5-fluoro-4-methylbenzoate (Example 252g) using a similar method to that described for Example 268d.

$^1$H NMR δ (DMSO-d$_6$) 7.83-7.76 (2H, m), 7.66-7.63 (1H, m), 7.55-7.49 (2H, m), 7.41-7.28 (4H, m), 7.08-7.00 (3H, m), 5.20 (2H, s), 3.85 (3H, s), 2.04 (3H, s), 1.29-1.10 (4H, m).

b) N-Cyclopropyl-3-fluoro-5-[3-{[1-(5-fluoro-2-hydroxyphenyl)cyclopropyl]amino}-2-oxopyrazin-1(2H)-yl]-4-methylbenzamide The subtitle compound was prepared from methyl 3-[3-({1-[2-(benzyloxy)-5-fluorophenyl]cyclopropyl}amino)-5-bromo-2-oxopyrazin-1(2H)-yl]-5-fluoro-4-methylbenzoate (Example 281a) using similar methods to that described for Example 259b and 259c.

$^1$H NMR δ (DMSO-d$_6$) 8.58 (1H, s), 8.48 (1H, d), 7.75 (1H, d), 7.65 (1H, s), 7.24 (1H, dd), 6.99-6.73 (4H, m), 2.90-2.77 (1H, m), 2.00 (3H, s), 1.31-1.13 (4H, m), 0.75-0.63 (2H, m), 0.59-0.50 (2H, m).

c) 3-[3-({1-[2-(2-Chloroethoxy)-5-fluorophenyl]cyclopropyl}amino)-2-oxopyrazin-1(2H)-yl]-N-cyclopropyl-5-fluoro-4-methylbenzamide The subtitle compound was prepared from N-cyclopropyl-3-fluoro-5-[3-{[1-(5-fluoro-2-hydroxyphenyl)cyclopropyl]amino}-2-oxopyrazin-1(2H)-yl]-4-methylbenzamide (Example 281b) using a similar method to that described for Example 259d.

$^1$H NMR δ (DMSO-d$_6$) 8.46 (1H, d), 7.73 (1H, d), 7.61 (1H, s), 7.35-7.26 (2H, m), 7.10-6.94 (2H, m), 6.90 (1H, d), 6.77 (1H, d), 4.32-4.24 (2H, m), 4.02-3.94 (2H, m), 2.88-2.78 (1H, m), 1.96 (3H, s), 1.41-1.09 (4H, m), 0.76-0.46 (4H, m)

d) N-Cyclopropyl-3-fluoro-5-{3-[(1-{5-fluoro-2-[2-(methylamino)ethoxy]phenyl}cyclopropyl)amino]-2-oxopyrazin-1(2H)-yl}-4-methylbenzamide The title compound was prepared from 3-[3-({1-[2-(2-chloroethoxy)-5-fluorophenyl]cyclopropyl}amino)-2-oxopyrazin-1(2H)-yl]-N-cyclopropyl-5-fluoro-4-methylbenzamide (Example 281c) using a similar method to that described for Example 259e.

MS: APCI (+ve) 510.2 (M+H)$^+$.

$^1$H NMR δ (DMSO-d$_6$) 8.47 (1H, d), 7.73 (1H, d), 7.65-7.61 (2H, m), 7.30 (1H, dd), 7.06-6.92 (2H, m), 6.90 (1H, d), 6.75 (1H, d), 4.03 (2H, t), 2.91-2.77 (3H, m), 2.35 (3H, s), 1.97 (3H, d), 1.28-1.05 (4H, m), 0.73-0.64 (2H, m), 0.59-0.47 (2H, m).

Example 282

N-Cyclopropyl-3-fluoro-5-[3-{[1-(5-fluoro-2-{2-[(2-hydroxyethyl)amino]ethoxy}phenyl)cyclopropyl]amino}-2-oxopyrazin-1(2H)-yl]-4-methylbenzamide

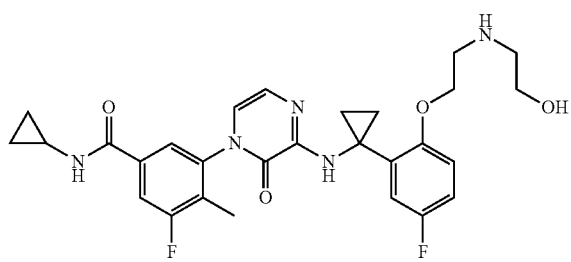

The title compound was prepared from 3-[3-({1-[2-(2-chloroethyl)-5-fluorophenyl]cyclopropyl}amino)-2-oxopyrazin-1(2H)-yl]-N-cyclopropyl-5-fluoro-4-methylbenzamide (Example 281c) and ethanolamine using a similar method to that described for Example 167f.

MS: APCI (+ve) 540 (M+H)$^+$.

$^1$H NMR δ (DMSO-d$_6$) 8.46 (1H, d), 7.73 (1H, d), 7.61 (1H, s), 7.53 (1H, s), 7.29 (1H, dd), 7.06-6.92 (2H, m), 6.90 (1H, d), 6.76 (1H, d), 4.42 (1H, t), 4.03 (2H, t), 3.46 (2H, q), 2.94 (2H, t), 2.89-2.78 (1H, m), 2.67 (2H, t), 1.97 (3H, d), 1.28-1.04 (4H, m), 0.72-0.61 (2H, m), 0.58-0.45 (2H, m)

Example 283

N-Cyclopropyl-3-[3-({1-[3-fluoro-2-(2-{[(2R)-2-hydroxypropyl]amino}ethoxy)phenyl]cyclopropyl}amino)-2-oxopyrazin-1(2H)-yl]-4-methylbenzamide

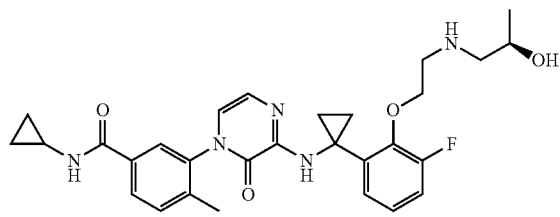

a) 2-(Benzyloxy)-3-fluorobenzonitrile

Benzyl alcohol (5.51 mL) was added dropwise over 20 min to a stirred suspension of sodium hydride (2.128 g of a 60% dispersion in mineral oil) and 2,3-difluorobenzonitrile (7.4 g) in THF (100 mL) with external ice bath cooling to maintain temperature around 25° C. After addition was complete, the reaction mixture was stirred at room temperature for 24 h, quenched with water (200 mL) and extracted into ethyl acetate (3×120 mL), combined organics were dried (MgSO$_4$) and evaporated. The residual oil was purified (SiO$_2$ chromatography eluting with 20% ether in isohexane) to give the subtitle compound as an oil (9.70 g).

$^1$H NMR δ (CDCl$_3$) 7.54-7.44 (2H, m), 7.40-7.26 (5H, m), 7.10-7.01 (1H, m), 5.33 (2H, s)

b) 1-[2-(Benzyloxy)-3-fluorophenyl]cyclopropanamine

A solution of ethylmagnesium bromide, 3M in diethyl ether (28.2 mL) was added as a slow stream to a mechanically stirred mixture of tetraisopropyl orthotitanate (13.09 mL,) and 2-(benzyloxy)-3-fluorobenzonitrile (Example 283a, 9.6 g) in diethyl ether (400 mL) cooled to −78° C. The resulting solution was stirred at −78° C. for 15 min and then warmed to room temperature over 1 h 30 min. An ice bath was placed around the reaction and boron trifluoride etherate (10.71 mL) was added as a slow stream (caution exothermic) and the mixture was stirred for 30 min. The reaction was cooled (ice bath) and quenched with 1 M aqueous HCl (400 mL added portionwise). The aqueous layer was separated and the diethyl ether layer further extracted into 1M HCl (2×200 mL) (ethyl acetate added to the diethyl ether to aid solubility). The aqueous layer was cooled in an ice bath and basified with stirring with a 10M aqueous NaOH solution. The resulting precipitate was filtered through Celite, washing the pad with water (200 mL) then DCM (4×200 mL) then DCM/MeOH (90:10, 300 mL). The combined filtrates were separated and the aqueous layer further extracted with DCM (2×200 mL). The combined organics were dried (MgSO$_4$) and evaporated, the residue was purified on SCX resin (50 g) eluting with DCM, methanol (discarded) and flushing with 20% ammonia in methanol to give the subtitle compound as an oil (2.54 g).

$^1$H NMR δ (CDCl$_3$) 7.54-7.50 (1H, m), 7.43-7.31 (2H, m), 7.06-6.89 (5H, m), 5.22 (2H, s), 0.96-0.93 (2H, m), 0.84-0.80 (2H, m).

c) Methyl 3-[3-({1-[2-(benzyloxy)-3-fluorophenyl]cyclopropyl}amino)-5-bromo-2-oxopyrazin-1(2H)-yl]-4-methylbenzoate Prepared using a similar method to Example 252h from 1-(2-(benzyloxy)-3-fluorophenyl)cyclopropanamine (Example 283b) and methyl 3-(3,5-dibromo-2-oxopyrazin-1(2H)-yl)-4-methylbenzoate (Example 252g).

$^1$H NMR δ (DMSO-d$_6$) 7.94 (1H, dd), 7.86 (1H, d), 7.72 (1H, s), 7.58-7.51 (3H, m), 7.44-7.32 (5H, m), 7.23-7.16 (1H, m), 7.11-7.03 (1H, m), 5.19 (2H, s), 3.83 (3H, s), 2.11 (3H, s), 1.26-1.14 (4H, m)

d) Methyl 3-[3-{[1-(3-fluoro-2-hydroxyphenyl)cyclopropyl]amino}-2-oxopyrazin-1(2H)-yl]-4-methylbenzoate Prepared using a similar method to Example 252j from methyl 3-[3-({1-[2-(benzyloxy)-3-fluorophenyl]cyclopropyl}amino)-5-bromo-2-oxopyrazin-1(2H)-yl]-4-methylbenzoate (Example 283c).

$^1$H NMR δ (DMSO-d$_6$)) 8.63 (1H, s), 7.96 (1H, dd), 7.86 (1H, d), 7.56 (1H, d), 7.27 (1H, d), 7.09-7.02 (1H, m), 6.90 (1H, d), 6.80 (1H, d), 6.79-6.74 (1H, m), 3.84 (3H, s), 2.13 (3H, s), 1.32-1.26 (2H, m), 1.12-1.09 (2H, m)

e) N-Cyclopropyl-3-[3-{[1-(3-fluoro-2-hydroxyphenyl)cyclopropyl]amino}-2-oxopyrazin-1(2H)-yl]-4-methylbenzamide The subtitle compound was prepared from methyl 3-[3-{[1-(3-fluoro-2-hydroxyphenyl)cyclopropyl]amino}-2-oxopyrazin-1(2H)-yl]-4-methylbenzoate (Example 283d) using a similar method to that described for Example 252i $^1$H NMR δ (DMSO-d$_6$) 8.75 (1H, s), 8.39 (1H, d), 7.85 (1H, dd), 7.73 (1H, d), 7.47 (1H, d), 7.28 (1H, d), 7.10-7.03

(1H, m), 6.92 (1H, d), 6.82 (1H, d), 6.80-6.74 (1H, m), 2.88-2.79 (1H, m), 2.10 (3H, s), 1.32-1.09 (4H, m), 0.72-0.65 (2H, m), 0.58-0.50 (2H, m)

f) 3-[3-({1-[2-(2-Chloroethoxy)-3-fluorophenyl]cyclopropyl}amino)-2-oxopyrazin-1(2H)-yl]-N-cyclopropyl-4-methyl benzamide The subtitle compound was prepared from N-cyclopropyl-3-[3-{[1-(3-fluoro-2-hydroxyphenyl)cyclopropyl]amino}-2-oxopyrazin-1(2H)-yl]-4-methylbenzamide (Example 283e) using a similar method to that described for Example 259d.

$^1$H NMR δ (DMSO-$d_6$) 8.41-8.36 (1H, m), 7.88-7.82 (1H, m), 7.71-7.67 (1H, m), 7.51-7.38 (2H, m), 7.24-6.99 (2H, m), 6.87-6.82 (1H, m), 6.74-6.70 (1H, m), 4.40-4.32 (2H, m), 4.07-4.00 (2H, m), 2.89-2.78 (1H, m), 2.07 (3H, s), 1.29-1.16 (4H, m), 0.71-0.63 (2H, m), 0.57-0.51 (2H, m)

g) N-cyclopropyl-3-[3-({1-[3-fluoro-2-(2-{[(2R)-2-hydroxypropyl]amino}ethoxy)phenyl]cyclopropyl}amino)-2-oxopyrazin-1(2H)-yl]-4-methylbenzamide 3-[3-({1-[2-(2-chloroethoxy)-3-fluorophenyl]cyclopropyl}amino)-2-oxopyrazin-1(2H)-yl]-N-cyclopropyl-4-methylbenzamide (Example 283f) (0.3 g) and 2-aminoethanol (0.147 g) were stirred together at 100° C. in dioxane (8 mL) in a sealed tube for 24 h. Purification by preparative HPLC (Xterra column 0.2% ammonia/MeCN eluent) give the title compound (0.094 g).

MS: APCI (+ve) 536 (M+H)$^+$.

$^1$H NMR δ (DMSO-$d_6$) 8.38 (1H, s), 8.30 (1H, d), 7.85 (1H, d), 7.69 (1H, s), 7.49-7.35 (2H, m), 7.14 (1H, t), 7.07-6.94 (1H, m), 6.89-6.83 (1H, m), 6.73-6.67 (1H, m), 4.49-4.42 (1H, m), 4.19-4.03 (2H, m), 3.80-3.66 (1H, m), 3.33 (2H, s), 2.95 (2H, s), 2.88-2.78 (1H, m), 2.58-2.54 (1H, m), 2.06 (3H, s), 1.32-1.08 (2H, m), 1.07-0.99 (2H, m), 0.89-0.78 (2H, m), 0.70-0.64 (2H, m), 0.58-0.48 (2H, m).

The following Examples 284-287 (Table 12) were prepared using a similar method to that described for Example 283:

Example 284

3-[3-({1-[2-(2-Aminoethoxy)-3-fluorophenyl]cyclopropyl}amino)-2-oxopyrazin-1(2H)-yl]-N-cyclopropyl-4-methylbenzamide Example 285

N-Cyclopropyl-3-[3-{[1-(3-fluoro-2-{2-[(2-hydroxyethyl)amino]ethoxy}phenyl)cyclopropyl]amino}-2-oxopyrazin-1(2H)-yl]-4-methylbenzamide Example 286

N-Cyclopropyl-3-{3-[(1-{2-[2-(ethylamino)ethoxy]-3-fluorophenyl}cyclopropyl)amino]-2-oxopyrazin-1(2H)-yl}-4-methylbenzamide Example 287

N-Cyclopropyl-3-{3-[(1-{3-fluoro-2-[2-(methylamino)ethoxy]phenyl}cyclopropyl)amino]-2-oxopyrazin-1(2H)-yl}-4-methylbenzamide

TABLE 12

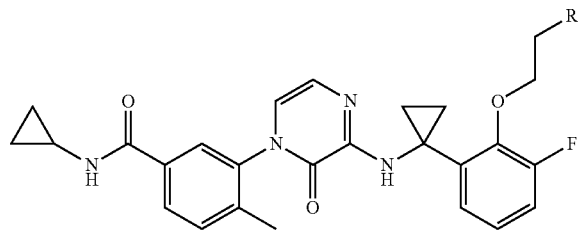

| Example | R | MS [M + H]$^+$ m/z | $^1$H NMR δ (DMSO-$d_6$) |
|---|---|---|---|
| 284 | ⤳N(H)H | 478 | 8.54-8.30 (2H, m), 7.84 (1H, d), 7.69 (1H, s), 7.45 (1H, d), 7.39 (1H, d), 7.12 (1H, t), 6.99 (1H, q), 6.85 (1H, d), 6.69 (1H, d), 4.07-3.99 (2H, m), 2.96 (2H, t), 2.88-2.77 (1H, m), 2.06 (3H, s), 1.27-1.06 (4H, m), 0.73-0.46 (4H, m) |
| 285 | ⤳N(H)CH₂CH₂OH | 522 | 8.38 (2H, s), 7.88-7.81 (1H, m), 7.71-7.67 (1H, m), 7.50-7.37 (2H, m), 7.20-7.08 (1H, m), 7.05-6.96 (1H, m), 6.86 (1H, t), 6.70 (1H, t), 4.49-4.41 (1H, m), 4.16-4.06 (2H, m), 3.55-3.45 (2H, m), 3.00-2.90 (2H, m), 2.88-2.79 (1H, m), 2.76-2.65 (2H, m), 2.06 (3H, d), 1.29-1.04 (4H, m), 0.75-0.59 (2H, m), 0.58-0.50 (2H, m) |

TABLE 12-continued

| Example | R | MS [M + H]+ m/z | 1H NMR δ (DMSO-d6) |
|---|---|---|---|
| 286 | (H, N-ethyl) | 506 | 8.45-8.34 (2H, m), 7.85 (1H, d), 7.69 (1H, s), 7.46 (1H, d), 7.39 (1H, d), 7.13 (1H, t), 7.06-6.95 (1H, m), 6.84 (1H, d), 6.69 (1H, d), 4.17-4.02 (2H, m), 2.97-2.88 (2H, m), 2.86-2.81 (1H, m), 2.73-2.58 (2H, m), 2.06 (3H, s), 1.28-1.10 (4H, m), 1.09-0.99 (3H, m), 0.74-0.61 (2H, m), 0.56-0.48 (2H, m) |
| 287 | (H, N-Me) | 492 | 8.45 (1H, s), 8.37 (1H, d), 7.84 (1H, d), 7.68 (1H, s), 7.46 (1H, d), 7.39 (1H, d), 7.12 (1H, t), 7.04-6.93 (1H, m), 6.85 (1H, d), 6.68 (1H, d), 4.18-4.02 (2H, m), 2.95-2.78 (2H, m), 2.38 (3H, s), 2.06 (3H, s), 1.26-1.07 (4H, m), 0.70-0.63 (2H, m), 0.57-0.50 (2H, m) |

Example 288

N-Cyclopropyl-4-ethyl-3-{3-[(1-methyl-1-{2-[2-(methylamino)ethoxy]phenyl}ethyl)amino]-2-oxopyrazin-1(2H)-yl}benzamide

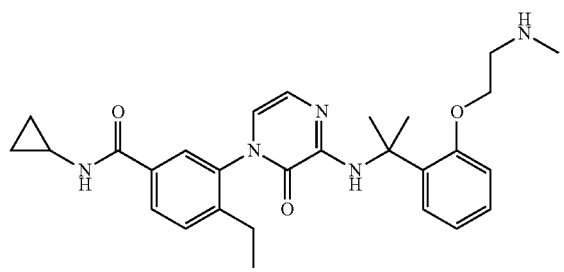

a) Methyl 3-[(cyanomethyl)amino]-4-ethylbenzoate

To a stirred solution of methyl 3-amino-4-ethylbenzoate (6.10 g) in THF (56.7 mL) at room temperature was added Hunig's Base (11.89 mL) followed by bromoacetonitrile (4.74 mL). The mixture was heated at reflux for 16 h. The reaction was cooled to room temperature and concentrated in vacuo. 1N aqueous HCl and DCM were added. The organic layer was separated, dried (MgSO4) and concentrated to give the subtitle compound as an oil (7.46 g).

1H NMR δ (DMSO-d6) 7.35 (d, 1H), 7.24-7.18 (m, 2H), 5.97 (t, 1H), 4.34 (d, 2H), 3.84 (d, 2H), 3.32 (d, 3H), 1.15 (t, 3H)

b) Methyl 3-(3,5-dibromo-2-oxopyrazin-1(2H)-yl)-4-ethylbenzoate

The subtitle compound was prepared from methyl 3-[(cyanomethyl)amino]-4-ethylbenzoate (Example 288a) using a similar method to that described for Example 252g.

1H NMR δ (DMSO-d6) 8.14 (d, 1H), 8.06 (s, 2H), 8.04-8.02 (m, 1H), 3.87 (s, 3H), 1.11 (t, 3H) Other resonances obscured under solvent peak (2.4 ppm)

c) Methyl 3-[3-({1-[2-(benzyloxy)phenyl]-1-methylethyl}amino)-5-bromo-2-oxopyrazin-1(2H)-yl]-4-ethyl benzoate The subtitle compound was prepared from methyl 3-(3,5-dibromo-2-oxopyrazin-1(2H)-yl)-4-ethylbenzoate (Example 288b) and α,α-dimethyl-2-(phenylmethoxy)-benzenemethanamine (Example 198d) using a similar method to that described for Example 252h.

MS: APCI (+ve) 576 (M+H)+.

d) 3-[3-({1-[2-(Benzyloxy)phenyl]-1-methylethyl}amino)-5-bromo-2-oxopyrazin-1(2H)-yl]-N-cyclopropyl-4-ethyl benzamide The subtitle compound was prepared from methyl 3-[3-({1-[2-(benzyloxy)phenyl]-1-methylethyl}amino)-5-bromo-2-oxopyrazin-1(2H)-yl]-4-ethylbenzoate (Example 288c) using a similar method to that described for Example 252i.

MS: APCI (+ve) 601 (M+H)+.
1H NMR δ (DMSO-d6) 8.42 (d, 1H), 7.91 (dd, 1H), 7.73 (d, 1H), 7.45-7.21 (m, 9H), 7.10 (t, 2H), 6.96 (t, 1H), 5.12 (s, 2H), 2.90-2.82 (m, 1H), 2.39 (q, 2H), 1.84 (d, 6H), 1.06 (t, 3H), 0.74-0.67 (m, 2H), 0.58-0.53 (m, 2H)

e) N-Cyclopropyl-4-ethyl-3-[3-{[1-(2-hydroxyphenyl)-1-methylethyl]amino}-2-oxopyrazin-1(2H)-yl]benzamide The subtitle compound was prepared from 3-[3-({1-[2-(benzyloxy)phenyl]-1-methylethyl}amino)-5-bromo-2-oxopyrazin-1(2H)-yl]-N-cyclopropyl-4-ethylbenzamide (Example 288d) using a similar method to that described for Example 252j.

MS: APCI (+ve) 433 (M+H)+..

f) 3-[3-({1-[2-(2-Chloroethoxy)phenyl]-1-methylethyl}amino)-2-oxopyrazin-1(2H)-yl]-N-cyclopropyl-4-ethylbenzamide The subtitle compound was prepared from N-cyclopropyl-4-ethyl-3-[3-{[1-(2-hydroxyphenyl)-1-methylethyl]amino}-2-oxopyrazin-1(2H)-yl]benzamide (Example 288e) using a similar method to that described for Example 252k.

MS: APCI (+ve) 495 (M+H)$^+$.

$^1$H NMR δ (DMSO-d$_6$) 8.43 (d, 1H), 7.91 (dd, 1H), 7.71 (d, 1H), 7.52 (d, 1H), 7.34 (dd, 1H), 7.21 (t, 1H), 6.97-6.91 (m, 3H), 6.65 (q, 2H), 4.26-4.13 (m, 2H), 3.93 (t, 2H), 2.89-2.81 (m, 1H), 2.45-2.38 (m, 2H), 1.87 (s, 3H), 1.84 (s, 3H), 1.06 (t, 3H), 0.70-0.67 (m, 2H), 0.57-0.54 (m, 2H)

g) N-Cyclopropyl-4-ethyl-3-{3-[(1-methyl-1-{2-[2-(methylamino)ethoxy]phenyl}ethyl)amino]-2-oxopyrazin-1(2H)-yl}benzamide The title compound was prepared from 3-[3-({1-[2-(2-chloroethoxy)phenyl]-1-methylethyl}amino)-2-oxopyrazin-1(2H)-yl]-N-cyclopropyl-4-ethylbenzamide (Example 288f) using a similar method to that described for Example 252i.

MS: APCI (+ve) 490.4 (M+H)$^+$.

$^1$H NMR δ (DMSO-d$_6$) 8.43 (d, 1H), 7.91 (dd, 1H), 7.69 (d, 1H), 7.51 (d, 1H), 7.34 (d, 1H), 7.20 (t, 1H), 6.98-6.88 (m, 3H), 6.67-6.62 (m, 2H), 4.02-3.88 (m, 2H), 2.90-2.80 (m, 3H), 2.45-2.35 (m, 2H), 2.26 (s, 3H), 1.82 (s, 6H), 1.06 (t, 3H), 0.70-0.66 (m, 2H), 0.55-0.53 (m, 2H).

The following Examples 289 to 292 (Table 13) were prepared using a similar method to that described for Example 288 from 3-[3-({1-[2-(2-chloroethoxy)phenyl]-1-methylethyl}amino)-2-oxopyrazin-1(2H)-yl]-N-cyclopropyl-4-ethylbenzamide (Example 288f) and suitable amine.

Example 289

N-Cyclopropyl-4-ethyl-3-[3-({1-[2-(2-{[(2S)-2-hydroxypropyl]amino}ethoxy)phenyl]-1-methylethyl}amino)-2-oxopyrazin-1(2H)-yl]benzamide

Example 290

N-Cyclopropyl-4-ethyl-3-{3-[(1-{2-[2-(ethylamino)ethoxy]phenyl}-1-methylethyl)amino]-2-oxopyrazin-1(2H)-yl}benzamide

Example 291

N-Cyclopropyl-4-ethyl-3-[3-{[1-(2-{2-[(2-hydroxyethyl)amino]ethoxy}phenyl)-1-methylethyl]amino}-2-oxopyrazin-1(2H)-yl]benzamide

Example 292

3-[3-({1-[2-(2-Aminoethoxy)phenyl]-1-methylethyl}amino)-2-oxopyrazin-1(2H)-yl]-N-cyclopropyl-4-ethylbenzamide

TABLE 13

| Example | R | MS [M + H]$^+$ m/z | $^1$H NMR δ (DMSO-d$_6$) |
|---|---|---|---|
| 289 | H-N-CH$_2$-CH(OH)-CH$_3$ | 534 | 8.44 (s, 1H), 7.91 (d, 1H), 7.71 (s, 1H), 7.51 (d, 1H), 7.33 (d, 1H), 7.22-7.17 (m, 1H), 6.98-6.90 (m, 3H), 6.65 (d, 2H), 4.38 (s, 1H), 3.98-3.94 (m, 2H), 3.61 (s, 1H), 2.95-2.81 (m, 4H), 2.45 (d, 2H), 1.84 (s, 6H), 1.06 (d, 3H), 1.00 (d, 3H), 0.69 (d, 2H), 0.56 (s, 2H) |
| 290 | H-N-ethyl | 504 | 8.43 (d, 1H), 7.91 (d, 1H), 7.70 (d, 1H), 7.51 (d, 1H), 7.34 (d, 1H), 7.19 (t, 1H), 6.98-6.88 (m, 3H), 6.65 (q, 2H), 4.02-3.89 (m, 2H), 2.91-2.82 (m, 3H), 2.54-2.51 (m, 2H), 2.45-2.35 (m, 2H), 1.84 (s, 3H), 1.83 (s, 3H), 1.06 (t,3H), 0.90 (t, 3H), 0.70-0.66 (m, 2H), 0.56-0.54 (m, 2H) |
| 291 | H-N-CH$_2$CH$_2$OH | 520.4 | 8.43 (d, 1H), 7.91 (dd, 1H), 7.70 (d, 1H), 7.51 (d, 1H), 7.33 (dd, 1H), 7.19 (t, 1H), 6.98-6.87 (m, 3H), 6.64 (q, 2H), 4.38 (t, 1H), 4.01-3.90 (m, 2H), 3.39 (q, 2H), 2.94-2.81 (m, 3H), 2.59 (t, 2H), 2.45-2.34 (m, 2H), 1.84 (s, 3H), 1.82 (s, 3H), 1.06 (t, 3H), 0.70-0.67 (m, 2H), 0.56-0.54 (m, 2H) |

TABLE 13-continued

| Example | R | MS [M + H]+ m/z | 1H NMR δ (DMSO-d6) |
|---|---|---|---|
| 292 | ⸨NH2 | 476 | 8.44 (d, 1H), 7.90 (dd, 1H), 7.69 (d, 1H), 7.51 (d, 1H), 7.34 (d, 1H), 7.19 (t, 1H), 6.97-6.88 (m, 3H), 6.67-6.62 (m, 2H), 3.91-3.84 (m, 2H), 2.89-2.83 (m, 3H), 2.42-2.38 (m, 2H), 1.84 (s, 3H), 1.83 (s, 3H), 1.06 (t, 3H), 0.70-0.66 (m, 2H), 0.57-0.54 (m, 2H) |

The following Examples 293 to 298 (Table 14) were prepared using a similar method to that described for Example 230 using 3-(3-(1-(2-(2-chloroethoxy)phenyl)cyclopropylamino)-2-oxopyrazin-1(2H)-yl)-N-cyclopropyl-4-methylbenzamide (Example 167e) and a suitable amine.

Example 293

N-Cyclopropyl-3-[3-({1-[2-(2-{[(1R)-1-(hydroxymethyl)-2-methylpropyl]amino}ethoxy)phenyl]cyclopropyl}amino)-2-oxopyrazin-1(2H)-yl]-4-methylbenzamide Example 294

N-Cyclopropyl-3-[3-({1-[2-(2-{[2-hydroxy-1-(hydroxymethyl)ethyl]amino}ethoxy)phenyl]cyclopropyl}amino)-2-oxopyrazin-1(2H)-yl]-4-methylbenzamide Example 295

N-Cyclopropyl-3-[3-{[1-(2-{2-[(1,1-dioxidotetrahydrothiophen-3-yl)amino]ethoxy}phenyl)cyclopropyl]amino}-2-oxopyrazin-1(2H)-yl]-4-methylbenzamide Example 296

N-Cyclopropyl-3-{3-[(1-{2-[2-(5,6-dihydroimidazo[1,2-a]pyrazin-7(8H)-yl)ethoxy]phenyl}cyclopropyl)amino]-2-oxopyrazin-1(2H)-yl}-4-methylbenzamide Example 297

N-Cyclopropyl-4-methyl-3-{3-[(1-{2-[2-(1-methyl-1,4,6,7-tetrahydro-5H-imidazo[4,5-c]pyridin-5-yl)ethoxy]phenyl}cyclopropyl)amino]-2-oxopyrazin-1(2H)-yl}benzamide Example 298

N-Cyclopropyl-4-methyl-3-{2-oxo-3-[(1-{2-[2-(propylamino)ethoxy]phenyl}cyclopropyl)amino]pyrazin-1(2H)-yl}benzamide

TABLE 14

| Example | R | MS [M+H]+ m/z | $^1$H NMR δ (DMSO-d$_6$) |
|---|---|---|---|
| 293 | (S)-NH-CH(CH(CH$_3$)$_2$)-CH$_2$OH | 546 | 8.02 (d, 1H), 7.81 (s, 1H), 7.77 (d, 1H), 7.64 (d, 1H), 7.40 (t, 1H), 7.14 (d, 1H), 7.11-7.04 (m, 2H), 6.75 (s, 1H), 4.38-4.31 (m, 2H), 3.92-3.84 (m, 1H), 3.72-3.64 (m, 2H), 3.51 (s, 2H), 3.35-3.26 (m, 2H), 3.04-2.97 (m, 1H), 2.73-2.66 (m, 1H), 2.31 (s, 3H), 2.11-2.01 (m, 1H), 1.52-1.26 (m, 4H), 1.21-1.07 (m, 6H), 0.97 (d, 2H), 0.82-0.75 (m, 2H). |
| 294 | NH-CH(CH$_2$OH)$_2$ | 534 | 8.37-8.32 (m, 1H), 7.87-7.81 (m, 1H), 7.69-7.65 (m, 1H), 7.54-7.42 (m, 2H), 7.39-7.34 (m, 1H), 7.23-7.14 (m, 1H), 6.98-6.92 (m, 1H), 6.89-6.81 (m, 2H), 6.72-6.66 (m, 1H), 4.43-4.34 (m, 2H), 4.10-4.02 (m, 2H), 3.05-2.96 (m, 2H), 2.86-2.79 (m, 1H), 2.65-2.58 (m, 1H), 2.22-2.10 (m, 5H), 1.25-1.13 (m, 4H), 1.12-0.99 (m, 2H), 0.70-0.62 (m, 2H), 0.56-0.49 (m, 2H). |
| 295 | NH-(tetrahydrothiophene-1,1-dioxide-3-yl) | 578 | 7.81 (d, 1H), 7.61 (d, 1H), 7.49 (d, 1H), 7.44 (d, 1H), 7.18 (t, 1H), 6.92 (d, 1H), 6.88-6.82 (m, 2H), 6.60-6.55 (m, 1H), 4.16-4.07 (m, 2H), 3.64-3.54 (m, 1H), 3.46 (q, 2H), 3.16-2.97 (m, 3H), 2.95-2.84 (m, 2H), 2.83-2.75 (m, 1H), 2.39-2.24 (m, 1H), 2.11 (d, 2H), 2.05-1.86 (m, 1H), 1.39-1.20 (m, 3H), 1.15 (t, 3H), 1.10-0.96 (m, 1H), 0.79-0.71 (m, 2H), 0.63-0.55 (m, 2H). |
| 296 | 5,6,7,8-tetrahydroimidazo[1,2-a]pyrazin-7-yl | 566 | 8.35 (d, 1H), 7.84 (dd, 1H), 7.68 (d, 1H), 7.48 (dd, 1H), 7.46 (d, 1H), 7.28 (s, 1H), 7.21 (td, 1H), 7.00 (d, 1H), 6.99 (d, 1H), 6.89-6.85 (m, 2H), 6.81 (d, 1H), 6.70 (d, 1H), 4.22 (t, 2H), 3.95 (t, 2H), 3.79 (d, 1H), 3.75 (d, 1H), 3.01 (d, 4H), 2.87-2.78 (m, 1H), 2.05 (s, 3H), 1.25-1.03 (m, 4H), 0.69-0.64 (m, 2H), 0.54-0.50 (m, 2H) |
| 297 | 1-methyl-4,5,6,7-tetrahydro-1H-imidazo[4,5-c]pyridin-5-yl | 580 | 8.35 (d, 1H), 7.84 (dd, 1H), 7.68 (d, 1H), 7.47 (m, 2H), 7.36 (s, 1H), 7.25 (s, 1H), 7.20 (dt, 1H), 7.00 (d, 1H), 6.86 (dt, 1H), 6.86 (d, 1H), 6.70 (d, 1H), 4.19 (t, 2H), 3.52 (s, 2H), 3.44 (s, 3H), 2.98 (t, 2H), 2.88 (t, 2H), 2.85-2.79 (m, 1H), 2.56 (t, 2H), 2.05 (s, 3H), 1.27-1.03 (m, 4H), 0.69-0.63 (m, 2H), 0.55-0.49 (m, 2H). |
| 298 | NH-propyl | 502 | d 7.81 (d, 1H), 7.61 (s, 1H), 7.53 (d, 1H), 7.43 (d, 1H), 7.19 (t, 1H), 6.92 (d, 1H), 6.89-6.83 (m, 2H), 6.57 (t, 2H), 4.14 (t, 2H), 3.09-3.01 (m, 2H), 2.84-2.75 (m, 1H), 2.61 (t, 2H), 2.10 (s, 3H), 1.66-1.32 (m, 3H), 1.31-1.05 (m, 5H), 0.86 (t, 4H), 0.78-0.71 (m, 2H), 0.60-0.54 (m, 2H). |

Example 299

N-Cyclopropyl-3-[3-({1-[2-({(2R)-2-hydroxy-3-[(2-hydroxyethyl)amino]propyl}oxy)phenyl]cyclopropyl}amino)-2-oxopyrazin-1(2H)-yl]-4-methylbenzamide

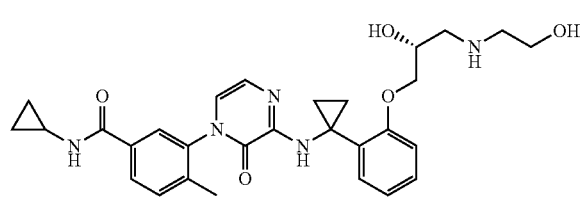

a) N-Cyclopropyl-4-methyl-3-{3-[(1-{2-[(2R)-oxiran-2-ylmethoxy]phenyl}cyclopropyl)amino]-2-oxopyrazin-1(2H)-yl}benzamide Potassium carbonate (216 mg) and cesium fluoride (36.5 mg) were added to N-cyclopropyl-3-(3-(1-(2-hydroxyphenyl)cyclopropylamino)-2-oxopyrazin-1(2H)-yl)-4-methylbenzamide (Example 167d, 500 mg) in DMF (9 mL) and stirred for 1 h. (R)-oxiran-2-ylmethyl 3-nitrobenzenesulfonate (311 mg) was added and the reaction stirred for 3 days. The reaction mixture was used without isolation/purification.

MS: APCI (+ve) 473 (M+H)+.

b) N-Cyclopropyl-3-[3-({1-[2-({(2R)-2-hydroxy-3-[(2-hydroxyethyl)amino]propyl}oxy)phenyl]cyclopropyl}amino)-2-oxopyrazin-1(2H)-yl]-4-methylbenzamide Ethanolamine (1 mL) was added to N-cyclopropyl-4-methyl-3-{3-[(1-{2-[(2R)-oxiran-2-ylmethoxy]phenyl}cyclopropyl)amino]-2-oxopyrazin-1(2H)-yl}benzamide (Example 299a, 7.81 g) in DMF (3 mL). The reaction was heated at 50° C. overnight. The reaction mixture was partitioned between water and DCM. The combined organics were dried (MgSO4), filtered and evaporated. Purification by preparative HPLC (Xbridge column, eluting with a gradient of acetonitrile in 0.2% (v/v) aqueous ammonia) gave the title product (0.102 g) after solvent removal and trituration with diethyl ether.

1H NMR δ (CD3OD) 7.82-7.76 (m, 1H), 7.61-7.52 (m, 2H), 7.45-7.39 (m, 1H), 7.21-7.14 (m, 1H), 6.93-6.81 (m, 3H), 6.57-6.53 (m, 1H), 4.20-4.11 (m, 1H), 4.03-3.98 (m, 2H), 3.64-3.56 (m, 2H), 2.96-2.88 (m, 1H), 2.85-2.68 (m, 4H), 2.11-2.07 (m, 3H), 1.28-1.07 (m, 4H), 0.79-0.71 (m, 2H), 0.60-0.53 (m, 2H).

MS: APCI (+ve) 534 (M+H)+.

Example 300

N-Cyclopropyl-3-[3-{[1-(2-{[(2R)-3-(ethylamino)-2-hydroxypropyl]oxy}phenyl)cyclopropyl]amino}-2-oxopyrazin-1(2H)-yl]-4-methylbenzamide

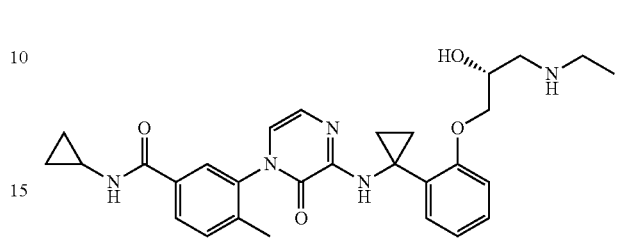

The title compound was prepared using a similar method to that described for Example 299b from (R)—N-cyclopropyl-4-methyl-3-(3-(1-(2-(oxiran-2-ylmethoxy)phenyl)cyclopropylamino)-2-oxopyrazin-1(2H)-yl)benzamide (Example 299a) and ethylamine.

MS: APCI (+ve) 518 (M+H)+.

1H NMR δ (CD3OD) 7.80 (dd, 1H), 7.59 (s, 1H), 7.55 (dd, 1H), 7.42 (d, 1H), 7.21-7.14 (m, 1H), 6.93-6.82 (m, 3H), 6.55 (d, 1H), 4.22-4.12 (m, 1H), 4.00 (d, 2H), 2.94-2.87 (m, 1H), 2.84-2.72 (m, 2H), 2.70-2.60 (m, 2H), 2.09 (s, 3H), 1.28-1.18 (m, 4H), 1.14-1.04 (m, 4H), 0.78-0.71 (m, 2H), 0.60-0.53 (m, 2H).

Example 301

N-Cyclopropyl-3-[3-{[1-(2-{[(2R)-2-hydroxy-3-(methylamino)propyl]oxy}phenyl)cyclopropyl]amino}-2-oxopyrazin-1(2H)-yl]-4-methylbenzamide

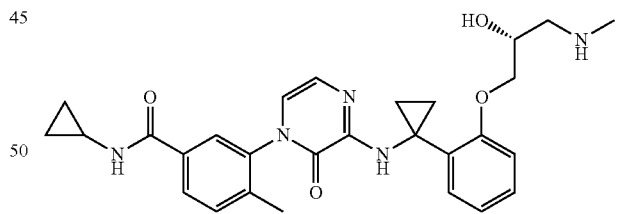

The title compound was prepared using a similar method to that described for Example 299b from (R)—N-cyclopropyl-4-methyl-3-(3-(1-(2-(oxiran-2-ylmethoxy)phenyl)cyclopropylamino)-2-oxopyrazin-1(2H)-yl)benzamide (Example 299a) and methylamine.

MS: APCI (+ve) 504 (M+H)+.

1H NMR δ (CD3OD) 7.81-7.79 (m, 1H), 7.60 (d, 1H), 7.57-7.54 (m, 1H), 7.43 (d, 1H), 7.21-7.16 (m, 1H), 6.93-6.83 (m, 3H), 6.57 (d, 1H), 4.20-4.12 (m, 1H), 4.02-3.99 (m, 2H), 2.91-2.83 (m, 1H), 2.84-2.72 (m, 2H), 2.40 (d, 3H), 2.10 (s, 3H), 1.28-1.13 (m, 4H), 1.14-1.09 (m, 1H), 0.79-0.71 (m, 2H), 0.61-0.54 (m, 2H).

Example 302

N-Cyclopropyl-3-[3-({1-[2-({(2S)-2-hydroxy-3-[(2-hydroxyethyl)amino]propyl}oxy)phenyl]cyclopropyl}amino)-2-oxopyrazin-1(2H)-yl]-4-methylbenzamide

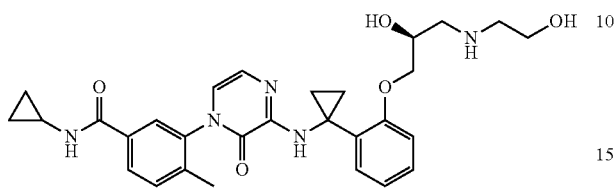

a) N-Cyclopropyl-4-methyl-3-{3-[(1-{2-[(2S)-oxiran-2-ylmethoxy]phenyl}cyclopropyl)amino]-2-oxopyrazin-1(2H)-yl}benzamide The subtitle compound was prepared using a similar method to that described for Example 299a from N-cyclopropyl-3-(3-(1-(2-hydroxyphenyl)cyclopropylamino)-2-oxopyrazin-1(2H)-yl)-4-methylbenzamide (Example 167d) and (S)-oxiran-2-ylmethyl 3-nitrobenzenesulfonate.

MS: APCI (+ve) 473 (M+H)$^+$.

b) N-Cyclopropyl-3-[3-({1-[2-({(2S)-2-hydroxy-3-[(2-hydroxyethyl)amino]propyl}oxy)phenyl]cyclopropyl}amino)-2-oxopyrazin-1(2H)-yl]-4-methylbenzamide The title compound was prepared using a similar method to that described for Example 299b from N-cyclopropyl-4-methyl-3-{3-[(1-{2-[(2S)-oxiran-2-ylmethoxy]phenyl}cyclopropyl)amino]-2-oxopyrazin-1(2H)-yl}benzamide (Example 302a).

MS: APCI (+ve) 534 (M+H)$^+$.

$^1$H NMR δ (CD$_3$OD) 7.80 (dd, 1H), 7.60 (d, 1H), 7.56 (dd, 1H), 7.43 (d, 1H), 7.21-7.15 (m, 1H), 6.92 (d, 2H), 6.89-6.83 (m, 1H), 6.56 (d, 1H), 4.23-4.12 (m, 1H), 4.01 (d, 2H), 3.63-3.58 (m, 2H), 2.97-2.90 (m, 1H), 2.85-2.67 (m, 4H), 2.10 (s, 3H), 1.27-1.07 (m, 4H), 0.79-0.71 (m, 2H), 0.60-0.54 (m, 2H).

Example 303

N-cyclopropyl-3-[3-{[1-(2-{[(2S)-3-(ethylamino)-2-hydroxypropyl]oxy}phenyl)cyclopropyl]amino}-2-oxopyrazin-1(2H)-yl]-4-methylbenzamide

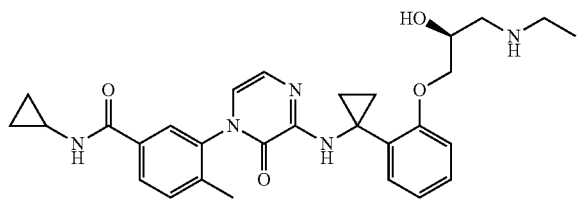

The title compound was prepared using a similar method to that described for Example 299b from N-cyclopropyl-3-[3-({1-[2-({(2S)-2-hydroxy-3-[(2-hydroxyethyl)amino]propyl}oxy)phenyl]cyclopropyl}amino)-2-oxopyrazin-1(2H)-yl]-4-methylbenzamide (Example 302a).

MS: APCI (+ve) 518 (M+H)$^+$.

$^1$H NMR δ (CD$_3$OD) 7.80 (dd, 1H), 7.59 (d, 1H), 7.55 (dd, 1H), 7.42 (d, 1H), 7.20-7.15 (m, 1H), 6.91 (d, 1H), 6.88-6.82 (m, 2H), 6.55 (d, 1H), 4.19-4.12 (m, 1H), 4.03-3.97 (m, 2H), 3.46 (q, 2H), 2.93-2.87 (m, 1H), 2.82-2.71 (m, 2H), 2.70-2.59 (m, 2H), 2.09 (s, 3H), 1.28-1.19 (m, 3H), 1.15 (t, 3H), 1.08 (td, 3H), 0.78-0.72 (m, 2H), 0.59-0.54 (m, 2H).

Example 304

N-Cyclopropyl-3-[3-{[1-(2-{[(2S)-2-hydroxy-3-(methylamino)propyl]oxy}phenyl)cyclopropyl]amino}-2-oxopyrazin-1(2H)-yl]-4-methylbenzamide

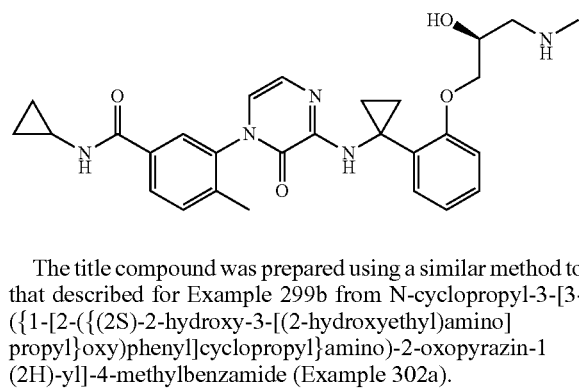

The title compound was prepared using a similar method to that described for Example 299b from N-cyclopropyl-3-[3-({1-[2-({(2S)-2-hydroxy-3-[(2-hydroxyethyl)amino]propyl}oxy)phenyl]cyclopropyl}amino)-2-oxopyrazin-1(2H)-yl]-4-methylbenzamide (Example 302a).

MS: APCI (+ve) 504 (M+H)$^+$.

$^1$H NMR δ (CD$_3$OD) 7.80 (dd, 1H), 7.60 (d, 1H), 7.56 (dd, 1H), 7.42 (d, 1H), 7.21-7.15 (m, 1H), 6.94-6.82 (m, 3H), 6.56 (d, 1H), 4.21-4.12 (m, 1H), 4.04-3.96 (m, 2H), 2.92-2.83 (m, 1H), 2.83-2.71 (m, 2H), 2.40 (d, 3H), 2.10 (s, 3H), 1.29-1.19 (m, 3H), 1.18-1.09 (m, 2H), 0.79-0.71 (m, 2H), 0.60-0.54 (m, 2H).

Example 305

3-[3-{[1-(2-{[(2R)-2-Amino-3-hydroxypropyl]oxy}phenyl)-1-methylethyl]amino}-2-oxopyrazin-1(2H)-yl]-N-cyclopropyl-4-methylbenzamide

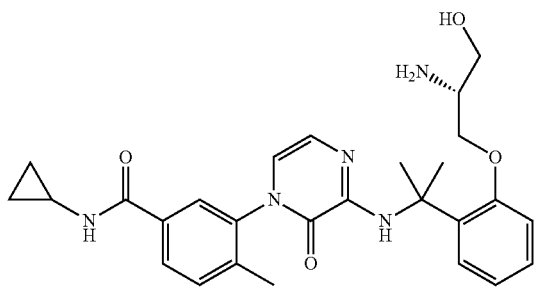

a) N-Cyclopropyl-4-methyl-3-[3-{[1-methyl-1-(2-{[(4S)-2-oxo-1,3-oxazolidin-4-yl]methoxy}phenyl)ethyl]amino}-2-oxopyrazin-1(2H)-yl]benzamide A solution of N-cyclopropyl-3-(3-(2-(2-hydroxyphenyl)propan-2-ylamino)-2-oxopyrazin-1(2H)-yl)-4-methylbenzamide (Example 134, 0.5 g) in acetonitrile (10 mL) was treated with potassium carbonate (0.495 g) and (S)-(2-oxooxazolidin-4-yl)methyl 4-methylbenzenesulfonate (0.324 g) under nitrogen. The resulting mixture was stirred at 80° C. for 16 h. The reaction mixture was diluted with water, and extracted with DCM. The organic layer was dried (MgSO$_4$), filtered and evaporated to afford the subtitle compound as a solid (0.6 g).

MS: APCI (+ve) 518 (M+H)$^+$.

b) 3-[3-{[1-(2-{[(2R)-2-Amino-3-hydroxypropyl]oxy}phenyl)-1-methylethyl]amino}-2-oxopyrazin-1(2H)-yl]-N-cyclopropyl-4-methylbenzamide A solution of N-cyclopropyl-4-methyl-3-[3-{[1-methyl-1-(2-{[(4S)-2-oxo-1,3-oxazolidin-4-yl]methoxy}phenyl)ethyl]amino}-2-oxopyrazin-1(2H)-yl]benzamide (Example 305a) (0.6 g) in water (10 mL) and MeOH (10 mL) was treated with potassium hydroxide (0.130 g) under nitrogen. The resulting mixture was stirred at 50° C. for 16 h. The reaction mixture was diluted with water (200 mL), and extracted with ethyl acetate (250 mL). The organic phase was dried (MgSO$_4$), filtered and evaporated. Purification by preparative HPLC (Phenomenex Gemini column, eluting with a gradient of acetonitrile in 0.2% (v/v) aqueous ammonia) gave the title compound as a solid (0.105 g).

MS: APCI (+ve) 492 (M+H)$^+$.

$^1$H NMR δ (DMSO-d$_6$) 8.49 (s, 1H), 7.93-7.82 (m, 1H), 7.79 (s, 1H), 7.55-7.44 (m, 1H), 7.41-7.30 (m, 1H), 7.27-7.16 (m, 1H), 7.03-6.86 (m, 3H), 6.73-6.59 (m, 2H), 4.74-4.53 (m, 1H), 4.00-3.85 (m, 1H), 3.86-3.72 (m, 1H), 3.38-3.24 (m, 1H), 3.14-2.99 (m, 1H), 2.94-2.80 (m, 1H), 2.17 (s, 3H), 1.94 (s, 6H), 1.74-1.52 (m, 2H), 0.76-0.64 (m, 2H), 0.63-0.51 (m, 2H).

Example 306

N-Cyclopropyl-3-[3-{[1-(2-{[(2R)-2-(dimethylamino)-3-hydroxypropyl]oxy}phenyl)-1-methylethyl]amino}-2-oxopyrazin-1(2H)-yl]-4-methylbenzamide

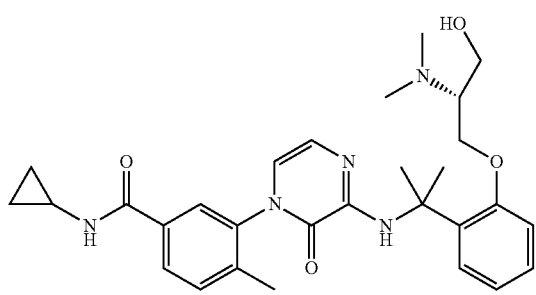

A solution of 3-[3-{[1-(2-{[(2R)-2-amino-3-hydroxypropyl]oxy}phenyl)-1-methylethyl]amino}-2-oxopyrazin-1(2H)-yl]-N-cyclopropyl-4-methylbenzamide (Example 305, 0.25 g) in dichloroethane (10 mL) was treated with 37% aqueous formaldehyde (0.021 mL) under nitrogen. The resulting mixture was stirred at 20° C. for 10 minutes before adding sodium triacetoxyborohydride (0.323 g). The resulting mixture was stirred at 20° C. for 16 h. The reaction mixture was diluted with water (125 mL), and extracted with DCM (250 mL). The organic phase was dried (MgSO$_4$), filtered and evaporated. Purification by preparative HPLC (Phenomenex Gemini column, eluting with a gradient of acetonitrile in 0.2% (v/v) aqueous ammonia) gave the title compound as a solid (0.069 g).

MS: APCI (+ve) 520 (M+H)$^+$.

$^1$H NMR δ (DMSO-d$_6$) 8.45 (s, 1H), 7.86 (d, 1H), 7.75-7.67 (m, 1H), 7.49 (d, 1H), 7.31 (d, 1H), 7.24-7.15 (m, 1H), 7.01 (d, 1H), 6.92-6.84 (m, 2H), 6.68-6.60 (m, 2H), 4.00-3.92 (m, 2H), 3.64-3.48 (m, 2H), 2.90-2.74 (m, 2H), 2.24 (s, 6H), 2.05 (s, 3H), 1.77 (s, 6H), 0.74-0.64 (m, 2H), 0.60-0.50 (m, 2H).

Example 307

N-Cyclopropyl-3-fluoro-5-[3-{[1-(2-{[(2R)-2-hydroxy-3-(methylamino)propyl]oxy}phenyl)-1-methylethyl]amino}-2-oxopyrazin-1(2H)-yl]-4-methylbenzamide

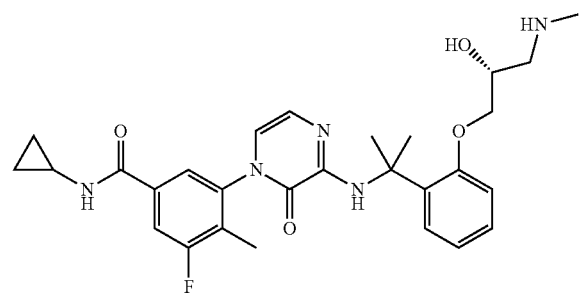

a) N-Cyclopropyl-3-fluoro-4-methyl-5-[3-({1-methyl-1-[2-(2R)-(oxiran-2-ylmethoxy)phenyl]ethyl}amino)-2-oxopyrazin-1(2H)-yl]benzamide Prepared from N-cyclopropyl-3-fluoro-5-[3-[[1-(2-hydroxyphenyl)-1-methylethyl]amino]-2-oxo-1(2H)pyrazinyl]-4-methyl-benzamide (Example 252j) and (R)-oxiran-2-ylmethyl 3-nitrobenzenesulfonate, using a similar method to that described in Example 299a.

MS: APCI (+ve) 493 (M+H)$^+$.

b) N-Cyclopropyl-3-fluoro-5-[3-{[1-(2-{[(2R)-2-hydroxy-3-(methylamino)propyl]oxy}phenyl)-1-methylethyl]amino}-2-oxopyrazin-1(2H)-yl]-4-methylbenzamide The title compound was prepared using a similar method to that described for Example 299b from N-cyclopropyl-3-fluoro-4-methyl-5-[3-({1-methyl-1-[2-(2R)-(oxiran-2-ylmethoxy)phenyl]ethyl}amino)-2-oxopyrazin-1(2H)-yl]benzamide (Example 307a).

MS: APCI (+ve) 524 (M+H)$^+$.

$^1$H NMR δ (DMSO-d$_6$) 8.53 (s, 1H), 7.71 (d, 2H), 7.26 (d, 2H), 6.98-6.89 (m, 3H), 6.68 (s, 2H), 4.84 (s, 1H), 3.93-3.88 (m, 3H), 2.91-2.78 (m, 1H), 2.59-2.57 (m, 2H), 2.23 (s, 3H), 2.00 (s, 3H), 1.85 (s, 6H), 0.64 (m, 4H).

Example 308

N-Cyclopropyl-3-[3-{[1-(2-{[(2R)-3-(ethylamino)-2-hydroxypropyl]oxy}phenyl)-1-methylethyl]amino}-2-oxopyrazin-1(2H)-yl]-5-fluoro-4-methylbenzamide

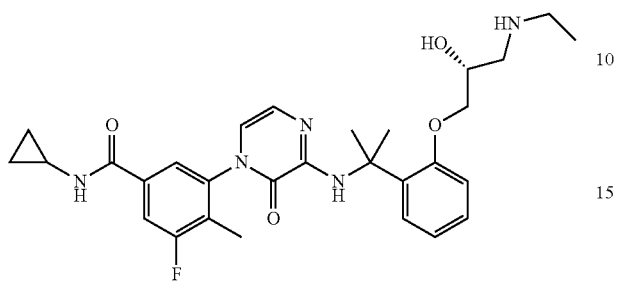

The title compound was prepared using a similar method to that described for Example 300 from N-cyclopropyl-3-fluoro-4-methyl-5-[3-({1-methyl-1-[2-(2R)-(oxiran-2-ylmethoxy)phenyl]ethyl}amino)-2-oxopyrazin-1(2H)-yl]benzamide (Example 307a).

MS: APCI (+ve) 538 (M+H)⁺.

$^1$H NMR δ (DMSO-d$_6$) 8.52 (s, 1H), 7.75 (d, 1H), 7.66 (s, 1H), 7.25 (d, 2H), 6.97-6.89 (m, 3H), 6.68 (s, 2H), 4.83 (s, 1H), 3.88 (s, 3H), 2.92-2.79 (m, 1H), 2.68-2.57 (m, 4H), 2.00 (s, 3H), 1.85 (s, 6H), 0.95 (s, 3H), 0.63 (m, 4H)

Example 309

N-Cyclopropyl-3-[3-{[1-(2-{[(2S)-3-(ethylamino)-2-hydroxypropyl]oxy}phenyl)-1-methylethyl]amino}-2-oxopyrazin-1(2H)-yl]-5-fluoro-4-methylbenzamide

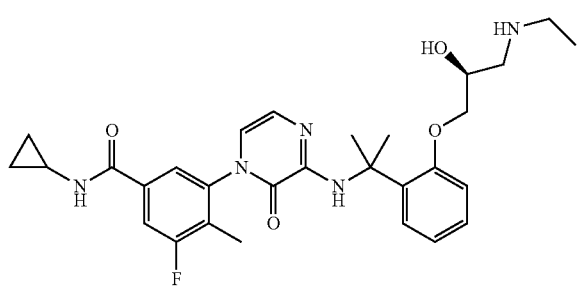

a) N-Cyclopropyl-3-fluoro-4-methyl-5-[3-({1-methyl-1-[2-(2S)-(oxiran-2-ylmethoxy)phenyl]ethyl}amino)-2-oxopyrazin-1(2H)-yl]benzamide The subtitle compound was prepared using a similar method to Example 299a from N-cyclopropyl-3-fluoro-5-[3-[[1-(2-hydroxyphenyl)-1-methylethyl]amino]-2-oxo-1(2H)-pyrazinyl]-4-methyl-benzamide (Example 252j) and (S)-oxiran-2-ylmethyl 3-nitrobenzenesulfonate.

MS: APCI (+ve) 493 (M+H)⁺.

b) N-Cyclopropyl-3-[3-{[1-(2-{[(2S)-3-(ethylamino)-2-hydroxypropyl]oxy}phenyl)-1-methylethyl]amino}-2-oxopyrazin-1(2H)-yl]-5-fluoro-4-methylbenzamide The title compound was prepared using a similar method to that described for Example 300 from N-cyclopropyl-3-fluoro-4-methyl-5-[3-({1-methyl-1-[2-(2S)-(oxiran-2-ylmethoxy)phenyl]ethyl}amino)-2-oxopyrazin-1(2H)-yl]benzamide (Example 309a).

MS: APCI (+ve) 538 (M+H)⁺

$^1$H NMR δ (DMSO-d$_6$) 8.52 (s, 1H), 7.75 (d, 1H), 7.66 (s, 1H), 7.32 (d, 1H), 7.19 (t, 1H), 6.97-6.86 (m, 3H), 6.68 (q, 2H), 4.83 (s, 1H), 3.93-3.81 (m, 3H), 2.88-2.82 (m, 1H), 2.68-2.55 (m, 4H), 1.99 (s, 3H), 1.84 (s, 6H), 0.97-0.92 (m, 3H), 0.70 (m, 2H), 0.55 (m, 2H).

Example 310

N-Cyclopropyl-3-fluoro-5-[3-{[1-(2-{[(2S)-2-hydroxy-3-(methylamino)propyl]oxy}phenyl)-1-methylethyl]amino}-2-oxopyrazin-1(2H)-yl]-4-methylbenzamide

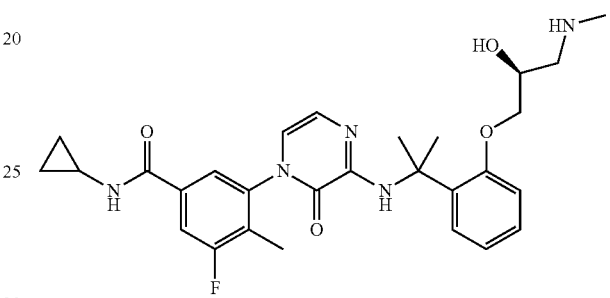

The title compound was prepared using a similar method to that described for Example 300 from N-cyclopropyl-3-fluoro-4-methyl-5-[3-({1-methyl-1-[2-(2S)-(oxiran-2-ylmethoxy)phenyl]ethyl}amino)-2-oxopyrazin-1(2H)-yl]benzamide (Example 309a).

MS: APCI (+ve) 524 (M+H)⁺.

$^1$H NMR δ (DMSO-d$_6$) 8.52 (s, 1H), 7.75 (d, 1H), 7.65 (s, 1H), 7.32 (d, 1H), 7.18 (t, 1H), 6.98-6.86 (m, 3H), 6.70-6.66 (m, 2H), 4.84 (s, 1H), 3.93-3.88 (m, 3H), 2.88-2.82 (m, 1H), 2.61-2.54 (m, 2H), 2.23 (d, 3H), 2.00 (s, 3H), 1.84 (s, 6H), 0.70 (m, 2H), 0.56 (m, 2H).

Example 311

3-[3-({1-[2-(2-Aminoethoxy)phenyl]-1-methylethyl}amino)-2-oxopyrazin-1(2H)-yl]-N-cyclopropyl-5-fluoro-4-methylbenzamide

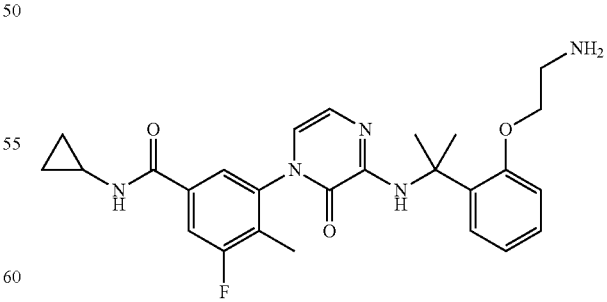

The title compound was prepared using a similar method to that described for Example 259e from 3-[3-[[1-[2-(2-chloroethoxy)phenyl]-1-methylethyl]amino]-2-oxo-1(2H)-pyrazinyl]-N-cyclopropyl-5-fluoro-4-methyl-benzamide (Example 252k).

MS: APCI (+ve) 480.2 (M+H)+.

¹H NMR δ (DMSO-d₆) 8.61-8.44 (m, 1H), 7.77 (d, 1H), 7.68 (s, 1H), 7.40-7.30 (m, 1H), 7.24-7.15 (m, 1H), 6.99-6.87 (m, 3H), 6.73-6.61 (m, 2H), 3.96-3.80 (m, 2H), 2.93-2.77 (m, 3H), 2.05 (s, 3H), 1.88 (s, 6H), 0.76-0.64 (m, 2H), 0.62-0.50 (m, 2H).

Example 312

N-(2-{2-[1-({4-[5-(Cyclopropylcarbamoyl)-3-fluoro-2-methylphenyl]-3-oxo-3,4-dihydropyrazin-2-yl}amino)-1-methylethyl]phenoxy}ethyl)glycine

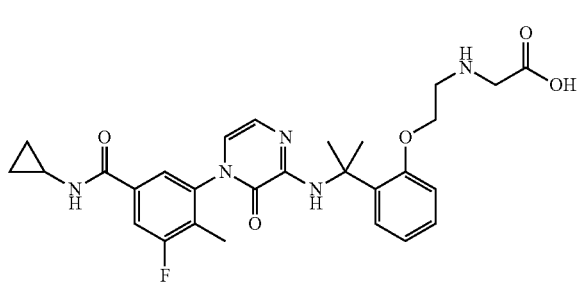

A solution of 3-(3-(2-(2-(2-aminoethoxy)phenyl)propan-2-ylamino)-2-oxopyrazin-1(2H)-yl)-N-cyclopropyl-5-fluoro-4-methylbenzamide (Example 311, 0.17 g) dissolved in THF (10 mL) was treated with triethylamine (0.049 mL) and methyl bromoacetate (0.034 mL) under nitrogen. The resulting mixture was stirred at 20° C. for 16 h. The reaction mixture was diluted with 2M aqueous NaOH (2 mL) and methanol (2 mL). The solution was stirred at room temperature for 1 h, acidified with acetic acid and extracted with ethyl acetate (50 mL).

The organic layer was dried (MgSO₄) and evaporated. Purification by preparative HPLC (Phenomenex Gemini column using a 95-5% gradient of aqueous 0.2% ammonia in acetonitrile as eluent) gave the title compound (0.03 g).

MS: APCI (+ve) 538 (M+H)+.

¹H NMR δ (DMSO-d₆) 8.61-8.50 (m, 1H), 7.74-7.64 (m, 2H), 7.36 (d, 1H), 7.24-7.14 (m, 1H), 7.01-6.85 (m, 3H), 6.69-6.62 (m, 1H), 6.58-6.52 (m, 1H), 4.11-3.99 (m, 2H), 3.15 (s, 2H), 3.03 (t, 2H), 2.91-2.82 (m, 1H), 1.94 (s, 3H), 1.81 (s, 6H), 0.71-0.57 (m, 4H)

Example 313

N-(2-{2-[1-({4-[5-(Cyclopropylcarbamoyl)-3-fluoro-2-methylphenyl]-3-oxo-3,4-dihydropyrazin-2-yl}amino)-1-methylethyl]phenoxy}ethyl)-beta-alanine

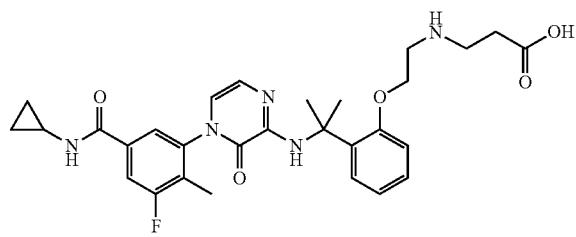

of the title compound was prepared from 3-(3-(2-(2-(2-aminoethoxy)phenyl)propan-2-ylamino)-2-oxopyrazin-1(2H)-yl)-N-cyclopropyl-5-fluoro-4-methylbenzamide (Example 311) and methyl bromopropanoate using a similar method to that described for Example 312.

MS: APCI (+ve) 552.4 (M+H)+.

¹H NMR δ (DMSO-d₆) 8.73-8.59 (m, 1H), 7.78-7.65 (m, 2H), 7.35 (d, 1H), 7.25-7.12 (m, 1H), 7.06-6.86 (m, 3H), 6.70-6.58 (m, 2H), 4.05-3.93 (m, 2H), 3.03-2.90 (m, 2H), 2.86-2.73 (m, 3H), 2.18 (t, 2H), 2.05 (s, 3H), 1.87 (s, 6H), 0.74-0.61 (m, 2H), 0.61-0.48 (m, 2H)

Example 314

3-[3-({1-[2-(2-Aminoethoxy)phenyl]cyclopropyl}amino)-2-oxopyrazin-1(2H)-yl]-N-cyclopropyl-5-fluoro-4-methylbenzamide

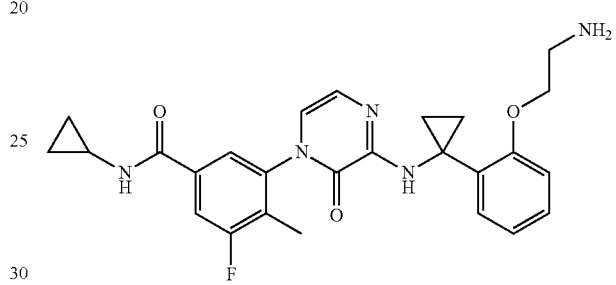

The title compound was prepared from 3-[3-[[1-[2-(2-chloroethoxy)phenyl]cyclopropyl]amino]-2-oxo-1(2H)-pyrazinyl]-N-cyclopropyl-5-fluoro-4-methyl-benzamide (Example 259d) using a similar method to Example 259e.

MS: APCI (+ve) 478.2 (M+H)+.

¹H NMR δ (DMSO-d₆) 8.45 (1H, d), 7.73 (1H, d), 7.60 (1H, s), 7.53-7.45 (2H, m), 7.19 (1H, t), 6.98-6.80 (4H, m), 6.76-6.72 (1H, m), 3.97 (2H, t), 2.94 (2H, t), 2.89-2.75 (1H, m), 1.96 (3H, s), 1.27-0.98 (4H, m), 0.72-0.64 (2H, m), 0.57-0.51 (2H, m)

Example 315

N-Cyclopropyl-3-fluoro-5-[3-{[1-(2-{2-[(2-hydroxyethyl)(methyl)amino]ethoxy}phenyl)cyclopropyl]amino}-2-oxopyrazin-1(2H)-yl]-4-methylbenzamide

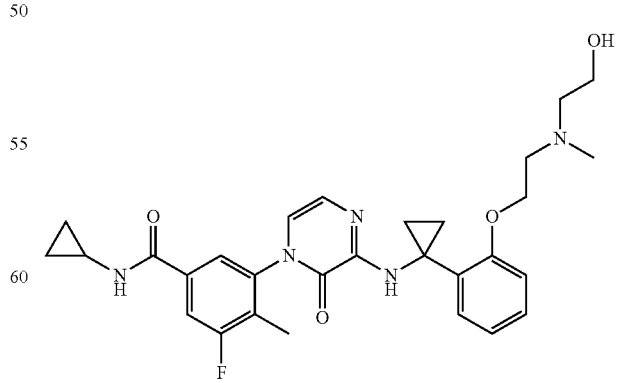

The title compound was prepared from 3-[3-[[1-[2-(2-chloroethoxy)phenyl]cyclopropyl]amino]-2-oxo-1(2H)- pyrazinyl]-N-cyclopropyl-5-fluoro-4-methyl-benzamide (Example 259d) using a similar method to Example 259e.

MS: APCI (+ve) 536.2 (M+H)⁺.

¹H NMR δ (DMSO-d₆) 8.45 (1H, d), 7.72 (1H, d), 7.60 (1H, s), 7.48 (1H, d), 7.28 (1H, s), 7.19 (1H, t), 6.96 (1H, d), 6.89-6.82 (2H, m), 6.74 (1H, d), 4.35-4.26 (1H, m), 4.08 (2H, t), 3.55-3.45 (2H, m), 2.83 (2H, t), 2.54 (2H, t), 2.31 (3H, s), 1.96 (3H, s), 1.21-1.02 (4H, m), 0.74-0.62 (2H, m), 0.57-0.48 (2H, m)

Example 316

3-Fluoro-N-methoxy-4-methyl-5-{3-[(1-methyl-1-{2-[2-(methylamino)ethoxy]phenyl}ethyl)amino]-2-oxopyrazin-1(2H)-yl}benzamide

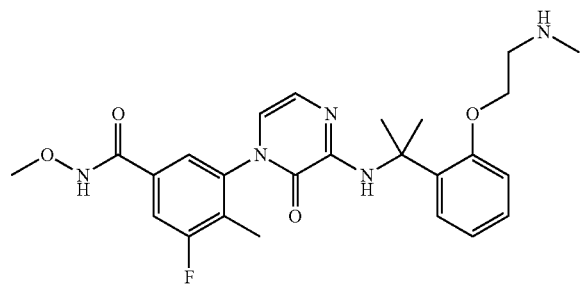

a) Methyl 3-fluoro-5-[3-{[1-(2-hydroxyphenyl)-1-methylethyl]amino}-2-oxopyrazin-1(2H)-yl]-4-methylbenzoate The subtitle compound was prepared from 3-[5-Bromo-3-[[1-methyl-1-[2-(phenylmethoxy)phenyl]ethyl]amino]-2-oxo-1(2H)-pyrazinyl]-5-fluoro-4-methyl-benzoic acid, methyl ester (Example 252h) using the method of Example 252j.

¹H NMR δ (DMSO-d₆) 9.55 (s, 1H), 7.82 (d, 1H), 7.77 (s, 1H), 7.25 (d, 1H), 7.09-6.94 (m, 2H), 6.80-6.66 (m, 4H), 3.94 (s, 3H), 2.10 (s, 3H), 1.89 (s, 6H)

b) Methyl 3-[3-({1-[2-(2-chloroethoxy)phenyl]-1-methylethyl}amino)-2-oxopyrazin-1(2H)-yl]-5-fluoro-4-methylbenzoate The subtitle compound was prepared from methyl 3-fluoro-5-[3-{[1-(2-hydroxyphenyl)-1-methylethyl]amino}-2-oxopyrazin-1(2H)-yl]-4-methylbenzoate (Example 316a) using the method of Example 252k.

MS: APCI (+ve) 474 (M+H)⁺.

c) 3-[3-({1-[2-(2-Chloroethoxy)phenyl]-1-methylethyl}amino)-2-oxopyrazin-1(2H)-yl]-5-fluoro-4-methyl benzoic acid Lithium hydroxide monohydrate (0.177 g) in water (5.00 mL) was added to methyl 3-[3-({1-[2-(2-chloroethoxy)phenyl]-1-methylethyl}amino)-2-oxopyrazin-1(2H)-yl]-5-fluoro-4-methylbenzoate (Example 316b, 1.17 g) in THF (10 mL) and the reaction mixture was stirred for 4 h at room temperature. Water was added and the solution acidified with 2M HCl. This was extracted into ethyl acetate (2×). The combined organics were dried (MgSO₄), filtered and evaporated to afford the subtitle compound as a solid (1 g).

MS: APCI (+ve) 460 (M+H)⁺.

d) 3-[3-({1-[2-(2-Chloroethoxy)phenyl]-1-methylethyl}amino)-2-oxopyrazin-1(2H)-yl]-5-fluoro-N-methoxy-4-methyl benzamide To 3-[3-({1-[2-(2-chloroethoxy)phenyl]-1-methylethyl}amino)-2-oxopyrazin-1(2H)-yl]-5-fluoro-4-methylbenzoic acid (Example 316c, 0.13 g) in DMF (3 mL) was added O-(Benzotriazol-1-yl)-N,N,N',N'-tetramethyluronium tetrafluoroborate (TBTU) (0.182 g) and N,N-diisopropylethylamine (0.148 mL). The reaction was stirred for 15 min, then O-methylhydroxylamine hydrochloride (0.047 g) was added. The reaction mixture was stirred at room temperature overnight, then diluted with water and extracted with ethyl acetate. The organic layer was dried (MgSO₄), filtered and evaporated to afford the subtitle compound (0.13 g).

MS: APCI (+ve) 489 (M+H)⁺.

e) 3-Fluoro-N-methoxy-4-methyl-5-{3-[(1-methyl-1-{2-[2-(methylamino)ethoxy]phenyl}ethyl)amino]-2-oxopyrazin-1(2H)-yl}benzamide The title compound was prepared from 3-[3-({1-[2-(2-chloroethoxy)phenyl]-1-methylethyl}amino)-2-oxopyrazin-1(2H)-yl]-5-fluoro-N-methoxy-4-methylbenzamide (Example 316d) using a similar method to that described for Example 167f but using dioxane as solvent and a reaction time of 5 min.

MS: APCI (+ve) 484.2 (M+H)⁺.

¹H NMR δ (DMSO-d₆) 7.60 (d, 2H), 7.26 (d, 2H), 6.95-6.91 (m, 3H), 6.67 (s, 2H), 3.96 (s, 2H), 3.70 (s, 3H), 2.84 (s, 2H), 2.27 (s, 3H), 2.00 (s, 3H), 1.83 (s, 6H).

Example 317

N-Methoxy-4-methyl-3-{3-[(1-{2-[2-(methylamino)ethoxy]phenyl}cyclopropyl)amino]-2-oxopyrazin-1(2H)-yl}benzamide

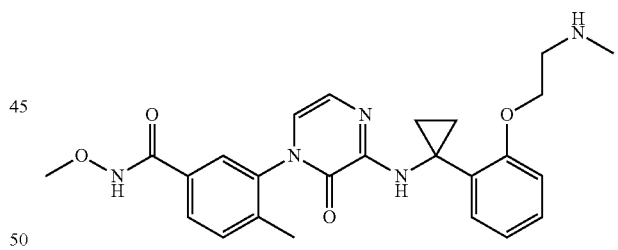

a) Methyl 3-[3-({1-[2-(2-chloroethoxy)phenyl]cyclopropyl}amino)-2-oxopyrazin-1(2H)-yl]-4-methylbenzoate A solution of methyl 3-(3-(1-(2-hydroxyphenyl)cyclopropylamino)-2-oxopyrazin-1(2H)-yl)-4-methylbenzoate (Example 167c) 0.45 g) dissolved in acetonitrile (8 mL) was treated with potassium carbonate (1.589 g) and 1-bromo-2-chloroethane (0.953 mL) under nitrogen. The resulting suspension was stirred at 83° C. for 10 h.

The reaction mixture was evaporated to dryness and diluted with water (300 mL), and extracted with DCM. The organic was dried (MgSO₄), filtered and evaporated to afford the subtitle compound as a foam (0.520 g)

MS: APCI (+ve) 454 (M+H)⁺..

b) 3-[3-({1-[2-(2-Chloroethoxy)phenyl]cyclopropyl}amino)-2-oxopyrazin-1(2H)-yl]-4-methylbenzoic acid The subtitle compound was prepared from methyl 3-[3-({1-[2-(2-chloroethoxy)phenyl]cyclopropyl}amino)-2-oxopyrazin-1(2H)-yl]-4-methylbenzoate (Example 317a) using a similar method to that described in Example 316c.

MS: APCI (+ve) 440 (M+H)$^+$.

$^1$H NMR δ (DMSO-d$_6$) 7.95 (dd, 1H), 7.86 (s, 1H), 7.66 (d, 1H), 7.55 (d, 1H), 7.29 (t, 1H), 7.05 (d, 1H), 6.99-6.94 (m, 2H), 6.86 (d, 1H), 4.35 (t, 2H), 4.07-4.00 (m, 2H), 1.99 (s, 3H), 1.18 (t, 4H).

c) 3-[3-({1-[2-(2-Chloroethoxy)phenyl]cyclopropyl}amino)-2-oxopyrazin-1(2H)-yl]-N-methoxy-4-methylbenzamide The subtitle compound was prepared from 3-[3-({1-[2-(2-chloroethoxy)phenyl]cyclopropyl}amino)-2-oxopyrazin-1(2H)-yl]-4-methylbenzoic acid (Example 317b) using a similar method to that described for Example 316d.

MS: APCI (+ve) 469 (M+H)$^+$.

d) N-Methoxy-4-methyl-3-{3-[(1-{2-[2-(methylamino)ethoxy]phenyl}cyclopropyl)amino]-2-oxopyrazin-1(2H)-yl}benzamide The title compound was prepared from 3-[3-({1-[2-(2-chloroethoxy)phenyl]cyclopropyl}amino)-2-oxopyrazin-1(2H)-yl]-4-methylbenzoic acid (Example 317c) using a similar method to that described for Example 316e.

MS: APCI (+ve) 464 (M+H)$^+$ $^1$H NMR δ (DMSO-d$_6$) 7.76 (d, 1H), 7.58 (s, 1H), 7.49 (d, 3H), 7.19 (t, 1H), 6.96 (d, 1H), 6.85-6.85 (m, 2H), 6.69 (d, 1H), 4.06 (t, 2H), 3.67 (s, 3H), 2.91 (t, 2H), 2.36 (s, 3H), 2.06 (s, 3H), 0.85 (d, 2H), 1.07 (s, 2H).

Example 318

N-cyclopropyl-5-{3-[(1-{2-[2-(ethylamino)ethoxy]phenyl}cyclopropyl)amino]-2-oxopyrazin-1(2H)-yl}-2-fluoro-4-methylbenzamide

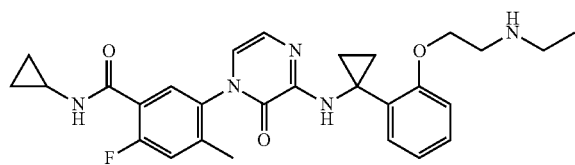

a) 5-Bromo-4-fluoro-2-methylaniline

A mixture of iron powder (4.30 g) and ammonium chloride (1.143 g) in water (23 mL) was heated under reflux at 100° C. for 30 minutes. To this hot mixture was added 1-bromo-2-fluoro-4-methyl-5-nitrobenzene (5.00 g) slowly and then the reaction mixture was heated under reflux at 100° C. overnight. The mixture was cooled to room temperature, filtered through a pad of celite, and extracted with ethyl acetate (3×50 mL). The organic solution was washed with water (3×100 mL) and brine (100 mL), dried (MgSO$_4$) and concentrated under reduced pressure to give the subtitle compound (3.59 g) as a solid.

$^1$H NMR δ (CDCl$_3$) 6.86-6.79 (m, 2H), 3.49 (s, 2H), 2.11 (s, 3H)

b) 2-(5-Bromo-4-fluoro-2-methylphenylamino)acetonitrile

Hunig's Base (6.15 mL) was added to 5-bromo-4-fluoro-2-methylaniline (Example 318a, 3.59 g) in THF (50 mL) at room temperature followed by bromoacetonitrile (2.451 mL). The reaction was heated to reflux overnight. The reaction was cooled to room temperature and concentrated. 2N HCl and DCM were added. The organic layer was separated and dried (MgSO$_4$) and concentrated to give the subtitle compound as a solid (6.61 g).

$^1$H NMR δ (CDCl$_3$) 6.92 (d, 1H), 6.80 (d, 1H), 4.13 (d, 2H), 3.78 (s, 1H), 2.13 (s, 3H).

c) [(5-Bromo-4-fluoro-2-methylphenyl)amino]acetonitrile

To a solution of 2-(5-bromo-4-fluoro-2-methylphenylamino)acetonitrile (Example 318b, 4.00 g) dissolved in ethyl acetate (12 mL) was added Hunig's Base (14.37 mL), methanol (4 mL) and PdCl$_2$(dppf) (0.351 g). The resulting mixture was stirred at 90° C. overnight under an atmosphere of carbon monoxide (5 bar). The cooled reaction mixture was evaporated to dryness and the residue passed through a pad of silica, eluting with 1:1 ethyl acetate:iso-hexane. The filtrate was evaporated in vacuo to give the subtitle compound as a solid (4.71 g).

$^1$H NMR δ (CDCl$_3$) 7.19 (d, 1H), 6.95 (d, 1H), 4.19 (d, 2H), 3.93 (s, 3H), 2.21 (s, 3H)

d) Methyl 5-(3,5-dibromo-2-oxopyrazin-1(2H)-yl)-2-fluoro-4-methylbenzoate

To a stirred solution of oxalyl bromide (5.97 mL) in DCM (88 mL) at 0° C. under nitrogen was added dropwise a solution of [(5-bromo-4-fluoro-2-methylphenyl)amino]acetonitrile (Example 318c, 4.71 g) in DCM (88 mL). The mixture was allowed to warm to room temperature and stirred for 30 min before addition of DMF (0.328 mL). The reaction mixture was then heated under reflux overnight. The reaction mixture was cooled to 0° C., water (100 mL) was added over 15 min (caution), then the organic layer (+2 further DCM extracts) was separated, dried (MgSO$_4$) and then poured onto a silica pad and eluted with DCM. The solvents were removed in vacuo to give the subtitle compound (4.96 g).

$^1$H NMR δ (DMSO-d$_6$) 8.09 (s, 1H), 8.00 (d, 1H), 7.48 (d, 1H), 3.86 (s, 3H), 2.18 (s, 3H)

e) Methyl 5-[3-({1-[2-(benzyloxy)phenyl]cyclopropyl}amino)-5-bromo-2-oxopyrazin-1(2H)-yl]-2-fluoro-4-methyl benzoate A solution of 1-(2-(benzyloxy)phenyl)cyclopropanamine (1.026 g) in dioxane (10 mL) was treated with methyl 5-(3,5-dibromo-2-oxopyrazin-1(2H)-yl)-2-fluoro-4-methylbenzoate (Example 318d, 1.500 g) and Hunig's Base (0.936 mL) under nitrogen. The resulting solution was stirred at 100° C. for 16 h. The cooled mixture was diluted with 2 M HCl and extracted with diethyl ether. The combined organics were dried (MgSO$_4$) and evaporated to afford the subtitle compound (2.310 g) as a foam MS: APCI (+ve) 580, 582 (M+H)$^+$.

¹H NMR δ (DMSO-d₆) 7.87-7.49 (m, 4H), 7.48-7.41 (m, 1H), 7.40-7.26 (m, 3H), 7.25-7.16 (m, 1H), 7.06-7.00 (m, 2H), 6.93-6.85 (m, 1H), 5.22 (s, 2H), 3.83 (s, 3H), 2.11 (s, 3H), 1.30-1.05 (m, 4H).

f) Methyl 2-fluoro-5-[3-{[1-(2-hydroxyphenyl)cyclopropyl]amino}-2-oxopyrazin-1(2H)-yl]-4-methylbenzoate To methyl 5-[3-({1-[2-(benzyloxy)phenyl]cyclopropyl}amino)-5-bromo-2-oxopyrazin-1(2H)-yl]-2-fluoro-4-methylbenzoate (Example 318e, 2.310 g) in ethanol (30 mL) was added ammonium formate (3.53 g) and Pd/C (0.042 g). The reaction was heated at 75° C. for 3 h. Hunig's Base (3 mL) was added, and the reaction was heated at 90° C. for 4 h. Additional catalyst, ammonium formate and hunigs base were added, and the reaction was heated at 90° C. for 4 h. The reaction mixture was then filtered warm, through a fibre glass filter, washing through with 500 mL ethanol, followed by 500 mL DCM, followed by 500 mL 10% methanol/DCM. The DCM and MeOH/DCM filtrates were combined, evaporated, and the resulting residue partitioned between DCM and water. The organic layer was separated, dried (MgSO₄), filtered, and evaporated to give the subtitle compound as a solid (1.063 g).

MS: APCI (+ve) 410 (M+H)⁺.

¹H NMR δ (CDCl₃) 11.29 (s, 1H), 7.77 (d, 1H), 7.39 (dd, 1H), 7.23-7.18 (m, 1H), 7.12 (d, 1H), 7.03 (s, 1H), 6.93-6.90 (m, 2H), 6.86 (td, 1H), 6.42 (d, 1H), 3.90 (s, 3H), 2.17 (s, 3H), 1.37-1.23 (m, 4H)

g) N-Cyclopropyl-2-fluoro-5-[3-{[1-(2-hydroxyphenyl)cyclopropyl]amino}-2-oxopyrazin-1(2H)-yl]-4-methylbenzamide Isopropylmagnesium chloride (5.19 mL of a 2.0 M solution in THF) was added over 20 min of a solution of cyclopropylamine (1.830 mL) and methyl 2-fluoro-5-[3-{[1-(2-hydroxyphenyl)cyclopropyl]amino}-2-oxopyrazin-1(2H)-yl]-4-methylbenzoate (Example 318f, 1.063 g) in THF (20 mL) stirring at room temperature under nitrogen. The reaction mixture was stirred for 1 h. Water and 2 M HCl were cautiously added and the volatiles removed in vacuo. The residue was basified with saturated aqueous sodium bicarbonate solution and extracted into DCM. The organics were combined, dried (MgSO₄) and evaporated to give the subtitle compound (1.189 g).

MS: APCI (+ve) 435 (M+H)⁺.

¹H NMR δ (CDCl₃) 11.35 (s, 1H), 7.92 (d, 1H), 7.41-7.36 (m, 1H), 7.24-7.17 (m, 1H), 7.08 (d, 1H), 7.03-7.01 (m, 1H), 6.94-6.92 (m, 1H), 6.92-6.89 (m, 1H), 6.89-6.82 (m, 1H), 6.79-6.72 (m, 1H), 6.43-6.41 (m, 1H), 2.97-2.86 (m, 1H), 2.18-2.14 (m, 3H), 1.41-1.23 (m, 4H), 0.92-0.83 (m, 2H), 0.65-0.57 (m, 2H).

h) 5-[3-({1-[2-(2-Chloroethoxy)phenyl]cyclopropyl}amino)-2-oxopyrazin-1(2H)-yl]-N-cyclopropyl-2-fluoro-4-methylbenzamide To a solution of N-cyclopropyl-2-fluoro-5-[3-{[1-(2-hydroxyphenyl)cyclopropyl]amino}-2-oxopyrazin-1(2H)-yl]-4-methylbenzamide (Example 318g, 1.189 g) in acetonitrile (30 mL) was added potassium carbonate (3.78 g) followed by 1-bromo-2-chloroethane (4.54 mL). The reaction was heated at 95° C. for 32 h under nitrogen. The reaction was cooled to room temperature, filtered through celite, and the cake washed with further acetonitrile. The filtrate was collected and the solvents removed in vacuo to give the subtitle compound (1.368 g).

MS: APCI (+ve) 497/498 (M+H)⁺.

¹H NMR δ (CDCl₃) 7.80 (d, 1H), 7.57 (dd, 1H), 6.98 (d, 1H), 6.87 (t, 1H), 6.84-6.82 (m, 1H), 6.74 (d, 1H), 6.69-6.63 (m, 1H), 6.23 (d, 1H), 4.25-4.20 (m, 2H), 3.84-3.80 (m, 2H), 2.86-2.80 (m, 1H), 2.08 (s, 3H), 1.23-1.16 (m, 3H), 1.10-1.06 (m, 1H), 0.83-0.76 (m, 2H), 0.56-0.50 (m, 2H).

i) N-Cyclopropyl-5-{3-[(1-{2-[2-(ethylamino)ethoxy]phenyl}cyclopropyl)amino]-2-oxopyrazin-1(2H)-yl}-2-fluoro-4-methylbenzamide A solution of ethylamine (2.012 mL of 2M in THF) and 5-[3-({1-[2-(2-chloroethoxy)phenyl]cyclopropyl}amino)-2-oxopyrazin-1(2H)-yl]-N-cyclopropyl-2-fluoro-4-methylbenzamide (Example 318h, 100 mg) in dioxane (3 mL) was heated for 24 h at 100° C. in a sealed tube. Further ethylamine (2.012 mL of a 2M solution in THF) was added and the reaction was heated for a further 24 h. Purification by preparative HPLC (Xbridge column eluting with a gradient of acetonitrile in 0.2% (v/v) aqueous ammonia) gave the title compound as a solid (10 mg).

MS: APCI (+ve) 506.2 (M+H)⁺.

¹H NMR δ (DMSO-d₆) 8.33 (s, 1H), 7.52-7.28 (m, 4H), 7.23-7.14 (m, 1H), 6.95 (d, 1H), 6.90-6.79 (m, 2H), 6.65 (s, 1H), 4.05 (s, 2H), 2.99-2.87 (m, 2H), 2.79 (s, 1H), 2.67-2.58 (m, 2H), 2.08-1.98 (m, 2H), 1.30-1.12 (m, 4H), 1.08-0.94 (m, 4H), 0.91-0.79 (m, 1H), 0.72-0.58 (m, 2H), 0.56-0.45 (m, 2H).

Example 319

N-Cyclopropyl-2-fluoro-4-methyl-5-{3-[(1-{2-[2-(methylamino)ethoxy]phenyl}cyclopropyl)amino]-2-oxopyrazin-1(2H)-yl}benzamide

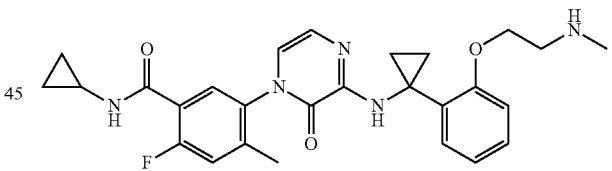

To a solution of 5-[3-({1-[2-(2-chloroethoxy)phenyl]cyclopropyl}amino)-2-oxopyrazin-1(2H)-yl]-N-cyclopropyl-2-fluoro-4-methylbenzamide (Example 318h, 100 mg) and methylamine, 40% by wt solution in water (0.1 mL) in dioxane (1 mL) was added potassium iodide (33.4 mg). The reaction mixture was stirred at room temperature overnight, then heated at 40° C. overnight. The reaction was heated at 50° C. for 48 h. Purification by preparative HPLC (Phenomenex Gemini, eluting with a gradient of acetonitrile in 0.2% (v/v) aqueous ammonia, followed by Xbridge column eluting with a gradient of acetonitrile in 0.2% (v/v) aqueous ammonia) gave the title compound as a solid (17 mg).

¹H NMR δ (DMSO-d₆) 8.34 (s, 1H), 7.51-7.41 (m, 3H), 7.33 (d, 1H), 7.19 (t, 1H), 6.95 (d, 1H), 6.88-6.81 (m, 2H), 6.64 (d, 1H), 4.09-4.00 (m, 2H), 2.94-2.85 (m, 2H), 2.83-2.75 (m, 1H), 2.35 (s, 3H), 2.03 (s, 3H), 1.24-1.00 (m, 4H), 0.71-0.61 (m, 2H), 0.55-0.48 (m, 2H)

MS: APCI (+ve) 492.2 (M+H)⁺..

Example 320

N-Cyclopropyl-3-fluoro-4-methyl-5-[3-{[1-methyl-1-(2-{[2-(methylamino)ethyl]sulfanyl}phenyl)ethyl]amino}-2-oxopyrazin-1(2H)-yl]benzamide

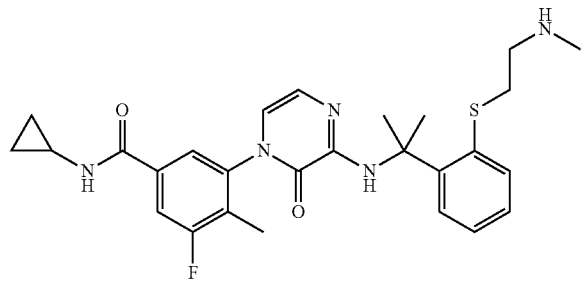

a) 2-(Benzyloxy)ethanethiol

Potassium carbonate (11.20 g) was added to S-2-(benzyloxy)ethyl ethanethioate (8.52 g) in methanol (170 mL)/water (85 mL) and the reaction was stirred for 20 min. Water was added and the mixture extracted with ethyl acetate. The organic layers were combined, washed with aqueous ammonium chloride and dried (MgSO$_4$) and concentrated in vacuo to give the subtitle compound (6.64 g).

$^1$H NMR δ (CDCl$_3$) 7.33-7.24 (m, 5H), 4.54 (s, 2H), 3.61 (q, 2H), 2.72 (q, 2H), 1.59 (t, 1H)

b) 2-{[2-(Benzyloxy)ethyl]sulfanyl}benzonitrile

A solution of 2-nitrobenzonitrile (5.85 g) in DMF (20 mL) was treated with 2-(benzyloxy)ethanethiol (Example 320a, 6.64 g) and a solution of potassium hydroxide (3.76 g) in water (5 mL) was added dropwise under nitrogen. The resulting mixture was stirred at 0° C. for 2 h. The reaction was quenched with water and extracted into ethyl acetate. The combined organics were washed with brine, dried (MgSO$_4$), and concentrated in vacuo. The residue was purified (SiO$_2$ chromatography eluting with 50% diethyl ether in iso-hexane) to afford the subtitle compound as a solid (7.08 g).

$^1$H NMR δ (CDCl$_3$) 7.60 (d, 1H), 7.46 (d, 2H), 7.32-7.23 (m, 6H), 4.54-4.53 (m, 2H), 3.72 (t, 2H), 3.24 (t, 2H)

c) 2-(2-{[2-(Benzyloxy)ethyl]sulfanyl}phenyl)propan-2-amine

A suspension of cerium (III) chloride (9.15 g) dissolved in THF (40 mL) was stirred at 50° C. for 3 h under nitrogen. The resulting suspension was cooled and 2-{[2-(benzyloxy)ethyl]sulfanyl}benzonitrile (Example 320b, 5 g) was added. The mixture was cooled to −10° C. before adding methyllithium (1.5M solution as complex with lithium bromide, 30.9 mL). The mixture was kept at −10° C. for 30 min before quenching with 880 ammonia (10 mL). The mixture was stirred at room temperature for 1 h then the solid was filtered off and discarded. The filtrate was diluted with water and extracted with ethyl acetate. The organic layer was dried (MgSO$_4$), filtered and evaporated to afford the crude product. The crude product was diluted with 2M aqueous HCl, extracted with diethyl ether (discarded). The aqueous layer was basified with 880 ammonia, extracted with ethyl acetate. The organic layer was dried (MgSO$_4$), filtered and evaporated to afford the subtitle compound as an oil (3.20 g).

$^1$H NMR δ (CDCl$_3$) 7.47-7.43 (m, 2H), 7.30-7.26 (m, 5H), 7.15 (t, 2H), 4.52 (s, 2H), 3.69 (t, 2H), 3.22 (t, 2H), 2.17 (s, 2H), 1.63 (s, 6H)

d) Methyl 3-[3-{[1-(2-{[2-(benzyloxy)ethyl]sulfanyl}phenyl)-1-methylethyl]amino}-5-bromo-2-oxopyrazin-1(2H)-yl]-5-fluoro-4-methyl benzoate The subtitle compound was prepared using a similar method to Example 252h from methyl 3-(3,5-dibromo-2-oxopyrazin-1(2H)-yl)-5-fluoro-4-methylbenzoate (Example 252g) and 2-(2-{[2-(benzyloxy)ethyl]sulfanyl}phenyl)propan-2-amine (Example 320c).

MS: APCI (−ve) 639 (M−H)$^-$.

e) 3-[3-{[1-(2-{[2-(Benzyloxy)ethyl]sulfanyl}phenyl)-1-methylethyl]amino}-5-bromo-2-oxopyrazin-1(2H)-yl]-N-cyclopropyl-5-fluoro-4-methylbenzamide The subtitle compound was prepared from methyl 3-[3-{[1-(2-{[2-(benzyloxy)ethyl]sulfanyl}phenyl)-1-methylethyl]amino}-5-bromo-2-oxopyrazin-1(2H)-yl]-5-fluoro-4-methylbenzoate (Example 320d) using a similar method to that described for Example 252i. The crude product was triturated in diethyl ether and the solid filtered off to give the substitle product (2.22 g) The filtrate was concentrated in vacuo then purified (SiO$_2$ chromatography eluting with 100% diethyl ether to 100% ethyl acetate). The product containing fractions were combined and concentrated in vacuo to yield further subtitle compound (1.7 g) as a solid.

MS: APCI (+ve) 665 (M+H)$^+$.

f) 3-[3-{[1-(2-{[2-(Benzyloxy)ethyl]sulfanyl}phenyl)-1-methylethyl]amino}-2-oxopyrazin-1(2H)-yl]-N-cyclopropyl-5-fluoro-4-methyl benzamide To 3-[3-{[1-(2-{[2-(Benzyloxy)ethyl]sulfanyl}phenyl)-1-methylethyl]amino}-5-bromo-2-oxopyrazin-1(2H)-yl]-N-cyclopropyl-5-fluoro-4-methylbenzamide (Example 320e, 1.7 g) in ethanol (35 mL) was added ammonium formate (2.255 g) and Pd/C (0.544 g) and the resulting solution heated at 75° C. for 1 h. After cooling to room temperature, type 490 paste 10% Pd/C (0.272 g) slurried in ethanol (5 mL) was added and the reaction heated to 75° C. for 1 hr. The reaction was filtered through celite then the filtrate concentrated in vacuo then extracted into DCM. The organic solution was dried (MgSO$_4$) and concentrated in vacuo to give the sub title compound (1.290 g).

MS: APCI (+ve) 587 (M+H)$^+$.

g) N-Cyclopropyl-3-fluoro-5-{3-[(1-{2-[(2-hydroxyethyl)sulfanyl]phenyl}-1-methylethyl)amino]-2-oxopyrazin-1(2H)-yl}-4-methylbenzamide 3-[3-{[1-(2-{[2-(Benzyloxy)ethyl]sulfanyl}phenyl)-1-methylethyl]amino}-2-oxopyrazin-1(2H)-yl]-N-cyclopropyl-5-fluoro-4-methylbenzamide (Example 320f, 1.2 g) was stirred in DCM (120 mL) and cooled to 0° C. Boron tribromide (0.387 mL of a 1M solution in DCM) was added dropwise at 0° C. and the reaction stirred for 30 min at 0° C. A further 4 eq of boron tribromide solution was added after 1 h and the reaction warmed to room temperature. The reaction mixture was diluted with ice water, and extracted with ethyl acetate. The organic layers were combined and dried (MgSO$_4$), filtered and evaporated in vacuo to afford the crude product. The crude product was purified (SiO2 chromatography eluting with 100% diethyl ether to 100% ethyl acetate) to afford the subtitle compound as a solid (0.6 g).

MS: APCI (+ve) 497 (M+H)$^+$.

h) N-Cyclopropyl-3-fluoro-4-methyl-5-[3-{[1-methyl-1-(2-{[2-(methylamino)ethyl]sulfanyl}phenyl)ethyl]amino}-2-oxopyrazin-1(2H)-yl]benzamide N-Cyclopropyl-3-fluoro-5-{3-[(1-{2-[(2-hydroxyethyl)sulfanyl]phenyl}-1-methylethyl)amino]-2-oxopyrazin-1(2H)-yl}-4-methylbenzamide (Example 320g, 0.15 g) was stirred in DCM (20 mL) and cooled to −40° C. before triethylamine (0.046 mL) and methanesulfonyl chloride (0.024 mL) were added. The reaction was warmed to room temperature and methylamine (40% in water) and ethanol (5 mL) were added. The reaction was then stirred for 18 h at 100° C. The reaction was concentrated in vacuo, then purified on SCX resin eluting with methanol (discarded) and flushing with 20% ammonia in methanol. The crude product was purified by preparative HPLC (Phenomenex Gemini column, eluent: 95-5% gradient of aqueous 0.2% aqueous ammonia in acetonitrile). The fractions containing the desired compound were evaporated to dryness to afford the title compound as a solid (3 mg).

$^1$H NMR δ (DMSO-d$_6$) 8.54 (s, 1H), 7.75 (d, 1H), 7.63 (s, 1H), 7.45 (d, 1H), 7.31 (d, 1H), 7.17 (s, 2H), 6.86 (s, 1H), 6.59 (d, 2H), 2.97 (s, 2H), 2.85 (s, 1H), 2.61 (s, 2H), 2.23 (s, 3H), 2.00 (s, 3H), 1.84 (d, 6H), 0.63 (d, 4H)

MS: APCI (+ve) 510 (M+H)$^+$.

Example 321

3-{3-[(1-{2-[(2-Aminoethyl)sulfanyl]phenyl}-1-methylethyl)amino]-2-oxopyrazin-1(2H)-yl}-N-cyclopropyl-5-fluoro-4-methylbenzamide

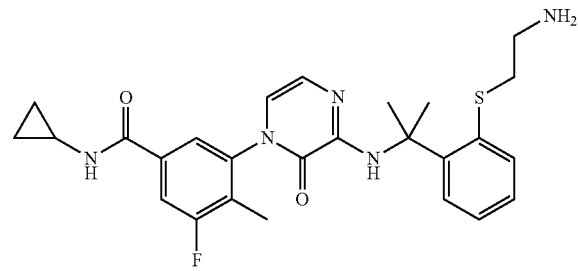

a) 3-{3-[(1-{2-[(2-chloroethyl)sulfanyl]phenyl}-1-methylethyl)amino]-2-oxopyrazin-1(2H)-yl}-N-cyclopropyl-5-fluoro-4-methylbenzamide A solution of N-cyclopropyl-3-fluoro-5-{3-[(1-{2-[(2-hydroxyethyl)sulfanyl]phenyl}-1-methylethyl)amino]-2-oxopyrazin-1(2H)-yl}-4-methylbenzamide (Example 320g, 0.15 g) dissolved in acetonitrile (2 mL) was treated with triethylamine (0.048 mL) and triethylamine hydrochloride (4.16 mg) under nitrogen. The resulting solution was stirred at 0° C. before adding p-toluenesulfonyl chloride (0.055 g) over 5 min. Lithium chloride (0.064 g) was then added and the mixture was stirred at room temperature for 16 h. The reaction mixture was diluted with water (200 mL), and extracted with DCM (200 mL). The organic layer was separated, dried (MgSO$_4$) and evaporated to afford the subtitle compound (0.14 g).

MS: APCI (+ve) 516 (M+H)$^+$.

b) 3-{3-[(1-{2-[(2-Aminoethyl)sulfanyl]phenyl}-1-methylethyl)amino]-2-oxopyrazin-1(2H)-yl}-N-cyclopropyl-5-fluoro-4-methylbenzamide The title compound was prepared from 3-{3-[(1-{2-[(2-chloroethyl)sulfanyl]phenyl}-1-methylethyl)amino]-2-oxopyrazin-1(2H)-yl}-N-cyclopropyl-5-fluoro-4-methylbenzamide (Example 320a) using a similar method to that described for Example 252l.

MS: APCI (+ve) 496 (M+H)$^+$.

$^1$H NMR δ (DMSO-d$_6$) 8.54 (d, 1H), 7.75 (d, 1H), 7.62 (s, 1H), 7.45 (dd, 1H), 7.32-7.29 (m, 1H), 7.19-7.14 (m, 2H), 6.86 (s, 1H), 6.59 (dd, 2H), 2.91 (t, 2H), 2.87-2.84 (m, 1H), 2.63 (t, 2H), 2.00 (d, 3H), 1.84 (d, 6H), 1.54 (s, 1H), 0.70 (q, 2H), 0.56 (q, 2H)

Example 322

N-Cyclopropyl-3-fluoro-5-[3-({1-[2-({2-[(2-hydroxyethyl)amino]ethyl}sulfanyl)phenyl]-1-methylethyl}amino)-2-oxopyrazin-1(2H)-yl]-4-methylbenzamide

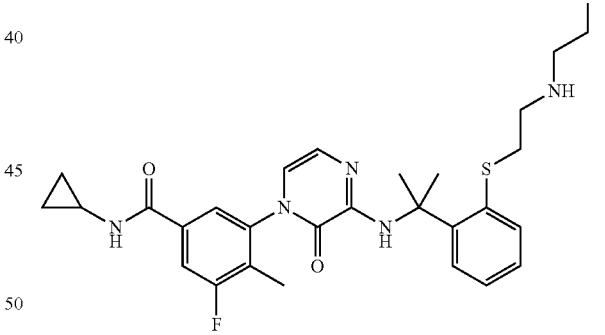

The title compound was prepared from ethanolamine and 3-{3-[(1-{2-[(2-chloroethyl)sulfanyl]phenyl}-1-methylethyl)amino]-2-oxopyrazin-1(2H)-yl}-N-cyclopropyl-5-fluoro-4-methylbenzamide (Example 321a) using a similar method to that described for Example 252l. The crude product was purified by preparative HPLC (X-Bridge column eluting with 95-5% gradient of aqueous 0.2% ammonia in acetonitrile) to give the title compound as a solid.

MS: APCI (+ve) 540 (M+H)$^+$.

$^1$H NMR δ (DMSO-d$_6$) 8.54 (d, 1H), 7.75 (d, 1H), 7.64 (s, 1H), 7.45 (d, 1H), 7.32 (d, 1H), 7.21-7.13 (m, 2H), 6.84 (s, 1H), 6.59 (dd, 2H), 4.42 (t, 1H), 3.39 (q, 2H), 2.98 (t, 2H), 2.85 (dq, 1H), 2.67 (t, 2H), 2.55 (d, 2H), 2.00 (s, 3H), 1.84 (d, 6H), 0.70 (q, 2H), 0.56 (q, 2H)

Example 323

N-Cyclopropyl-3-fluoro-4-methyl-5-{3-[(1-methyl-1-{2-[3-(methylamino)propyl]phenyl}ethyl)amino]-2-oxopyrazin-1(2H)-yl}benzamide

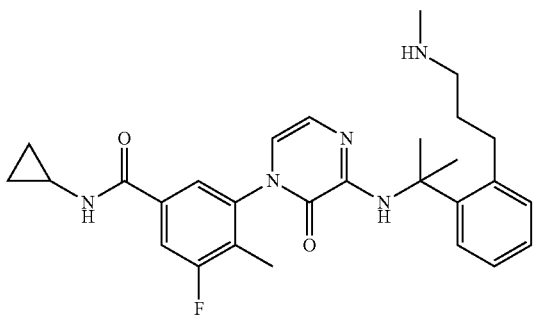

a) (Z)-3-(2-Cyanophenyl)acrylic acid

A solution of 1-nitrosonaphthalen-2-ol (5 g) dissolved in THF (30 mL) was treated with p-toluenesulfonyl chloride (6.61 g) under nitrogen. The resulting mixture was stirred at 20° C. for 1 h. The mixture was treated with a solution of sodium hydroxide (4.04 g) in water (30 mL) dropwise over 30 min to keep temperature below 25° C. The reaction mixture was diluted with water (200 mL), and extracted with diethyl ether (200 mL) (discarded). The aqueous layer was acidified with 2M HCl, extracted with ethyl acetate (200 mL), dried (MgSO$_4$), filtered and evaporated. The residue was triturated with 50% diethyl ether in isohexane to give the subtitle compound as a solid (4.75 g).

$^1$H NMR δ (DMSO-d$_6$) 12.87 (s, 1H), 7.90-7.47 (m, 4H), 7.19 (d, J=79.0 Hz, 1H), 6.24 (d, J=79.0 Hz, 1H).

b) 3-(2-Cyanophenyl)propanoic acid

A slurry of (Z)-3-(2-cyanophenyl)acrylic acid (Example 323a, 4.75 g) in ethanol (50 mL) was added to 5% Palladium (0.292 g) in ethanol (50 mL) and hydrogenated under 2.0 bar hydrogen pressure for 2 h. The reaction mixture was filtered and the filtrate evaporated to dryness to afford the sub title compound as a solid (4.36 g).

$^1$H NMR δ (DMSO-d$_6$) 7.78 (d, 1H), 7.68-7.62 (m, 1H), 7.50 (d, 1H), 7.44-7.38 (m, 1H), 3.02 (t, 2H), 2.62 (t, 2H)

c) 2-(3-hydroxypropyl)benzonitrile

A solution of 3-(2-cyanophenyl)propanoic acid (Example 323b, 4.36 g) in DCM (40 mL) was treated with oxalyl chloride (3.26 mL) under nitrogen. The resulting solution was stirred at 20° C. for 1 h. The reaction mixture was evaporated to dryness, azeotroped with toluene. The solid was dissolved in THF (30 mL) and sodium borohydride (1.883 g) was added. The mixture was stirred at 20° C. for 16 h. Further Sodium borohydride (1.883 g) added and stirred for 4 h. The reaction required a further 3 days and a further sodium borohydride (18.83 g). The reaction mixture was evaporated, diluted with water (200 mL), and extracted with ethyl acetate (200 mL). The organic was dried (MgSO$_4$), filtered and evaporated to give the subtitle compound as an oil (3.83 g).

$^1$H NMR δ (DMSO-d$_6$) 7.78 (d, 1H), 7.68-7.62 (m, 1H), 7.50 (d, 1H), 7.44-7.38 (m, 1H), 3.02 (t, 2H), 2.62 (t, 2H)

d) 2-(3-(Benzyloxy)propyl)benzonitrile

A solution of 2-(3-hydroxypropyl)benzonitrile (Example 323c, 3.83 g) in DMF (40 mL) under nitrogen was treated with 60% Sodium hydride (1.140 g) and stirred at room temperature for 1 h before adding benzyl bromide (2.83 mL). The resulting solution was stirred at 20° C. for 60 h. The reaction mixture was diluted with water (200 mL), and extracted with ethyl acetate (200 mL). The organic was dried (MgSO$_4$), filtered and evaporated. The residue was purified (SiO$_2$ chromatography eluting with 30% diethyl ether in isohexane). Pure fractions were evaporated to dryness to afford the subtitle compound as an oil (2.3 g).

$^1$H NMR δ (CDCl$_3$) 7.60 (d, 1H), 7.51-7.45 (m, 1H), 7.39-7.33 (m, 3H), 7.32-7.25 (m, 4H), 4.53 (s, 2H), 3.52 (t, 2H), 2.97 (t, 2H), 2.03-1.96 (m, 2H)

e) 2-{2-[3-(Benzyloxy)propyl]phenyl}propan-2-amine

A suspension of Cerium(III) chloride (4.51 g) dissolved in THF (20 mL) was stirred at 50° C. for 3 h under nitrogen. The resulting suspension was cooled and 2-(3-(benzyloxy)propyl)benzonitrile (Example 323d, 2.3 g) added. The mixture was cooled to −10° C. before adding a 1.5 M Methyllithium as complex with lithium bromide (15.25 mL). The mixture was kept at −10° C. for 30 min before quenching with 880 ammonia (10 mL). The mixture was stirred at room temperature for 1 h before filtering off the solids (discarded). The filtrate was diluted with water (100 mL), and extracted with ethyl acetate (200 mL). The organic was dried (MgSO$_4$), filtered and evaporated to afford the subtitle compound as an oil (2.05 g).

$^1$H NMR δ (CDCl$_3$) 7.48 (d, 1H), 7.40-7.07 (m, 8H), 4.57 (s, 2H), 3.59 (t, 2H), 3.16-3.04 (m, 2H), 2.04-1.92 (m, 2H), 1.83-1.63 (m, 2H), 1.62 (s, 6H).

f) Methyl 3-{3-[(1-{2-[3-(benzyloxy)propyl]phenyl}-1-methylethyl)amino]-5-bromo-2-oxopyrazin-1(2H)-yl}-5-fluoro-4-methyl benzoate The subtitle compound was prepared using a similar method to Example 252h from methyl 3-(3,5-dibromo-2-oxopyrazin-1(2H)-yl)-5-fluoro-4-methylbenzoate (Example 252g) and 2-(2-(3-(benzyloxy)propyl)phenyl)propan-2-amine (Example 323e).

MS: APCI (+ve) 622 (M+H)$^+$.

g) 3-{3-[(1-{2-[3-(Benzyloxy)propyl]phenyl}-1-methylethyl)amino]-5-bromo-2-oxopyrazin-1(2H)-yl}-N-cyclopropyl-5-fluoro-4-methylbenzamide The subtitle compound was prepared using a similar method to Example 252i from methyl 3-{3-[(1-{2-[3-(benzyloxy)propyl]phenyl}-1-methylethyl)amino]-5-bromo-2-oxopyrazin-1(2H)-yl}-5-fluoro-4-methylbenzoate (Example 323f).

$^1$H NMR δ (CDCl$_3$) 7.59-7.44 (m, 2H), 7.39-7.15 (m, 10H), 6.80 (s, 1H), 6.29 (s, 1H), 4.52 (s, 2H), 3.56-3.44 (m, 2H), 2.97-2.78 (m, 3H), 2.08 (s, 3H), 1.98-1.81 (m, 8H), 0.90-0.78 (m, 2H), 0.64-0.51 (m, 2H)

h) N-Cyclopropyl-3-fluoro-5-[3-({1-[2-(3-hydroxypropyl)phenyl]-1-methylethyl}amino)-2-oxopyrazin-1(2H)-yl]-4-methyl benzamide The subtitle compound was prepared using a similar method to Example 252j from 3-{3-[(1-{2-[3-(benzyloxy) propyl]phenyl}-1-methylethyl)amino]-5-bromo-2-oxopyrazin-1(2H)-yl}-N-cyclopropyl-5-fluoro-4-methylbenzamide (Example 323g).
MS: APCI (+ve) 479 (M+H)$^+$.

i) 3-[3-({1-[2-(3-Bromopropyl)phenyl]-1-methylethyl}amino)-2-oxopyrazin-1(2H)-yl]-N-cyclopropyl-5-fluoro-4-methylbenzamide A solution of N-cyclopropyl-3-fluoro-5-[3-({1-[2-(3-hydroxypropyl)phenyl]-1-methylethyl}amino)-2-oxopyrazin-1(2H)-yl]-4-methylbenzamide (Example 323h) (0.4 g) dissolved in THF (10 mL) was treated with carbon tetrabromide (0.277 g) under nitrogen. The resulting mixture was cooled to 0° C. before adding triphenylphosphine (0.219 g). The reaction mixture was stirred at room temperature for 16 h. The reaction mixture was evaporated and the residue purified (SiO$_2$ chromatography eluting with 50% DCM in ethyl acetate) to give the subtitle compound as a solid (0.135 g).
$^1$H NMR δ (CDCl$_3$) 7.65-7.56 (m, 1H), 7.55-7.46 (m, 1H), 7.43-7.34 (m, 1H), 7.26-7.17 (m, 4H), 6.80-6.71 (m, 1H), 6.64-6.55 (m, 1H), 3.38 (t, 2H), 3.08-2.82 (m, 3H), 2.14 (s, 3H), 1.91 (d, 6H), 1.29-1.18 (m, 2H), 0.91-0.81 (m, 2H), 0.66-0.55 (m, 2H)

j) N-Cyclopropyl-3-fluoro-4-methyl-5-{3-[(1-methyl-1-{2-[3-(methylamino)propyl]phenyl}ethyl) amino]-2-oxopyrazin-1(2H)-yl}benzamide The title compound was prepared from 3-[3-({1-[2-(3-bromopropyl)phenyl]-1-methylethyl}amino)-2-oxopyrazin-1 (2H)-yl]-N-cyclopropyl-5-fluoro-4-methylbenzamide (Example 323g) using a similar method to that described for Example 259e.
MS: APCI (+ve) 492.4 (M+H)$^+$.
$^1$H NMR δ (DMSO-d$_6$) 8.65-8.55 (m, 1H), 7.82 (d, 1H), 7.74 (s, 1H), 7.51-7.41 (m, 1H), 7.25-7.14 (m, 3H), 7.10-6.99 (m, 1H), 6.76-6.65 (m, 2H), 2.98-2.79 (m, 3H), 2.51-2.39 (m, 2H), 2.31 (s, 3H), 2.10 (s, 3H), 1.91-1.79 (m, 6H), 1.59-1.47 (m, 2H), 0.81-0.69 (m, 2H), 0.67-0.55 (m, 2H).

Example 324

N-Cyclopropyl-4-methyl-3-[3-(2-{2-[3-(methylamino)propoxy]phenyl}pyrrolidin-1-yl)-2-oxopyrazin-1(2H)-yl]benzamide

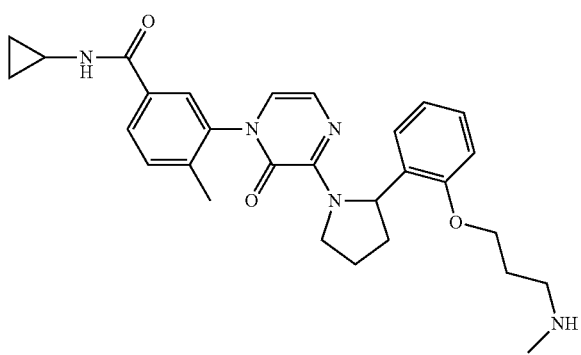

a) N-Cyclopropyl-3-{3-[2-(2-hydroxyphenyl)pyrrolidin-1-yl]-2-oxo-3,4-dihydropyrazin-1(2H)-yl}-4-methyl benzamide To N-cyclopropyl-3-(3-(2-(2-methoxyphenyl)pyrrolidin-1-yl)-2-oxopyrazin-1(2H)-yl)-4-methylbenzamide (Example 97, 0.993 g) in DCM (10 mL) was added boron tribromide (4.47 mL of a 1M solution in DCM) at 0° C. and the reaction stirred for 3 h. Further Boron tribromide (4.47 mL of a 1M solution in DCM) was added and the reaction stirred for 3 h. Ice was added followed by water and the aqueous layer extracted with DCM then EtOAc. The aqueous layer was neutralised to pH 7 and extracted with DCM then EtOAc and all the combined organics dried (Na$_2$SO$_4$) and the solvent removed to give the subtitle compound as a solid (0.786 g).
MS: APCI (+ve) 432 (M+H)$^+$.

b) 3-[3-{2-[2-(3-Chloropropoxy)phenyl]pyrrolidin-1-yl}-2-oxopyrazin-1(2H)-yl]-N-cyclopropyl-4-methylbenzamide A solution of N-cyclopropyl-3-{3-[2-(2-hydroxyphenyl) pyrrolidin-1-yl]-2-oxo-3,4-dihydropyrazin-1(2H)-yl}-4-methylbenzamide (Example 324a, 0.2 g) in acetonitrile (5 mL) was treated with potassium carbonate (0.642 g) and 1-bromo-3-chloropropane (0.459 mL) under nitrogen. The resulting suspension was stirred at 83° C. for 10 h. The reaction mixture was diluted with water and extracted with ethyl acetate. The organic layer was dried (MgSO$_4$), filtered and evaporated to give the subtitle compound (0.23 g).
MS: APCI (+ve) 507 (M+H)$^+$.

c) N-Cyclopropyl-4-methyl-3-[3-(2-{2-[3-(methylamino)propoxy]phenyl}pyrrolidin-1-yl)-2-oxopyrazin-1(2H)-yl]benzamide 3-[3-{2-[2-(3-Chloropropoxy)phenyl]pyrrolidin-1-yl}-2-oxopyrazin-1(2H)-yl]-N-cyclopropyl-4-methylbenzamide (Example 324b, 0.23 g) and methylamine (1 mL) were heated in a CEM microwave in dioxane at 110° C. for 15 min. The resulting solution was concentrated in vacuo and purification by preparative HPLC (X-Bridge column using a 95-5% gradient of aqueous 0.2% ammonia in acetonitrile) gave the title compound as a solid (0.028 g).
MS: APCI (+ve) 502 (M+H)$^+$.
$^1$H NMR δ (DMSO-d$_6$) 8.14 (s, 1H), 7.77 (d, 1H), 7.65-7.56 (m, 1H), 7.42-7.31 (m, 1H), 7.10 (t, 1H), 6.92-6.77 (m, 4H), 6.57-6.57 (m, 1H), 5.97-5.94 (m, 1H), 4.13-4.03 (m, 3H), 3.93-3.77 (m, 1H), 3.01 (s, 4H), 2.87-2.81 (m, 1H), 2.65 (t, 2H), 2.28 (s, 3H), 2.09 (s, 1H), 1.88-1.79 (m, 5H), 0.70-0.64 (m, 2H), 0.58-0.53 (m, 2H)

Example 325 and Example 326

(R)—N-Cyclopropyl-4-methyl-3-(3-(2-(2-(3-(methylamino)propoxy)phenyl)pyrrolidin-1-yl)-2-oxopyrazin-1(2H)-yl)benzamide and (S)—N-Cyclopropyl-4-methyl-3-(3-(2-(2-(3-(methylamino)propoxy) phenyl)pyrrolidin-1-yl)-2-oxopyrazin-1(2H)-yl) benzamide The racemic mixture from Example 324 was purified by chiral HPLC (Chirobiotic V column, eluting 80:20 0.1% triethylamine in MeOH:0.1% acetic acid in methanol) to give the two unassigned single enantiomers.
Isomer 1:
MS: APCI (+ve) 502.2 (M+H)$^+$.

Chiral Purity 95.5% @ 220 nM by HPLC and

Isomer 2

MS: APCI (+ve) 502.2 (M+H)⁺.

Chiral Purity 97.1% @ 220 nM by HPLC

Example 327

N-Cyclopropyl-4-methyl-3-[3-(2-{2-[2-(methylamino)ethoxy]phenyl}pyrrolidin-1-yl)-2-oxopyrazin-1(2H)-yl]benzamide Trifluoroacetate salt

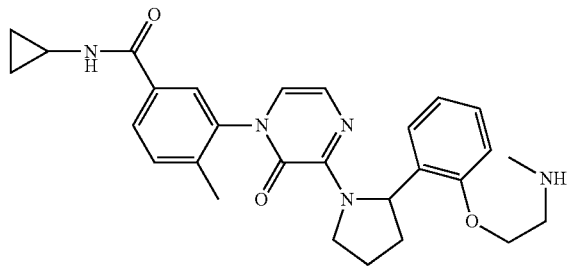

a) Benzyl 2-(2-(1-(4-(5-(cyclopropylcarbamoyl)-2-methylphenyl)-3-oxo-3,4-dihydropyrazin-2-yl)pyrrolidin-2-yl)phenoxy)ethyl(methyl)carbamate Cesium carbonate (0.274 g) was added to a solution of N-cyclopropyl-3-{3-[2-(2-hydroxyphenyl)pyrrolidin-1-yl]-2-oxo-3,4-dihydropyrazin-1(2H)-yl}-4-methylbenzamide (Example 324a, 0.18 g) and benzyl 2-chloroethyl(methyl)carbamate (0.096 g) in acetonitrile (4 mL), and the reaction was heated at 90° C. for 72 h. DCM and water were added, and the organic layer was separated, dried (Na₂SO₄) and the solvent removed in vacuo. Purification (SiO₂ chromatography eluting with 30-50% EtOAc in DCM) gave the subtitle compound as an oil (0.122 g).

MS: APCI (+ve) 622 (M+H)⁺.

b) N-Cyclopropyl-4-methyl-3-[3-(2-{2-[2-(methylamino)ethoxy]phenyl}pyrrolidin-1-yl)-2-oxopyrazin-1(2H)-yl]benzamide Trifluoroacetate Salt A solution of benzyl 2-(2-(1-(4-(5-(cyclopropylcarbamoyl)-2-methylphenyl)-3-oxo-3,4-dihydropyrazin-2-yl)pyrrolidin-2-yl)phenoxy)ethyl(methyl)carbamate (Example 327a, 0.122 g) in ethanol (10 mL) was pumped through a Pd/C cartridge at 2 ml/min under max Hydrogen at 40° C. on an H cube hydrogenator. The solvents were evaporated. Purification by preparative HPLC (Xbridge column, eluting with a gradient of acetonitrile in 0.2% (v/v) aqueous TFA) gave the title product as a solid (45 mg).

MS: APCI (+ve) 488 (M+H)⁺.

¹H NMR δ (CD₃OD) 7.78 (dt, 1H), 7.70-7.38 (m, 1H), 7.34 (d, 1H), 7.28-7.18 (m, 1H), 7.03-6.90 (m, 4H), 6.67-6.63 (m, 1H), 6.36-6.28 (m, 1H), 4.49-4.27 (m, 2H), 4.24-4.07 (m, 1H), 3.97-3.79 (m, 1H), 3.44-3.33 (m, 2H), 2.90-2.79 (m, 1H), 2.55-2.37 (m, 4H), 2.22-1.54 (m, 6H), 0.85-0.75 (m, 2H), 0.66-0.56 (m, 2H).

Example 328

N-Cyclopropyl-3-fluoro-4-methyl-5-[3-{[(1R,2S)-2-methyl-1-phenyl-3-pyrrolidin-1-ylpropyl]amino}-2-oxopyrazin-1(2H)-yl]benzamide

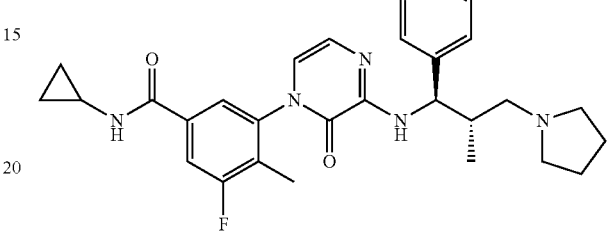

a) (2R,3R)-3-Amino-2-methyl-3-phenylpropan-1-ol

N-[(1R,2R)-3-{[tert-butyl(diphenyl)silyl]oxy}-2-methyl-1-phenylpropyl]-2-methylpropane-2-sulfinamide (Example 136b, 1.46 g) was stirred in methanol (10 mL) and then Hydrogen chloride (4M in dioxane) (10 mL) added. The reaction was stirred at 70° C. for 7 h and then concentrated in vacuo. The crude product was azeotroped with toluene then triturated in ether for 2 days after which the solvent was concentrated in vacuo to give the subtitle compound (0.47 g).

¹H NMR δ (DMSO-d₆) 8.51 (s, 2H), 7.71-7.67 (m, 1H), 7.49-7.35 (m, 4H), 4.18-4.14 (m, 1H), 3.24-3.07 (m, 2H), 2.14-2.10 (m, 1H), 0.97 (s, 3H)

b) Methyl 3-[5-bromo-3-{[(1R,2R)-3-hydroxy-2-methyl-1-phenylpropyl]amino}-2-oxopyrazin-1(2H)-yl]-5-fluoro-4-methylbenzoate To methyl 3-(3,5-dibromo-2-oxopyrazin-1(2H)-yl)-5-fluoro-4-methylbenzoate (Example 252g, 0.9 g) in THF (3 mL) was added (2R,3R)-3-amino-2-methyl-3-phenylpropan-1-ol (Example 328a, 0.389 g) and Hunig's Base (0.374 mL) and the reaction stirred at 50° C. for 8 h. The reaction mixture was diluted with ethyl acetate and washed with aqueous NaHCO₃. The organics were dried (MgSO₄) and concentrated in vacuo to leave the crude product which was triturated overnight in 2:1 isohexane/diethyl ether to give the subtitle compound. Purification of the filtrate (SiO₂ chromatography eluting with 50-100% diethyl ether in isohexane) to give further subtitle compound (total 0.820 g).

MS: APCI (+ve) 506 (M+H)⁺.

c) Methyl 3-[5-bromo-3-{[(1R,2R)-3-hydroxy-2-methyl-1-phenylpropyl]amino}-2-oxopyrazin-1(2H)-yl]-5-fluoro-4-methylbenzoate The subtitle compound was prepared from methyl 3-(5-bromo-3-((1R,2R)-3-hydroxy-2-methyl-1-phenylpropylamino)-2-oxopyrazin-1(2H)-yl)-5-fluoro-4-methylbenzoate (Example 259b) using a similar method to that described in Example 259b MS: APCI (+ve) 426 (M+H)⁺..

d) N-Cyclopropyl-3-fluoro-5-[3-{[(1R,2R)-3-hydroxy-2-methyl-1-phenylpropyl]amino}-2-oxopyrazin-1(2H)-yl]-4-methylbenzamide The subtitle compound was prepared from methyl 3-fluoro-5-[3-{[(1R,2R)-3-hydroxy-2-methyl-1-phenylpropyl]amino}-2-oxopyrazin-1(2H)-yl]-4-methylbenzoate (Example 328c) using a similar method to that described for Example 252i.

MS: APCI (+ve) 451 (M+H)$^+$.

e) N-cyclopropyl-3-fluoro-4-methyl-5-[3-{[(1R,2R)-2-methyl-3-oxo-1-phenylpropyl]amino}-2-oxopyrazin-1(2H)-yl]benzamide A solution of Dess-Martin Periodinane (0.911 g) in DCM (8 mL) was added dropwise to a solution of N-cyclopropyl-3-fluoro-5-[3-{[(1R,2R)-3-hydroxy-2-methyl-1-phenylpropyl]amino}-2-oxopyrazin-1(2H)-yl]-4-methylbenzamide (Example 328d, 0.64 g) in DCM (8 mL) at 22° C. The resulting mixture was stirred at 22° C. for 30 min. The reaction mixture was quenched with sat. aqueous $Na_2S_2O_3$ and sat. aqeuous $NaHCO_3$ and stirred for a further 15 min and then extracted into DCM. The organic extracts were combined, dried ($MgSO_4$) and concentrated in vacuo to give the subtitle compound as a solid (0.6 g).

MS: APCI (+ve) 449 (M+H)$^+$.

f) N-Cyclopropyl-3-fluoro-4-methyl-5-[3-{[(1R,2S)-2-methyl-1-phenyl-3-pyrrolidin-1-ylpropyl]amino}-2-oxopyrazin-1(2H)-yl]benzamide Sodium triacetoxyborohydride (0.284 g) was added to N-cyclopropyl-3-fluoro-4-methyl-5-[3-{[(1R,2R)-2-methyl-3-oxo-1-phenylpropyl]amino}-2-oxopyrazin-1(2H)-yl]benzamide (Example 328e, 0.3 g), pyrrolidine (0.221 mL) and Hunig's Base (0.467 mL) in DCM (15 mL). The resulting suspension was stirred at 22° C. for 2 h. The reaction mixture was basified with satd sodium bicarbonate solution before extracting with DCM. The combined organic phases were concentrated in vacuo and the residue purified by preparative HPLC (Phenominex column using a 75-5% gradient of aqueous 0.2% ammonia in acetonitrile as eluent). The fractions containing the desired compound were evaporated to dryness to afford the title compound as a solid (0.046 g).

MS: APCI (+ve) 504 (M+H)$^+$.

$^1$H NMR δ (DMSO-$d_6$) 9.14 (dd, 1H), 8.52 (dd, 1H), 7.77-7.62 (m, 2H), 7.36-7.24 (m, 5H), 6.75-6.65 (m, 2H), 5.07-5.05 (m, 1H), 2.85 (q, 1H), 2.56-2.53 (m, 4H), 2.45-2.37 (m, 3H), 2.01 (s, 2H), 1.95 (s, 1H), 1.73 (t, 3H), 0.79 (d, 3H), 0.69 (t, 2H), 0.58-0.54 (m, 2H).

Example 329

N-Cyclopropyl-3-fluoro-4-methyl-5-[3-{[(1R,2S)-2-methyl-1-phenyl-3-piperidin-1-ylpropyl]amino}-2-oxopyrazin-1(2H)-yl]benzamide

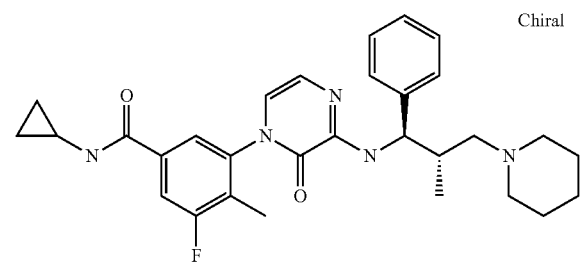

Chiral

The title compound was prepared from N-cyclopropyl-3-fluoro-4-methyl-5-[3-{[(1R,2R)-2-methyl-3-oxo-1-phenylpropyl]amino}-2-oxopyrazin-1(2H)-yl]benzamide (Example 328e) and piperidine using a similar method to that described for Example 328f.

MS: APCI (+ve) 518 (M+H)$^+$.

$^1$H NMR δ (DMSO-$d_6$) 9.30 (dd, 1H), 8.52 (dd, 1H), 7.78-7.74 (m, 1H), 7.65 (d, 1H), 7.36-7.22 (m, 5H), 6.69 (dd, 2H), 5.08-5.05 (m, 1H), 2.84 (s, 1H), 2.54-2.45 (m, 2H), 2.23-1.88 (m, 7H), 1.74-1.64 (m, 2H), 1.62-1.53 (m, 2H), 1.41-1.34 (m, 2H), 0.86-0.75 (m, 3H), 0.72-0.67 (m, 2H), 0.58-0.54 (m, 2H).

Example 330

4-Chloro-N-cyclopropyl-3-[3-[(1-methyl-1-{2-[2-(methylamino)ethoxy]phenyl}ethyl)amino]-2-oxopyrazin-1(2H)-yl]benzamide

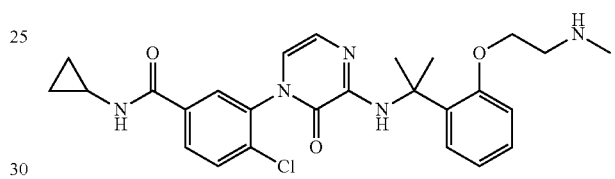

a) Methyl 3-amino-4-chlorobenzoate

A solution of methyl 4-chloro-3-nitrobenzoate (10 g) dissolved in acetic acid (100 mL) was treated with Iron powder (10.36 g) under nitrogen. The resulting mixture was stirred vigorously at 20° C. for 2 h. The reaction mixture was filtered through celite and the filtrate evaporated to dryness to afford crude product. The residue was diluted with aqueous sodium bicarbonate solution (200 mL), and extracted with dichloromethane (250 mL). The organic layer was separated, dried ($MgSO_4$), filtered and evaporated to afford the sub title compound (8.41 g).

$^1$H NMR δ ($CDCl_3$) 7.47 (s, 1H), 7.37-7.24 (m, 3H), 4.29-3.95 (m, 2H), 3.90 (s, 3H)

b) Methyl 4-chloro-3-{[ethoxy(oxo)acetyl]amino}benzoate

A suspension of methyl 3-amino-4-chlorobenzoate (Example 330a, 8.41 g) dissolved in ethyl acetate (80 mL) was treated with triethylamine (9.47 mL) under nitrogen. The resulting mixture was stirred at 0° C. before adding ethyl oxalyl chloride (5.57 mL) dropwise over 5 min. The resulting mixture was stirred for 1 h. The reaction mixture was diluted with water (100 mL), and extracted with ethyl acetate. The organic layer was washed with 2M hydrochloric acid followed by saturated sodium bicarbonate solution. The organic layer was dried ($MgSO_4$), filtered and evaporated to afford the crude product. The solid was triturated with diethyl ether to give the subtitle compound (11.20 g).

$^1$H NMR δ ($CDCl_3$) 9.53-9.42 (m, 1H), 9.12 (s, 1H), 7.82 (d, 1H), 7.50 (d, 1H), 4.45 (q, 2H), 3.96 (s, 3H), 1.45 (t, 3H)

c) Methyl 4-chloro-3-{[[(2,2-dimethoxyethyl)amino](oxo)acetyl]amino}benzoate A solution of methyl 4-chloro-3-{[ethoxy(oxo)acetyl]amino}benzoate (Example 330b, 11.2 g) dissolved in ethyl acetate (80 mL) was treated with aminoacetaldehyde dimethyl acetal (5.08 mL) under nitrogen. The resulting mixture was stirred at 20° C. for 3 h. The reaction mixture was diluted with diethyl ether (100 mL) and stirred at room temperature overnight. The solid formed was filtered off and dried under vacuum to afford the subtitle compound (12.64 g).

$^1$H NMR δ (CDCl$_3$) 9.92 (s, 1H), 9.12 (s, 1H), 7.81 (d, 1H), 7.70-7.56 (m, 1H), 7.50 (d, 1H), 4.44 (t, 1H), 4.00 (s, 3H), 3.54 (t, 2H), 3.48 (s, 6H)

d) methyl 4-chloro-3-(2,3-dioxo-3,4-dihydropyrazin-1(2H)-yl)benzoate

A suspension of methyl 4-chloro-3-{[[(2,2-dimethoxyethyl)amino](oxo)acetyl]amino}benzoate (Example 330c, 8.5 g) in acetic acid (26 mL) was treated with trifluoroacetic acid (8.5 mL) under nitrogen. The resulting mixture was stirred at 120° C. for 3 h. The mixture was quenched with water (20 mL) and the resulting solid filtered off to give the subtitle compound (8.00 g).

$^1$H NMR δ (DMSO-d$_6$) 8.13-8.01 (m, 2H), 7.84 (d, 1H), 6.52-6.40 (m, 2H), 3.93 (s, 3H)

e) methyl 3-(3-bromo-2-oxopyrazin-1(2H)-yl)-4-chlorobenzoate

A suspension of methyl 4-chloro-3-(2,3-dioxo-3,4-dihydropyrazin-1(2H)-yl)benzoate (Example 330d, 8 g) in DCM (80 mL) was treated with N,N-dimethylformamide (0.220 mL) and oxalyl bromide (2.94 mL) dropwise over 5 min at room temperature under nitrogen. The resulting mixture was stirred at 20° C. for 16 h. The reaction mixture turned black and was evaporated to afford crude product. Purification (SiO$_2$ chromatography eluting with 30% diethyl ether in dichloromethane) gave the subtitle compound (6.33 g).

$^1$H NMR δ (DMSO-d$_6$) 8.28 (s, 1H), 8.10 (d, 1H), 7.90 (d, 1H), 7.77 (d, 1H), 7.32 (d, 1H), 3.83 (s, 1H)

f) Methyl-3-[3-({1-[2-(benzyloxy)phenyl]-1-methylethyl}amino)-2-oxopyrazin-1(2H)-yl]-4-chlorobenzoate A solution of methyl 3-(3-bromo-2-oxopyrazin-1(2H)-yl)-4-chlorobenzoate (Example 330e, 3 g) dissolved in toluene (15 mL) was treated with N-ethyldiisopropylamine (2.99 mL) and 2-(2-(benzyloxy)phenyl)propan-2-amine (Example 198d 2.107 g) under nitrogen. The resulting mixture was stirred at 125° C. for 8 h in a sealed tube. The reaction mixture was diluted with water (150 mL), and extracted with ethyl acetate (250 mL). The organic was dried (MgSO$_4$), filtered and evaporated to afford crude product. Purification (SiO$_2$ chromatography eluting with 50% diethyl ether in isohexane) gave the subtitle compound (2.230 g).

$^1$H NMR δ (DMSO-d$_6$) 8.10-7.99 (m, 2H), 7.85 (d, 1H), 7.43-7.27 (m, 5H), 7.23-7.15 (m, 1H), 7.03 (d, 1H), 6.95-6.82 (m, 2H), 6.73-6.64 (m, 2H), 5.16 (s, 2H), 3.92 (s, 3H), 1.81 (d, 6H)

g) 3-[3-({1-[2-(Benzyloxy)phenyl]-1-methylethyl}amino)-2-oxopyrazin-1(2H)-yl]-4-chloro-N-cyclopropylbenzamide A solution of methyl-3-[3-({1-[2-(benzyloxy)phenyl]-1-methylethyl}amino)-2-oxopyrazin-1(2H)-yl]-4-chlorobenzoate (Example 330f, 2.23 g) dissolved in THF (30 mL) was treated with cyclopropylamine (2.261 mL) and 2.0M Isopropylmagnesium chloride (11.06 mL) under nitrogen. The resulting solution was stirred at 20° C. for 2 h. The reaction mixture was diluted with aqueous ammonium chloride (150 mL), and extracted with dichloromethane (250 mL). The organic was dried (MgSO$_4$), filtered and evaporated to afford the subtitle compound (2.40 g).

$^1$H NMR δ (DMSO-d$_6$) 8.61-8.54 (m, 1H), 7.99-7.93 (m, 2H), 7.81-7.75 (m, 1H), 7.38-7.28 (m, 5H), 7.25-7.16 (m, 1H), 7.09-7.02 (m, 1H), 6.94-6.84 (m, 2H), 6.73-6.66 (m, 2H), 2.90-2.83 (m, 1H), 1.86 (s, 6H), 0.74-0.66 (m, 2H), 0.60-0.53 (m, 2H)

h) N-(sec-butyl)-4-chloro-3-[3-{[1-(2-hydroxyphenyl)-1-methylethyl]amino}-2-oxopyrazin-1(2H)-yl]benzamide A solution of 3-[3-({1-[2-(benzyloxy)phenyl]-1-methylethyl}amino)-2-oxopyrazin-1(2H)-yl]-4-chloro-N-cyclopropylbenzamide (Example 330g, 2.23 g) dissolved in DCM (30 mL) was treated with boron tribromide (8.43 mL of a 1M solution in DCM) at 0° C. under nitrogen. The resulting mixture was stirred at 0° C. for 1 h. The reaction mixture was diluted with water (200 mL), and extracted with dichloromethane (250 mL). The organic was dried (MgSO$_4$), filtered and evaporated to afford crude product. The crude product was triturated with diethyl ether (50 mL) to afford the subtitle compound (1.760 g).

$^1$H NMR δ (DMSO-d$_6$) 9.59-9.50 (m, 1H), 8.62-8.53 (m, 1H), 8.03-7.94 (m, 2H), 7.84-7.75 (m, 1H), 7.29-7.20 (m, 1H), 7.10-7.01 (m, 2H), 6.83-6.69 (m, 4H), 2.96-2.82 (m, 1H), 1.93 (s, 6H), 0.77-0.67 (m, 2H), 0.64-0.54 (m, 2H)

i) 4-Chloro-3-[3-({1-[2-(2-chloroethoxy)phenyl]-1-methylethyl}amino)-2-oxopyrazin-1(2H)-yl]-N-cyclopropylbenzamide A solution of N-(sec-butyl)-4-chloro-3-[3-{[1-(2-hydroxyphenyl)-1-methylethyl]amino}-2-oxopyrazin-1(2H)-yl]benzamide (Example 330h, 1 g) dissolved in acetonitrile (10 mL) was treated with potassium carbonate (3.15 g) and 1-bromo-2-chloroethane (1.896 mL) under nitrogen. The resulting suspension was stirred at 75° C. for 10 h. The reaction mixture was evaporated to dryness, diluted with water (300 mL), and extracted with DCM. The organic layer was separated, dried (MgSO$_4$), filtered and evaporated to afford the crude product. The crude product was triturated with 50% ether in isohexane to afford the subtitle compound (1.100 g).

$^1$H NMR δ (DMSO-d$_6$) 8.61-8.52 (m, 1H), 8.02-7.93 (m, 2H), 7.78 (d, 1H), 7.39-7.30 (m, 2H), 6.97-6.88 (m, 3H), 6.65 (d, 2H), 4.24-4.15 (m, 2H), 3.98-3.89 (m, 2H), 2.90-2.81 (m, 1H), 1.89-1.81 (m, 6H), 0.74-0.65 (m, 2H), 0.62-0.53 (m, 2H)

j) 4-Chloro-N-cyclopropyl-3-[3-[(1-methyl-1-{2-[2-(methylamino)ethoxy]phenyl}ethyl)amino]-2-oxopyrazin-1(2H)-yl]benzamide A solution of 4-chloro-3-[3-({1-[2-(2-chloroethoxy)phenyl]-1-methylethyl}amino)-2-oxopyrazin-1(2H)-yl]-N-cyclopropylbenzamide (Example 330i, 0.22 g) dissolved in acetonitrile (3 mL) was treated with 40% aqueous methylamine (0.380 mL). The resulting mixture was stirred at 100° C. for 16 h in a sealed tube. The reaction mixture was filtered and purified by preparative HPLC (Phenominex Gemini column using a 95-5% gradient of aqueous 0.2% ammonia in acetonitrile as eluent). The fractions containing the desired compound were evaporated to afford the title compound (0.087 g).

MS: APCI (+ve) 496 (M+H)+.

$^1$H NMR δ (DMSO-$d_6$) 8.62-8.52 (m, 1H), 8.02-7.92 (m, 2H), 7.78 (d, 1H), 7.33 (d, 1H), 7.19 (t, 1H), 6.99-6.85 (m, 3H), 6.71 (s, 2H), 4.03-3.89 (m, 2H), 2.91-2.76 (m, 3H), 2.31 (s, 3H), 1.87 (s, 6H), 0.74-0.65 (m, 2H), 0.60-0.51 (m, 2H)

The following Examples 331 to 334 (Table 15) were prepared using a similar method to that described for Example 330 using 4-chloro-3-[3-({1-[2-(2-chloroethoxy)phenyl]-1-methylethyl}amino)-2-oxopyrazin-1(2H)-yl]-N-cyclopropylbenzamide (Example 330i) and a suitable amine.

Example 331

4-Chloro-N-cyclopropyl-3-[3-{[1-(2-{2-[(2-hydroxyethyl)amino]ethoxy}phenyl)-1-methylethyl]amino}-2-oxopyrazin-1(2H)-yl]benzamide

Example 332

4-Chloro-N-cyclopropyl-3-[3-({1-[2-(2-{[(2R)-2-hydroxypropyl]amino}ethoxy)phenyl]-1-methylethyl}amino)-2-oxopyrazin-1(2H)-yl]benzamide

Example 333

4-Chloro-N-cyclopropyl-3-[3-[(1-{2-[2-(ethylamino)ethoxy]phenyl}-1-methylethyl)amino]-2-oxopyrazin-1(2H)-yl]benzamide

Example 334

3-[3-({1-[2-(2-Aminoethoxy)phenyl]-1-methylethyl}amino)-2-oxopyrazin-1(2H)-yl]-4-chloro-N-cyclopropylbenzamide

TABLE 15

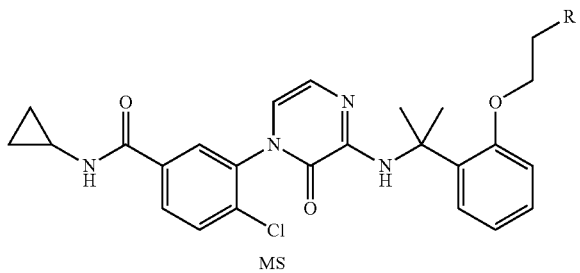

MS [M + H]+

| Example | R | m/z | $^1$H NMR δ (DMSO-$d_6$) |
|---|---|---|---|
| 331 | H\N\~\~OH | 526 | 8.66-8.56 (m, 1H), 8.07-7.96 (m, 2H), 7.84 (d, 1H), 7.38 (d, 1H), 7.24 (t, 1H), 7.06-6.89 (m, 3H), 6.76 (s, 2H), 4.43 (t, 1H), 4.08-3.95 (m, 2H), 3.52-3.38 (m, 2H), 3.01-2.88 (m, 3H), 2.73-2.60 (m, 2H), 1.94 (s, 6H), 0.82-0.69 (m, 2H), 0.68-0.55 (m, 2H) |
| 332 | H\N\~\~OH (2R) | 540 | 8.65-8.56 (m, 1H), 8.06-7.97 (m, 2H), 7.82 (d, 1H), 7.37 (d, 1H), 7.23 (t, 1H), 7.05-6.88 (m, 3H), 6.67 (s, 2H), 4.45-4.36 (m, 1H), 4.10-3.93 (m, 2H), 3.74-3.57 (m, 1H), 3.01-2.85 (m, 3H), 2.52-2.45 (m, 2H), 1.85 (s, 6H), 1.04 (d, 3H), 0.78-0.71 (m, 2H), 0.65-0.59 (m, 2H) |
| 333 | H\N\~ | 510 | 8.68-8.57 (m, 1H), 8.07-7.96 (m, 2H), 7.83 (d, 1H), 7.39 (d, 1H), 7.24 (t, 1H), 7.07-6.91 (m, 3H), 6.76 (s, 2H), 4.10-3.93 (m, 2H), 3.01-2.84 (m, 3H), 2.67-2.56 (m, 2H), 1.93 (s, 6H), 0.95 (t, 3H), 0.81-0.70 (m, 2H), 0.66-0.56 (m, 2H) |
| 334 | H\N\H | 482 | 8.58 (d, 1H), 7.99-7.92 (m, 2H), 7.77 (d, 1H), 7.33 (d, 1H), 7.18 (t, 1H), 6.99-6.85 (m, 3H), 6.65 (s, 2H), 3.95-3.79 (m, 2H), 2.95-2.79 (m, 3H), 1.78 (s, 6H), 0.77-0.65 (m, 2H), 0.59-0.50 (m, 2H) |

PHYSICAL FORM DATA

Description of Figures

FIG. 1: X-ray powder diffraction pattern of Form A of Example 167 free base
FIG. 2: X-ray powder diffraction pattern of Form B of Example 167 free base
FIG. 3: X-ray powder diffraction pattern of Form A of Example 259 free base
FIG. 4: X-ray powder diffraction pattern of Form A of Example 260 free base
FIG. 5: X-ray powder diffraction pattern of Form A of Example 163 free base
FIG. 6: X-ray powder diffraction pattern of Form B of Example 163 free base
FIG. 7: X-ray powder diffraction pattern of Form C of Example 163 free base
FIG. 8: X-ray powder diffraction pattern of Form D of Example 163 free base
FIG. 9: X-ray powder diffraction pattern of Form A of Example 163 Saccharide Salt
FIG. 10: X-ray powder diffraction pattern of Form A of Example 163 Tosylate Salt
FIG. 11: X-ray powder diffraction pattern of Form B of Example 163 Tosylate Salt
FIG. 12: X-ray powder diffraction pattern of Form A of Example 163 Hydrochloride Salt Instrument Details:
XRPD data were collected using a PANalytical CubiX PRO machine.
XRPD—PANalytical CubiX PRO
Data was collected with a PANalytical CubiX PRO machine in θ-2θ configuration over the scan range 2° to 40° 2θ with 100-second exposure per 0.02° increment. The X-rays were generated by a copper long-fine focus tube operated at 45 kV and 40 mA. The wavelength of the copper X-rays was 1.5418 Å. The Data was collected on zero background holders on which ~2 mg of the compound was placed. The holder was made from a single crystal of silicon, which had been cut along a non-diffracting plane and then polished on an optically flat finish. The X-rays incident upon this surface were negated by Bragg extinction.

DSC thermograms were measured using a TA Q1000 Differential Scanning calorimeter, with aluminium pans and pierced lids. The sample weights varied between 0.5 to 5 mg. The procedure was carried out under a flow of nitrogen gas (50 ml/min) and the temperature studied from 25 to 300° C. at a constant rate of temperature increase of 10° C. per minute.

GVS profiles were measured using a Dynamic Vapour Sorption DVS-1 instrument. The solid sample ca. 1-5 mg was placed into a glass vessel and the weight of the sample was recorded during a dual cycle step method (40 to 90 to 0 to 90 to 0% relative humidity (RH), in steps of 10% RH).

Preparation of Example 167 Free Base: N-Cyclopropyl-4-methyl-3-[3-[[1-[2-[2-(methylamino)ethoxy]phenyl]cyclopropyl]amino]-2-oxo-1(2H)-pyrazinyl]-benzamide Crystalline Form A 3-(3-(1-(2-(2-Chloroethoxy)phenyl)cyclopropylamino)-2-oxopyrazin-1(2H)-yl)-N-cyclopropyl-4-methylbenzamide (Example 167e, 5.00 g) dissolved in dioxane (15 mL) was treated with methylamine (15 mL of a 40 wt % solution in water). The resulting suspension was stirred at 100° C. for 4 h in an autoclave. The solution was evaporated to dryness. The crude product was purified ($SiO_2$ chromatography, eluting with a 5:1:94 (v/v) mixture of methanol:triethylamine:dichloromethane respectively). The product containing fractions were evaporated in vacuo and re-purified by RPHPLC (Xterra column, 95-5% gradient of aqueous 0.2% ammonia in acetonitrile as mobile phase). The product containing fractions were combined and freeze dried to leave a solid. Trituration with diethyl ether followed by drying in vacuo overnight gave the title compound as a white powder (3.14 g).

$^1$H NMR consistent with that described above in example 167

MS: APCI (+ve) 474 (M+H)$^+$.

Elemental Analysis—Found (calculated): % C, 68.0 (68.5); % H, 6.7 (6.6); % N, 14.2 (14.8).

Analysis of Example 167 Free Base: N-Cyclopropyl-4-methyl-3-[3-[[1-[2-[2-(methylamino)ethoxy]phenyl]cyclopropyl]amino]-2-oxo-1(2H)-pyrazinyl]-benzamide Crystalline Form A A sample of example 167 crystalline form A obtained by the procedure described above was analysed by XRPD, DSC and GVS.

The melting temperature of example 167 Crystalline Form A as determined by DSC gave a single endothermic event, occurring at 166° C. (±2° C.), with a water uptake of 1% (±0.2%) between RH of 0%-80%, as measured by GVS. An XRPD diffraction pattern of example 167 Crystalline Form A is presented in FIG. 1.

Preparation and Analysis of Example 167 Free Base: N-Cyclopropyl-4-methyl-3-[3-[[1-[2-[2-(methylamino)ethoxy]phenyl]cyclopropyl]amino]-2-oxo-1(2H)-pyrazinyl]-benzamide Crystalline Form B A sample of example 167 crystalline form B was obtained by slurrying example 167 crystalline Form A in dioxane at room temperature (~25° C.) and was analysed by XRPD. An XRPD diffraction pattern of example 167 crystalline form B is presented in FIG. 2.

Preparation of Example 259 Free Base: N-Cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide Crystalline Form A 3-[3-[[1-[2-(2-chloroethoxy)phenyl]cyclopropyl]amino]-2-oxo-1(2H)-pyrazinyl]-N-cyclopropyl-5-fluoro-4-methyl-benzamide (Example 259d, 10 g) in dioxane (25 mL) was treated with methylamine (15 mL of a 40 wt % aqueous solution). The resulting mixture was stirred at 100° C. for 16 h in a sealed tube. The reaction mixture was cooled, filtered and the solvents removed in vacuo to give crude product (~10 g). The crude product (~8.0 g) was purified by RPHPLC (Waters X-Bridge column, 95-5% gradient of aqueous 0.2% ammonia in acetonitrile as mobile phase). The product containing fractions were combined, evaporated and triturated with diethyl ether overnight. The white solid was collected by filtration and dried in vacuo to afford the title compound (4.14 g). NMR consistent with that described above in example 259.

MS: APCI (+ve) 492 (M+H)$^+$.

Elemental Analysis—Found (calculated): % C, 65.9 (66.0); % H, 6.1 (6.2); % N, 14.2 (14.3).

Analysis of Example 259 Free Base: N-Cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide Crystalline Form A A sample of example 259 crystalline form A obtained by the procedure described above was analysed by XRPD, DSC and GVS.

The melting temperature of example 259 crystalline form A as determined by DSC gave a single endothermic event, occurring at 163° C. (±2° C.), with a water uptake of 0.4% (±0.2%) between RH of 0%-80%, as measured by GVS. An XRPD diffraction pattern of example 259 crystalline form A is presented in FIG. 3

Preparation of Example 260 Free Base: N-Cyclopropyl-3-fluoro-5-[3-[[1-[2-[2-[(2-hydroxyethyl)amino]ethoxy]phenyl]cyclopropyl]amino]-2-oxo-1(2H)-pyrazinyl]-4-methyl-benzamide Crystalline Form A 3-[3-[[1-[2-(2-chloroethoxy)phenyl]cyclopropyl]amino]-2-oxo-1(2H)-pyrazinyl]-N-cyclopropyl-5-fluoro-4-methyl-benzamide (Example 259d, 5 g) and ethanolamine (6.1 mL) were heated at 100° C. in dioxane (20 mL) in a sealed tube for 16 h. Purification of the cooled solution by preparative HPLC (Xterra column, eluting with a gradient of acetonitrile in 0.2% (v/v) aqueous ammonia) gave the title product (2.95 g) after solvent removal in vacuo and trituration with isohexane/diethyl ether (1:1 80 mL).

MS: APCI (+ve) 522 (M+H)+.

$^1$H NMR δ (DMSO-$d_6$) 8.46 (1H, d), 7.73 (1H, d), 7.61 (1H, s), 7.51 (1H, d), 7.43 (1H, s), 7.19 (1H, t), 6.95 (1H, d), 6.92-6.80 (2H, m), 6.74 (1H, d), 4.44 (1H, s), 4.06 (2H, t), 3.51-3.43 (2H, m), 3.42-3.30 (1H, m), 2.97 (2H, t), 2.90-2.77 (1H, m), 2.69 (2H, t), 1.97 (3H, s), 1.27-1.01 (4H, m), 0.75-0.63 (2H, m), 0.57-0.50 (2H, m).

Elemental Analysis—Found (calculated): % C, 63.8 (64.5); H, 6.3 (6.2); N, 13.0 (13.4).

Analysis of Example 260 Free Base: N-Cyclopropyl-3-fluoro-5-[3-[[1-[2-[2-[(2-hydroxyethyl)amino]ethoxy]phenyl]cyclopropyl]amino]-2-oxo-1(2H)-pyrazinyl]-4-methyl-benzamide Crystalline Form A A sample of example 260 crystalline Form A obtained by the procedure described above was analysed by XRPD, DSC and GVS.

The melting temperature of example 260 crystalline form A as determined by DSC gave a single endothermic event, occurring at 206° C. (±2° C.), with a water uptake of 1.2% (±0.2%) between RH of 0%-80%, as measured by GVS. An XRPD diffraction pattern of example 260 crystalline form A is presented in FIG. 4.

Preparation of Example 163 Free Base Crystalline Form A: N-Cyclopropyl-4-methyl-3-[3-[[1-methyl-1-[2-[2-(methylamino)ethoxy]phenyl]ethyl]amino]-2-oxo-1(2H)-pyrazinyl]-benzamide Crystalline Form A To N-cyclopropyl-3-(3-(2-(2-hydroxyphenyl)propan-2-ylamino)-2-oxopyrazin-1(2H)-yl)-4-methylbenzamide (Example 134, 4.3 g) in acetonitrile (5 mL) was added potassium carbonate (2.84 g) followed by benzyl 2-chloroethyl(methyl)carbamate (2.69 g) and the reaction heated at 85° C. for 16 h under nitrogen. After cooling to room temperature, the mixture was evaporated to dryness and the residue partitioned between water (20 mL) and DCM (20 mL). The aqueous layer was separated and further extracted into DCM (2×20 mL). The combined organics were evaporated to leave crude benzyl 2-(2-(2-(4-(5-(cyclopropylcarbamoyl)-2-methylphenyl)-3-oxo-3,4-dihydropyrazin-2-ylamino)propan-2-yl)phenoxy)ethyl(methyl)carbamate (3.50 g) as a gum. Ethanol (150 mL) and P/C (0.611 g of 5%) were added and the reaction stirred under H2 atmosphere (2 bar) for 4 h. The mixture was filtered through Celite (washing pad with aliquots of ethanol) and the combined filtrates evaporated to leave the crude product (2.1 g). Recrystallisation from ethyl acetate gave the title product (1.15 g) as a white solid.

MS: APCI (+ve) 476 (M+H)+.

Analysis of Example 163 Free Base Crystalline Form A: N-Cyclopropyl-4-methyl-3-[3-[[1-methyl-1-[2-[2-(methylamino)ethoxy]phenyl]ethyl]amino]-2-oxo-1(2H)-pyrazinyl]-benzamide Crystalline Form A A sample of crystalline example 163 crystalline form A obtained by the procedure described above was analysed by XRPD (measured using Philips X-Pert MPD), DSC and GVS. The crystalline form was slurried in n propylacetate, Toluene and Methyl tertiary-butyl ether, with no change in crystal form.

The melting temperature of example 163 crystalline form A as determined by DSC gave a double endothermic event, occurring at 155° C. ($1^{st}$ onset) and 236° C. ($2^{nd}$ onset) (±2° C.). GVS determination gave 5% weight increase (% w/w) at 80% RH (±0.2%).

An XRPD diffraction pattern of example 163 crystalline form A is presented in FIG. 5.

Preparation of Example 163 Free Base Crystalline Form B: N-Cyclopropyl-4-methyl-3-[3-[[1-methyl-1-[2-[2-(methylamino)ethoxy]phenyl]ethyl]amino]-2-oxo-1(2H)-pyrazinyl]-benzamide Crystalline Form B 3-[3-[[1-[2-(2-Chloroethoxy)phenyl]-1-methylethyl]amino]-2-oxo-1(2H)-pyrazinyl]-N-cyclopropyl-4-methyl-benzamide (Example 198e, 17.5 g) in dioxane (50 mL) was treated with 40% Methylamine solution (50 mL) under nitrogen. The resulting suspension was heated in a sealed system at 100° C. for 4 h. After cooling to room temperature, the solution was evaporated to dryness. The crude product was purified by flash chromatography (SiO$_2$, eluent 10% methanol in dichloromethane and 1% triethylamine). Evaporation of the relevant fractions to dryness and trituration of the residue in diethyl ether gave a solid which was filtered off and dried to give the title compound (12.5 g) as an off white solid.

MS: APCI (+ve) 476 (M+H)+.

Analysis of Example 163 Free Base Crystalline Form B: N-Cyclopropyl-4-methyl-3-[3-[[1-methyl-1-[2-[2-(methylamino)ethoxy]phenyl]ethyl]amino]-2-oxo-1(2H)-pyrazinyl]-benzamide Crystalline Form B A sample of crystalline example 163 crystalline form B obtained by the procedure described above was analysed by XRPD (measured using PANalytical CubiX PRO), DSC and GVS.

The melting temperature of example 163 crystalline form B as determined by DSC gave a double endothermic event, occurring at 162° C. and 225° C. (±2° C.). GVS determination gave 4.3% weight increase (% w/w) at 80% RH (±0.2%).

An XRPD diffraction pattern of example 163 crystalline form B is presented in FIG. 6.

Preparation of Example 163 Free Base Crystalline
Form C: N-Cyclopropyl-4-methyl-3-[3-[[1-methyl-
1-[2-[2-(methylamino)ethoxy]phenyl]ethyl]amino]-
2-oxo-1(2H)-pyrazinyl]-benzamide Crystalline Form
C 3-[3-[[1-[2-(2-Chloroethoxy)phenyl]-1-methylethyl] amino]-2-oxo-1(2H)-pyrazinyl]-N-cyclopropyl-4-methyl-benzamide (Example 198e, 17.5 g) in dioxane (50 mL) was treated with 40% Methylamine solution (50 ml) under nitrogen. The resulting suspension was heated in a sealed system at 100° C. for 4 h. After cooling to room temperature, the solution was evaporated to dryness. The crude product was purified by flash chromatography (SiO$_2$, eluent 10% methanol in dichloromethane and 1% triethylamine). Evaporation of the relevant fractions to dryness and trituration of the residue in diethyl ether gave a solid which was filtered off. The filtrate was collected and evaporated. This residue was purified by preparative HPLC (Waters X-Terra column using a 95-5% gradient of aqueous 0.2% ammonia in acetonitrile as eluent). The fractions containing the desired compound were evaporated to dryness. Further purification by preparative HPLC (phenomenex column, aqueous 0.2% ammonia in acetonitrile as eluent) and freeze-drying of the relevant fractions gave a solid. This freeze dried material readily dissolved in ethyl acetate (30 mL) at room temperature and after stirring for 1 h some solid precipitated. The mixture was then heated to at 85° C. for 1 h to effect dissolution and then cooled and stirred at room temperature for 1 week. The solid was filtered off and dried in vacuo at 40° C. to afford the title compound (2.20 g).

Analysis of Example 163 Free Base Crystalline
Form C: N-Cyclopropyl-4-methyl-3-[3-[[1-methyl-
1-[2-[2-(methylamino)ethoxy]phenyl]ethyl]amino]-
2-oxo-1(2H)-pyrazinyl]-benzamide Crystalline Form
C A sample of crystalline example 163 crystalline form C obtained by the procedure described above was analysed by XRPD (measured using PANalytical CubiX PRO), DSC and GVS.

The melting temperature of example 163 crystalline form C as determined by DSC gave a single endothermic event, occurring at 168° C. (±2° C.). GVS determination gave 0.3% weight increase (% w/w) at 80% RH (±0.2%).

An XRPD diffraction pattern of example 163 crystalline form C is presented in FIG. 7.

Preparation and Analysis of Example 163 Free Base
Crystalline Form D: N-Cyclopropyl-4-methyl-3-[3-
[[1-methyl-1-[2-[2-(methylamino)ethoxy]phenyl]
ethyl]amino]-2-oxo-1(2H)-pyrazinyl]-benzamide
Crystalline Form D N-Cyclopropyl-4-methyl-3-[3-[[1-methyl-1-[2-[2-(methylamino)ethoxy]phenyl]ethyl]amino]-2-oxo-1(2H)-pyrazinyl]-benzamide Crystalline Form B was slurried in ethyl acetate for 1 week. The solid was filtered off and dried in vacuo at 40° C. to give the title compound.

A sample of this example 163 crystalline form D obtained by the procedure described above was analysed by XRPD (measured using PANalytical CubiX PRO).

An XRPD diffraction pattern of example 163 crystalline form D is presented in FIG. 8.

Preparation and Analysis of Example 163 Saccharide
Salt Crystalline Form A: N-Cyclopropyl-4-methyl-3-
[3-[[1-methyl-1-[2-[2-(methylamino)ethoxy]phenyl]
ethyl]amino]-2-oxo-1(2H)-pyrazinyl]-benzamide
Saccharide Salt Crystalline Form A N-Cyclopropyl-4-methyl-3-[3-[[1-methyl-1-[2-[2-(methylamino)ethoxy]phenyl]ethyl]amino]-2-oxo-1(2H)-pyrazinyl]-benzamide was dissolved in methanol, treated with saccharin (1 equiv), evaporated to dryness and slurried in acetonitrile (0.5 mL) for 1 week. The mixture was centrifuged and the solid filtered off to give the title compound. A sample of crystalline example 163 saccharide salt crystalline form A obtained by the procedure described above was analysed by XRPD (measured using Philips X-Pert MPD) and DSC.

The melting temperature of example 163 saccharide salt crystalline form A as determined by DSC gave three endothermic events, occurring at 148° C., 167° C. and 207° C. (±2° C.).

An XRPD diffraction pattern of example 163 saccharide salt crystalline form A is presented in FIG. 9.

Preparation and Analysis of Example 163 Tosylate
Salt Crystalline Form A: N-Cyclopropyl-4-methyl-3-
[3-[[1-methyl-1-[2-[2-(methylamino)ethoxy]phenyl]
ethyl]amino]-2-oxo-1(2H)-pyrazinyl]-benzamide
Tosylate Salt Crystalline Form A N-Cyclopropyl-4-methyl-3-[3-[[1-methyl-1-[2-[2-(methylamino)ethoxy]phenyl]ethyl]amino]-2-oxo-1(2H)-pyrazinyl]-benzamide was dissolved in methanol, treated with p-toluenesulfonic acid (1 equiv), evaporated to dryness and slurried in acetonitrile (0.5 mL) for 1 week. The mixture was centrifuged and the solid filtered off to give the title compound.

A sample of crystalline example 163 tosylate salt crystalline form A obtained by the procedure described above was analysed by XRPD (measured using Philips X-Pert MPD), DSC and GVS.

The melting temperature of example 163 tosylate salt crystalline form A as determined by DSC gave a single endothermic event, occurring at 206° C. (±2° C.). GVS determination gave 0.1% weight increase (% w/w) at 80% RH (±0.2%).

An XRPD diffraction pattern of example 163 tosylate salt crystalline form A is presented in FIG. 10.

Preparation and Analysis of Example 163 Tosylate
salt Crystalline Form B: N-Cyclopropyl-4-methyl-3-
[3-[[1-methyl-1-[2-[2-(methylamino)ethoxy]phenyl]
ethyl]amino]-2-oxo-1(2H)-pyrazinyl]-benzamide
Tosylate salt Crystalline Form B N-Cyclopropyl-4-methyl-3-[3-[[1-methyl-1-[2-[2-(methylamino)ethoxy]phenyl]ethyl]amino]-2-oxo-1(2H)-pyrazinyl]-benzamide was dissolved in methanol, treated with p-toluenesulfonic acid (1 equiv), evaporated to dryness and slurried in THF (0.5 mL) for 1 week. The mixture was centrifuged and the solid filtered off to give the title compound. A sample of crystalline example 163 tosylate salt crystalline form B obtained by the procedure described above was analysed by XRPD (measured using Philips X-Pert MPD) and DSC.

The melting temperature of example 163 tosylate salt crystalline form B as determined by DSC gave three endothermic events, occurring at 88° C., 166° C. and 177° C. (±2° C.)

An XRPD diffraction pattern of example 163 tosylate salt crystalline form B is presented in FIG. 11.

Preparation and Analysis of Example 163 Hydrochloride Salt Crystalline Form A: N-Cyclopropyl-4-methyl-3-[3-[[1-methyl-1-[2-[2-(methylamino)ethoxy]phenyl]ethyl]amino]-2-oxo-1(2H)-pyrazinyl]-benzamide Hydrochloride Salt Crystalline Form A N-Cyclopropyl-4-methyl-3-[3-[[1-methyl-1-[2-[2-(methylamino)ethoxy]phenyl]ethyl]amino]-2-oxo-1(2H)-pyrazinyl]-benzamide was dissolved in methanol, treated with 4N HCl in dioxane (excess), evaporated to dryness and slurried in THF (0.5 mL) for 1 week. The mixture was centrifuged and the solid filtered off to give the title compound. A sample of crystalline example 163 HCl salt polymorph A obtained by the procedure described above was analysed by XRPD (measured using Philips X-Pert MPD) and DSC.

The melting temperature of example 163 HCl salt polymorph A as determined by DSC gave three endothermic events, occurring at 43° C., 90° C. and 177° C. (±2° C.)

An XRPD diffraction pattern of example 163 HCl salt polymorph A is presented in FIG. 12.

Pharmacological Analysis

The ability of the compounds of formula (I) to inhibit p38 kinase may be determined using the following biological assay:

P38 Alpha Enzyme Assay

Enzyme assays were performed in polypropylene 96 well plates. The following solutions were added to each well; 10 µL of compound dilutions in assay buffer (20 mM HEPES pH 7.4, containing 20 mM magnesium acetate, 0.005% (w/v) Tween-20, 10 mM DTT) containing 1% (v/v) DMSO or assay buffer containing 1% (v/v) DMSO alone, 70 µL of assay buffer containing 36 nM substrate (biotinylated-ATF2) and 10 µL of an appropriate dilution of human active recombinant p38α-6H is tagged. Depending on batch of p38, an appropriate dilution was typically a 5 nM solution to give a final enzyme concentration of 0.5 nM. At this stage, background control wells also received 50 µL of AlphaScreen quench buffer (10 mM HEPES pH 7.4 containing 100 mM EDTA, 0.2% (w/v) bovine serum albumin). The plate was covered, pre-incubated for 4 h at 37° C. and the enzyme reaction initiated by addition of 10 µL 1 mM ATP. After incubation for a further 45 minutes at 37° C., the reaction was stopped by addition of 50 µL quench reagent and 50 µL of the quenched reaction mixture transferred to an opaque, white 96-well plate. Detection reagent, 25 µL of 10 mM HEPES pH 7.4 containing 100 mM EDTA, 0.2% (w/v) bovine serum albumin, 0.3 nM anti phosphoATF2 antibody and 25 µg/mL of AlphaScreen protein A acceptor and donor beads, was added to all wells in a darkened room, the plate sealed and left in the dark for between 5 and 24 h before AlphaScreen readings were taken using a Perkin Elmer EnVision reader. The compounds of the examples show greater than or equal to 50% inhibition of p38α and/or p38β at concentrations less than 10 µM.

The following table shows $pIC_{50}$ figures for the compounds of the present invention.

| Example number | $pIC_{50}$* | Example number | $pIC_{50}$* | Example number | $pIC_{50}$* | Example number | $pIC_{50}$* |
|---|---|---|---|---|---|---|---|
| 1 | 7.4 | 83 | 7.7 | 165 | 9.3 | 247 | 9.8 |
| 2 | 6.4 | 84 | 8.6 | 166 | 7.6 | 248 | 10 |
| 3 | 6.1 | 85 | 6.4 | 167 | 9.7 | 249 | 9.9 |
| 4 | 6.1 | 86 | 8.1 | 168 | 9.9 | 250 | 9.7 |
| 5 | 5.9 | 87 | 7.7 | 169 | 9.9 | 251 | 10.1 |
| 6 | 6.5 | 88 | 6.4 | 170 | 8.9 | 252 | 10.1 |
| 7 | 6.2 | 89 | 7.6 | 171 | 8.8 | 253 | 10.2 |
| 8 | 6.4 | 90 | 6.4 | 172 | 9.6 | 254 | 10.2 |
| 9 | 6.3 | 91 | 7.9 | 173 | 9 | 255 | 10.2 |
| 10 | 7.3 | 92 | 7.6 | 174 | 8.9 | 256 | 10.5 |
| 11 | 7.6 | 93 | 6.9 | 175 | 9 | 257 | 10.3 |
| 12 | 7 | 94 | 7.5 | 176 | 8.7 | 258 | 10.4 |
| 13 | 7.2 | 95 | 7.7 | 177 | 9 | 259 | 10 |
| 14 | 6 | 96 | 8.5 | 178 | 8.8 | 260 | 10.3 |
| 15 | 7.8 | 97 | 8.7 | 179 | 8.9 | 261 | 10.5 |
| 16 | 6.7 | 98 | 7.8 | 180 | 9.6 | 262 | 10.2 |
| 17 | 6.6 | 99 | 7.1 | 181 | 9.2 | 263 | 10.3 |
| 18 | 8.2 | 100 | 7.3 | 182 | 9 | 264 | 10.1 |
| 19 | 6.6 | 101 | 7.4 | 183 | 9 | 265 | 9.7 |
| 20 | 6.1 | 102 | 6.3 | 184 | 8.7 | 266 | 9.4 |
| 21 | 6.7 | 103 | 6.1 | 185 | 9.1 | 267 | 9.5 |
| 22 | 7 | 104 | 7.2 | 186 | 9 | 268 | 10 |
| 23 | 6.9 | 105 | 6.2 | 187 | 9.8 | 269 | 9.9 |
| 24 | 6.3 | 106 | 6.2 | 188 | 9.2 | 270 | 9.9 |
| 25 | 5.5 | 107 | 6.1 | 189 | 9.2 | 271 | 9.9 |
| 26 | 7.8 | 108 | 6.3 | 190 | 9 | 272 | 8.5 |
| 27 | 6.4 | 109 | 7.2 | 191 | 9.6 | 273 | 9 |
| 28 | 6.2 | 110 | 6.7 | 192 | 9.2 | 274 | 8.7 |
| 29 | 7 | 111 | 7.1 | 193 | 9.3 | 275 | 8.6 |
| 30 | 6.9 | 112 | 9.4 | 194 | 9.1 | 276 | 8.8 |
| 31 | 7 | 113 | 9.8 | 195 | 8.8 | 277 | 8.5 |
| 32 | 6.8 | 114 | 6.6 | 196 | 8.9 | 278 | 9.9 |
| 33 | 7.5 | 115 | 6.9 | 197 | 9 | 279 | 10.1 |
| 34 | 6.4 | 116 | 6.4 | 198 | 9.6 | 280 | 10.1 |
| 35 | 6.6 | 117 | 6.8 | 199 | 9.1 | 281 | 10.4 |
| 36 | 6.8 | 118 | 7.3 | 200 | 9.2 | 282 | 10.3 |
| 37 | 6.1 | 119 | 6.6 | 201 | 9.1 | 283 | 9.7 |
| 38 | 8.9 | 120 | 6.4 | 202 | 9.2 | 284 | 9.5 |
| 39 | 7.5 | 121 | 6 | 203 | 8.9 | 285 | 9.6 |
| 40 | 6.7 | 122 | 5.6 | 204 | 9.8 | 286 | 9.3 |
| 41 | 7 | 123 | 7 | 205 | 9 | 287 | 9.3 |
| 42 | 6.4 | 124 | 6.9 | 206 | 9.3 | 288 | 8.4 |
| 43 | 7.1 | 125 | 6.2 | 207 | 8.9 | 289 | 8.9 |
| 44 | 7.6 | 126 | 8.1 | 208 | 9.1 | 290 | 8.5 |
| 45 | 6.5 | 127 | 7.3 | 209 | 8.9 | 291 | 8.5 |
| 46 | 8 | 128 | 8.2 | 210 | 9.5 | 292 | 8.4 |
| 47 | 7.2 | 129 | 7.7 | 211 | 9.6 | 293 | 9.5 |
| 48 | 7.5 | 130 | 8.2 | 212 | 9.6 | 294 | 10 |
| 49 | 6.9 | 131 | 7.6 | 213 | 9.9 | 295 | 9.5 |
| 50 | 7 | 132 | 7.5 | 214 | 9.1 | 296 | 9.1 |
| 51 | 7.5 | 133 | 6.8 | 215 | 9.6 | 297 | 9.4 |
| 52 | 6.3 | 134 | 8.9 | 216 | 9.4 | 298 | 10.2 |
| 53 | 7.4 | 135 | 9.5 | 217 | 9.6 | 299 | 10 |
| 54 | 6.5 | 136 | 8.6 | 218 | 9.1 | 300 | 10.3 |
| 55 | 6.5 | 137 | 8.1 | 219 | 9.3 | 301 | 10.1 |
| 56 | 6.4 | 138 | 8.9 | 220 | 8.3 | 302 | 10 |
| 57 | 7.1 | 139 | 8.7 | 221 | 6.7 | 303 | 10.1 |
| 58 | 7 | 140 | 8.6 | 222 | 9 | 304 | 10.2 |
| 59 | 7.2 | 141 | 8.8 | 223 | 8.1 | 305 | 9.9 |
| 60 | 7.3 | 142 | 8.8 | 224 | 8.4 | 306 | 10.1 |
| 61 | 6.3 | 143 | 8.8 | 225 | 8.2 | 307 | 10.3 |
| 62 | 7 | 144 | 7.9 | 226 | 6.6 | 308 | 10.4 |
| 63 | 6.3 | 145 | 8.2 | 227 | 8.5 | 309 | 10.2 |
| 64 | 6.8 | 146 | 8.9 | 228 | 6.8 | 310 | 10 |
| 65 | 7 | 147 | 9 | 229 | 8.6 | 311 | 10.1 |
| 66 | 6.5 | 148 | 8.1 | 230 | 10 | 312 | 9.8 |
| 67 | 6.6 | 149 | 8.9 | 231 | 9.9 | 313 | 9.9 |
| 68 | 7.6 | 150 | 7.9 | 232 | 9.1 | 314 | 10.4 |
| 69 | 6.2 | 151 | 9.1 | 233 | 9.9 | 315 | 10 |
| 70 | 6.8 | 152 | 8.9 | 234 | 10.3 | 316 | 10.4 |
| 71 | 6.8 | 153 | 9.2 | 235 | 9.7 | 317 | 10.1 |
| 72 | 7.2 | 154 | 9 | 236 | 10 | 318 | 8.2 |
| 73 | 7.1 | 155 | 9.1 | 237 | 9.9 | 319 | 8.1 |
| 74 | 6.7 | 156 | 8.9 | 238 | 9.7 | 320 | 9.5 |
| 75 | 7.1 | 157 | 9 | 239 | 9.6 | 321 | 9.7 |
| 76 | 6.8 | 158 | 9 | 240 | 8.8 | 322 | 9.8 |
| 77 | 7.5 | 159 | 9.6 | 241 | 9.5 | 323 | 9.5 |

-continued

| Example number | pIC$_{50}$* | Example number | pIC$_{50}$* | Example number | pIC$_{50}$* | Example number | pIC$_{50}$* |
|---|---|---|---|---|---|---|---|
| 78 | 7.8 | 160 | 9.8 | 242 | 9.7 | 324 | 8.1 |
| 79 | 7.7 | 161 | 9.2 | 243 | 9.4 | 325 | 8.9 |
| 80 | 7.9 | 162 | 9.4 | 244 | 9.2 | 326 | 7.6 |
| 81 | 6.3 | 163 | 9.6 | 245 | 9.5 | 327 | 8 |
| 82 | 7.5 | 164 | 9.6 | 246 | 9.8 | 328 | 9 |
| 329 | 9.6 | 330 | 9.4 | 331 | 9.6 | 332 | 9.7 |
| 333 | 9.5 | 334 | 9.3 | | | | |

* The standard deviation of the p38 enzyme inhibition assay is between 0.2 and 0.3 log units. The pIC50 values in the above table are means of replicate determinations which were within 2 × SD (95% confidence) of each other.

The invention claimed is:

1. A compound, wherein said compound is N-Cyclopropyl-3-fluoro-4-methyl-5-[3-[[1-[2-[2 (methylamino)ethoxy]phenyl]cyclopropyl]amino]-2-oxo-1(2H)-pyrazinyl]-benzamide or a pharmaceutically acceptable salt thereof.

2. The compound of claim 1, wherein said pharmaceutically acceptable salt is acetate, adipate, alginate, ascorbate, aspartate, benzenesulfonate (besylate), benzoate, butyrate, camphorate, camphorsulfonate, camsylate, citrate, p-chlorobenzenesulfonate, cyclopentate, 2,5-dichlorobesylate, digluconate, edisylate, esylate, fumarate, formate, gluconate, glucoheptanoate, glutamate, glutarate, glycerophosphate, glycolate, heptanoate, hexanoate, hippurate, 2-hydroxyethane sulfonate, lactate, lactobionate, laurate, malate, maleate, malonate, mandelate, methanesulfonate, 2-naphthalenesulfonate, napsylate, nicotinate, orotate, oxalate, pantothenate, pamoate, pamoic, pectinate, 3-phenylpropionate, pivalate, propionate, pivalate, saccharin, salicylate, stearate, succinate, tartrate, trans-cinnamate, trifluoroacetate, xinafoate, xylate (p-xylene-2-sulfonic acid), undecanoate, hydrobromide, hydrochloride, hydroiodide, sulphate, bisulfate, phosphate, nitrate, hemisulfate, thiocyanate, persulfate, phosphoric acid or sulfonic acid.

3. The compound of claim 1, wherein said compound is N-Cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide.

4. A pharmaceutical composition comprising the compound of claim 1, or a pharmaceutically acceptable salt thereof, and a pharmaceutically acceptable adjuvant, diluent, or carrier.

* * * * *